US010266844B2

(12) United States Patent
Anderson et al.

(10) Patent No.: US 10,266,844 B2
(45) Date of Patent: Apr. 23, 2019

(54) ACTIVITY-DEPENDENT EXPRESSION OF NUCLEIC ACIDS

(71) Applicant: California Institute of Technology, Pasadena, CA (US)

(72) Inventors: David J. Anderson, Altadena, CA (US); Todd E. Anthony, Pasadena, CA (US)

(73) Assignee: California Institute of Technology, Pasadena, CA (US)

(*) Notice: Subject to any disclaimer, the term of this patent is extended or adjusted under 35 U.S.C. 154(b) by 260 days.

(21) Appl. No.: 15/222,554

(22) Filed: Jul. 28, 2016

(65) Prior Publication Data

US 2017/0029848 A1 Feb. 2, 2017

Related U.S. Application Data

(60) Provisional application No. 62/199,836, filed on Jul. 31, 2015.

(51) Int. Cl.
 C12N 15/86 (2006.01)
 A01K 67/027 (2006.01)
 C07K 14/82 (2006.01)
 C12N 7/00 (2006.01)
 A61K 31/65 (2006.01)

(52) U.S. Cl.
 CPC .......... *C12N 15/86* (2013.01); *A01K 67/0275* (2013.01); *C07K 14/82* (2013.01); *A01K 2217/052* (2013.01); *C07K 2319/00* (2013.01); *C07K 2319/80* (2013.01); *C12N 2750/14143* (2013.01); *C12N 2800/30* (2013.01); *C12N 2830/002* (2013.01); *C12N 2830/003* (2013.01); *C12N 2830/006* (2013.01); *C12N 2830/32* (2013.01)

(58) Field of Classification Search
 CPC ......... C12N 15/86; C07K 14/82; A61K 31/65
 See application file for complete search history.

(56) References Cited

U.S. PATENT DOCUMENTS

2007/0116690 A1 5/2007 Yang et al.
2012/0232133 A1 9/2012 Balazs et al.

FOREIGN PATENT DOCUMENTS

WO WO 1992015694 A1 9/1992

OTHER PUBLICATIONS

Blesch et al.; Neurite Outgrowth Can Be Modulated In Vitro Using a Tetracycline-Repressible Gene Therapy Vector Expressing Human Nerve Growth Factor; Journal of Neuroscience Research 59:402-409 (2000) (Year: 2000).*
Drane et al.; A transgenic mouse line for collecting ribosome-bound mRNA using the tetracycline transactivator system; Frontiers in Molecular Neuroscience, vol. 7, article 82, Oct. 2014, pp. 1-10 (Year: 2014).*
Reijmers et al. Localization of a Stable Neural Correlate of Associative Memory; Science, vol. 317, pp. 1230-1233; Aug. 31, 2007 (Year: 2007).*
International Search Report and Written Opinion dated Oct. 21, 2016 for International Application No. PCT/US2016/044587, filed Jul. 28, 2016.
Abremski et al., 'Bacteriophage P1 site-specific recombination. Purification and properties of the Cre recombinase protein.' 1984, J. Biol. Chem. 259:1509-1514.
Barth, A.L., Gerkin, R.C., and Dean, K.L. (2004). Alteration of neuronal firing properties after in vivo experience in a FosGFP transgenic mouse. J Neurosci 24, 6466-6475.
Cantor et al. 'Ribozyme cleaves rex/tax mRNA and inhibits bovine leukemia virus expression.' (1993) Proc. Natl. Acad. Sci. USA 90:10932-10936.
Carrasco et al. Depolarization-induced slow calcium trnasients activate early genes in skeletal muscle cells. (2003), Am J Physiol Cell Physiol, 284, C1438-C1447.
Chao, et al., 'Development of single-vector Tet-on inducible systems with high sensitivity to doxycycline', Molecular Biotechnology, 2012, vol. 51, Issue 3, pp. 240-246.
Chtarto, a. et al., 'Tetracycline-inducible transgene expression mediated by a single AAV vector', Gene Therapy, 2003, vol. 10, No. 1, pp. 84-94.
De Felipe. 'Skipping the co-expression problem: the new 2A "CHYSEL" technology.' (2004) Genetic Vaccines and Ther. 2:13.
DeFelipe et al. 'Targeting of proteins derived from self-processing polyproteins containing multiple signal sequences.' (2004) Traffic 5:616-626.
Distel et al. 'Nucleoprotein complexes that regulate gene expression in adipocyte differentiation: direct participation of c-fos.' (1987) Cell 49: 835-844.
Freundlieb, S., Schirra-Muller, C., and Bujard, H. (1999). A tetracycline controlled activation/repression system with increased potential for gene transfer into mammalian cells. J Gene Med 1, 4-12.
Garner, A.R., Rowland, D.C., Hwang, S.Y., Baumgaertel, K., Roth, B.L., Kentros, C., and Mayford, M. (2012). Generation of a synthetic memory trace. Science (New York, NY) 335, 1513-1516.
Gossen, M. & Bujard, H., 'Tight control of gene expression in mammalian cells by tetracycline-responsive promoters.' (1992) Proc. Natl. Acad. Sci. USA 89:5547-5551.
Goverdhana, S. et al., 'Regulatable gene expression systems for gene therapy applications: progress and future challenges', Molecular Therapy, 2005, vol. 12, No. 2, pp. 189-211.

(Continued)

*Primary Examiner* — Antonio Galisteo Gonzalez
(74) *Attorney, Agent, or Firm* — Knobbe Martens Olson & Bear LLP

(57) ABSTRACT

According to some embodiments herein, expression systems and methods for activity-dependent transcription of nucleic acids are provided. In some embodiments, adeno-associated viral vector systems comprise an immediate early gene promoter operably linked to a transcriptional activator. The transcription activator can be fused to an N-terminal portion of an immediate early gene, for example fos.

14 Claims, 69 Drawing Sheets

Specification includes a Sequence Listing.

(56) References Cited

OTHER PUBLICATIONS

Greenberg, M.E., and Ziff, E.B. (1984). Stimulation of 3T3 cells induces transcription of the c-fos proto-oncogene. Nature 311, 433-438.

Guenthner, C.J., Miyamichi, K., Yang, H.H., Heller, H.C., and Luo, L. (2013). Permanent genetic access to transiently active neurons via TRAP: targeted recombination in active populations. Neuron 78, 773-784.

Gius et al. 'Transcriptional activation and repression by Fos are independent functions: the C terminus represses immediate-early gene expression via CArG elements.' (1990) Mol. Cell. Biol. 10:4243-4255.

Gurney et al. 'Opposing actions of Fos and Jun on transcription of the phosphoenolpyruvate carboxykinase (GTP) gene. Dominant negative regulation by Fos.' (1992) J. Biol. Chem. 267:18133-18139.

Guzowski, J.F., Setlow, B., Wagner, E.K., and McGaugh, J.L. (2001). Experience-dependent gene expression in the rat hippocampus after spatial learning: a comparison of the immediate-early genes Arc, c-fos, and zif268. J Neurosci 21, 5089-5098.

Hay et al. 'A FOS protein is present in a complex that binds a negative regulator of MYC.' (1989) Genes Dev. 3:293-303.

Hayakawa, T., Yusa, K., Kouno, M., Takeda, J., and Horie, K. (2006). Bloom's syndrome genedeficient phenotype in mouse primary cells induced by a modified tetracyclinecontrolled transsilencer. Gene 369, 80-89.

Hinrichs, W., et al., 'Structure of the Tet repressor-tetracycline complex and regulation of antibiotic resistance.' (1994) Science 264:418-420.

Holt et al. "Inducible Production c-Fos Antisense RNA Inhibits 3T3 Cell Proliferation," (1986) Proc. Natl. Acad. Sci. USA 831:4794-4798.

Lakso et al., 'Targeted oncogene activation by site-specific recombination in transgenic mice.' 1992, Proc. Natl. Acad. Sci. USA 89: 6232-6236.

Lord et al. 'Proto-oncogenes of the fos/jun family of transcription factors are positive regulators of myeloid differentiation.' (1993) Mol Cell. Biol. 13:841-851.

Liu, et al., 'Optogenetic stimulation of a hippocampal engram activates fear memory recall', Nature, 2012, vol. 484, No. 7394, pp. 381-385.

Livet et al., 'Transgenic strategies for combinatorial expression of fluorescent proteins in the nervous system.' 2007, Nature, 450, 56-62.

Miller et al. 'c-fos protein can induce cellular transformation: a novel mechanism of a cellular oncogene.' (1984) Cell 36:51-60.

Morgan, J.I., Cohen, D.R., Hempstead, J.L., and Curran, T. (1987). Mapping patterns of c-fos expression in the central nervous system after seizure. Science 237, 192-197.

O'Gorman et al., 'Recombinase-mediated gene activation and site-specific integration in mammalian cells.' 1991, Science 251: 1351-1355.

Orban et al., 'Tissue- and site-specific DNA recombination in transgenic mice.' 1992, Proc. Natl. Acad. Sci. USA 89: 6861-6865.

Ramirez, S., Liu, X., Lin, P.A., Suh, J., Pignatelli, M., Redondo, R.L., Ryan, T.J., and Tonegawa, S. (2013). Creating a False Memory in the Hippocampus. Science (New York, NY) 341, 387-391.

Reijmers, et al., 'Localization of a stable neural correlate of associative memory', Science, 2007, vol. 317, No. 5842, pp. 1230-1233.

Riabowol et al. 'Microinjection of fos-specific antibodies blocks DNA synthesis in fibroblast cells.' (1988) Mol. Cell. Biol. 8:1670-1676.

Root, C.M., Denny, C.A., Hen, R., and Axel, R. (2014). The participation of cortical amygdala in innate, odour-driven behaviour. Nature 515, 269-273.

Rüüther et al. 'c-fos expression induces bone tumors in transgenic mice.' (1989) Oncogene 4:861-865.

Sassone-Corsi et al. 'Transcriptional autoregulation of the proto-oncogene fos .' (1988) Nature 334:314-319.

Schuermann, M. et al. The leucine repeat motif in Fos protein mediates complex formation with Jun/AP-1 and is required for transformation. Cell, 1989, 56, 507-516.

Smeyne, et al. (1992). fos-lacZ transgenic mice: mapping sites of gene induction in the central nervous system. Neuron 8, 13-23.

Urlinger, S., et al. (2000). Exploringthe sequence space for tetracycline-dependent transcriptional activators: novel mutations yield expanded range and sensitivity. Proc Natl Acad Sci U S A 97, 7963-7968.

Zeng, H., and Madisen, L. (2012). Mouse transgenic approaches in optogenetics. Progress in Brain Research 196, 193-213.

Gore et al., "Neural Representations of Unconditioned Stimuli in Basolateral Amygdala Mediate Innate and Learned Responses", Cell, Vo. 162, pp. 134-145, Jul. 2, 2015.

Roy et al., "Memory retrieval by activating engram cells in mouse models of early Alzheimer's disease", Nature, vol. 531, Mar. 24, 2016, pp. 508-524.

Kawashima et al., "Functional labeling of neurons and their projections using the synthetic activity-dependent promoter E-SARE", Nature Methods, vol. 10, No. 9, Sep. 2013, pp. 889-911.

\* cited by examiner

AAV_cfos-FmTB-comp+5'pA nucleotide sequence

FRR-ChR2-YFP nucleotide sequence

TRE-FLPo nucleotide sequence

FIG. 6 (continued)

DESIGN USED TO GENERATE Fos::FmTB TRANSGENICS

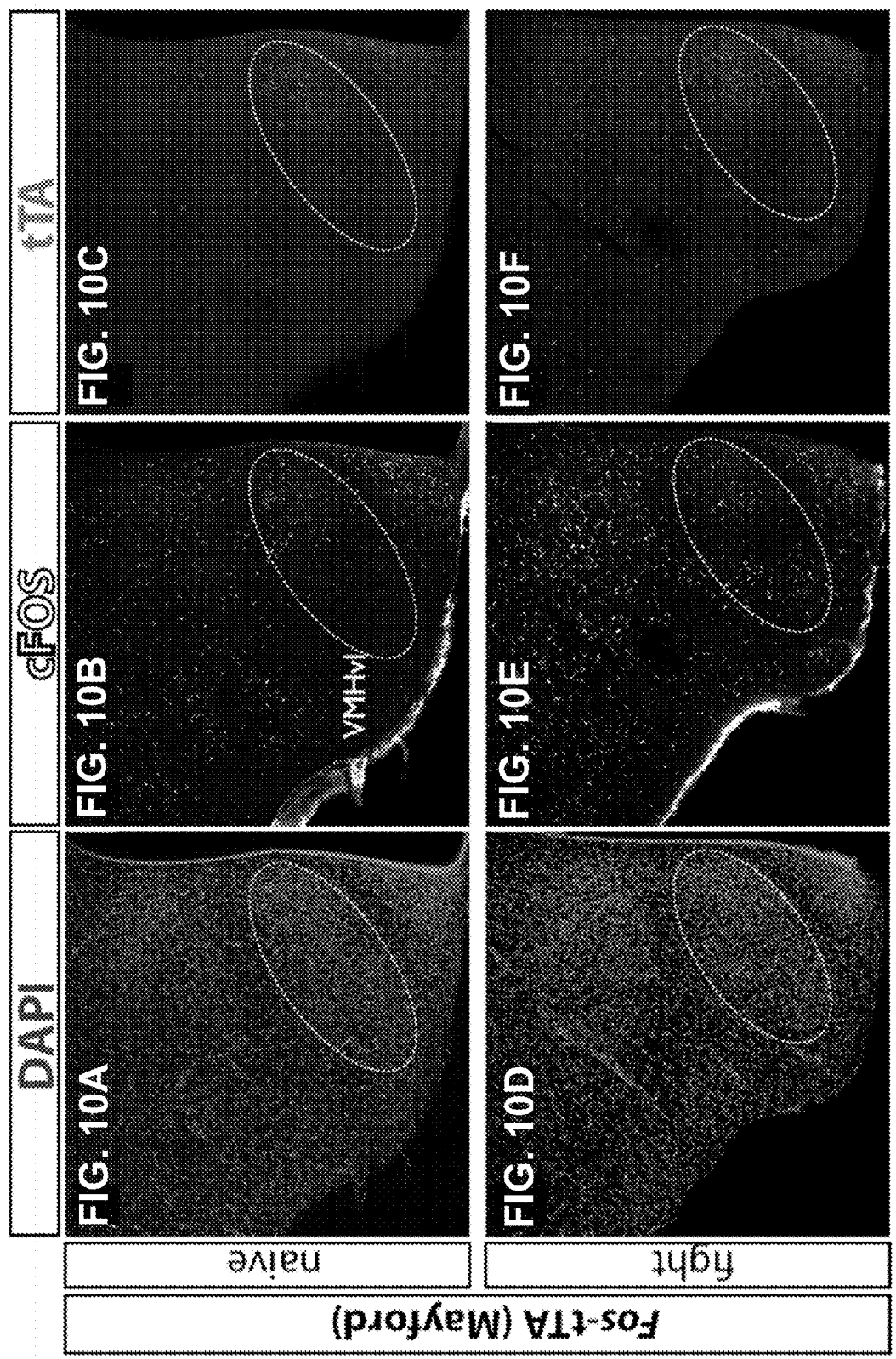

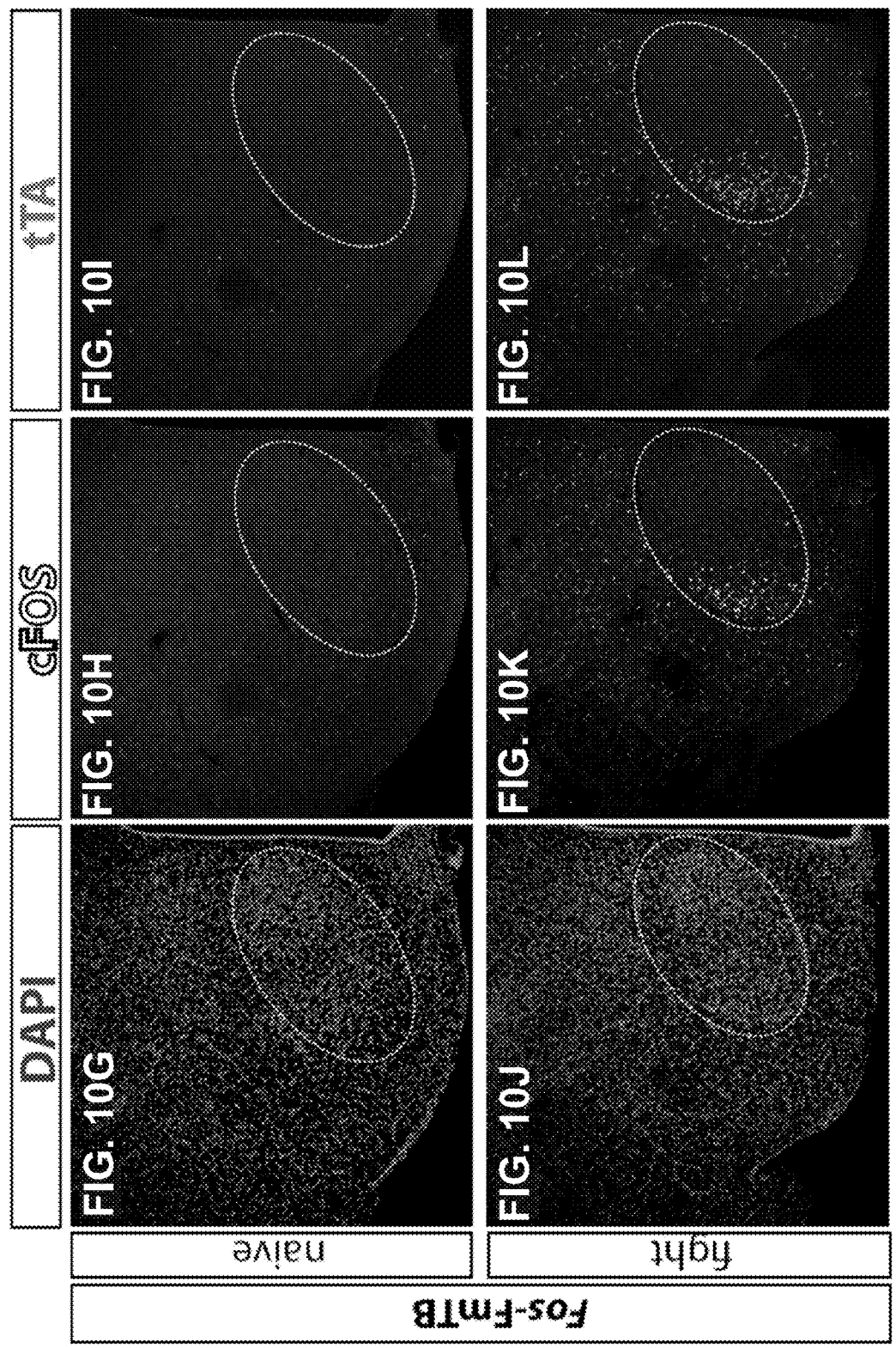

Transgene

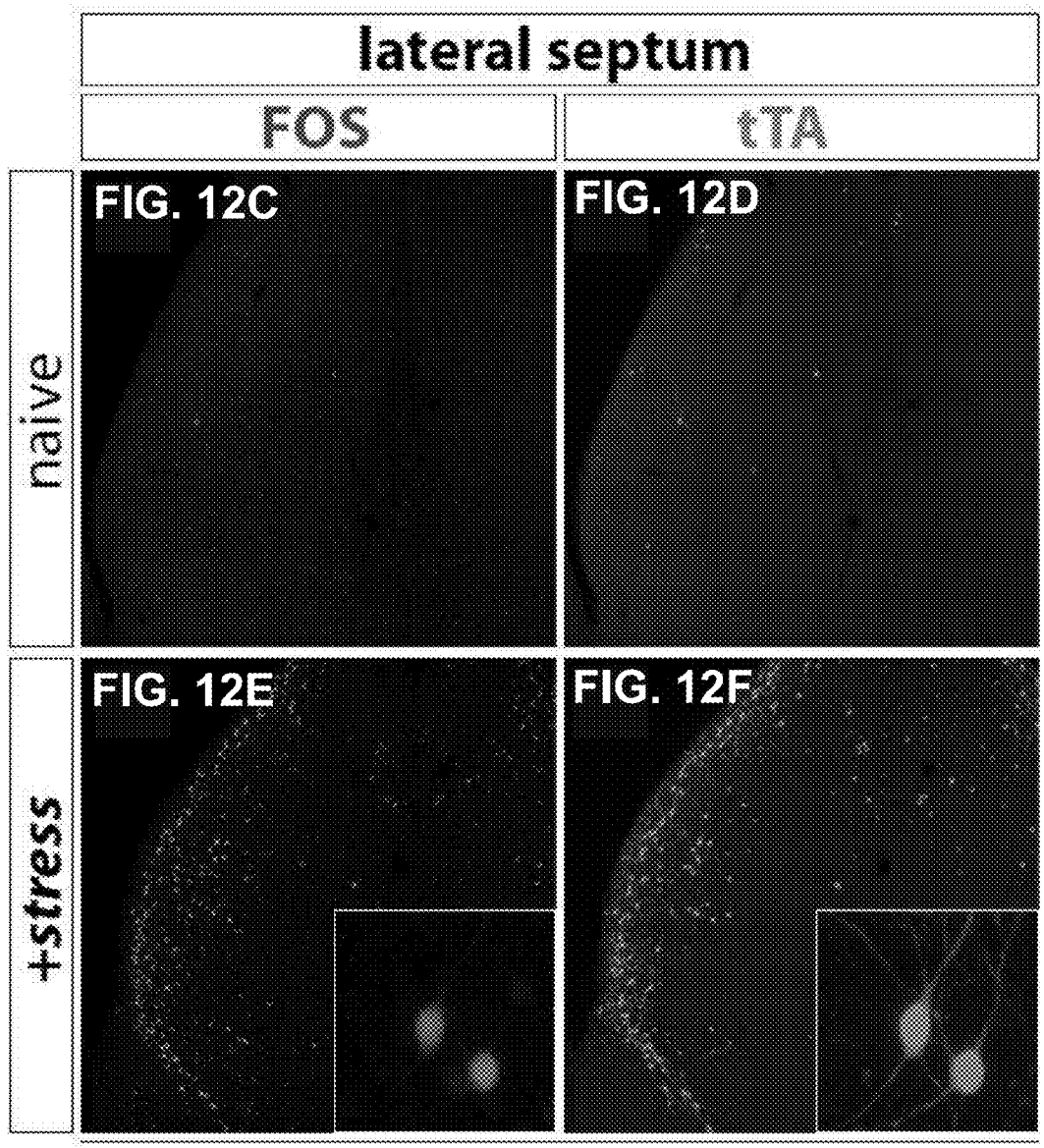

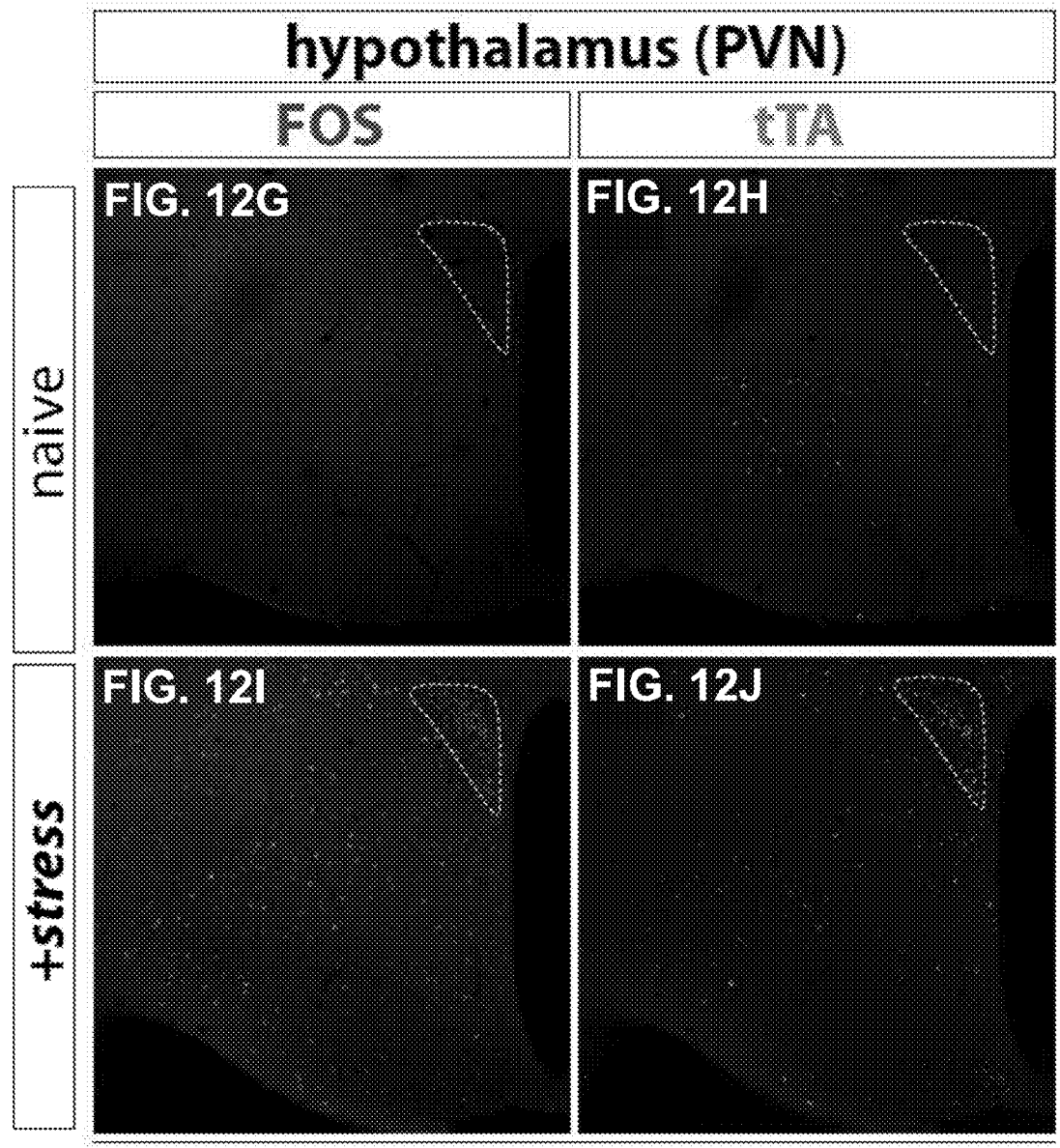

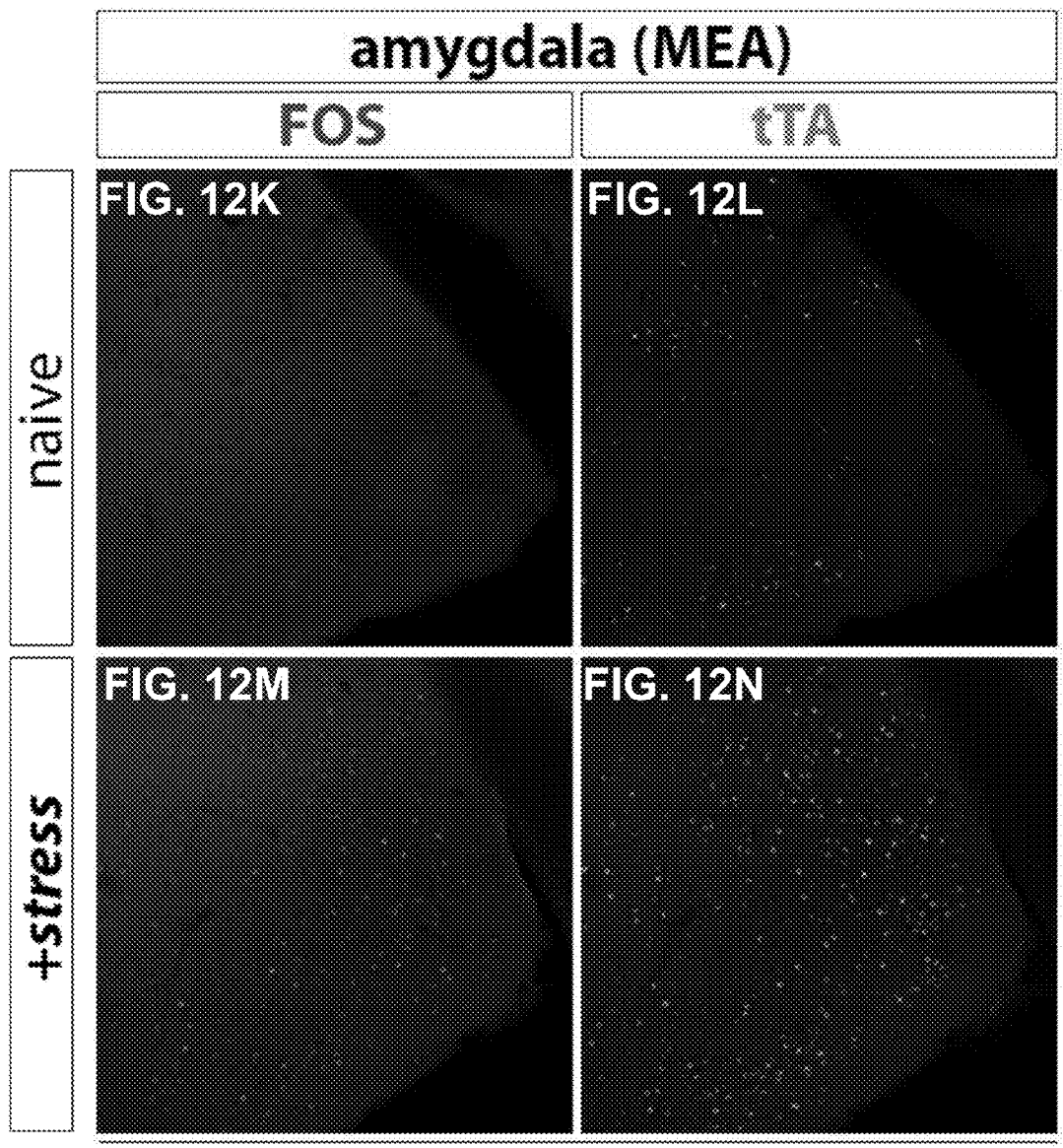

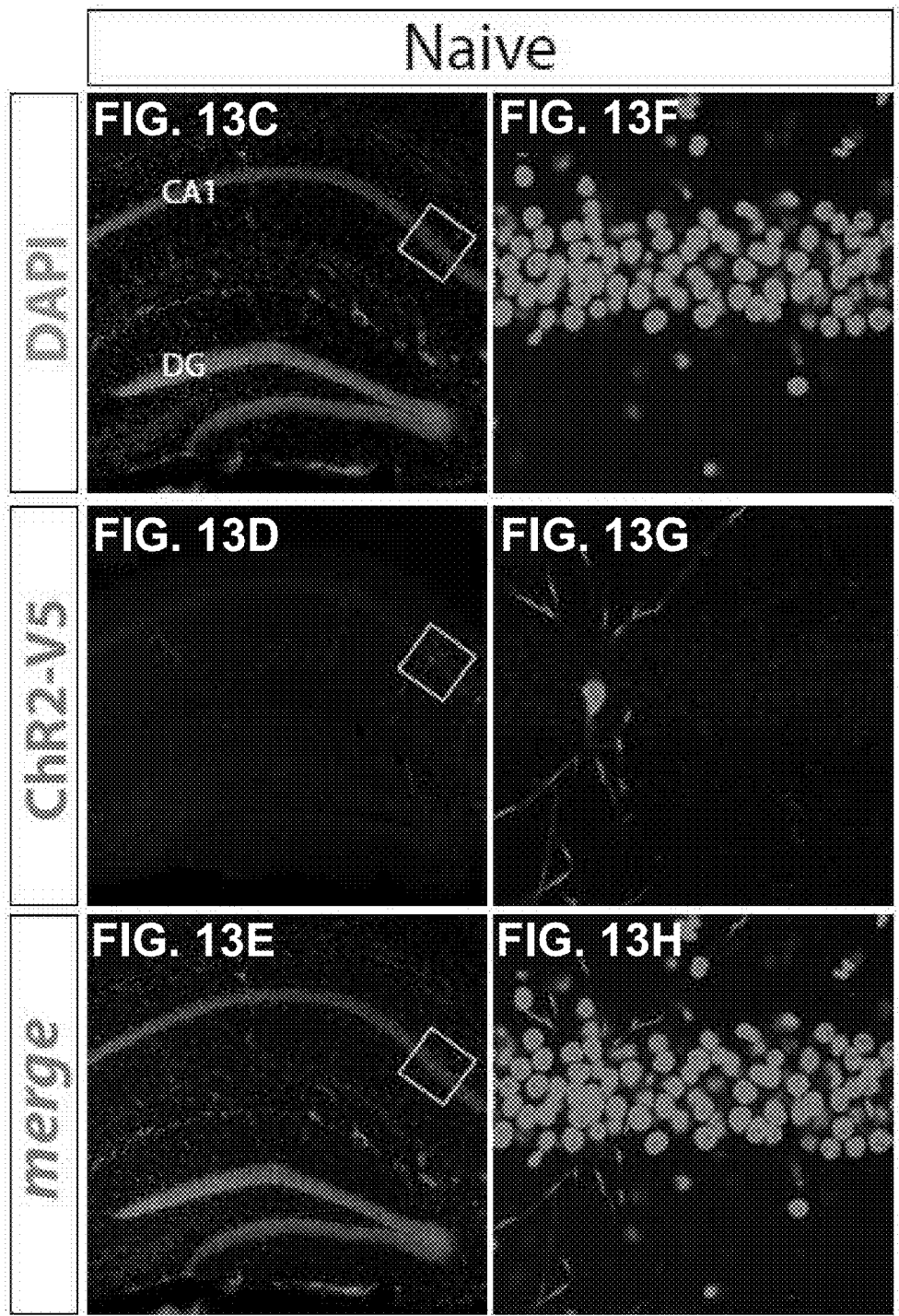

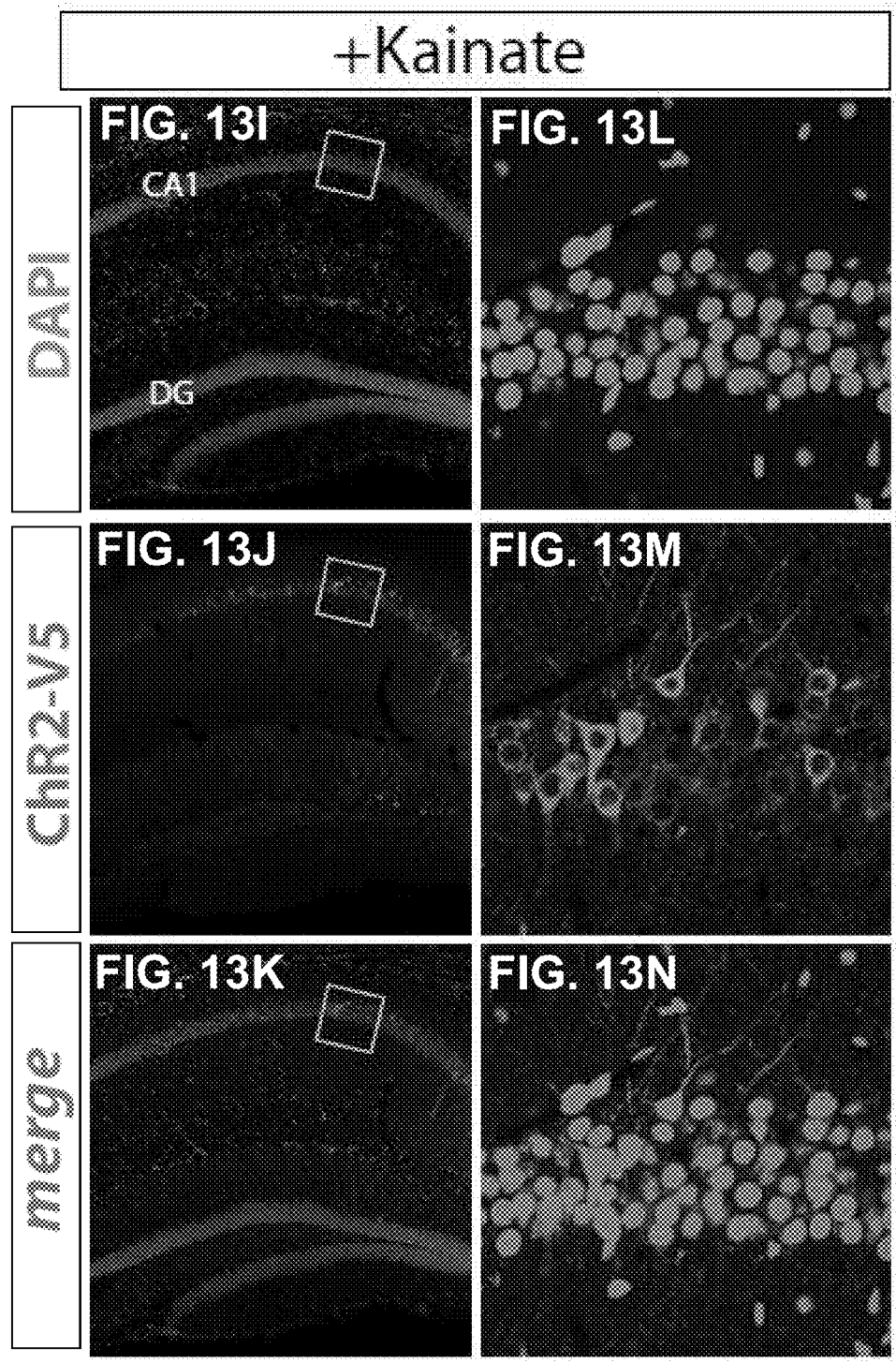

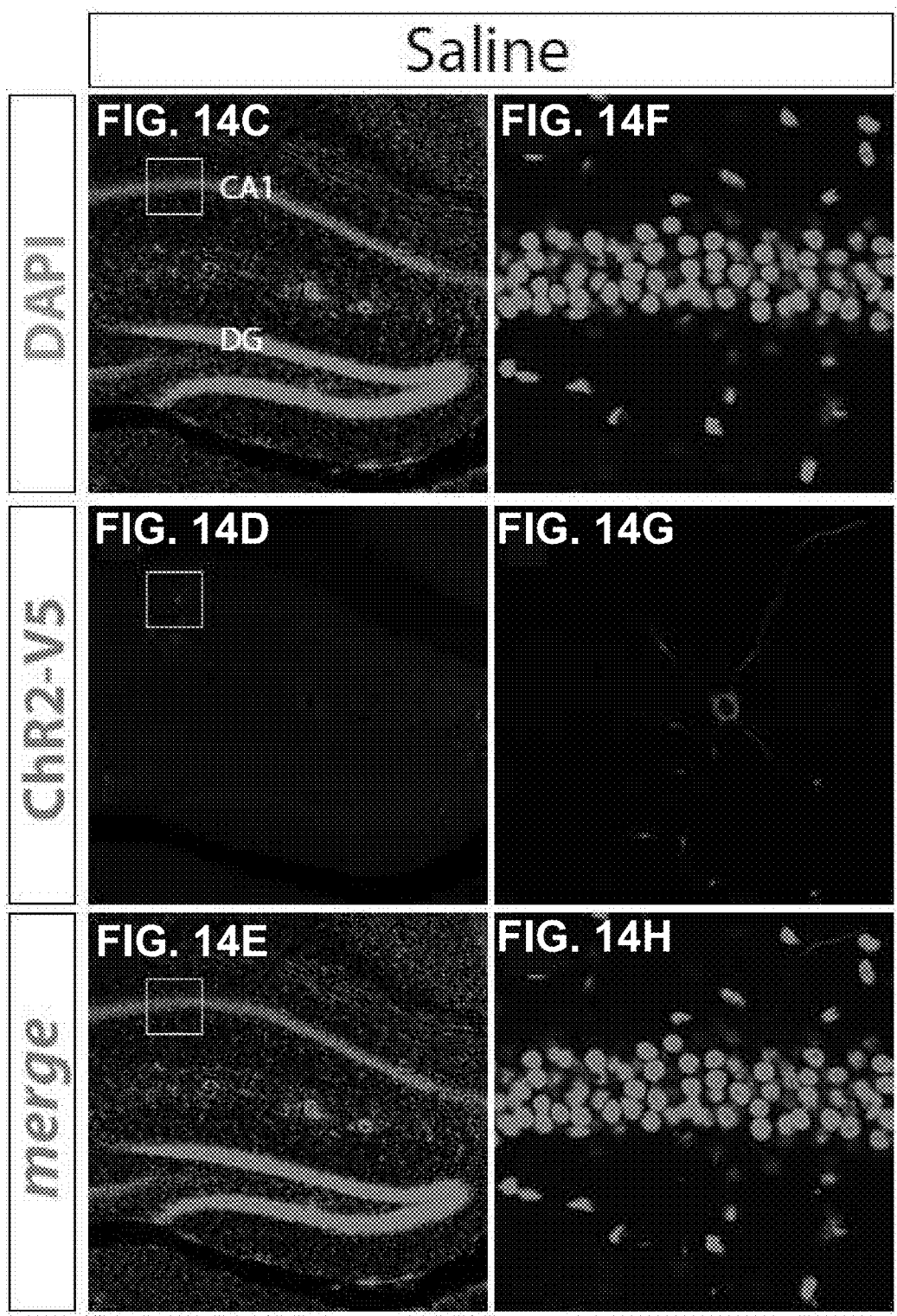

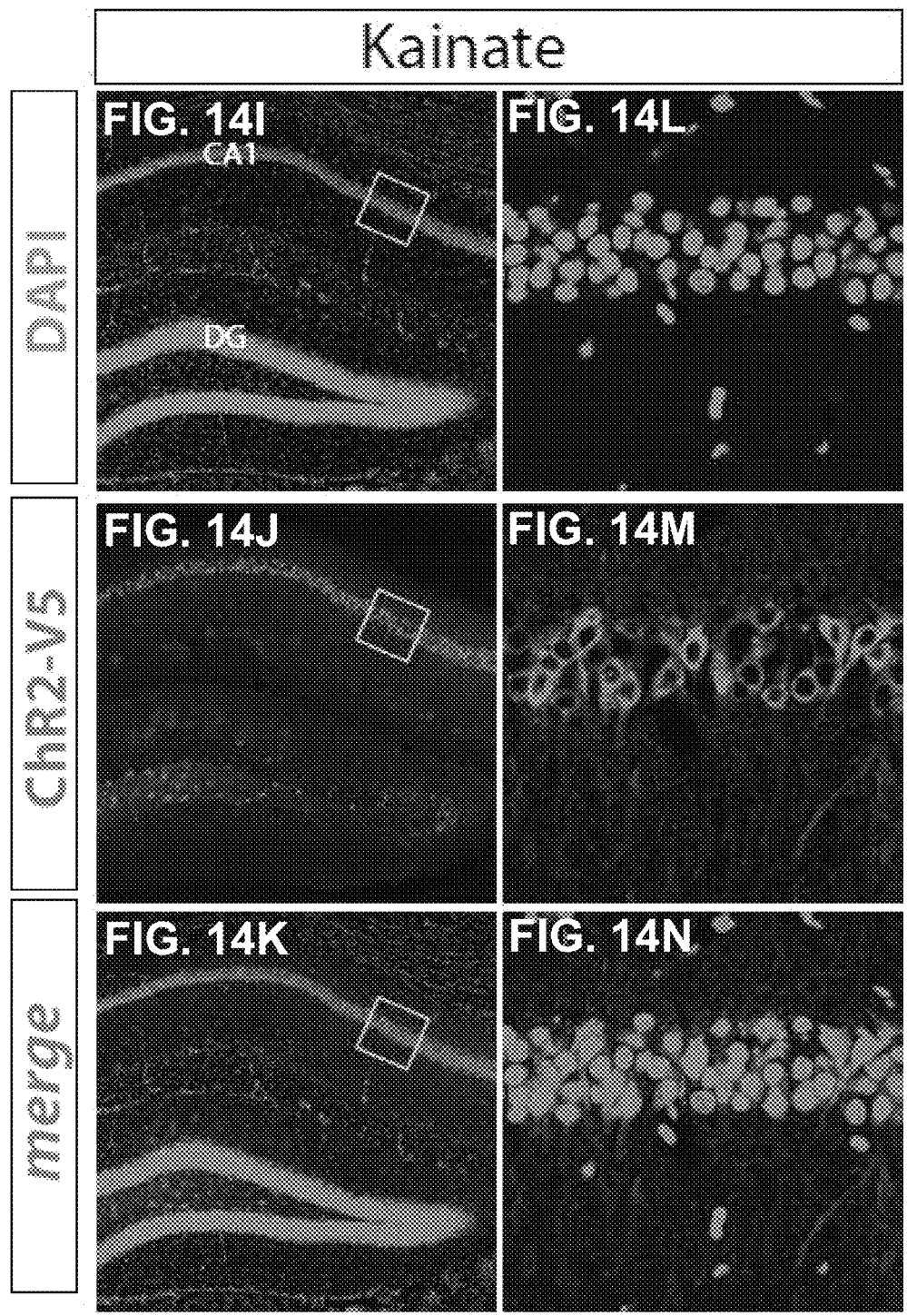

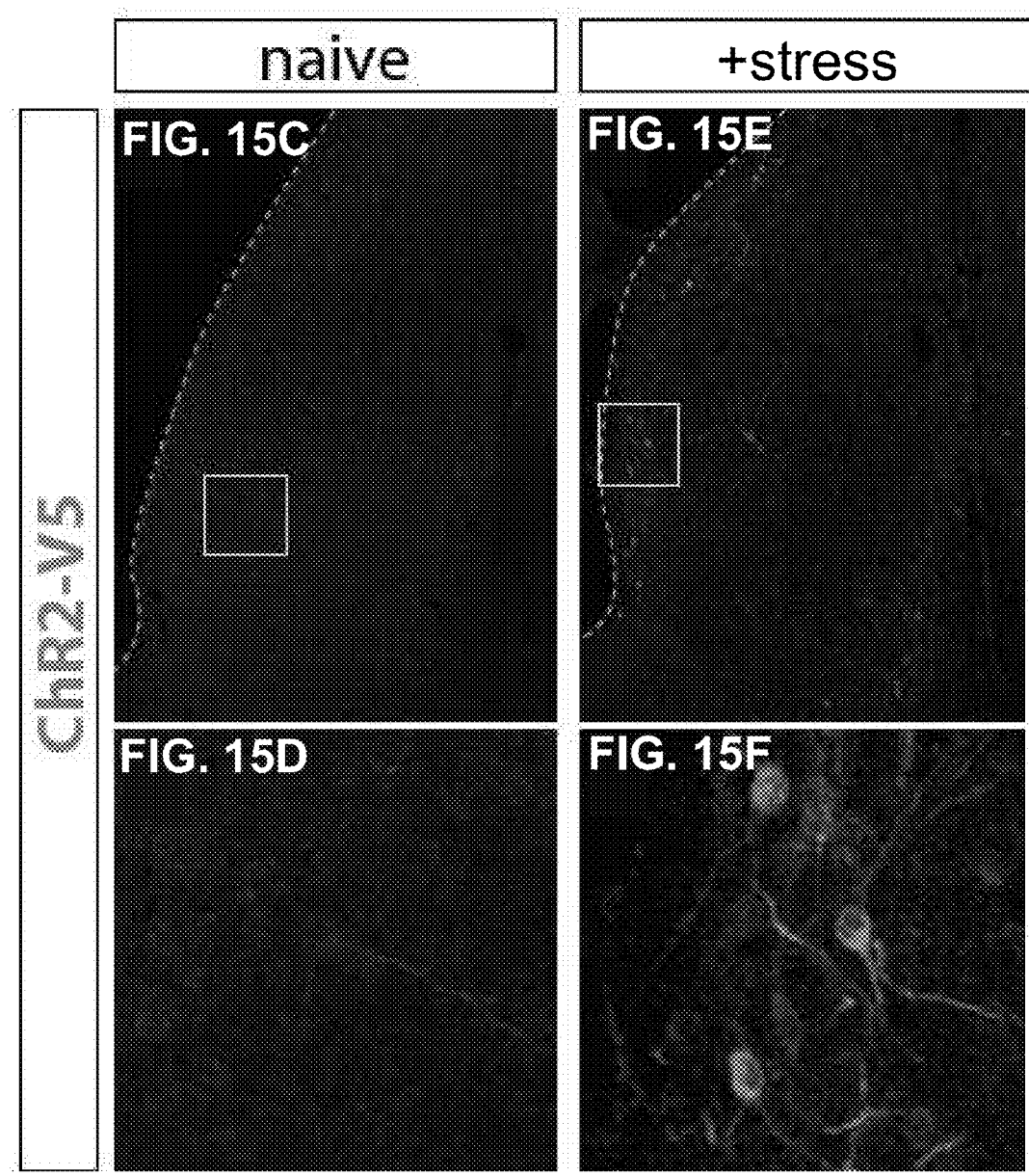

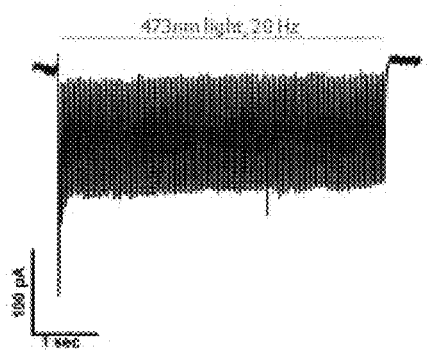
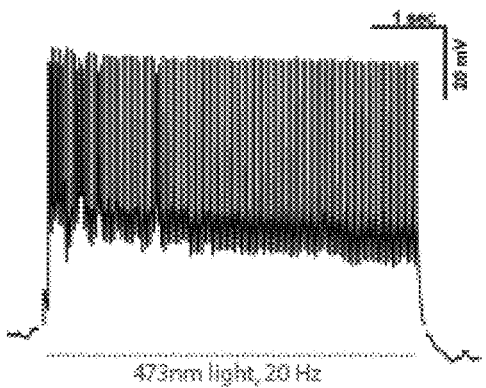
FIG. 15J
FIG. 15K
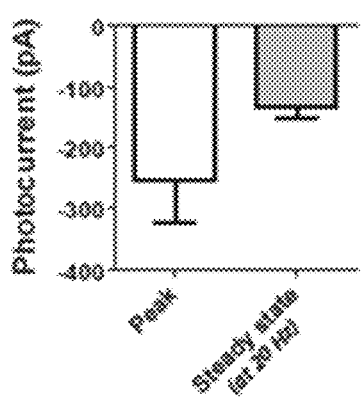
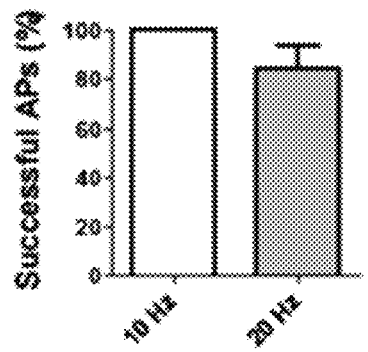
FIG. 15L
FIG. 15M

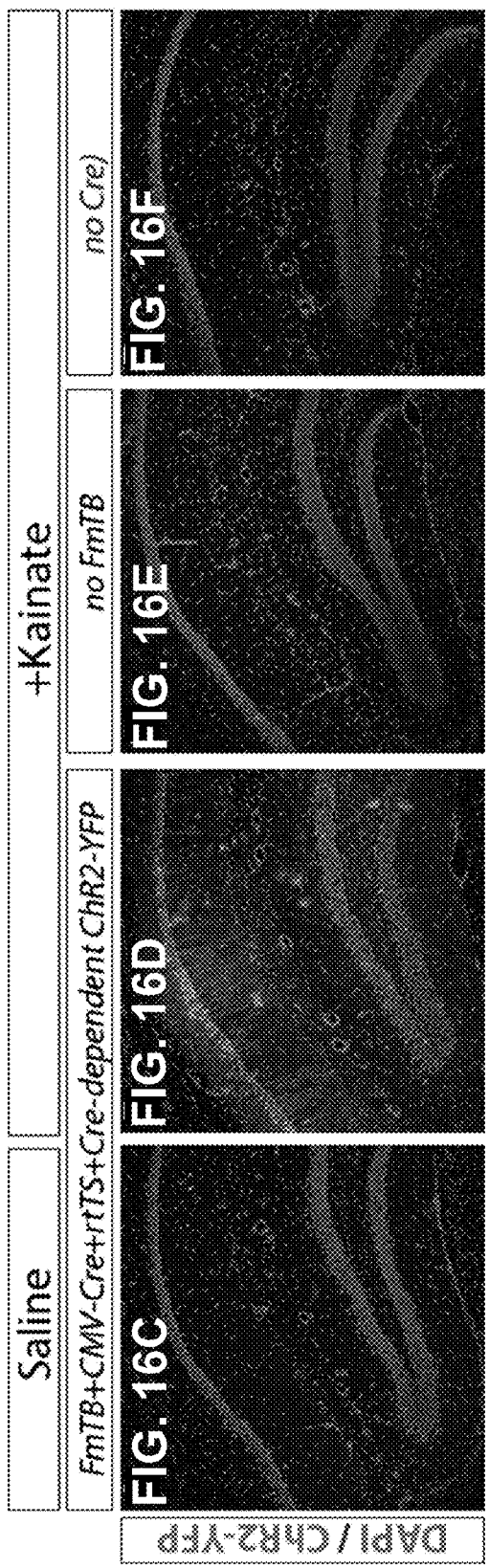

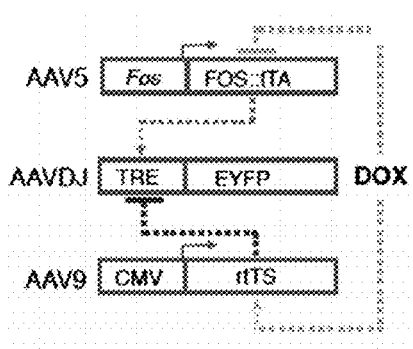
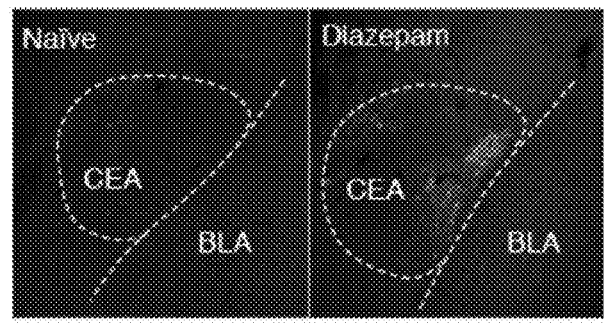
FIG. 17A                FIG. 17B
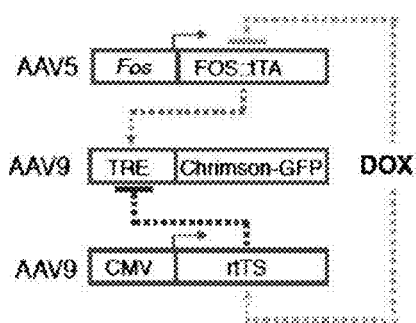
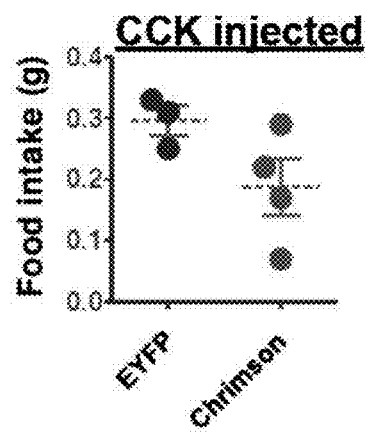
FIG. 17C                FIG. 17D

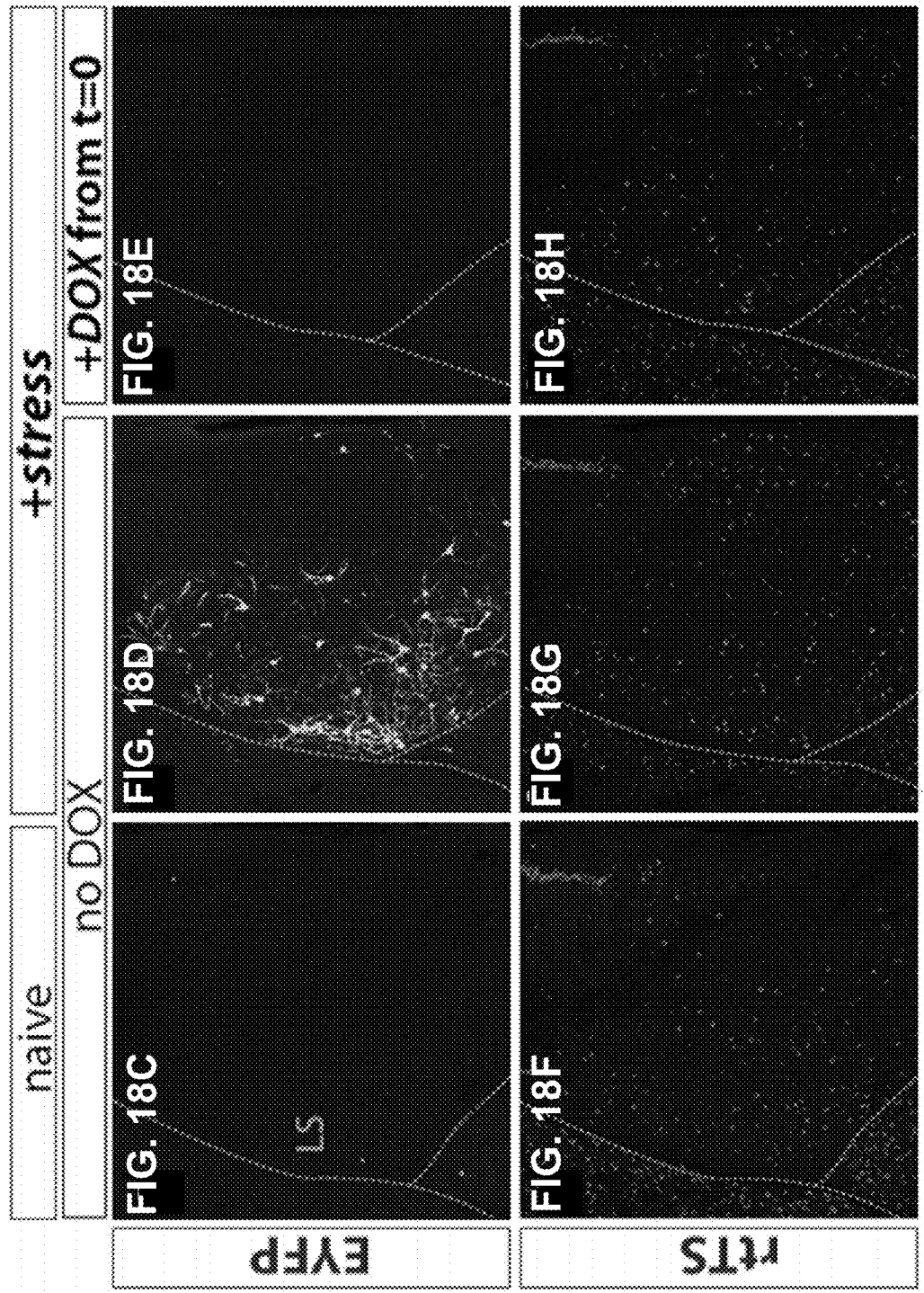

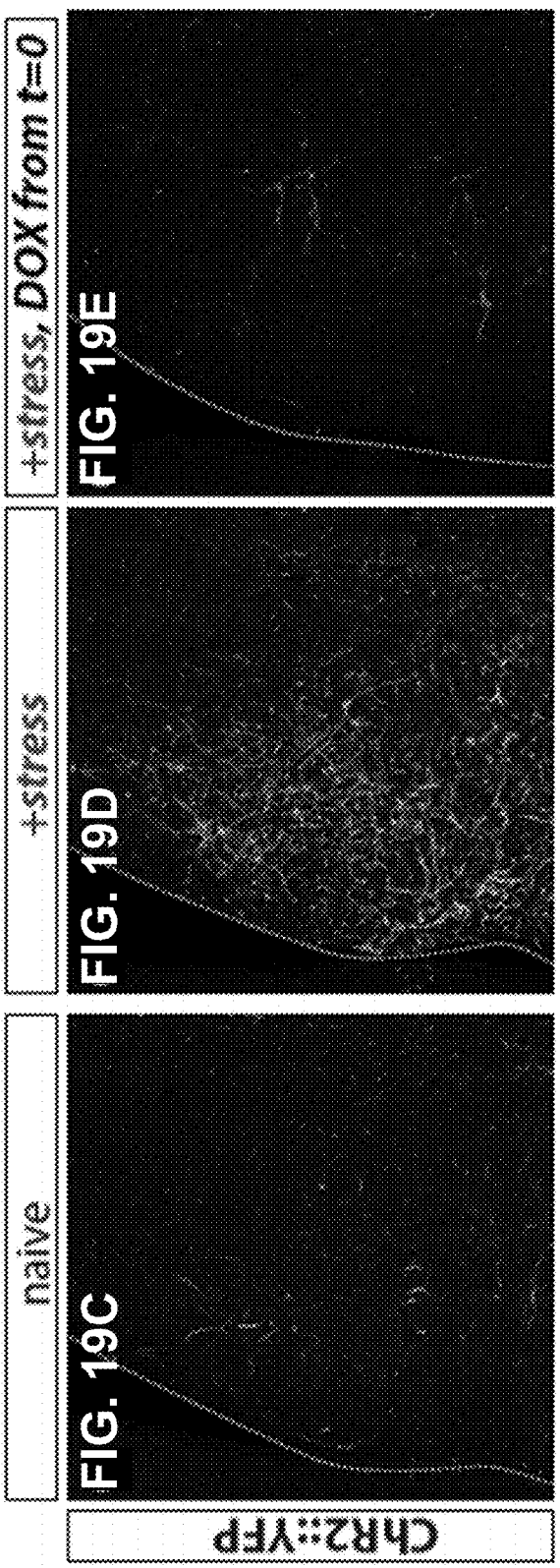

ACTIVITY-DEPENDENT EXPRESSION OF NUCLEIC ACIDS

CROSS-REFERENCE TO RELATED APPLICATIONS

The present Application claims the benefit of priority to U.S. Provisional Appl. No. 62/199,836 filed Jul. 31, 2015, which is hereby incorporated by reference in its entirety.

STATEMENT REGARDING FEDERALLY SPONSORED R&D

This invention was made with government support under Grant No. MH070053 awarded by the National Institutes of Health. The government has certain rights in the invention.

REFERENCE TO SEQUENCE LISTING

The present application is being filed along with a Sequence Listing in electronic format. The Sequence Listing is provided as file CALTE117A_SEQLIST.TXT created and last modified on Jul. 28, 2016, which is 50,294 bytes in size, and updated by a file entitled CALTE117AREPLACEMENT.TXT, created and last modified on Aug. 10, 2016, which is 50,320 bytes in size. The information in the electronic format of the Sequence Listing is incorporated herein by reference in its entirety.

Field

Embodiments herein relate generally to inducible adeno-associated virus (AAV) vector systems and methods for activity-dependent nucleic acid expression, for example expression of labels in cells.

SUMMARY

According to some aspects, an activity-dependent adeno-associated virus (AAV) vector expression system is provided. The AAV vector system can comprise an immediate early gene (IEG) promoter operably linked to a converter nucleic acid encoding a converter comprising an N-terminal portion of FOS fused to a nucleic acid encoding an activator, in which the activator is downstream of the N terminal portion of FOS. The AAV vector system can comprise a regulatable promoter operably linked to an insertion site for a transcript-encoding nucleic acid, in which transcription by the regulatable promoter is activated by the activator, in which the activator's activation of the regulatable promoter is modulated by a transcriptional modulator compound, if present. In some embodiments, the activity-dependent AAV vector expression system further comprises an other promoter operably linked to a silencer nucleic acid encoding a silencer, in which the silencer inhibits transcription by the regulatable promoter, and in which wherein the silencer's inhibition of the regulatable promoter is modulated by the transcriptional modulator compound, if present. In some embodiments, the activator comprises tTA, wherein the silencer comprises rtTS, and the regulatable promoter comprises a tetracycline regulatable element (TRE) promoter. In some embodiments, the activator comprises rtTA, the regulatable promoter comprises a tetracycline regulatable element (TRE) promoter, and the transcriptional modulator compound (if present) induces the activator's activation of the regulatable promoter. In some embodiments, the activator comprises tTA, the regulatable promoter comprises a tetracycline regulatable element (TRE) promoter, and wherein the transcriptional modulator compound, if present, inhibits the activator's activation of the regulatable promoter. In some embodiments, the converter nucleic acid comprises fos exons I, II, III, and IV. In some embodiments, the IEG promoter comprises a fos promoter or a cyclic AMP response element (CRE) promoter. In some embodiments, the insertion site contains a polynucleotide encoding a label. In some embodiments, the silencer nucleic acid is positioned immediately 3' of the other promoter. In some embodiments, a single AAV vector comprises the converter nucleic acid, the silencer nucleic acid, the regulatable promoter, and the insertion site. In some embodiments, two or more different AAV vectors collectively comprise the converter nucleic acid, the silencer nucleic acid, the regulatable promoter, and the insertion site. In some embodiments, the converter nucleic acid and the silencer nucleic acid are on a first AAV vector and the regulatable promoter and insertion site are on a second AAV vector. In some embodiments, the converter nucleic acid encodes an FmTB converter as in SEQ ID NO: 12. In some embodiments, the AAV vector system further comprises a first inverted terminal repeat (ITR) sequence located 5' of the IEG promoter, and a second ITR sequence located 3' of the insertion site. In some embodiments, the transcript-encoding nucleic acid comprises a polypeptide-encoding nucleic acid. In some embodiments, the transcript-encoding nucleic acid encodes a label.

According to some aspects, a kit for activity-dependent nucleic acid expression is provided. The kit can comprise any of the AAV vector systems as described in the paragraph above. The kit can comprise a transcriptional modulator compound, for example tetracycline or doxycycline. In some embodiments, the transcriptional modulator compound comprises doxycycline or tetracycline.

According to some aspects, a method of activity-dependent expression of a nucleic acid in an animal cell is provided. The method can comprise contacting an adeno-associated virus (AAV) vector system in the animal cell with a transcriptional modulator compound. The AAV vector system can comprise an immediate early gene (IEG) promoter operably linked to a converter nucleic acid encoding an N-terminal portion of FOS fused to an activator, in which the activator is downstream of the N terminal portion of FOS. The AAV vector system can comprise a regulatable promoter operably linked to a transcript-encoding nucleic acid, in which the activator activates transcription by the regulatable promoter, and in which the activator's activation of transcription is inhibited by the transcriptional modulator compound. The AAV vector system can comprise another promoter operably linked to a silencer nucleic acid encoding a silencer; in which the silencer represses transcription by the regulatable promoter, and in which the silencer's repression of transcription is induced by the transcriptional modulator compound. The method can comprise ceasing said contacting by said transcriptional modulator compound, so that the activator is no longer inhibited, thereby expressing the nucleic acid from the IEG promoter when the animal cell is activated. In some embodiments, the transcript-encoding nucleic acid comprises a polypeptide-encoding nucleic acid. In some embodiments, the transcript-encoding nucleic acid encodes a label.

According to some aspects, a method of activity-dependent nucleic acid expression in an animal cell is provided. The method can comprise contacting an adeno-associated virus (AAV) vector system in the animal cell with a transcriptional modulator compound. The AAV vector system can comprise an immediate early gene (IEG) promoter operably linked to a converter nucleic acid encoding an N-terminal portion of FOS fused to an activator, in which the activator is downstream of the N terminal portion of FOS. The AAV vector system can comprise a regulatable promoter operably linked to a transcript-encoding nucleic acid, in which the activator activates transcription by the regulatable promoter, and in which the activator's activation of transcription is activated by the transcriptional modulator compound. Thus, the method can result in expressing the transcript-encoding nucleic acid from the IEG promoter when the animal cell is activated. In some embodiments, the transcript-encoding nucleic acid is not transcribed when the animal cell is not activated. In some embodiments, the activator comprises tTA, and the silencer comprises rtTS. In some embodiments, the activator comprises rtTA. In some embodiments, the converter comprises a FmTB converter. In some embodiments, the method comprises an in vivo method. In some embodiments, the animal comprises a mammal. In some embodiments, the animal comprises a non-human mammal. In some embodiments, the animal comprises a human. In some embodiments, the animal cell is activated by a sensory cue, a behavioral experience, or a chemical. In some embodiments, the animal cell is activated by a change in polarity. In some embodiments, the ceasing is for at least about 10 seconds. In some embodiments, the method further comprises administering the AAV vector system to the animal cell, thereby disposing the AAV vector system in the animal cell. In some embodiments, the transcript-encoding nucleic acid comprises a polypeptide-encoding nucleic acid. In some embodiments, the transcript-encoding nucleic acid encodes a label.

BRIEF DESCRIPTION OF THE DRAWINGS

Figure 2:
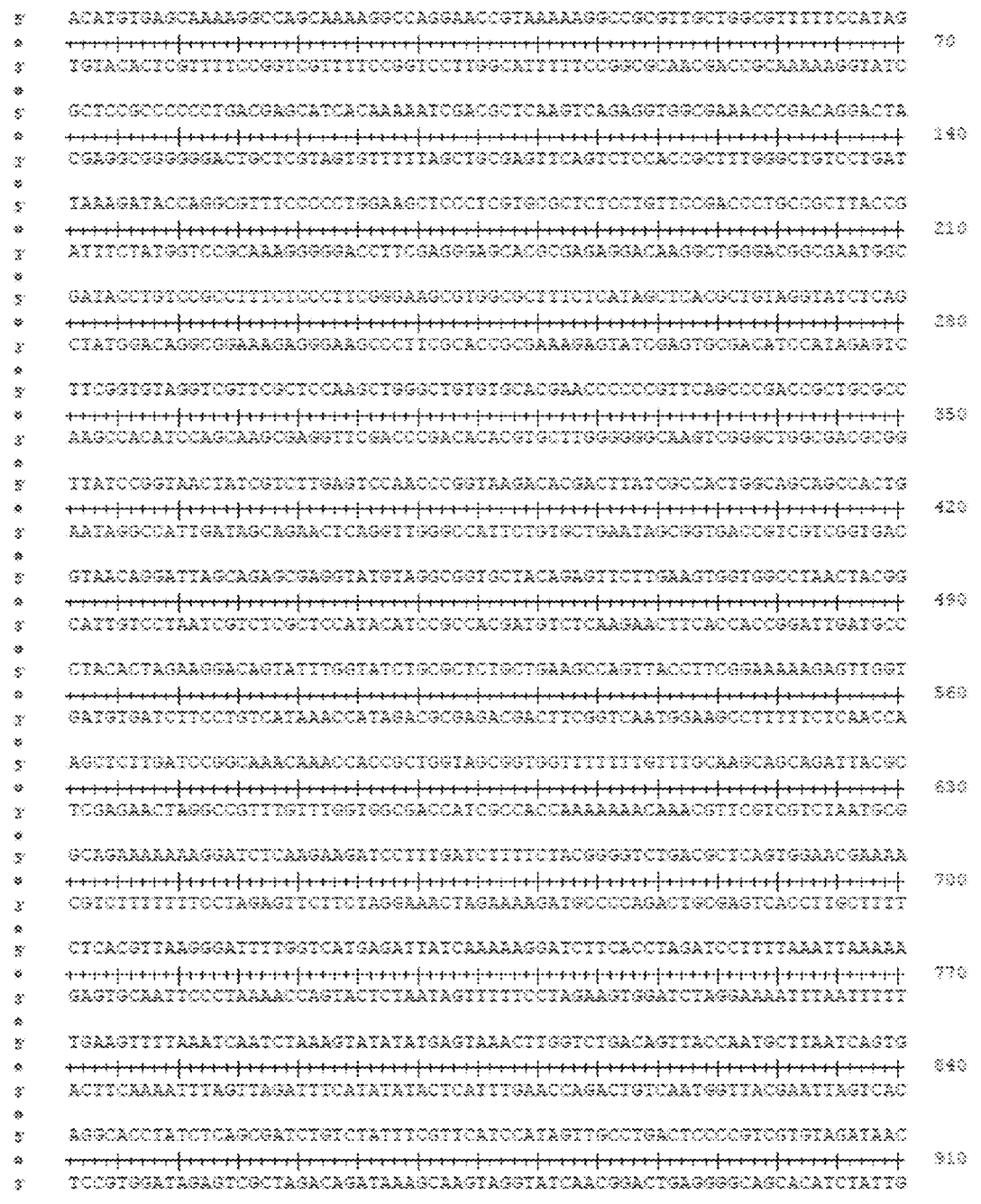
Figure 2:
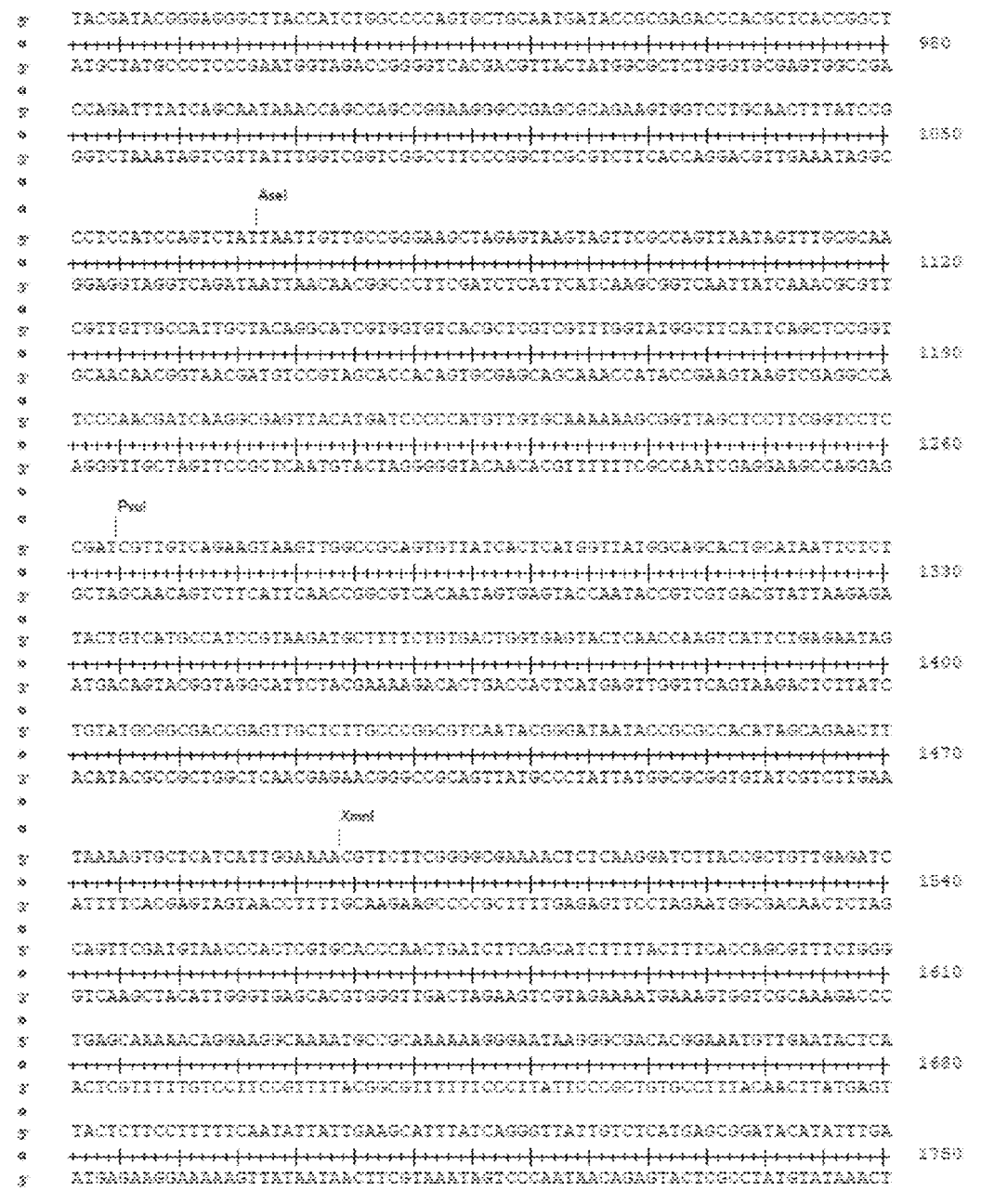
Figure 2:
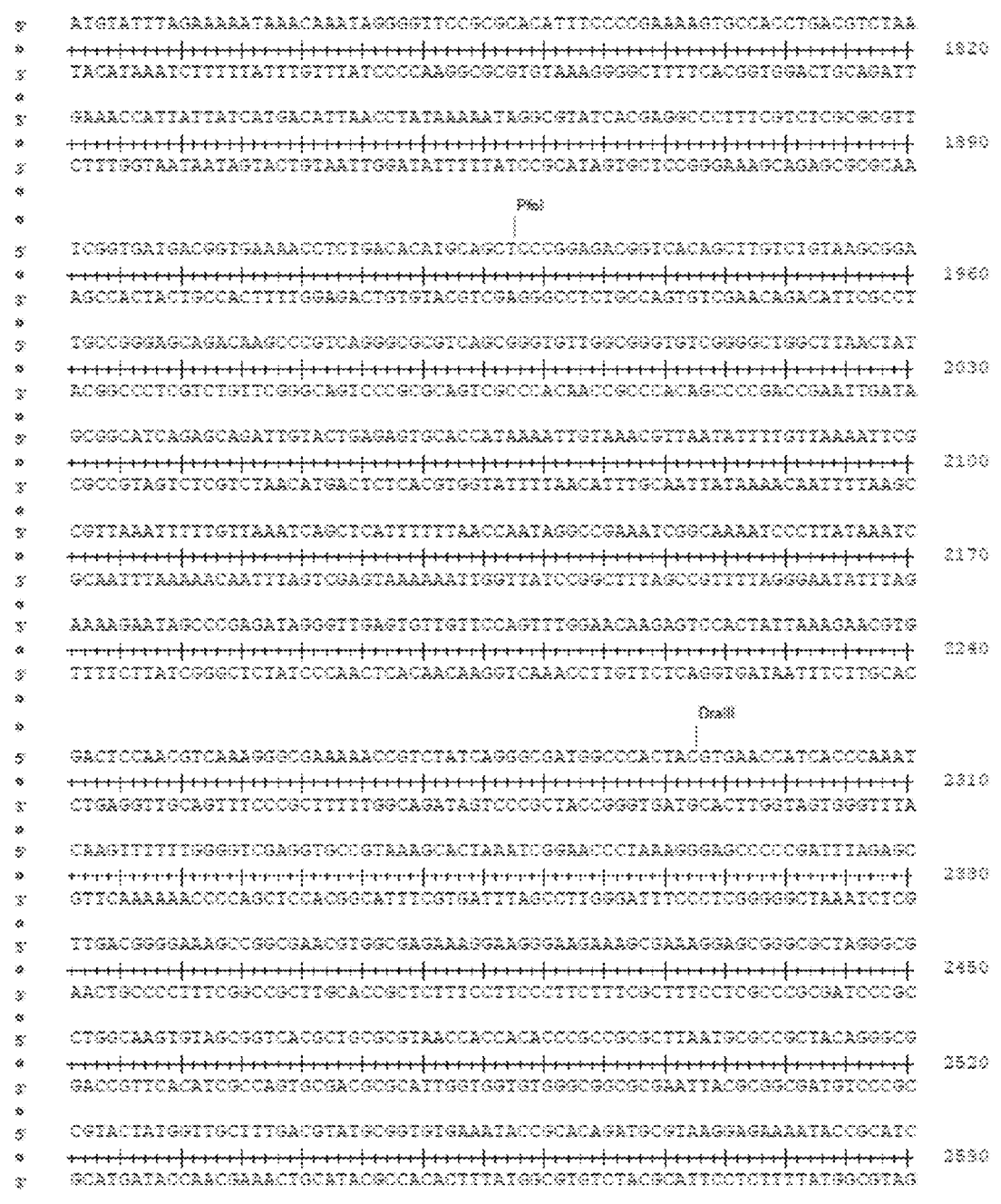
Figure 2:
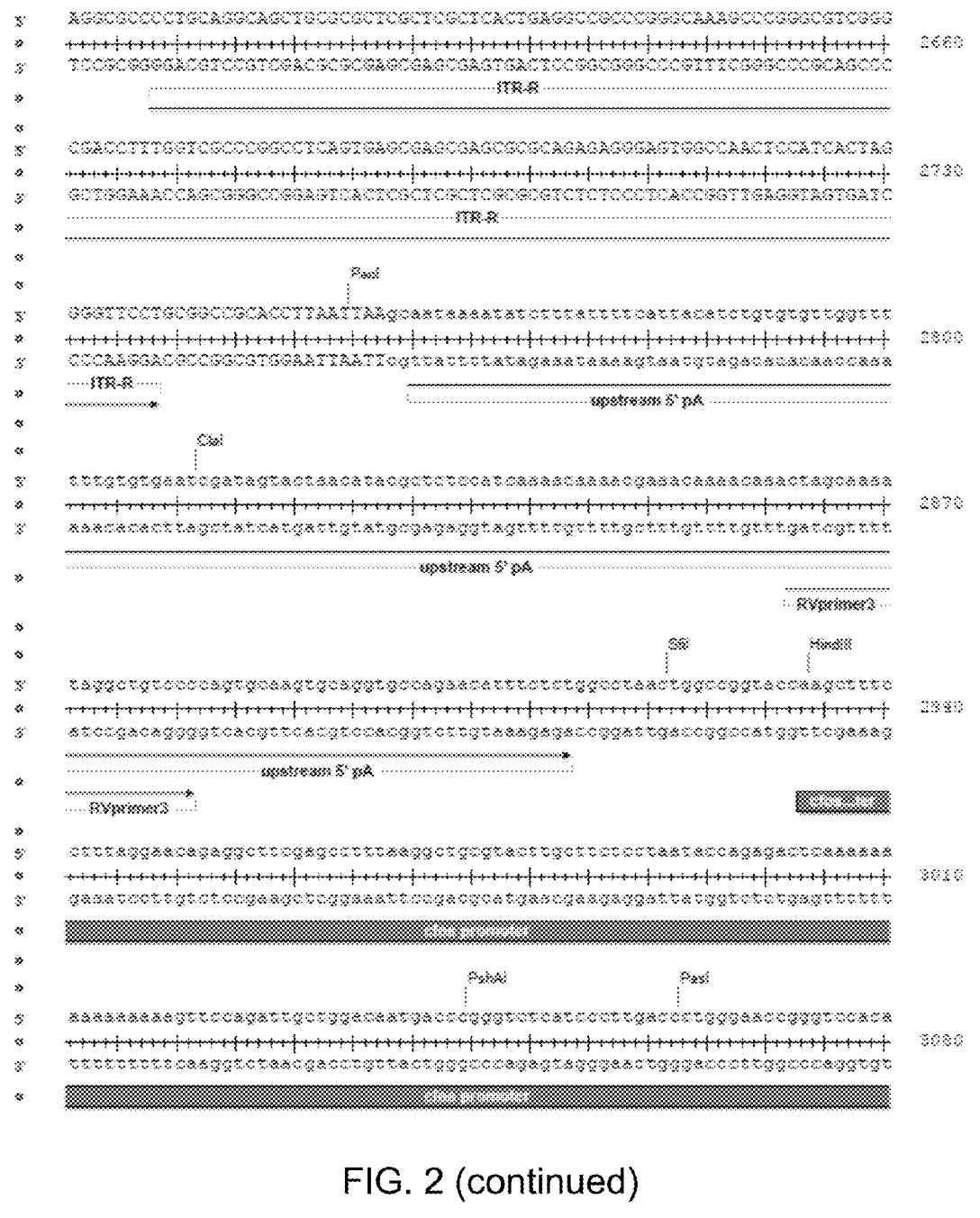
Figure 2:
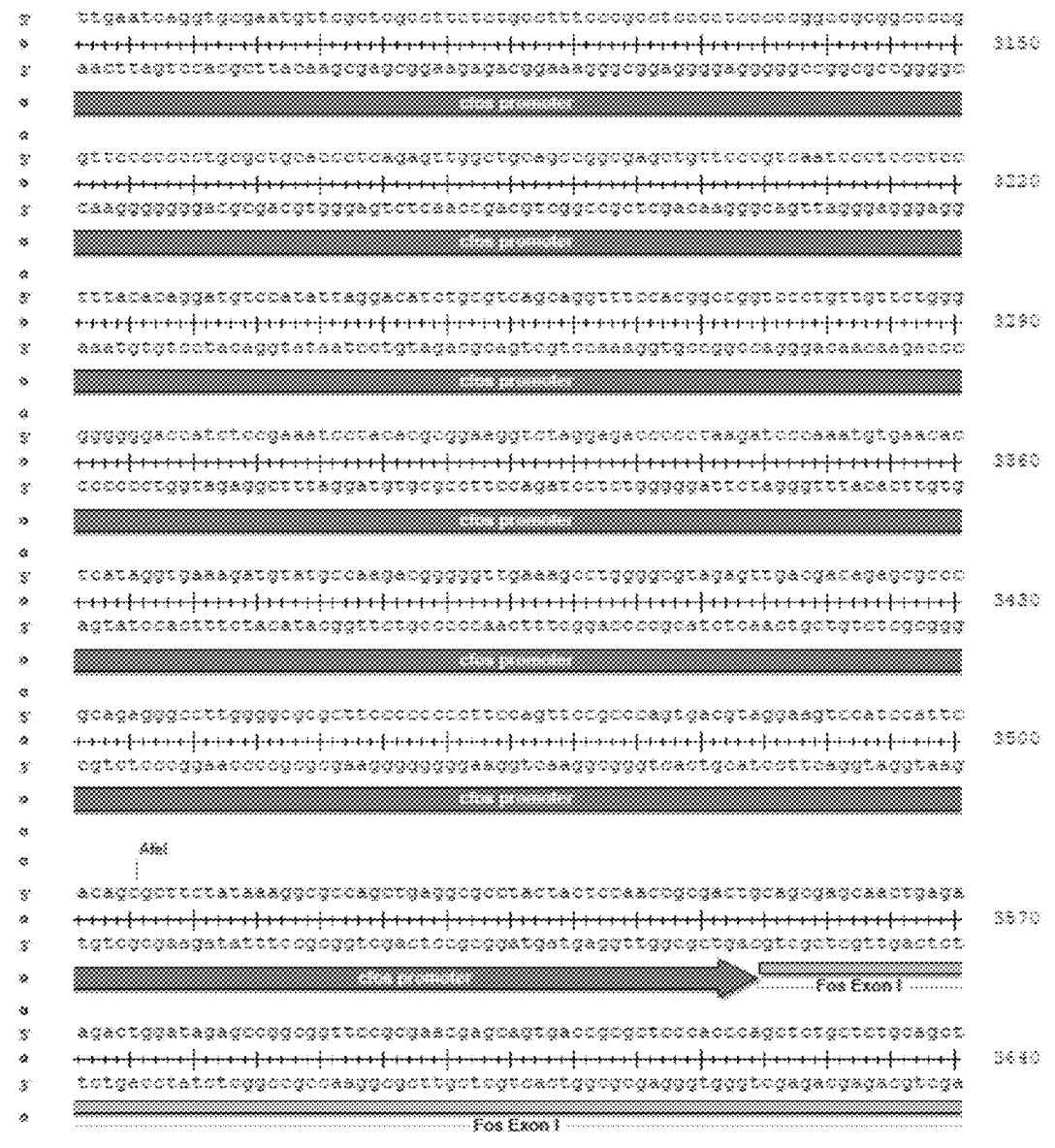
Figure 2:
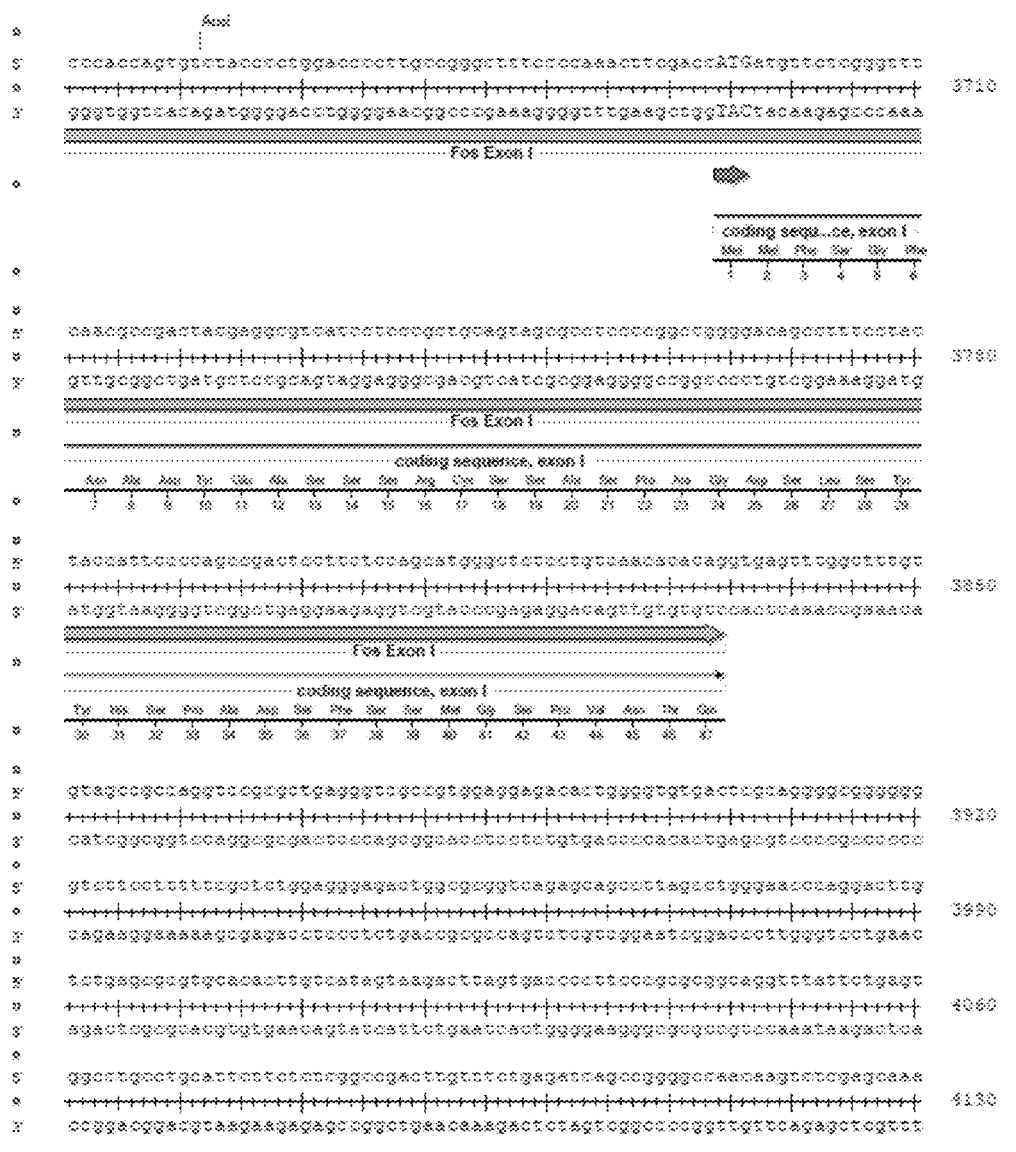
Figure 2:
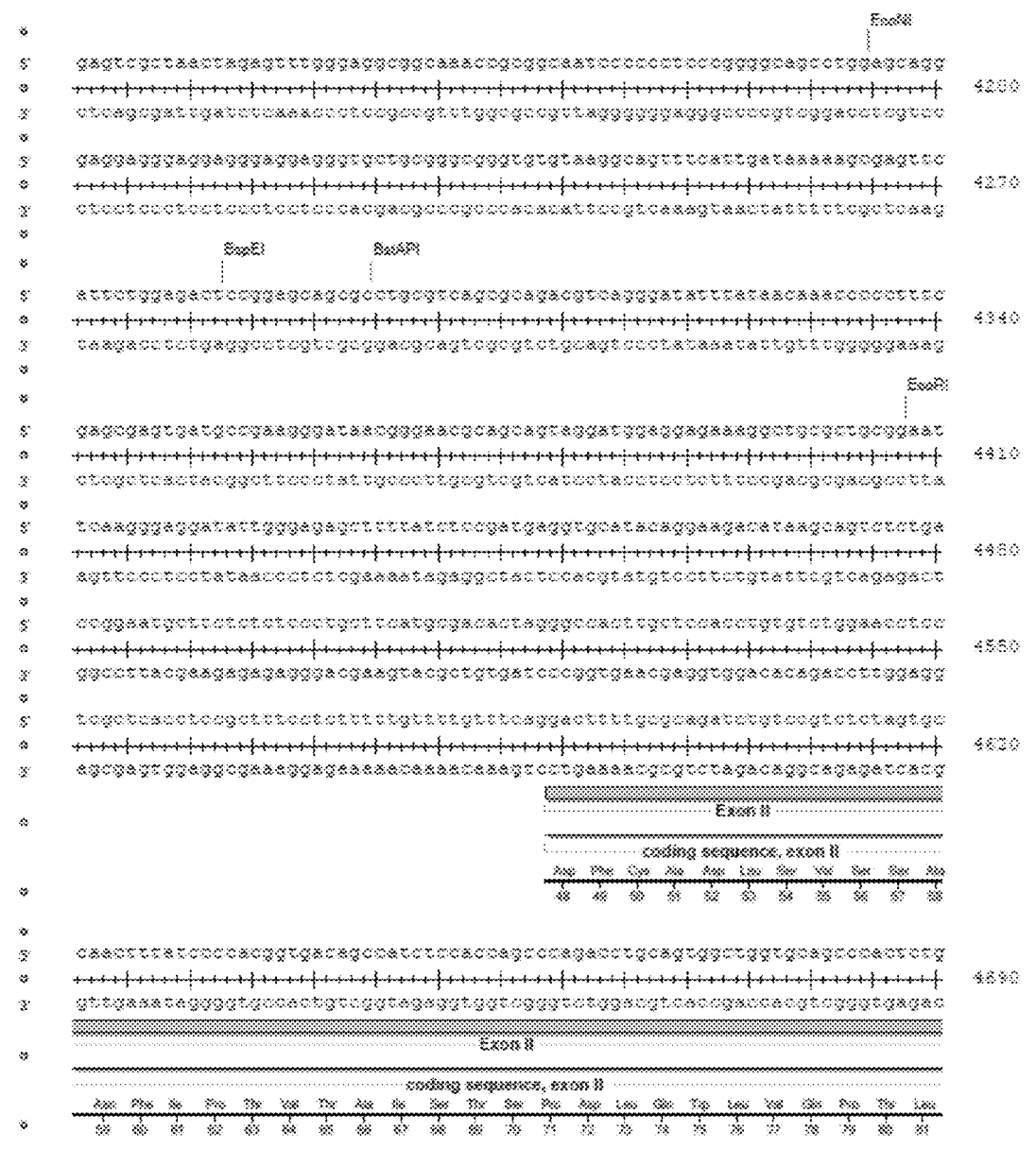
Figure 2:
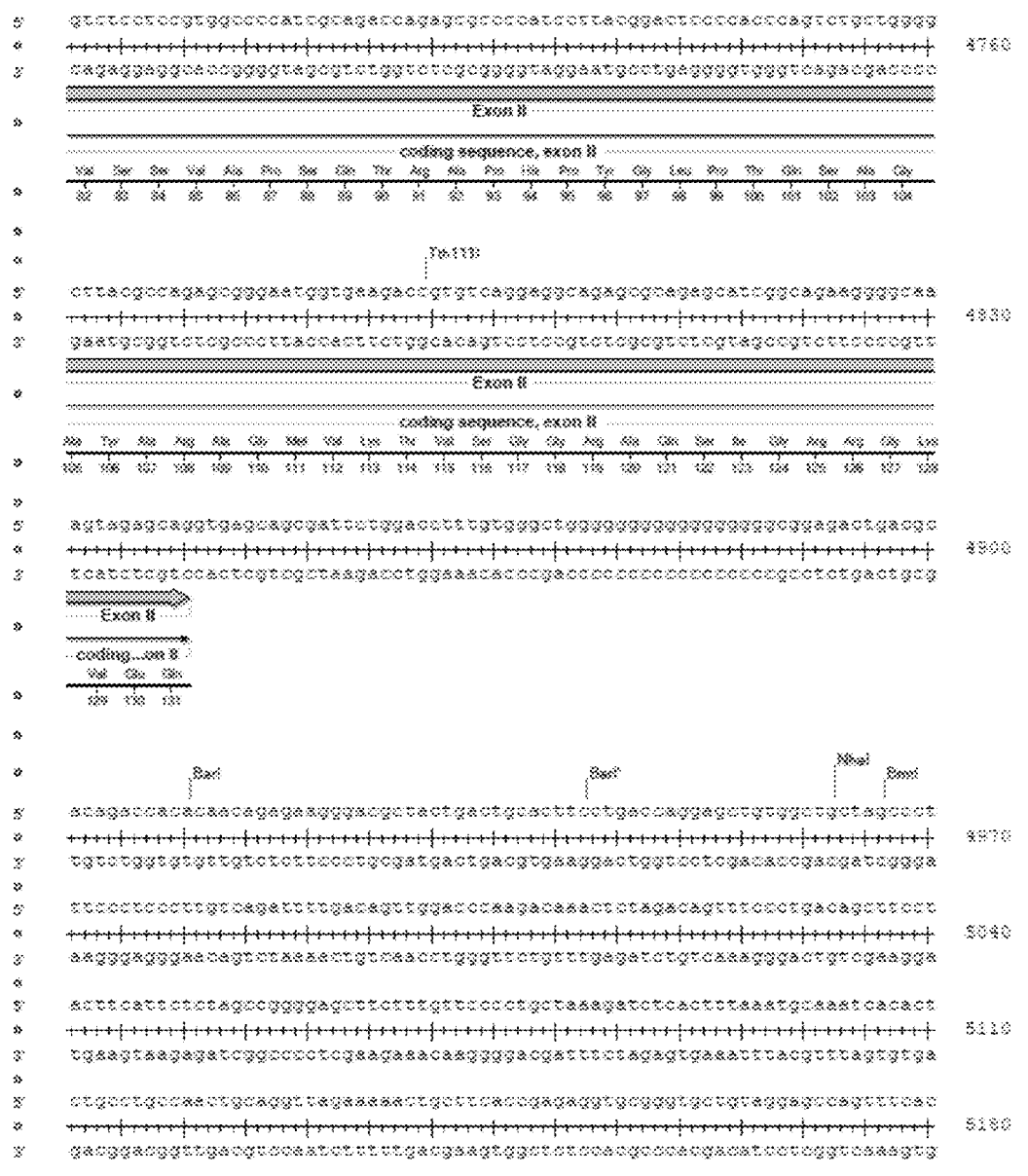
Figure 2:
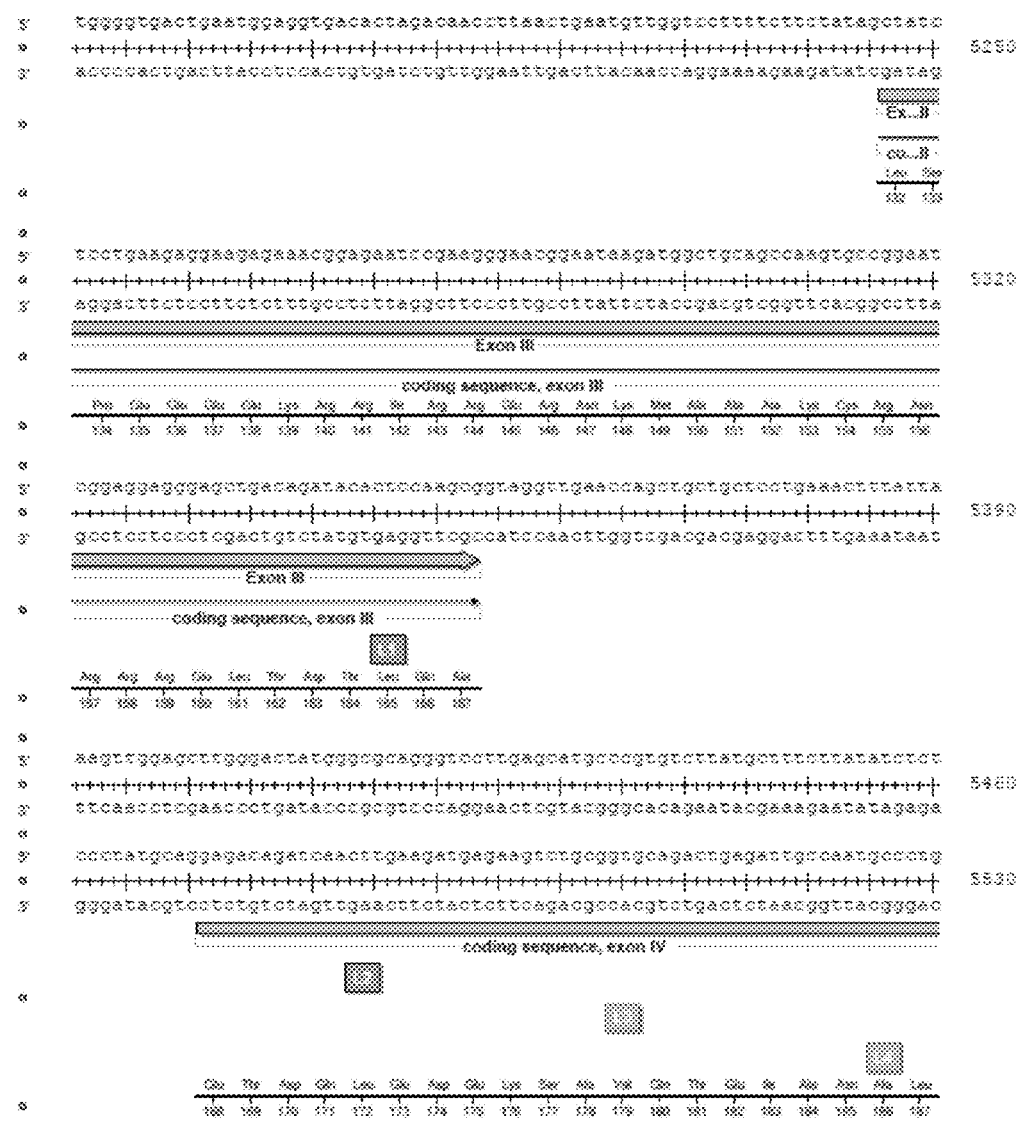
Figure 2:
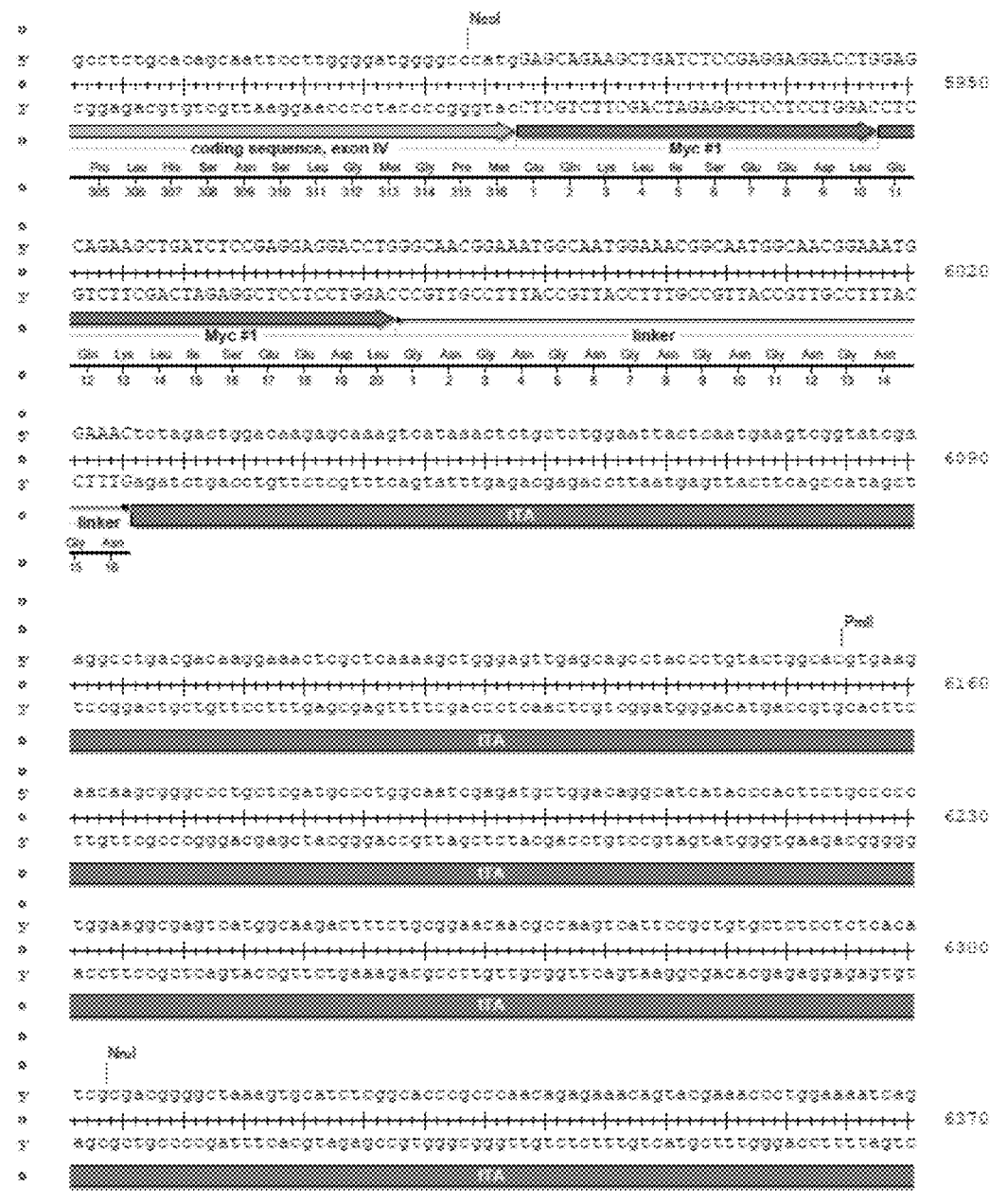
Figure 2:
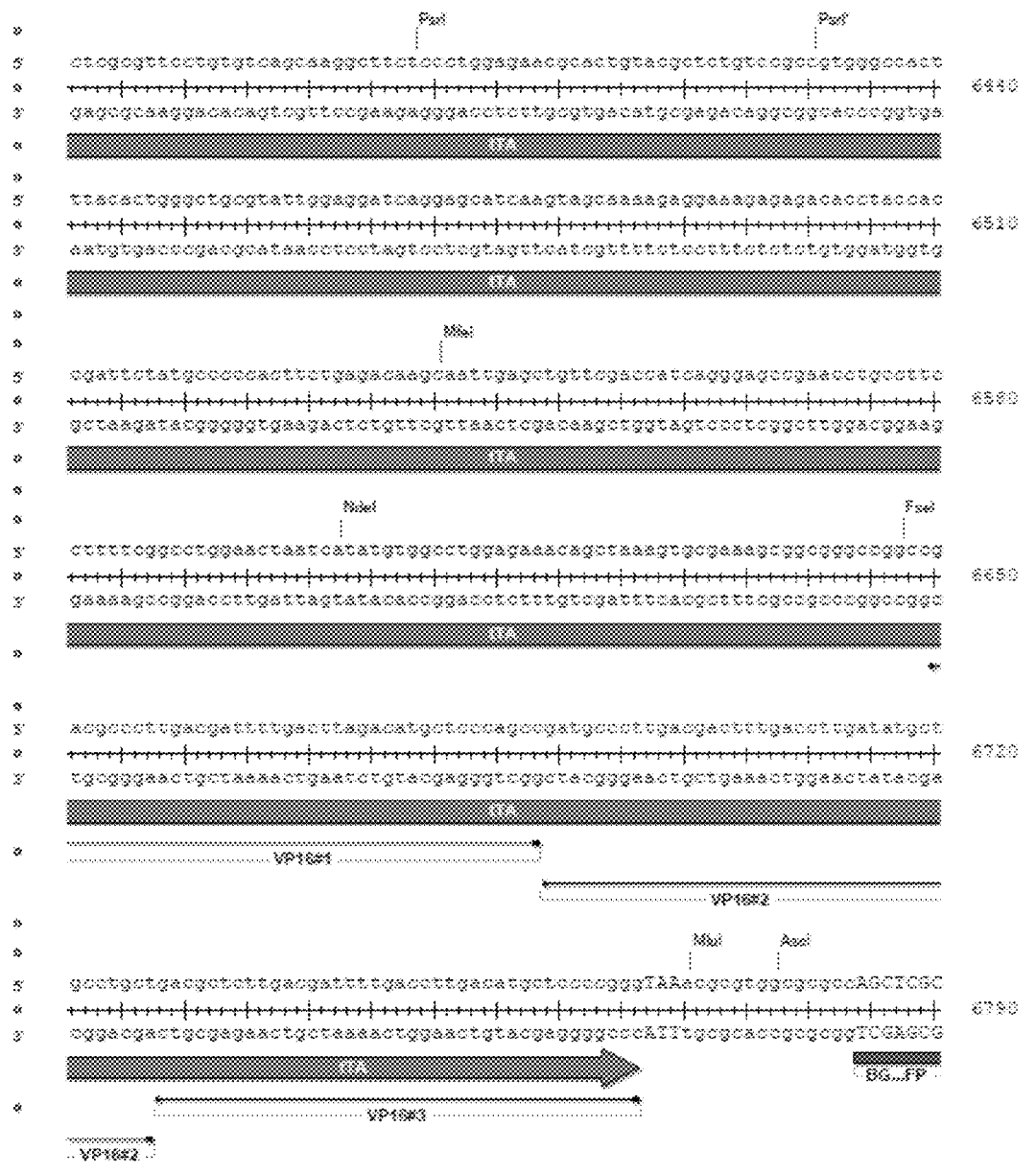
Figure 2:
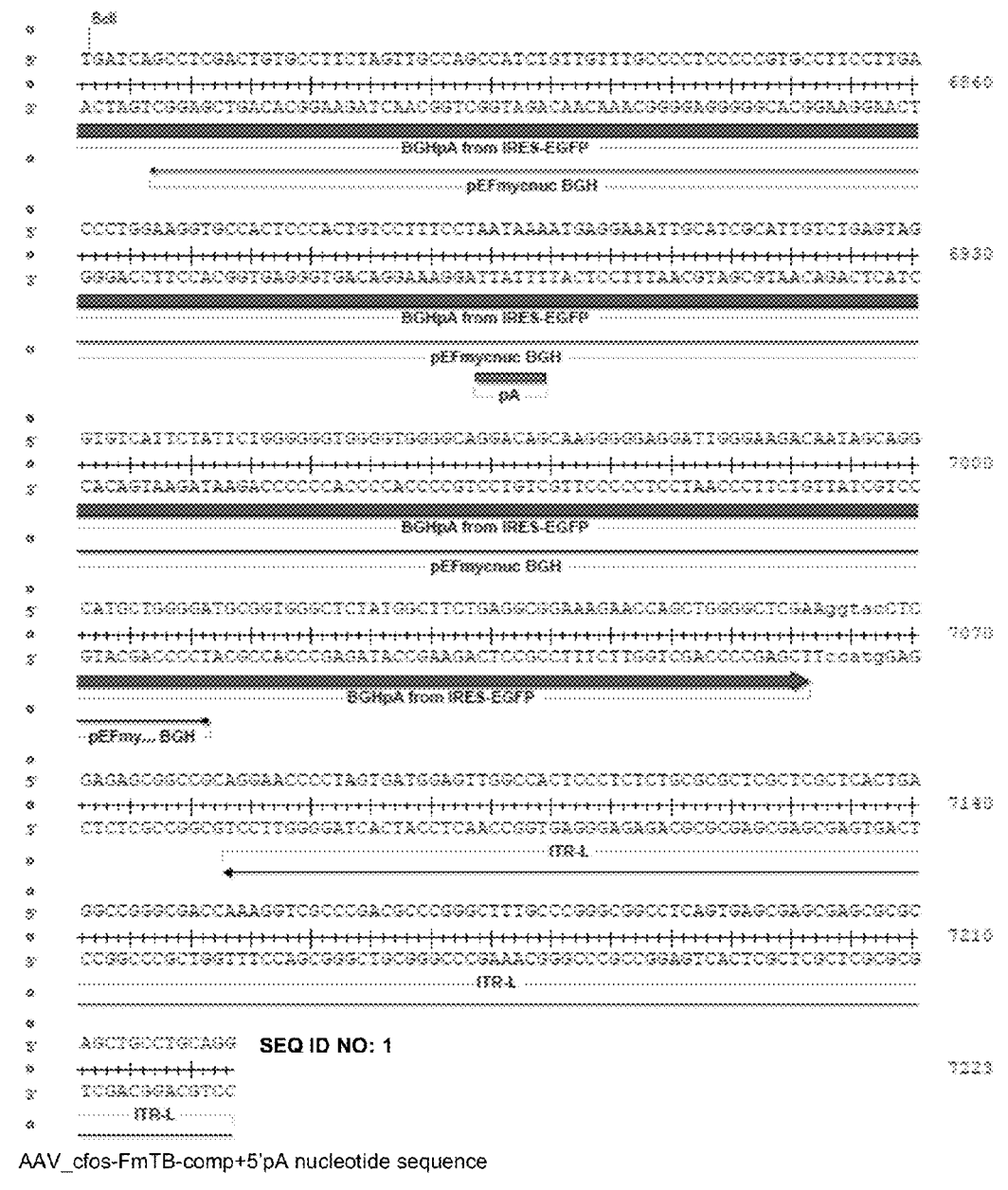

FIG. 2 shows the nucleotide sequence for the AAV vector of FIG. 1 (SEQ ID NO: 1). The ITR-R (SEQ ID NO: 16) is located at 2598-2738. The upstream 5' polyadenylation (SEQ ID NO: 2) is located at positions 2760-2913. The FOS coding sequence (SEQ ID NO: 3) is comprised within the nucleic acids of positions 2933-5917, which also comprises the c-fos promoter (SEQ ID NO: 4), located at positions 2933-3554; Fos exon I (SEQ ID NO: 5), located at positions 3555-3884, with the coding sequence from 3694-3834; Fos exon II (SEQ ID NO: 6), located at positions 4589-4840; Fos exon III (SEQ ID NO: 7), located at positions 5246-5353; and Fos exon IV (SEQ ID NO: 8), located at positions 5471-5917. The FmTB converter sequence (SEQ ID NO: 12) is located at positions 3555-6766, and comprises fos exons I-IV; Myc #1 (x2) (SEQ ID NO: 9), located at positions 5918-5947 and 5948-5977; a linker (SEQ ID NO: 10), located at positions 5978-6025, and tTA (SEQ ID NO: 11), located at positions 6026-6766. In some embodiments, the FmTB converter sequence comprises rtTA (SEQ ID NO: 13) in place of tTA. BGHpA (SEQ ID NO: 14) is located at positions 6784-7061. The ITR-L (SEQ ID NO: 25) is located at positions 7083-7223.

Figure 4:
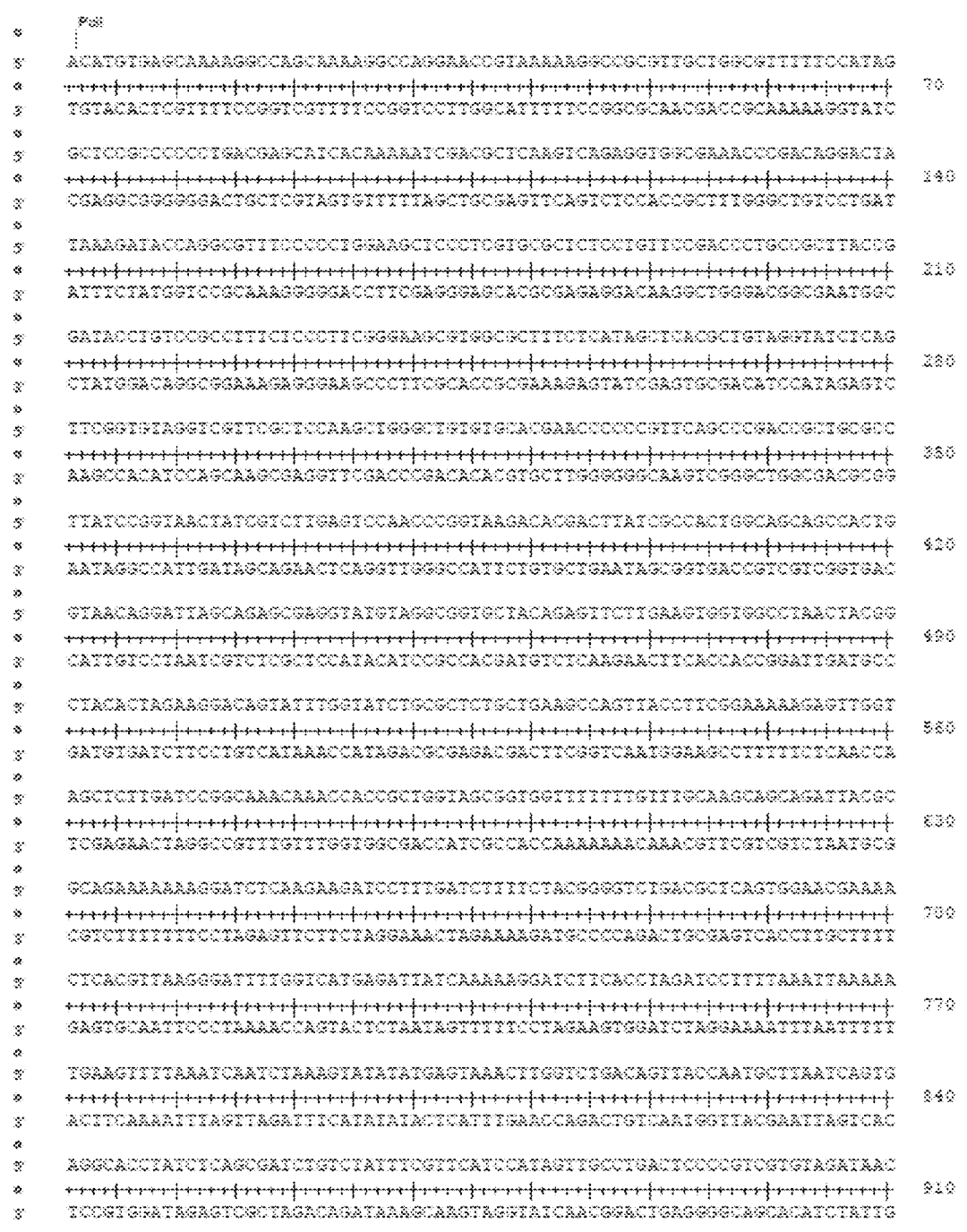
Figure 4:
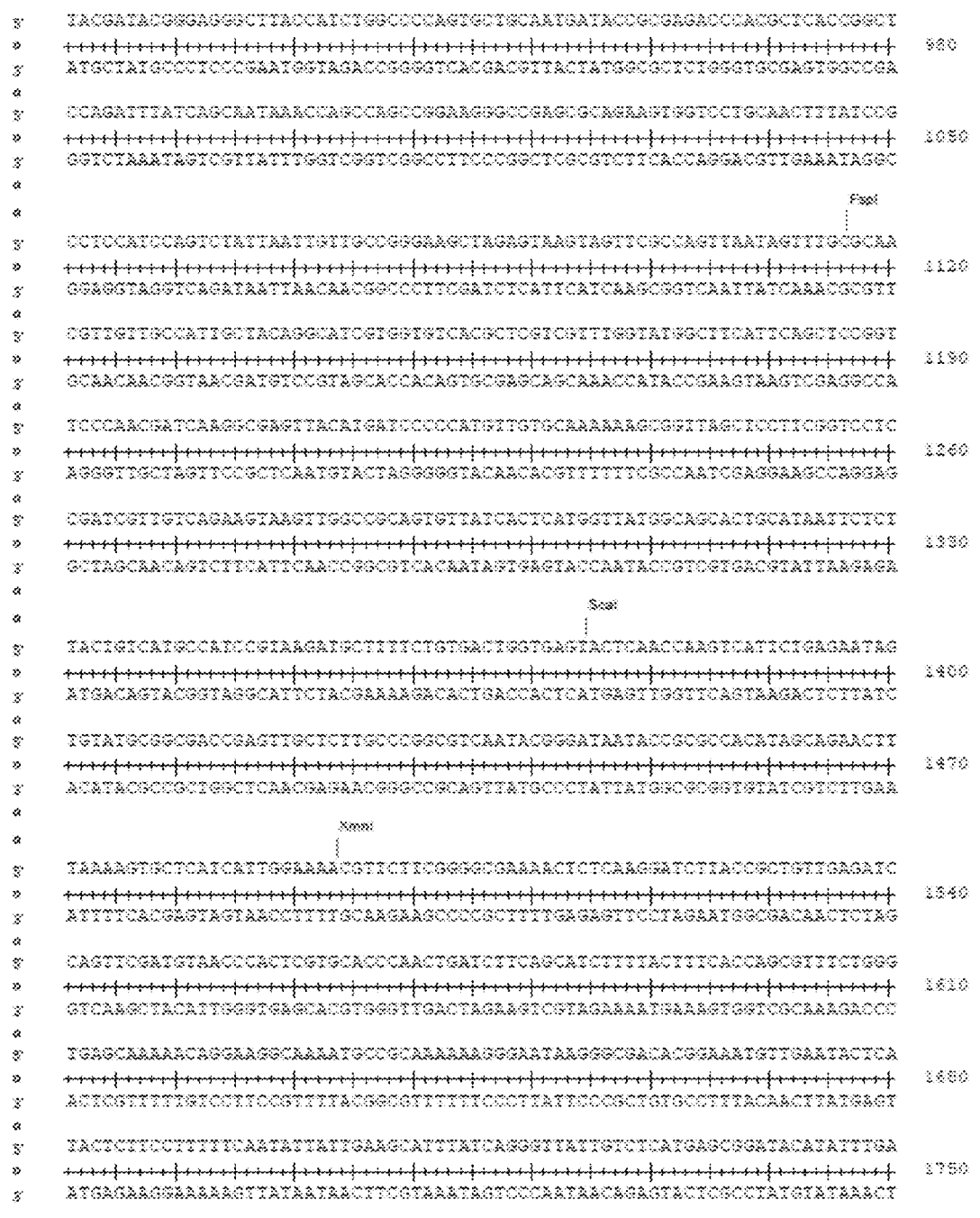
Figure 4:
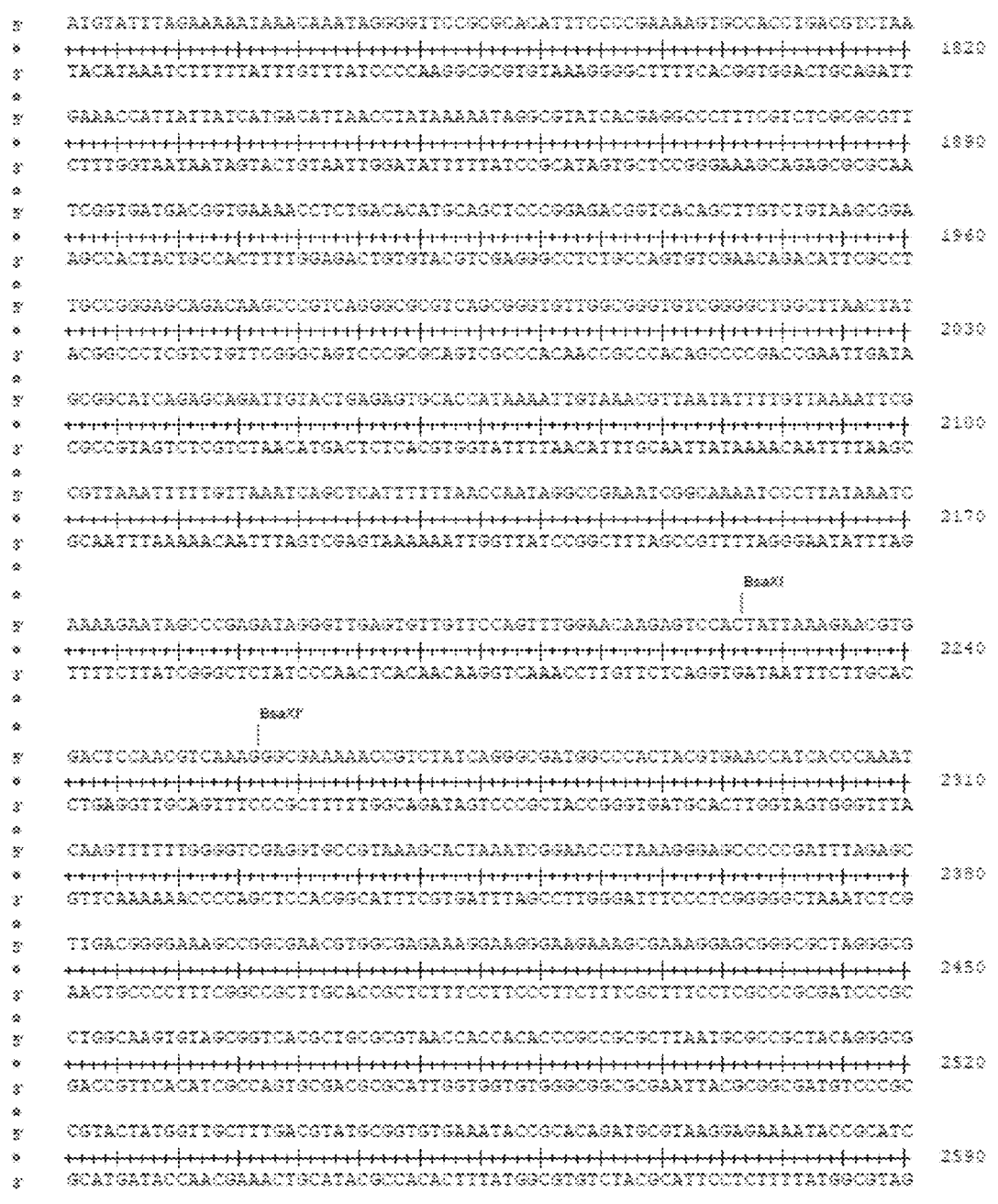
Figure 4:
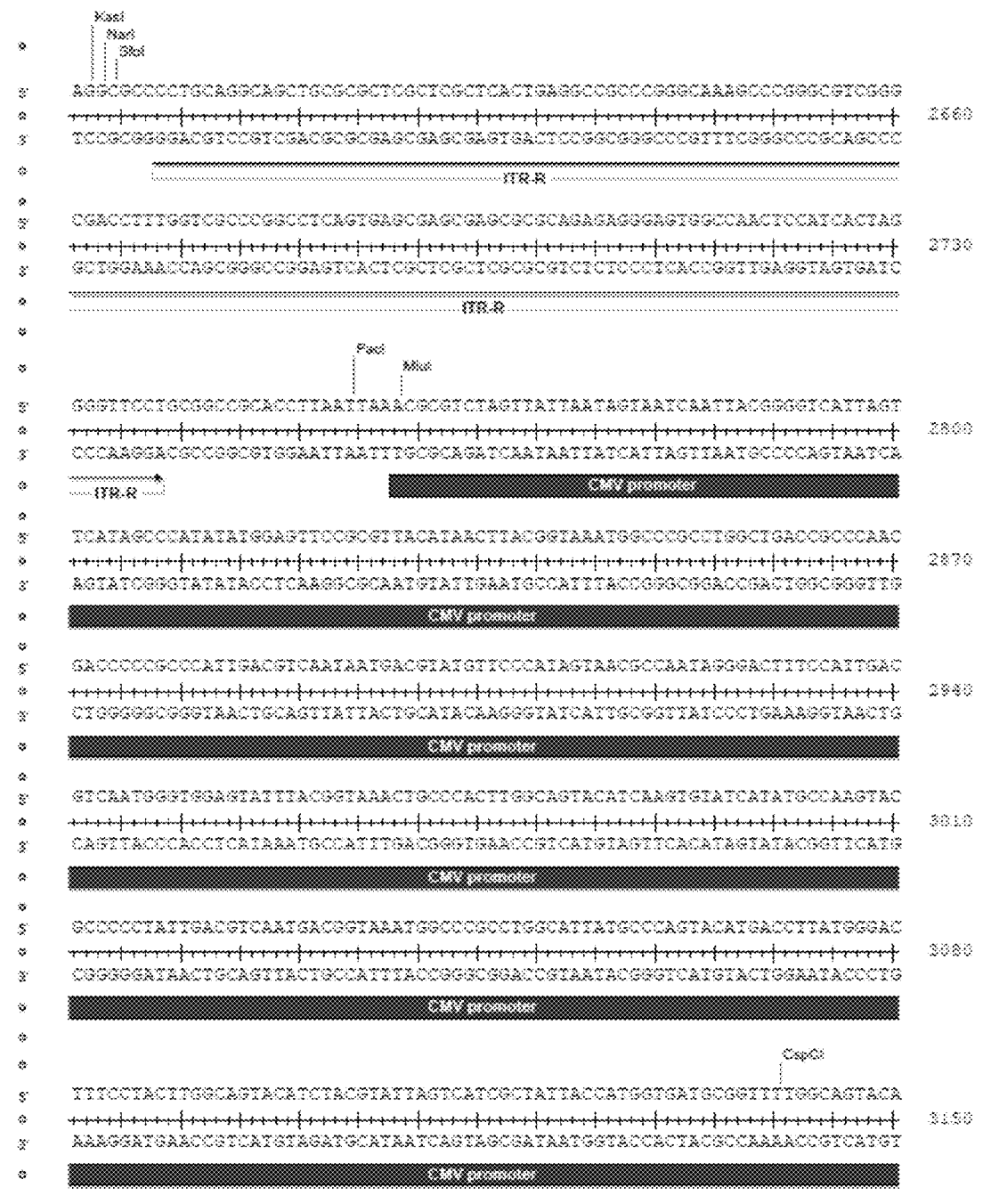
Figure 4:
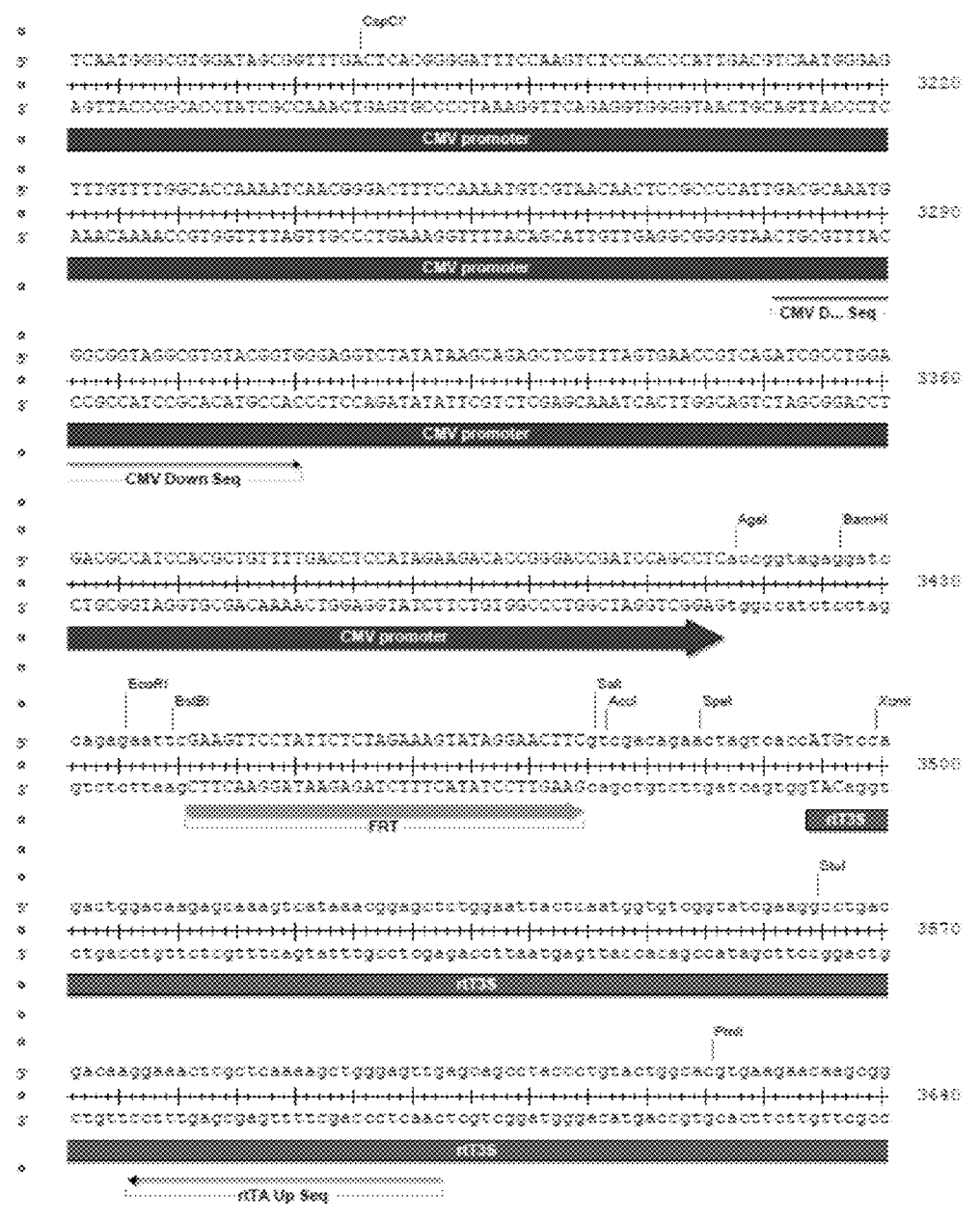
Figure 4:
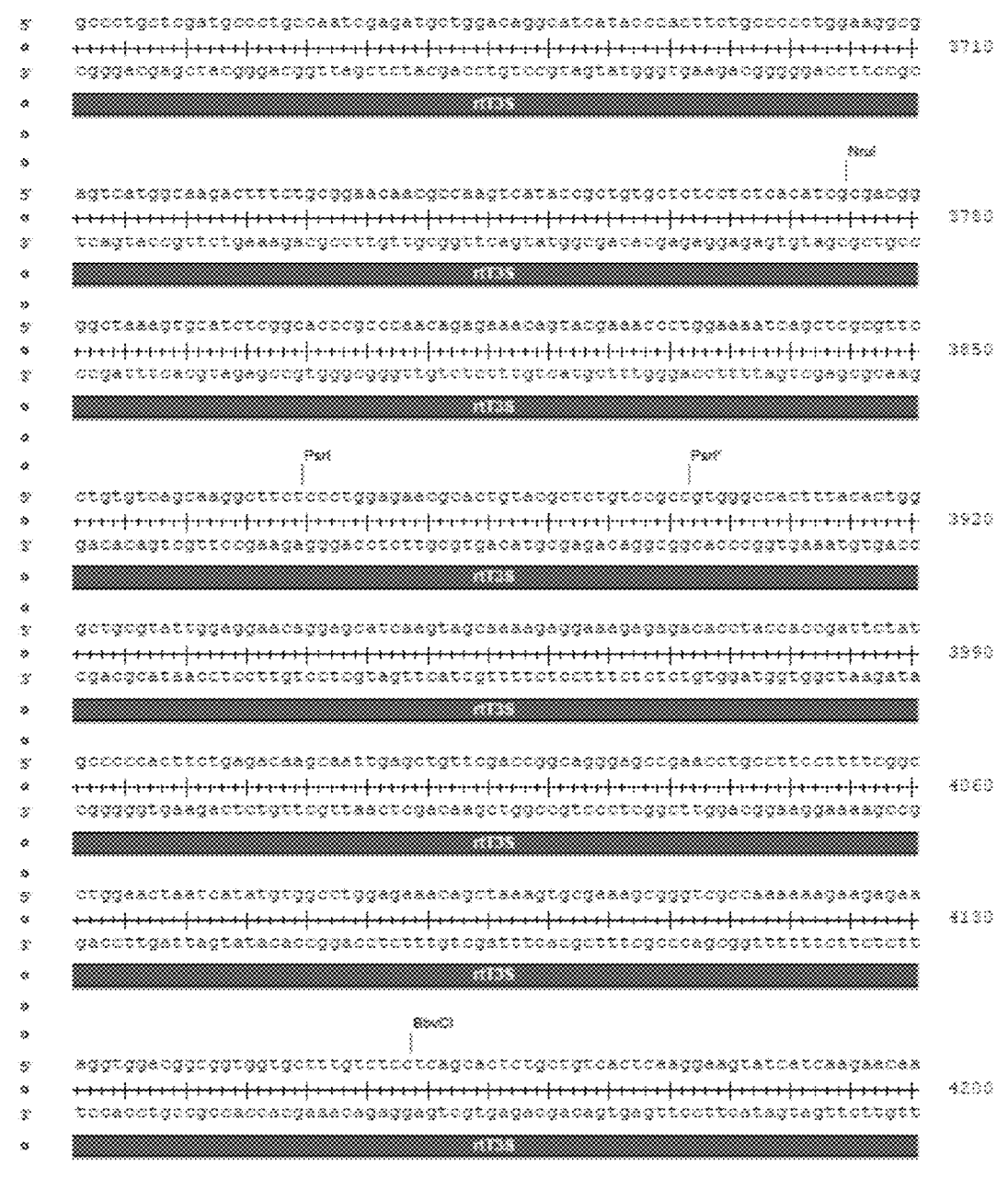
Figure 4:
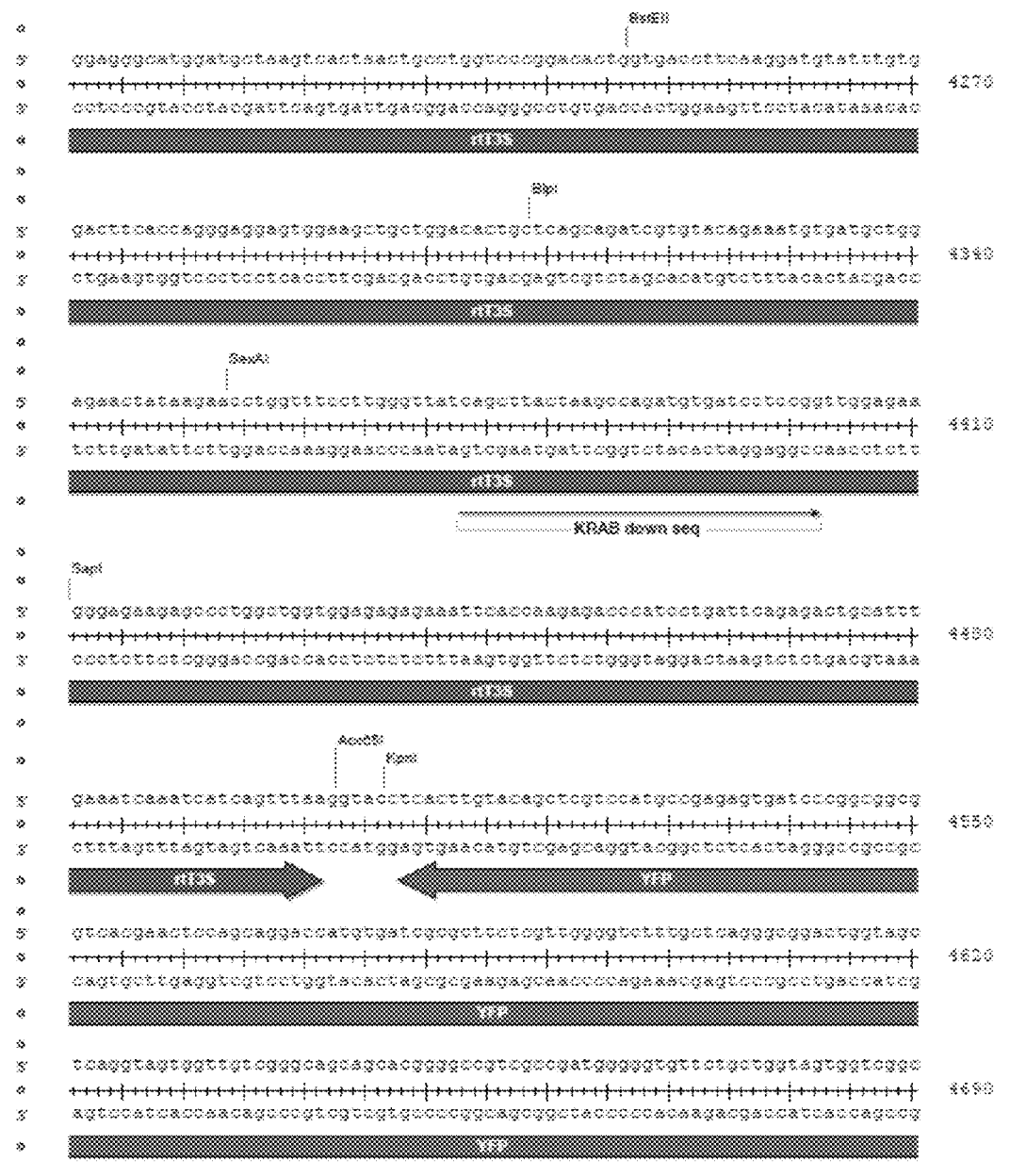
Figure 4:
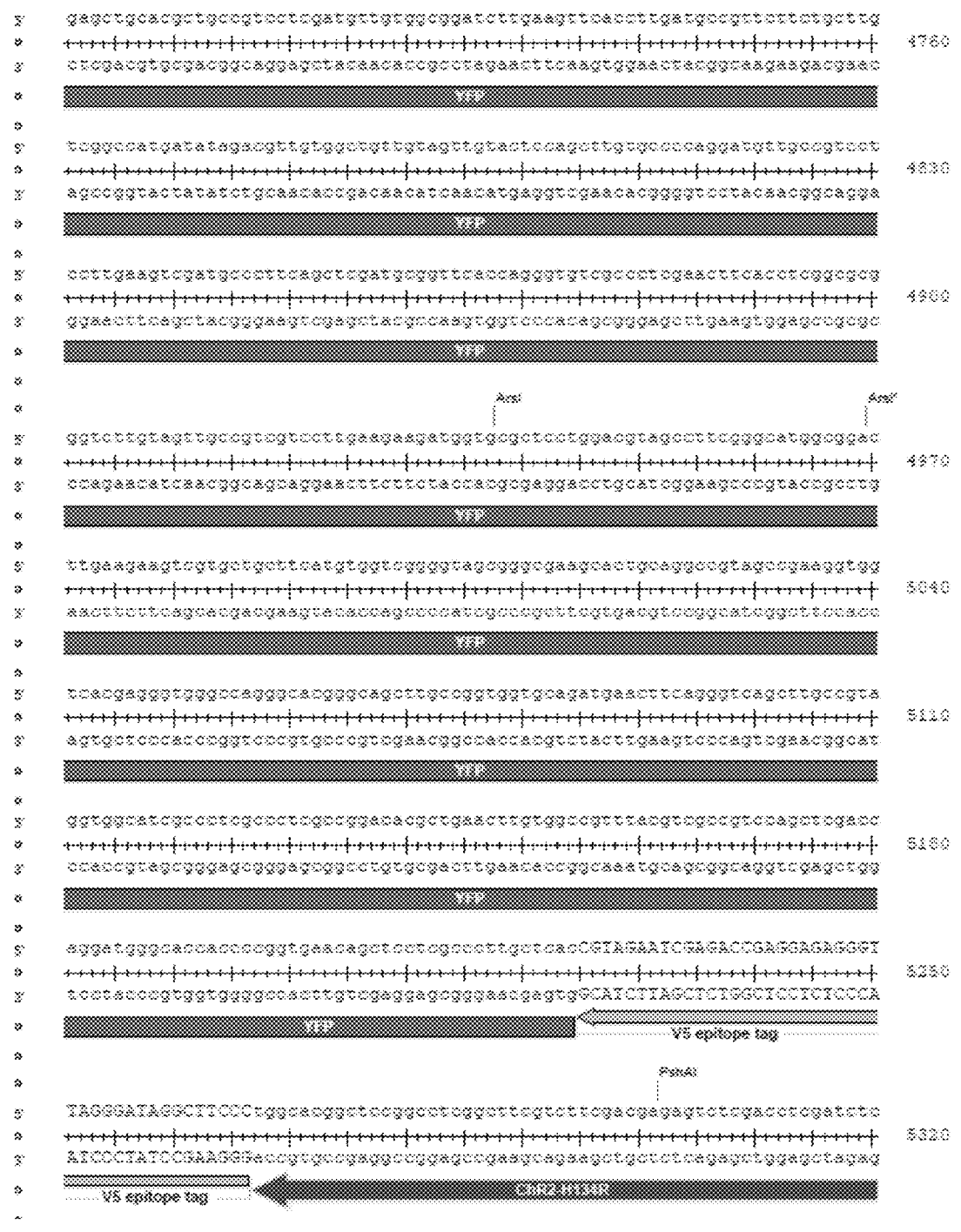
Figure 4:
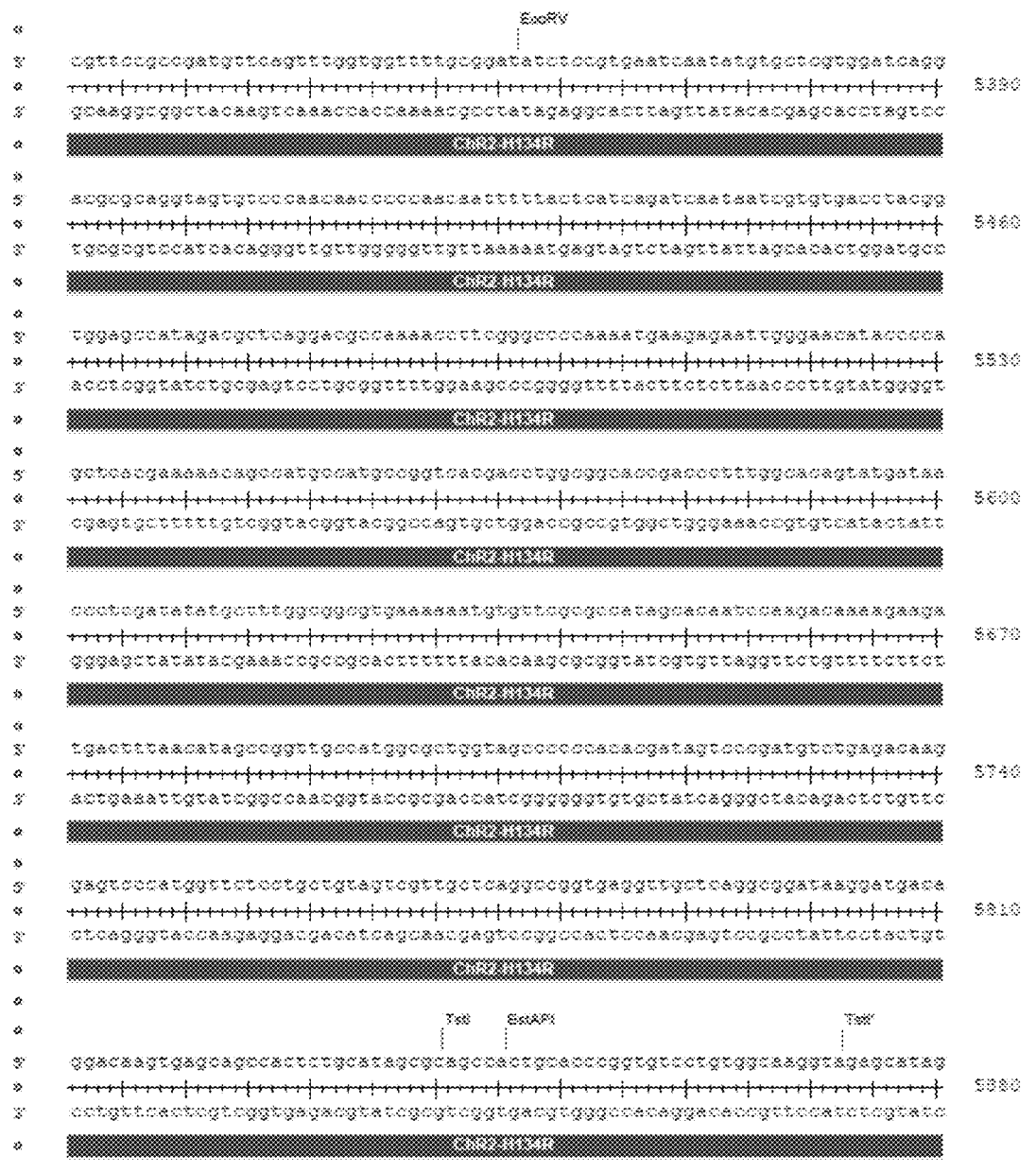
Figure 4:
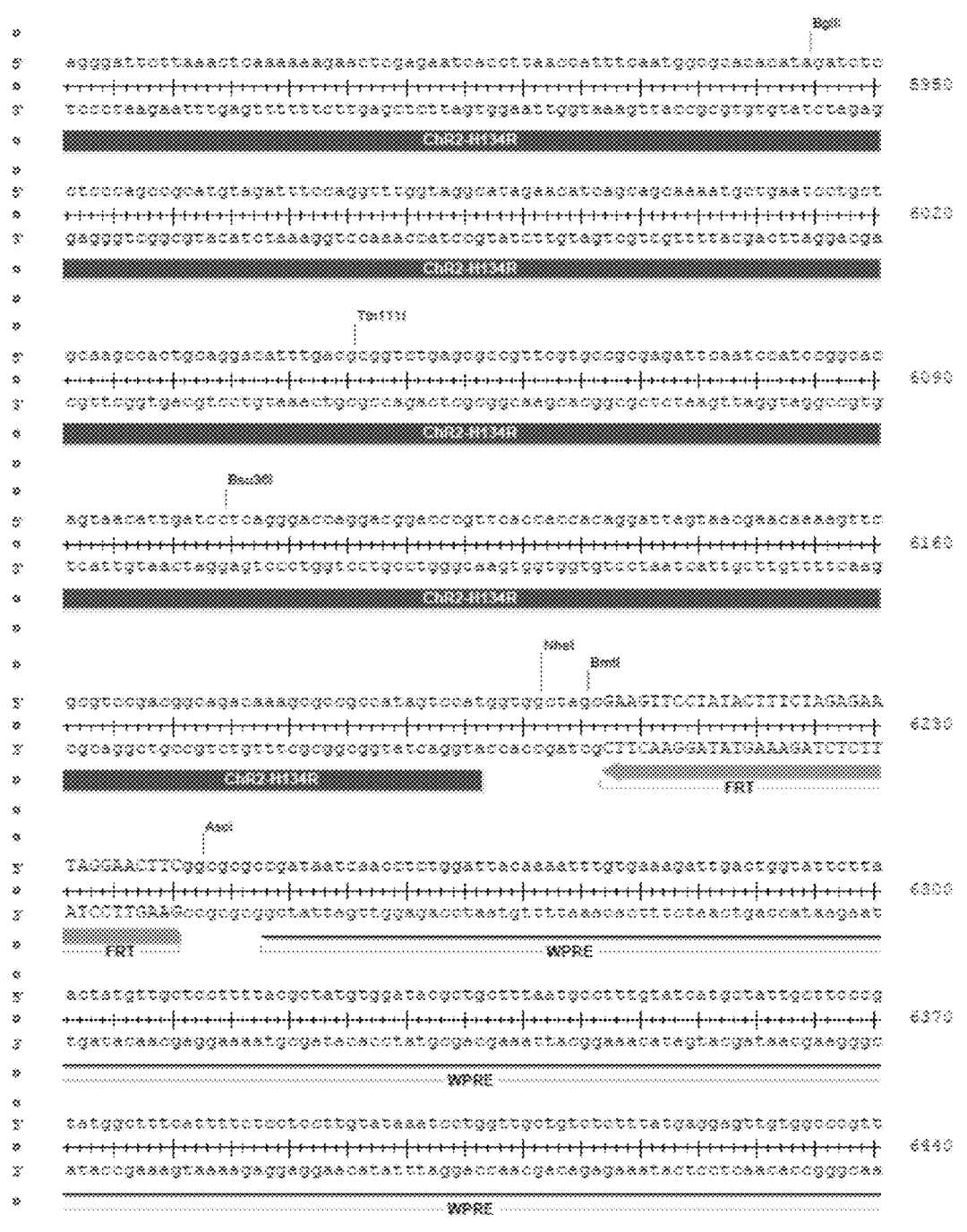
Figure 4:
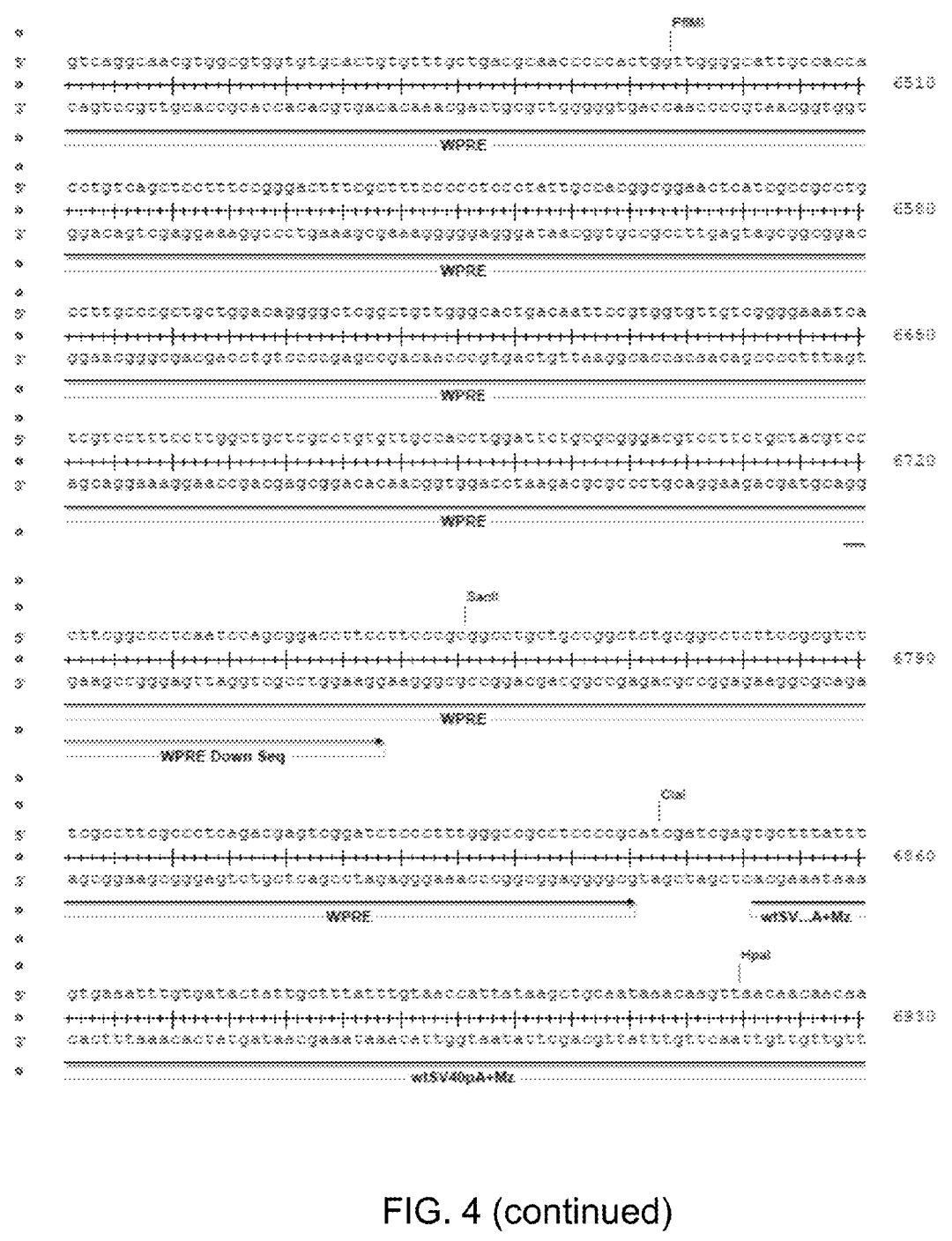
Figure 4:
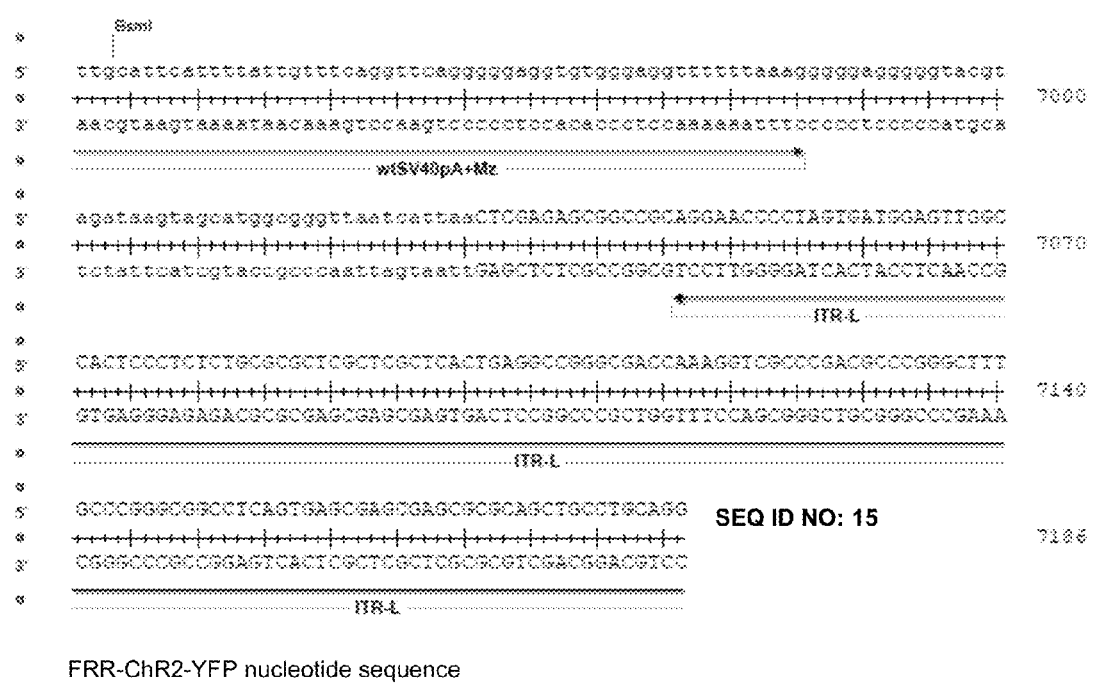

FIG. 4 shows the nucleotide sequence for the AAV vector of FIG. 3 (SEQ ID NO: 15). The ITR-R (SEQ ID NO: 16) is located at positions 2598-2738. The CMV promoter (SEQ ID NO: 17) is located at positions 2758-3416. The FRT (SEQ ID NO: 18) is located at positions 3441-3474 and 6207-6240. The rtT3S (SEQ ID NO: 19) is located at positions 3494-4501. The YFP (SEQ ID NO: 20) is located at positions 4508-5224. The V5 epitope tag (SEQ ID NO: 21) is located at positions 5225-5266. The ChR2-H134R (SEQ ID NO: 22) is located at positions 5267-6197. The WPRE (SEQ ID NO: 24) is located at positions 6248-6840. The wtSV40pA+Mz (SEQ ID NO: 24) is located at positions 6851-6985. The ITR-L (SEQ ID NO: 25) is located at positions 7046-7186.

Figure 6:
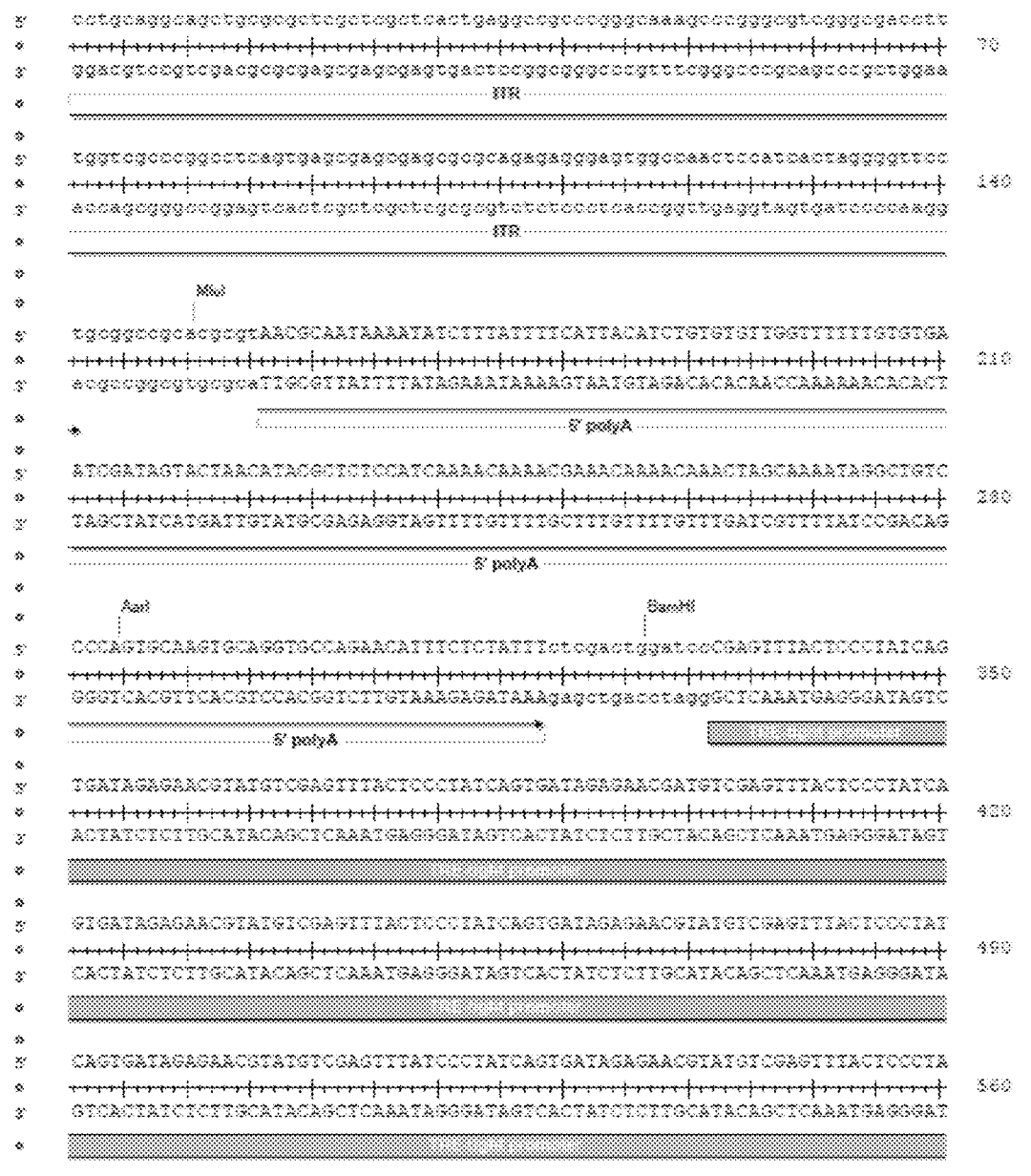
Figure 6:
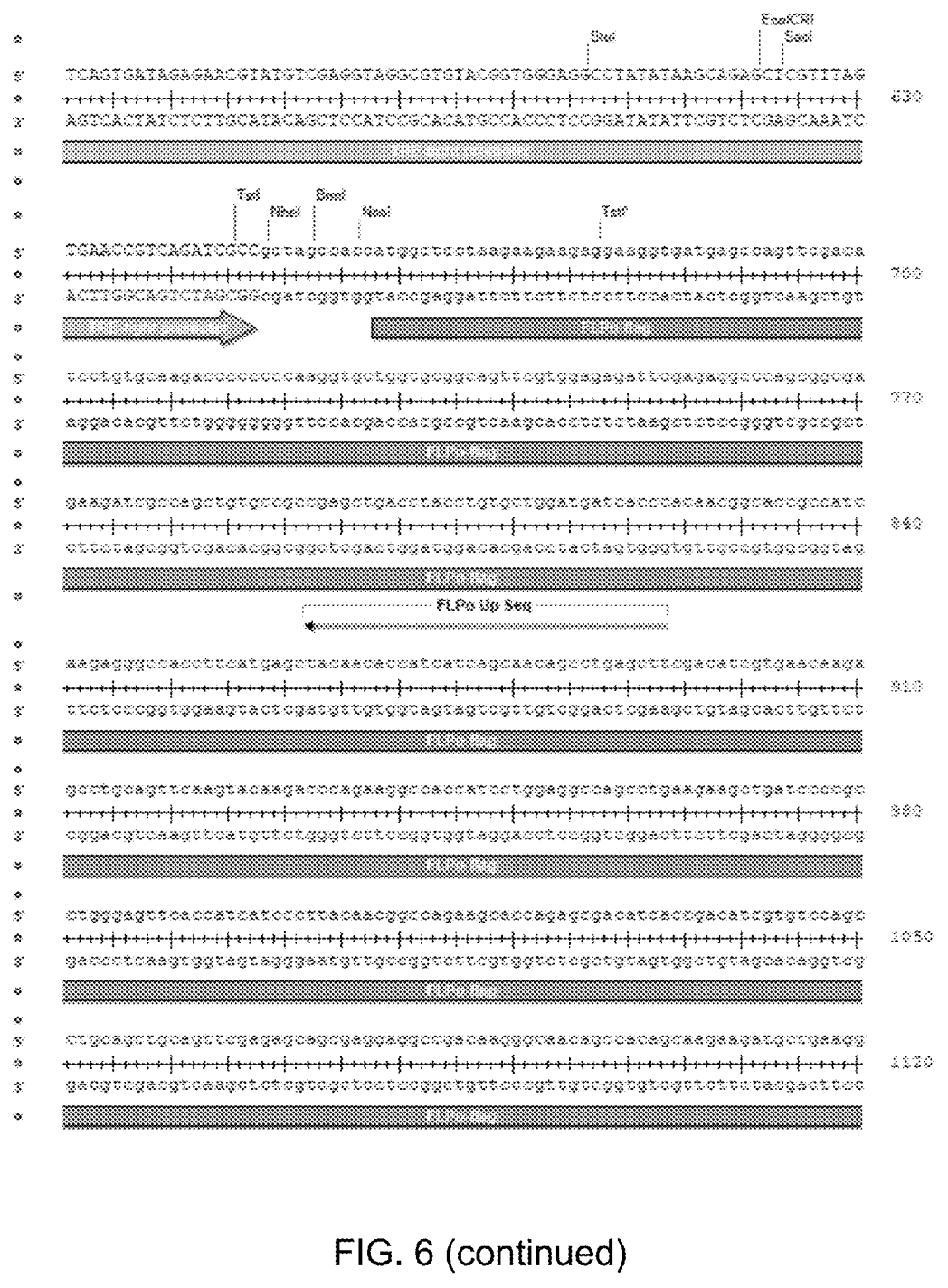
Figure 6:
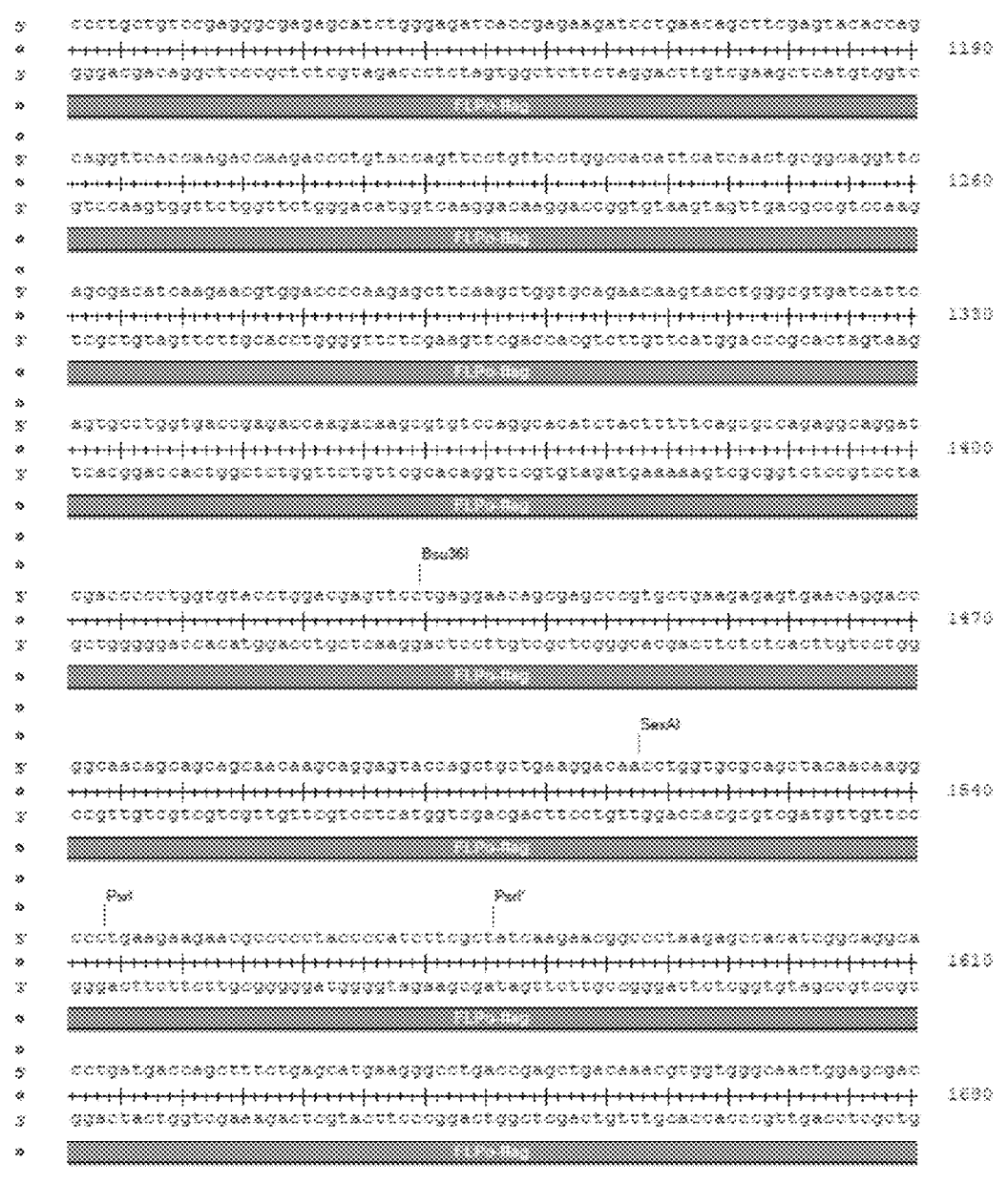
Figure 6:
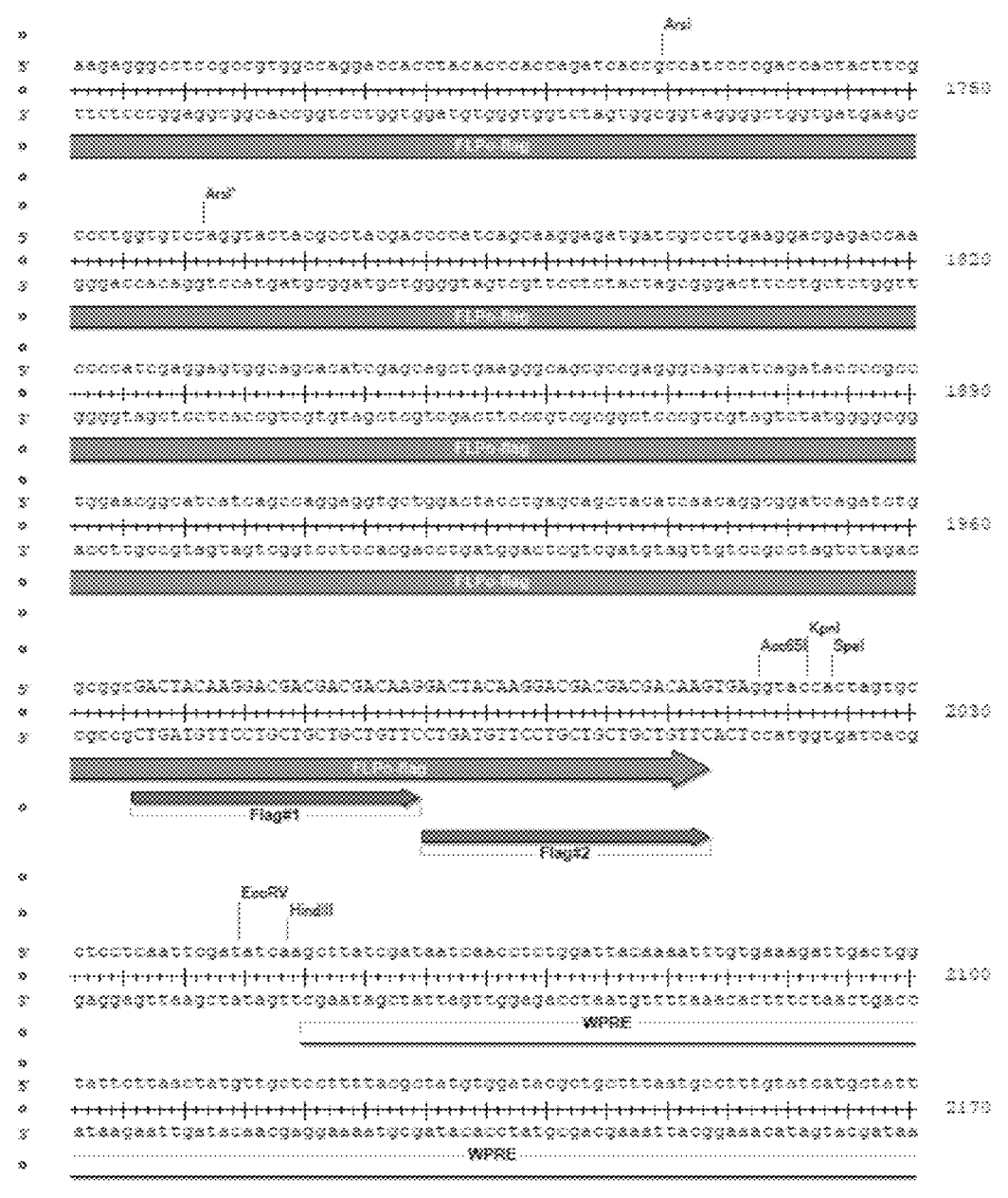
Figure 6:
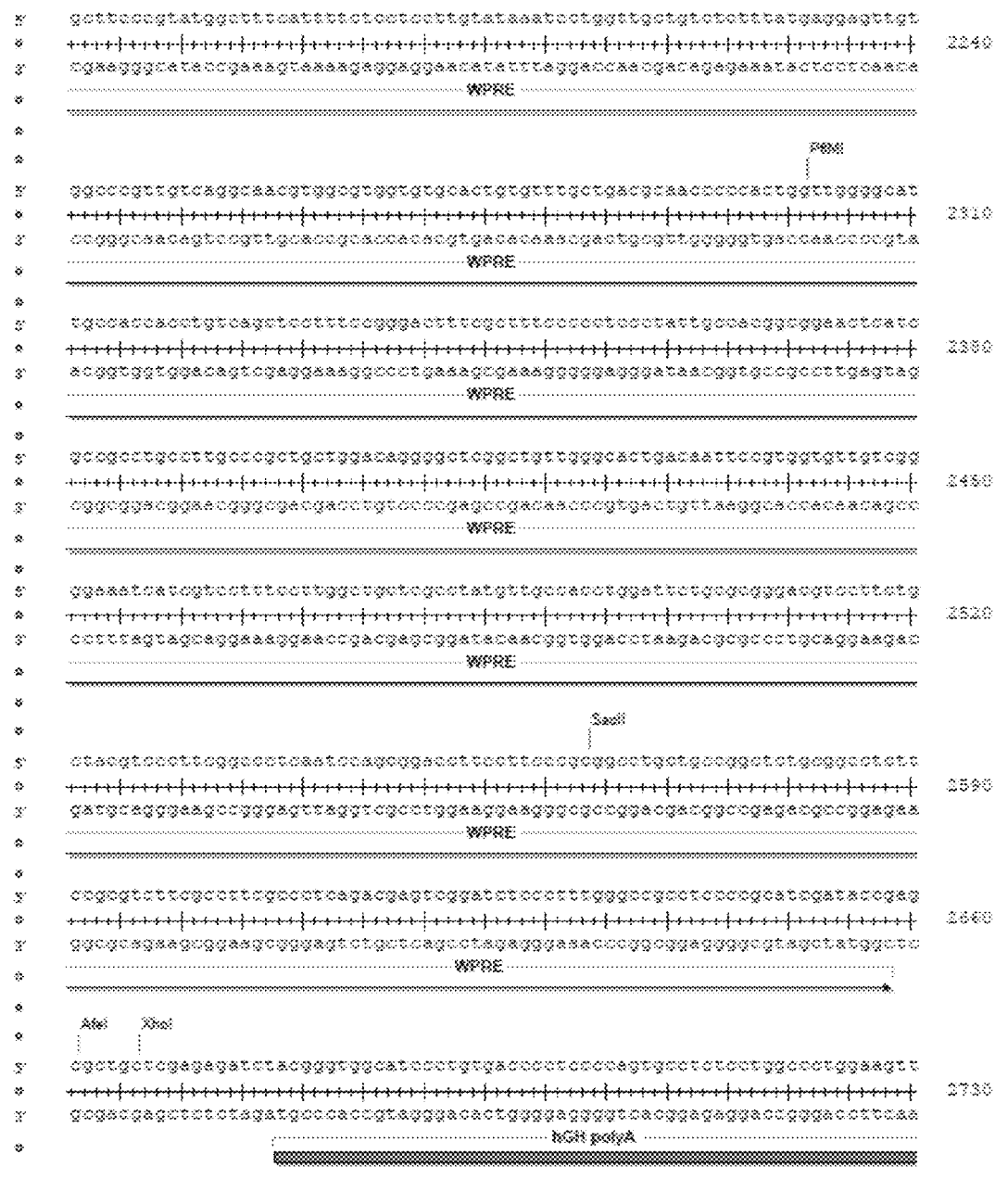
Figure 6:
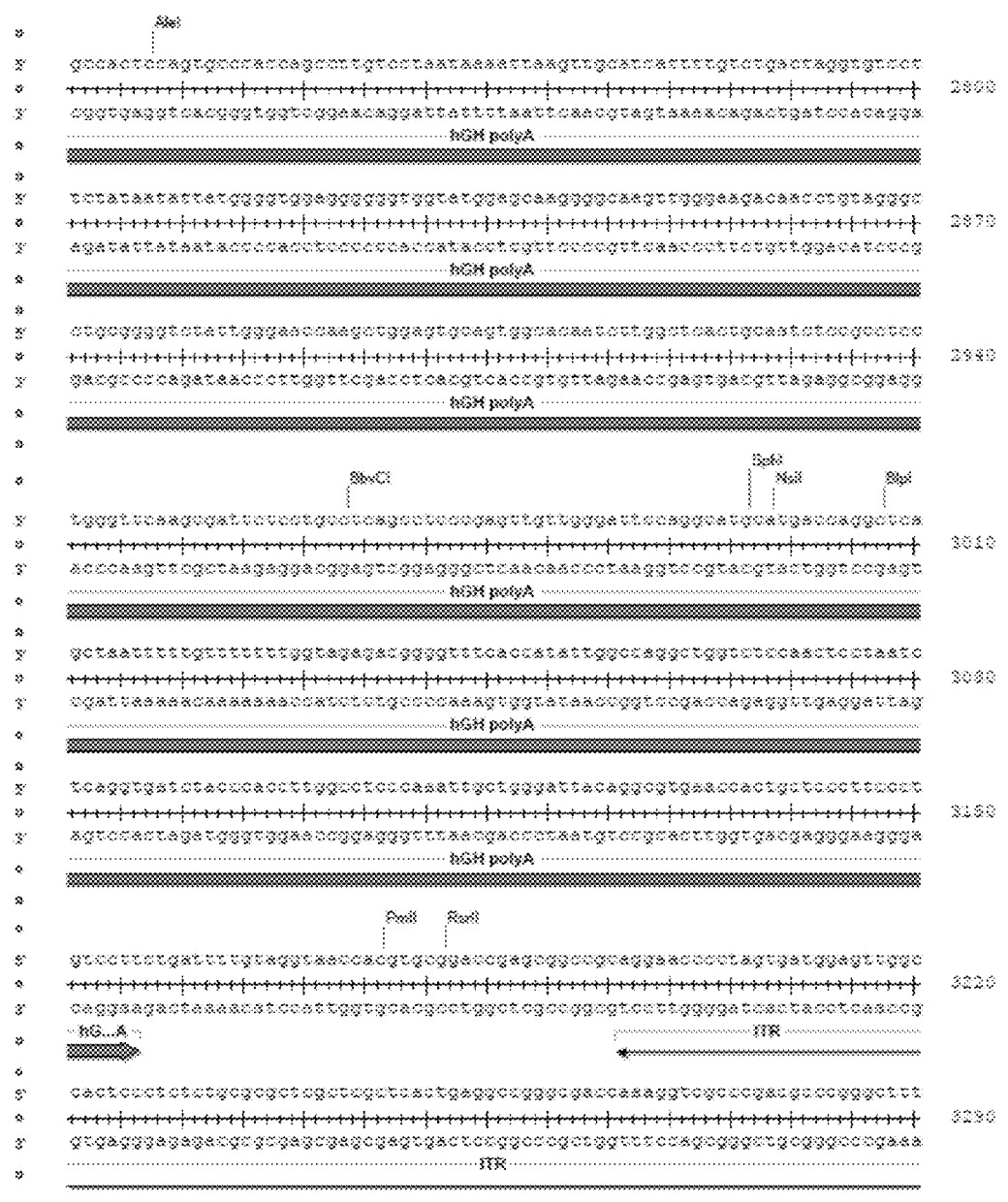
Figure 6:
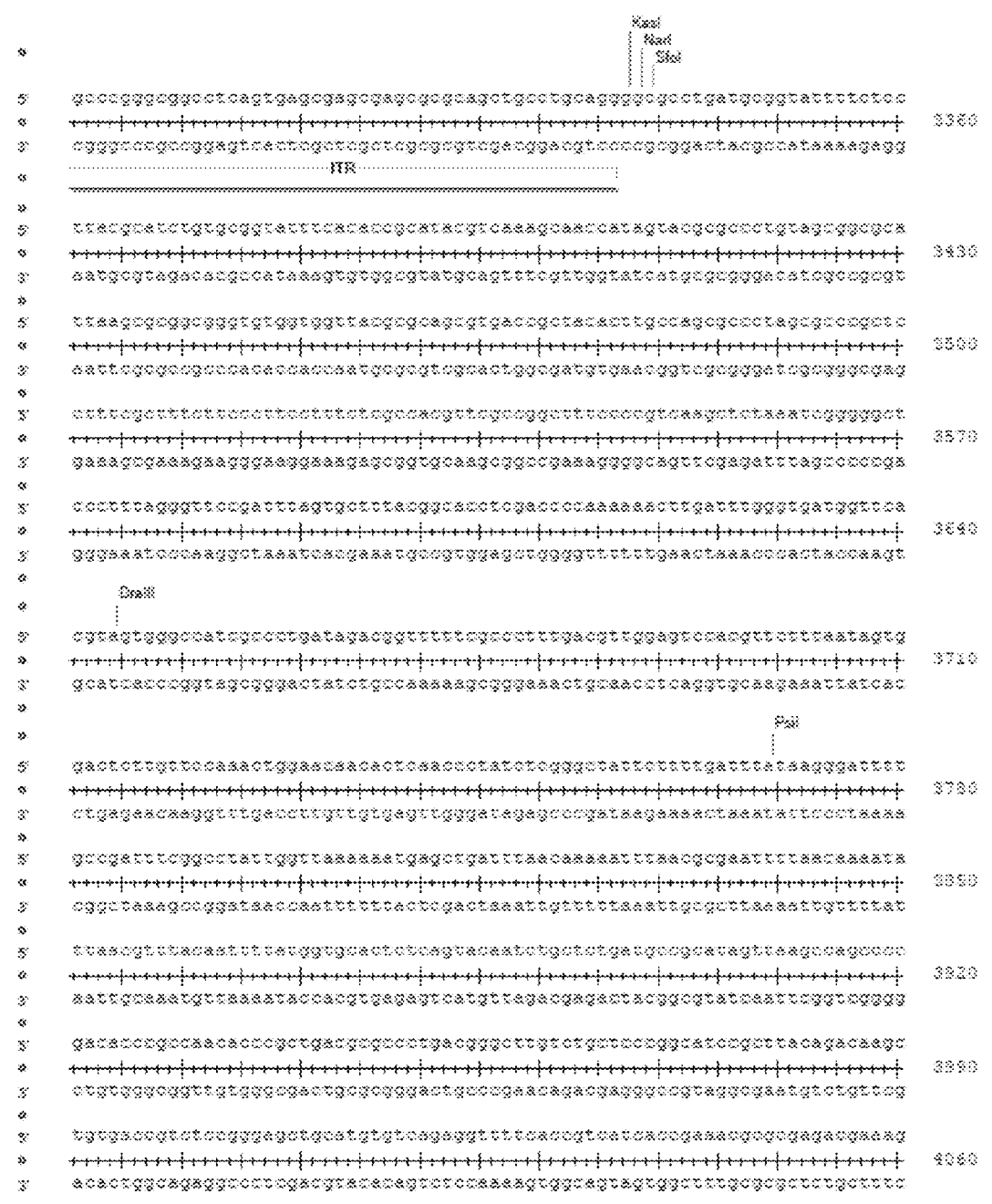
Figure 6:
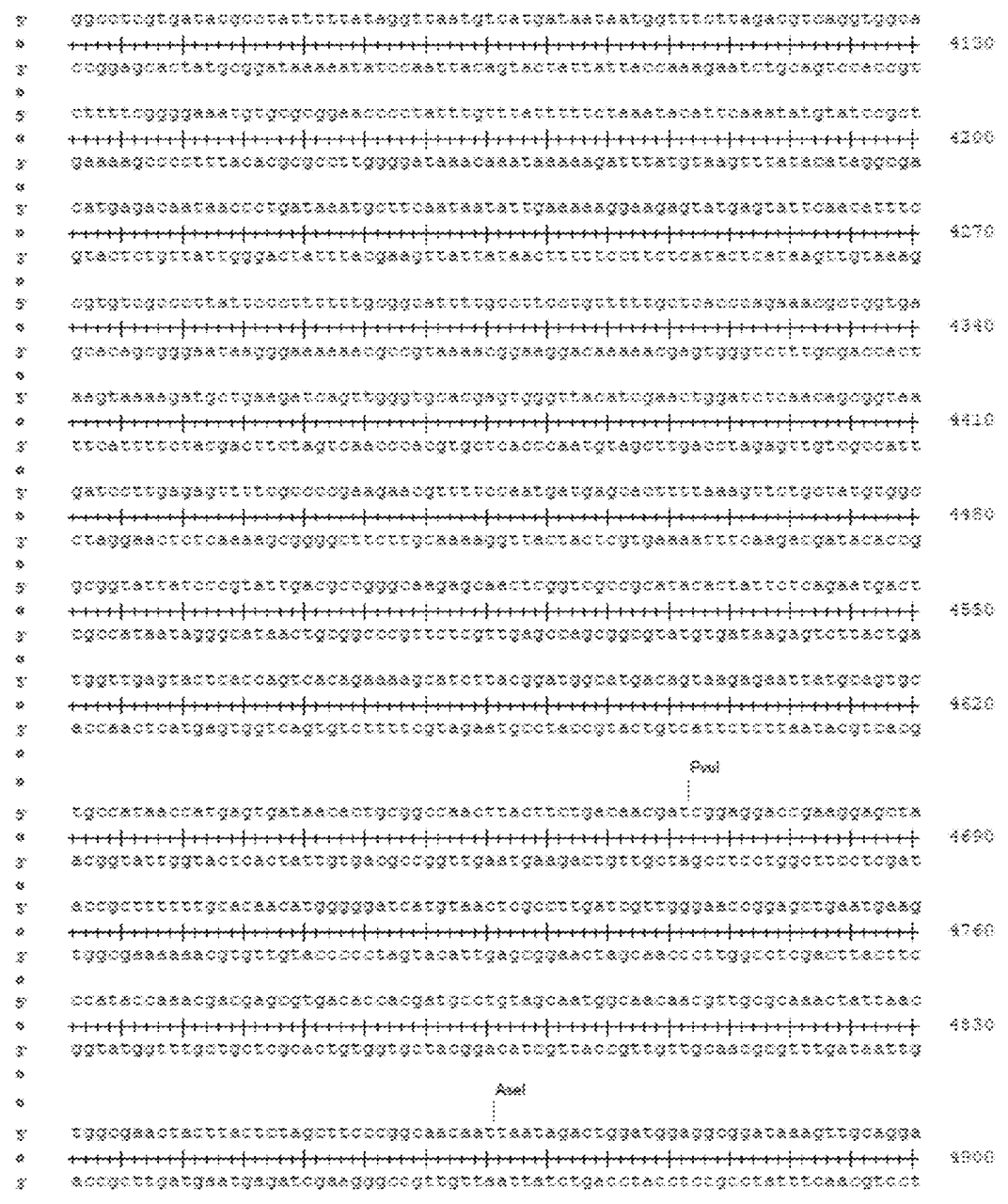
Figure 6:
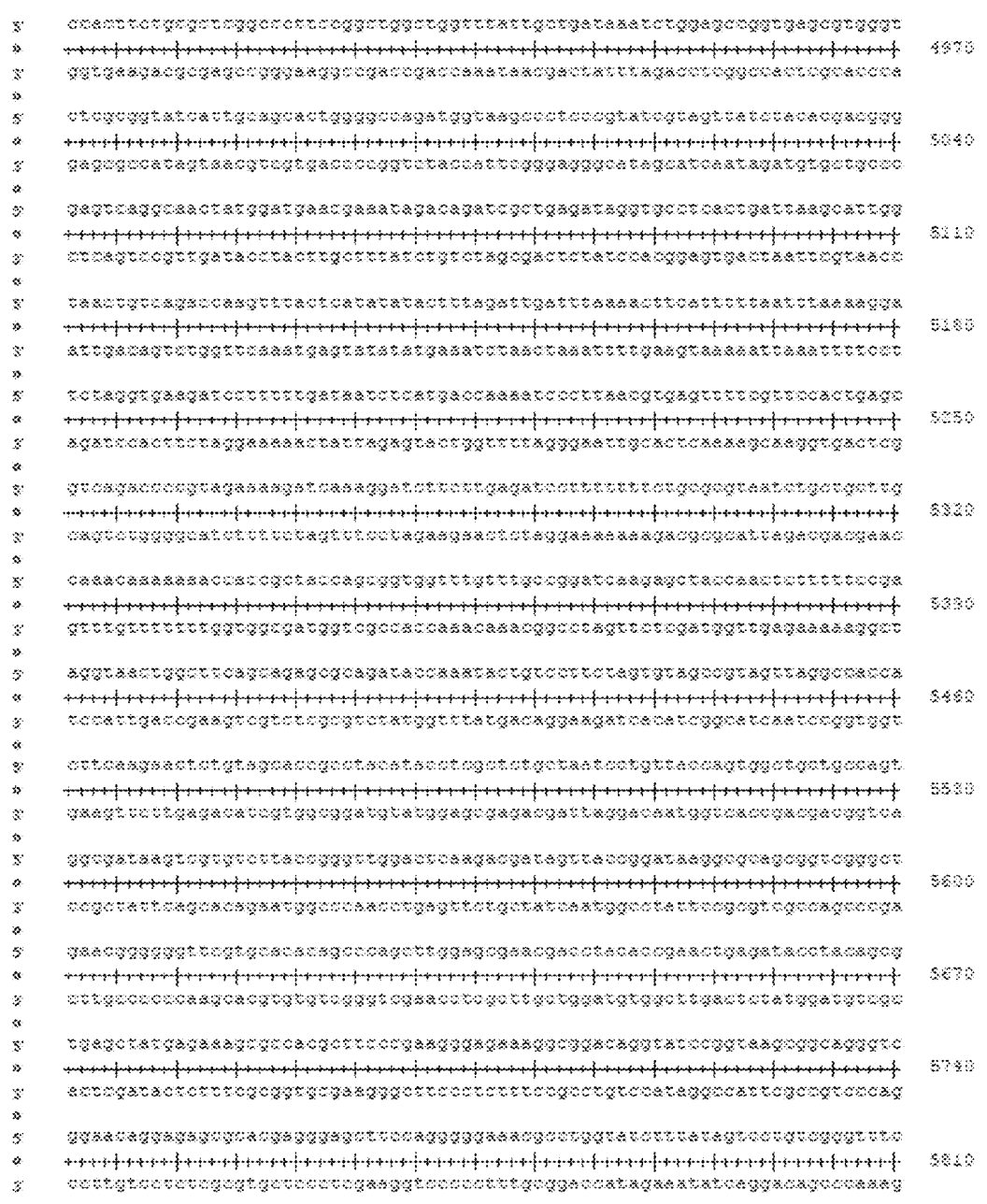
Figure 6:
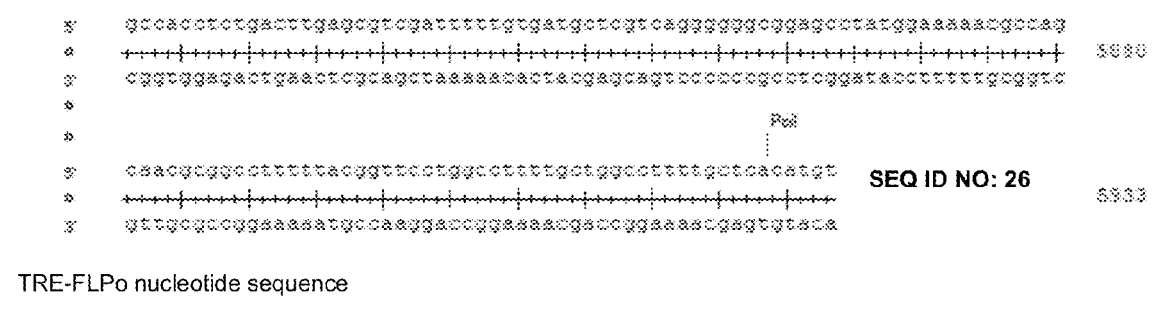

FIG. 6 show the nucleotide sequence for the AAV vector of FIG. 5 (SEQ ID NO: 26). The ITR-R (SEQ ID NO: 16) is located at positions 1-141 and ITR-L (SEQ ID NO: 25) is located at positions 3196-3336. The 5' polyadenylation site (SEQ ID NO: 27) is located at positions 156-318. The TRE-tight promoter (SEQ ID NO: 28) is located at positions 332-647. The FLPo-flag (SEQ ID NO: 29) is located at positions 658-2013, with Flag#1 located at 1966-1989 and Flag#2 located at 1990-2013. An FLPo up sequence is located at positions 792-823. The TRE WPRE (SEQ ID NO: 30) is located at positions 2050-2658. The hGH polyadenylation (SEQ ID NO: 31) is located at positions 2678-3156.

FIGS. 10A-10L are a series of microscope images showing a comparison of induction of tTA expressed from a "full length Fos" Fos-tTA transgenic mouse (FIGS. 10A-10F) developed by Mayford (Reijmers et al. (2007), Science, 317, 1230-1233, incorporated herein by reference in its entirety) and Fos-FmTB transgenic mouse (FIGS. 10G-10L), in accordance with some embodiments herein, in the hypothalamus. The dashed oval delineates the boundary of the ventromedial hypothalamic nucleus (VMH), in which cFos expression is induced following an aggressive interaction ("fight") in the ventrolateral region (panel B, VMHvl). DAPI is a nuclear stain, cFOS is endogenous c-FOS protein, and tTA is antibody staining for tTA. Note that tTA is poorly induced in VMHvl after fighting in the Mayford mouse line (FIG. 10F), but strongly induced in the Fos-FmTB transgenic line according to some embodiments herein (FIG. 10L).

FIGS. 12C-12N are a series of microscope images illustrating tTA induction from the FmTB transgene (FIG. 12A) in different brain regions following restraint stress of 30 minutes. tTA is induced in the lateral septum (FIGS. 12C-12F), paraventricular nucleus of the hypothalamus (PVN; FIGS. 12G-12J), and medial amygdala (MEA; FIGS. 12K-12N). FOS represents staining with an antibody to c-FOS, which recognizes both endogenous c-FOS protein and FmTB FOS-tTA fusion protein.

FIG. 14A shows the three viral components, which include construct "a", an AAV encoding the FmTB transgene, construct "b", a TRE-drive ChR2 virus, and construct "c", a CMV-driven rtTS. The rtTS is activated by DOC, and binds to the TRE to prevent leakage expression when FmTB is not induced. All three viruses are injected in the hippocampus. The neurons are activated in the hippocampus by injecting the animal with kainate. ChR2 expression is visualized using an antibody to the V5 epitope tag. This demonstrates a strong induction in kainate-treated animals (FIG. 14M) compared to saline-injected controls (FIG. 14G).

FIGS. 15A-15M demonstrate that an all-viral TRACM system can generate functionally relevant levels of ChR2 expression following induction by a natural stressor according to some embodiments herein. Viruses as provided in FIG. 15A were co-injected into the hippocampus and animals were treated as summarized in FIG. 15B. Antibody staining reveals that ChR2-V5 is induced in the lateral septum by restrains stress (FIG. 15F and FIG. 15G). FIG. 15I is a schematic illustration of a hippocampus slice, with the setup in which ChR2-expressing cells can be prospectively visualized using the hrGFP reporter as shown in panel G. Voltage-clamp FIG. 15J) and current-clamp (FIG. 15K) show recordings of optogenetically induced spiking in FmTB-ChR2-expressing cells. Peak and steady state photocurrents (FIG. 15L) and action potentials (FIG. 15M) are recorded from the cells.

FIGS. 16A-16F demonstrate Cre-dependent TRACM system for intersectional marking of active neurons that also express Cre recombinase according to some embodiments herein. An all-viral system is used, with a Cre-dependent CR2-YFP virus (construct "b"), and a CMV-driven Cre-recombinase virus (construct "d") together with the FmTB virus (construct "a") and the rtTS "leak suppressor" virus (construct "c"). The experimental flow-chart is shown below the virus constructs. Kainate treatment induces ChR2-YFP expression in the hippocampus in mice co-injected with all four viruses (FIG. 16D) compared to saline-injected controls (FIG. 16C). Omission of FmTB (FIG. 16E) or Cre (FIG. 16F) viruses prevents kainate induction of ChR2-YFP.

FIGS. 17A-17D illustrate the use of TRACM to achieve drug-induced cell marking (FIG. 17A and FIG. 17B) or behavioral responses (FIG. 17C and FIG. 17D) according to some embodiments herein. FIG. 17A is a schematic representation of a three-component all-viral system used in mice injected with the anxiolytic drug diazepam, which induced c-FOS in the central amygdala (CEA). FIG. 17B shows the strong induction of the TRE-driven EYFP reporter in CEA compared to naïve control animals. FIG. 17C and FIG. 17D illustrate optogenetic activation of TRACM-marked cells by a drug recapitulates the behavioral response to the drug. Animals were injected with a three-component all-viral TRACM system in which TRE drives Chrimson, a red-shifted opsin, or TRE-EYFP as a control. Following viral injection, animals were injected with cholecystokinin (CCK), a drug that suppresses food intake. Twenty-four hours following CCK injection, Chrimson activation in CEA reduces food intake in starved animals (panel D). Although Chrimson data points do not differ significantly from EYFP at $p<0.05$, a clear trend is evident.

FIGS. 18A-18J illustrate that an all viral TRACM system according to some embodiments herein robustly and specifically marks lateral septum (LS) acute stress-activated neurons. FIG. 18A shows the TRACM adeno-associated viral (AAV) vectors used for transient expression of reporter or effector molecules, as shown in FIGS. 1-6; neural activity-induced Fos expression produces a DOX-suppressible tetracycline transactivator (tTA) fusion protein ("i") that in turn activates expression from TRE-driven reporter vectors ("ii"). Inclusion of the DOX-activated reverse tetracycline silencer (rtTS, "iii") increases signal to noise by actively suppressing expression from the TRE promoter. FIGS. 18C-18H show that in the absence of DOX, significant induction of YFP native fluorescence is observed in immobilization stressed (+S) but not unstressed naive (N) mice (FIG. 18C and FIG. 18D); stress does not induce YFP in the presence of DOX (+S, +DOX) (FIG. 18E). *$P<0.001$; one-way ANOVA with Tukey's Multiple Comparisons Test. FIG. 18G** illustrates that constitutively expressed rtTS serves as an internal control; no significant differences in LS rtTS$^-$ cell counts are detectable, demonstrating comparable infections across all experimental groups. Total DAPI$^+$ cells: N=5,580; +S=5,076; +S, +DOX=3,164.

FIGS. 19A-19F illustrate stable activity-dependent genetic marking using TRACM according to some embodiments herein. FIG. 19A shows the TRACM transgene and AAV vectors used for stable expression of reporter or effector molecules. In this scheme, the AAV that expresses rtTS also contains a second gene (here, ChR2::YFP) which is in the reverse 3' to 5' orientation relative to rtTS and the CMV promoter; both rtTS and ChR2::YFP are flanked by inverted FRT sites. Therefore, neural activity results in the induction of codon optimized FLPo recombinase, which mediates inversion of the rtTS-ChR2 cassette such that ChR2::YFP is inverted into the correct, 5' to 3' orientation. Upon placing subjects onto high concentrations of DOX, cells in which such a recombination event occurred will yield stable expression of the reporter, whereas cells that did not undergo a recombination event will be stably silenced. FIG. 19B-19F show that 8 days following stereotactic injections of AAV constructs "a"+"b" into Fos-FmTB transgenics, mice were either left undisturbed in their home cages (naive) or subjected to immobilization stress (+stress). At 24 hours following completion of immobilization, all animals were placed onto DOX, and 12 days later, perfused for histological analysis. Stressed animals showed significantly more ChR2-YFP+ neurons than naive mice (FIG. 19C, FIG. 19D, and FIG. 19F), and stressed mice that received DOX from day 0 (FIG. 19E) showed similar ChR2-YFP expression as naives. Total DAPI+ cells: naive=2,922; +stress=2,879.

DETAILED DESCRIPTION

Figure 1:
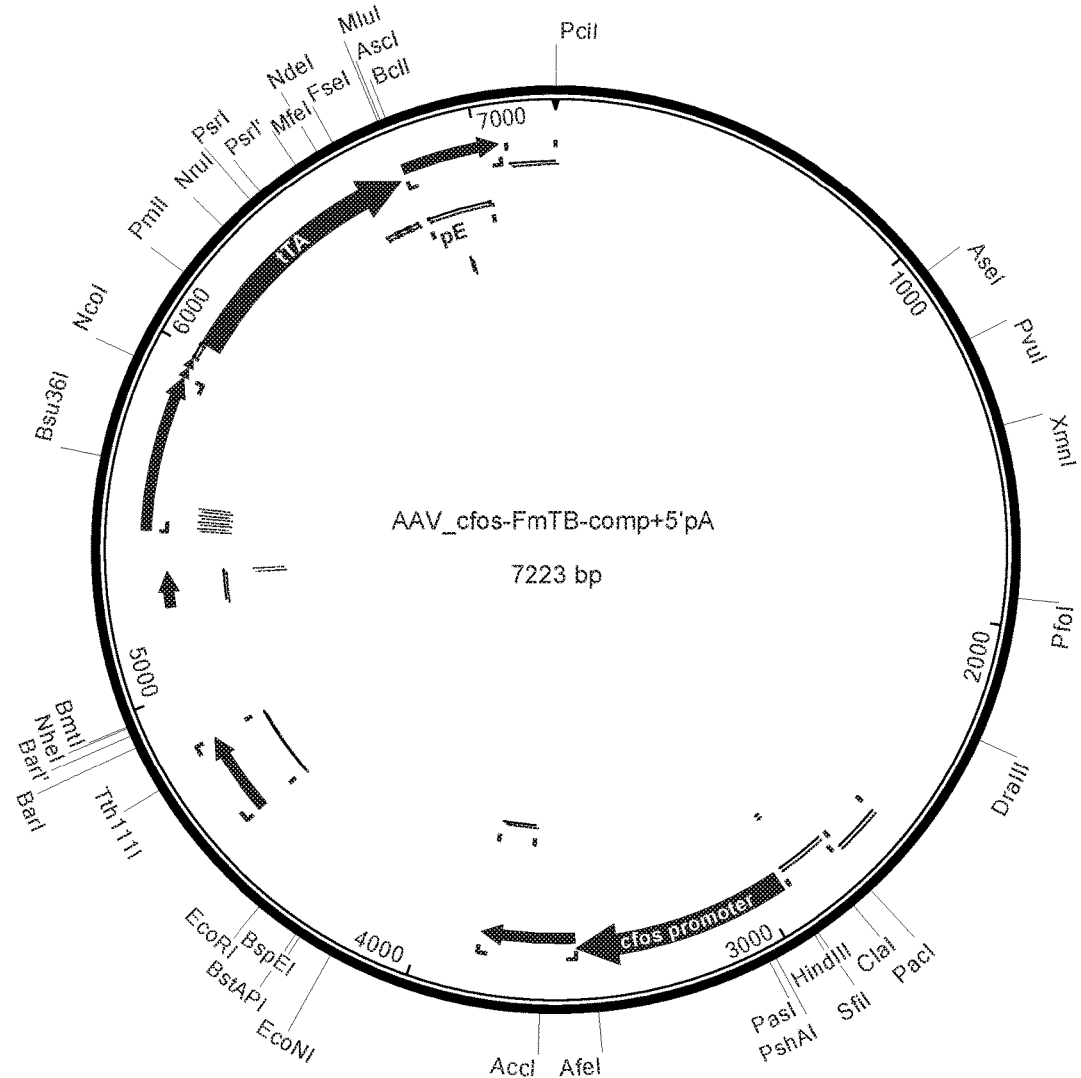
FIG. 1 is a vector map illustrating an AAV vector according to some embodiments herein. Depicted is vector cfos-FmTB (Fos mutant tetracycline regulated transcriptional activator (tTA) with the bovine growth hormone polyadenylation site (BGHpA)) (SEQ ID NO: 1).

According to some embodiments herein are activity-dependent adeno-associated virus (AAV) vector expression systems. The activity-dependent AAV vector expression systems can be useful for identifying, marking, and manipulating activated cells such as neurons in a mammal based on the neurons' pattern of prior activity. The AAV vector expression system can comprise an immediate early gene (IEG) promoter operably linked to a converter nucleic acid encoding an N-terminal portion of FOS fused to a downstream nucleic acid encoding an activator. Without being limited by any theory, it has been observed that AAV expression systems comprising an N-terminal portion of FOS fused to an activator as described herein recapitulate activity-dependent nucleic acid expression timing and expression patterns more accurately and robustly than an IEG promoter alone (in the absence of the N-terminal portion of FOS fused to the activator). Optionally, the AAV vector system can also comprise an other promoter operably linked to a silencer nucleic acid encoding a silencer. The silencer and/or activator can be controlled by a transcriptional modulator compound for example doxycycline, so that a regulatable promoter is only active in the absence of the transcriptional modulator compound (for example, if the activator is tTA and the silencer is rtTS), or only active in the presence of the transcriptional modulator compound (for example, if the activator is rtTA). The regulatable promoter can be operably linked to an insertion site configured to comprise, or comprising, a nucleic acid encoding a gene product of interest. If permitted by the presence of absence of the transcriptional modulator compound, upon a change of potential in the cell, the converter nucleic acid can be transcribed, resulting in the production of the N-terminal portion of fos fused to the activator. The activator can induce activator of a regulatable promoter, and optionally, the silencer can be prevented from silencing the regulatable promoter. Without being limited by any theory, it is observed that the presence of a silencer and minimize leakiness of a regulatable promoter (for example minimizing transcription in the absence of cell activity). Thus, the addition and removal of the transcriptional modulator compound can restrict activity-dependent activity of the IEG promoter (and subsequent production of any gene product encoded in the insertion site) to a desired window of time.

For example, in some embodiments, a tetracycline-regulatable element (TRE) can be upstream of a nucleic acid encoding a gene product of interest, so that expression of the gene product is regulated by a tetracycline regulated transcriptional activator (tTA). Upon insertion of the AAV vector system into a mammalian cell (in vivo or in vitro), the gene product of interest can be reversibly expressed. In some embodiments, activity-dependent gene expression can be inhibited by the presence of a transcriptional modulator compound such as an antibiotic (e.g., tetracycline, doxycycline, or another tetracycline analog). As such, when the transcriptional modulator compound ceases to be present, activity-dependent gene expression can occur upon activation or stimulation of an animal cell containing the AAV vector system. Because AAV vectors do not integrate into the host genome, and as such, do not modify the host cell genome, there is minimal danger of the system inducing rearrangements in the host genome. In contrast, if multiple copies of an integrating vector (e.g. lentivirus) were to be integrated into a host genome, the vector system could cause rearrangements. The tTA nucleic acid can be fused to a fos coding sequence, for example an N terminal portion of fos. The fos coding sequence can be upstream (3') of the tTA nucleic acid. For example, in some embodiments, an activator is fused to the fos coding sequence encoded by the nucleic acid of SEQ ID NO: 3. Thus, a promoter drives not only expression of the activator but also the encoded FOS polypeptide sequence. Without being limited by any theory, it is contemplated that this construct provides signals when expressed in cells that are closer to endogenous expression of protein. Accordingly, constructs as described in some embodiments herein provide the ability to mark cells more specifically than other approaches. Indeed, nearly all cells that respond to stimuli and having the expression system are marked. In contrast, the cells lacking the expression system, but being exposed to stimuli exhibit no signal, as described herein.

In some embodiments, the activator comprises a reverse tTA (rtTA), for example as encoded by SEQ ID NO: 13

(CTACCCACCGTACTCGTCAATTCCAAGGGCATCGGTAAACATCTGCTCAAACTCG AAGTCGGCCATATCCAGAGCGCCGTAGGGGGCGGAGTCGTGGGGGGTAAATCCC
GGACCCGGGGAATCCCCGTCCCCCAACATGTCCAGATCGAAATCGTCTAGCGCGT CGGCATGCGCCATCGCCACGTCCTCGCCGTCTAAGTGGAGCTCGTCCCCCAGGCT
GACATCGGTCGGGGGGCCGTCGACAGTCTGCGCGTGTGTCCCGCGGGAGAAA GGACAGGCGCGGAGCCGCCAGCCCCGCCTCTTCGGGGGCGTCGTCGTCCGGGAG
ATCGAGCAGGCCCTCGATGGTAGACCCGTAATTGTTTTTCGTACGCGCGGCTG TACGCGGACCCACTTTCACATTTAAGTTGTTTTTCTAATCCGCATATGATCAATTC
AAGGCCGAATAAGAAGGCTGGCTCTGCACCTTGGTGATCAAATAATTCGATAGCT TGTCGTAATAATGGCGGCATACTATCAGTAGTAGGTGTTTCCCTTTCTTCTTTAGC
GACTTGATGCTCTTGATCTTCCAATACGCAACCTAAAGTAAAATGCCCCACAGCG CTGAGTGCATATAACGCGTTCTCTAGTGAAAAACCTTGTTGGCATAAAAAGGCTA
ATTGATTTTCGAGAGTTTCATACTGTTTTTCTGTAGGCCGTGTATCTGAATGTACT TTTGCTCCATTGCGATGACTTAGTAAAGCACATCTAAAACTTTTAGCGTTATTGCG
TAAAAAATCTTGCCAGCTTTCCCCTTTTAAAGGGCAAAAGTGAGTATGGTGCCTA
TCTAACATCTCAATGGCTAAGGCGTCGAGCAAAGCCCGCTTATTTTTTACATGCC AATACAGTGTAGGCTGCTCTACACCAAGCTTCTGGGCGAGTTTACGGGTTGTTAA
ACCTTCGATTCCGACCTCATTAAGCAGCTCTAATGCGCTGTTAATCACTTTACTTT TATCTAATCTAGACAT). Thus, in some embodiments, upon insertion of the AAV vector system into a mammalian cell (in vivo or in vitro), the gene product of interest can be expressed in the presence of a transcriptional modulator compound. For example, doxycycline can induce rtTA to activate transcription by a TRE promoter. By way of example, it is contemplated that an rtTA activator can be useful in vivo, at least in that transcription by the TRE promoter in the presence of cell activation can be achieved by a single step of adding doxycycline, in contrast to adding and subsequently removing doxycycline for a tTA system.

In some embodiments, the regulatable promoter transcribes a nucleic acid encoding the gene product of interest in the presence of the transcriptional modulator compound such as an antibiotic (e.g., tetracycline, doxycycline, or another tetracycline analog). As such, when the transcriptional modulator compound is present, activity-dependent gene expression can occur upon activation or stimulation of an animal cell containing the AAV vector system. The rtTA nucleic acid can be fused to a fos coding sequence, for example an N terminal portion of fos. The fos coding sequence can be upstream (3') of the rtTA nucleic acid. For example, in some embodiments, an activator nucleic acid is fused to the fos coding sequence of SEQ ID NO: 3. The activator nucleic acid can be downstream of the fos coding sequence. Thus, a promoter drives not only expression of the activator but also the encoded FOS polypeptide sequence. Without being limited by any theory, it is contemplated that this construct provides signals when expressed in cells that are closer to endogenous expression of protein. Accordingly, constructs as described in some embodiments herein provide the ability to mark cells more specifically than other approaches. Indeed, nearly all cells that respond to stimuli and having the expression system are marked. In contrast, the cells lacking the expression system, but being exposed to stimuli exhibit no signal, as described herein.

In neuropsychiatry and/or neurology, there are many uses for targeting therapies for brain disorders to specific circuits or cell types. This targeting can minimize or avoid side-effects that can cause non-compliance with some drugs. Some drugs, such as PROZAC™ drug, can act broadly throughout the brain at many undesired sites as well as the desired site of action. Deep brain stimulation (DBS) is an example of a therapy (e.g., for Parkinson Disease, OCD, Depression) targeted to specific brain sites, but it is not cell type-specific and also can produce side effects.

Specific cell types in the brain can be targeted by their "genetic address," i.e., by identifying promoters that are specific to that cell type. However it can be challenging to find the address/promoter for each cell type of potential therapeutic interest. An alternative approach, in accordance with some embodiments herein, is to target cells according to their activity profile. That is, if the cells (e.g., neurons) are specifically activated during a particular behavior, or in response to a particular drug, they could potentially be tagged to express a therapeutically relevant gene (e.g., an optogenetic effector such as channelrhodopsin-2, ChR2), by virtue of an activity-dependent promoter. Activity-dependent promoters are found in immediate early genes (IEGs) (Greenberg and Ziff, 1984), which are rapidly induced in response to calcium influx (which accompanies neuronal activation), or elevated levels of second messengers such as cAMP (Morgan et al., 1987; Guzowski et al., 2001).

Without being limited by any theory, signaling mechanisms by which skeletal muscle electrical activity can leads to changes in gene expression remain largely undefined. Myotube depolarization induces calcium signals in the cytosol and nucleus via inositol 1,4,5-trisphosphate (IP(3)) and phosphorylation of both ERK1/2 and cAMP-response element-binding protein (CREB). (Carrasco et al., (2003), Am J Physiol Cell Physiol, 284, C1438-1447). P-CREB and P-ERK induction are calcium dependent and increases mRNA of the early genes c-fos, c-jun, and egr-1. Increased phosphorylation and early gene activation are maintained in the absence of extracellular calcium, whereas an increase in intracellular calcium induced by caffeine mimics the depolarization stimulus. Depolarization performed either in the presence of the IP(3) inhibitors 2-aminoethoxydiphenyl borate or xestospongin C or on cells loaded with BAPTA-AM, in which slow calcium signals were abolished, results in decreased activation of the early genes. Both early gene activation and CREB phosphorylation are inhibited by ERK phosphorylation blockade. Taken together, this suggests a role for calcium in the transcription-related events that follow membrane depolarization in muscle cells. As such, in some embodiments, activity-dependent expression by AAV vector systems in accordance with some embodiments herein is performed in muscle cells.

As used herein, the term "optogenetics" is the combination of genetic and optical methods to control specific events in targeted cells of living tissue, particularly within living organisms such as mammals and other animals, with the temporal and spatial precision needed to keep pace with functioning intact biological systems. Millisecond-scale temporal precision and micrometer-scale spatial resolution are central to optogenetics. This allows experimenters to keep pace with fast biological information processing, for example, by probing the causal role of specific action potential patterns in defined neurons. Optogenetics comprises the introduction of fast light-responsive channel or pump proteins to the plasma membranes of target neuronal cells that allow temporally precise manipulation of neuronal membrane potential while maintaining cell-type resolution through the use of specific targeting mechanisms. Any microbial opsin that can be used to promote neural cell membrane hyperpolarization or depolarization in response to light may be used.

A promoter of an IEG, c-fos, has been used to drive expression of optogenetic effectors, or other effectors that control neuronal activity, in transgenic mice. In one version of this method, a strain of transgenic mice was engineered in which the c-fos promoter drives expression of tTA (Urlinger et al., (2000), 97, 7963-7968). tTA drives transcription by recognizing a specific DNA sequence element, TRE (Freundlieb et al., J Gene Med, (1999), 1, 4-12). By placing the TRE upstream of any gene of interest, that gene can be regulated by tTA. tTA itself binds a small molecule antibiotic called doxycycline (DOX), which crosses the blood-brain barrier (BBB); binding of DOX inhibits the activity of tTA, thereby preventing it from binding to the TRE. Reijmers et al. showed that by crossing fos-tTA transgenic mice to mice expressing a TRE-driven reporter or effector, activity-dependent expression of the reporter or effector could be achieved within a time-window defined by the removal of DOX. This system has been exploited by Mayford and others (e.g., S. Tonegawa, MIT) to express virally encoded TRE-driven effectors such as ChR2 or hM3DREADD (Garner et al., Science, (2012), 335, 1513-1516; Liu et al., Nature, (2012), 484, 381-385; Ramirez et al., Science, (2013), 341, 387-391). A variant of tTA, reverse-tTA (rtTA) is activated in the presence of DOX. Accordingly, in some embodiments, for example if the IEG promoter is operably linked to an N-terminal portion of FOS fused to an rtTA element, expression of the regulatable promoter (e.g. TRE) is induced by contacting a cell containing the AAV vector system with a transcriptional modulator compound, such as DOX.

Described in some embodiments herein is a method for artificially re-activating a cell that has recently been activated by a natural stimulus, such as a sensory cue, behavioral experience, or a drug. This is a powerful method, because it allows one to identify, mark, and manipulate neurons for therapeutic purposes purely based on their pattern of prior activity. Several laboratories have generated germline-modified variants of fos-tTA mice for permanent marking of active cells, e.g., the TRAP system developed by Luo and colleagues at Stanford (Guenthner et al., Neuron, (2013), 78, 773-784) and Root et al., Nature, (2014), 515, 269-273).

However, conventional methods based on transgenic animal strains are restricted to particular lines of transgenic animals (such as mice) in which the fos-tTA transgene is integrated into chromosomal DNA and transmitted through the germline (Reijmers et al., (2007), Science, 317, 1230-1233, incorporated herein by reference in its entirety; Guenthner et al., Neuron, (2013), 78, 773-784; Root et al., Nature, (2014), 515, 269-273). Activity-dependent expression systems that require integration of expression system constructs into host DNA are generally inapplicable to organisms where germline modifications of the genome have traditionally been difficult, such as rats or monkeys, and/or otherwise undesirable or prohibited. However, even with the advent of widespread genome editing techniques, such as with CRISPR/Cas9 technology, the requirement to use the technology in a transgenic line is cumbersome and inconvenient, because it makes it difficult to apply the technique in different genetic backgrounds or in mutant animals, without extensive and expensive interbreeding. Furthermore, the application of germline modification in humans is controversial, and may be prohibited by law. Therefore if activity-dependent gene expressions are applied to humans (e.g., for therapeutic purposes), there are numerous advantages to forms that do not require or cause heritable modifications of the genome.

Conventional approaches for activity-dependent gene expression, in addition to restriction to germline modification, can also be limited by: 1) the level of induction of the effector/reporter gene is often low, precluding functional manipulations which would require high-level expression; 2) background levels of expression, due to "leakage" in the system, are often high; and 3) versions such as TRAP that are based on Cre-mediated recombination (Guenthner et al., Neuron, (2013), 78, 773-784; Root et al., Nature, (2014), 515, 269-2732014) cannot be combined with mouse lines expressing Cre in specific classes of cell types (e.g. neurons or classes of neurons), a widespread technology for targeting specific cell types (Zeng and Madisen, Prog Brain Res, (2012), 196, 193-213).

Accordingly, provided in some embodiments herein is a portable, all-viral system for activity-dependent marking of neurons that frees the user from the need to employ a specific line of transgenic mice to obtain IEG promoter-driven transcriptional activator expression (e.g. fos-driven expression of tTA). In some embodiments is provided a compact version of fos-tTA, called FmTB (Fos mutant fused to an activator, such as tTA, or rtTA with the bovine growth hormone poly adenylation site). It is noted that "FmTB" as used herein can further refer to a fos-promoter upstream of a FmTB converter that comprises mutant fos fused upstream of an activator such as tTA or rtTA. FmTB can comprise the FOS coding sequence through amino acid residue 315. Additionally, FmTB can comprise a mutation in the leucine zipper motif of exon IV. Without being limited by any theory, it is contemplated that mutating the leucine zipper motif of exon IV can minimize or abolish interactions with Jun and the ability to transactivate target genes. In some embodiments, leucine residues L3, L4 and L5 of the leucine zipper of fos exon IV are mutated. In some embodiments, leucine residues L3, L4 and L5 of the leucine zipper of fos exon IV are non-conservatively mutated. In embodiments, leucine residues L3, L4 and L5 of the leucine zipper of fos exon IV are mutated into V3-A4-V5. In some embodiments, FmTB or an FmTB converter is packaged and expressed using an AAV vector. The AAV vector system is a safe and efficient option for gene transfer in humans. Provided in some embodiments herein are methods for tetracycline-regulated activity-dependent cell marking (TRACM). Provided in some embodiments herein is a virally based TRACM system for use in a number of different brain regions, behaviors, and drug treatments to mark and functionally manipulate active cells (e.g., using optogenetics).

As described in accordance with some embodiments herein, the Fos-FmTB system employs a number of advantageous features. In some embodiments, the Fos-FmTB system comprises a fusion of tTA to the N-terminus of the FOS protein in a construct that contains all genomic elements sufficient to recapitulate Fos induction in vivo (Smeyne et al., Neuron, (1992), 8, 13-23; Barth et al., J Neurosci, (2004), 24, 6466-6475, each of which is hereby incorporated by reference in its entirety). Thus, all elements necessary for both transcriptional (upstream promoter and full length Fos introns) and post-transcriptional (within the FOS protein itself) regulation of expression are present in the same construct. This Fos-FmTB construct has been shown to be robustly induced in many brain regions in response to both natural and pharmacological stimuli, and shows an onset and offset of expression similar to endogenous FOS protein (see FIGS. 10A-10L, 11A-11C, 12A-12N, 13A-13N, 14A-14N, 15A-15M, 16A-16F, and 17A-17D). The Fos-FmTB design therefore yields specific marking of activated neurons and avoids drawbacks of other systems that suffer from poor inducibility and/or high background levels of transgene expression that are likely due to the absence of various regulatory elements.

Another difference between conventional methods and activity-dependent AAV vector expression systems as described in some embodiments herein (e.g., the TRACM system) is the incorporation of a silencer, which allows for strong transcriptional modulator compound-induced suppression of regulatable promoter-driven reporter constructs, and thus can minimize or prevent leakiness by the regulatable promoter. For example, a reverse tetracycline transcriptional silencer (rtTS) (Hayakawa et al., Gene, (2006), 369, 80-89), which allows for strong DOX-induced suppression of TRE promoter-driven reporter constructs, and thus can minimize or prevent leakiness by the TRE promoter is suitable for use in embodiments herein. Although the TRE promoter is strongly activated by tTA, it also shows low levels of tTA-independent expression that can accumulate to significant levels over time. By including the rtTS, such tTA-independent leak can be efficiently suppressed, thus enhancing the specificity of activity-dependent marking by permitting tight control over the time window during which marking can occur.

Due to the compact size of AAV vectors, not just any gene expression system will fit in AAV vectors. AAV is a small construct, and suitable inserted nucleic acids generally total about 3 kb or less. Therefore, it will be understood that the AAV system is not amenable to insertion of nucleic acids of unlimited size, and that the design of an AAV vector system will also carefully take into account the total size of nucleic acids inserted in the AAV vector system. The genetic tools described in some embodiments herein are fully functional when packaged in AAV vectors and are amenable to application in a broad range of species, including humans. Moreover, in contrast to conventional fos promoter-based expression systems, for example germline-transformations, AAV systems in accordance with embodiments herein do not need to be stably incorporated into the host genome.

The TRACM system in accordance with some embodiments herein provides genomic transgene-independent activity-dependent marking and manipulation of neurons in the vertebrate brain. To the best of Applicant's knowledge, this expression system is the first viral construct encoding any c-fos-tTA/rtTS gene fusion. Additionally, as described in more detail herein, the-fos-tTA/rtTS gene has been demonstrated to be functional in the brain. In addition, some embodiments provide for a modified c-fos-tTA transgene that comprises mutations to wild-type tTA, and regulatory elements (FmTB). Some embodiments described herein include a combination of an AAV vector encoding CMV-rtTS together with AAV vectors encoding FmTB and TRE-reporter/effectors to reduce "leakage" expression. Some embodiments provided herein demonstrate an intersectional combination of a fos-tTA-driven and Cre recombinase-dependent system.

As used herein, the term "converter" refers to a molecule that comprises an N-terminal portion of an induced early gene product such as fos, fused to an activator, such as tTA or rtTA. In some embodiments, a converter comprises a FmTB converter, which comprises a fusion of an N-terminal portion of FOS to an activator, downstream of the FOS. The N-terminal portion of the induced early gene product can be upstream of the activator. Optionally, the FmTB converter comprises Exons I-IV of c-fos. Optionally, the FmTB converter comprises the first 315 amino acids of the N terminus of FOS. Optionally, the FmTB converter comprising the first 315 amino acids of the N terminus of FOS comprises Exons I-IV of FOS. Optionally, the FmTB converter can further comprise mutations in the leucine zipper motif of FOS, for example mutation of some or all of leucine residues L3, L4, and L5. For example, the FmTB converter can comprise mutations in leucine residues L3, L4, and L5, such as mutations of L3→V3, L4→A4, and/or L5→V5. Without being limited by any theory it is contemplated that such mutations in the leucine can minimize or abolish interactions with Jun and/or transactivation. In some embodiments, the FmTB converter comprises a converter encoded by the nucleic acid of SEQ ID NO: 3. Optionally, the FmTB converter can be under the control of an IEG promoter, for example the fos promoter or CRE promoter. Suitable CRE promoters can comprise multimerized CRE elements (for example CRE×3 or CRE×6) placed upstream of a minimal promoter. Thus, a converter nucleic acid sequence can comprise exons and/or introns of an IEG N-terminus, and an activator.

As used herein, the term "fusion" or "fused" refers to a first nucleic acid linked to a second nucleic acid by a phosphodiester bond, so that a coding sequence at the 3' end of the first nucleic acid is in frame with a coding sequence at the 5' end of the second nucleic acid, and by extension can further refer to a first polypeptide linked by a peptide bond to a second polypeptide at the C-terminus of the first polypeptide. As such, a "fused" (or "fusion of a") nucleic acid or peptide as used herein refers to a configuration of molecules, and does not necessarily involve performing the act of joining two molecules together. By way of example, the fusion of the first nucleic acid to the second nucleic acid can encode a single polypeptide in which a first polypeptide sequence (encoded by the first nucleic acid) is fused to a second polypeptide sequence (encoded by the second nucleic acid). In some embodiments, the molecule comprising the fused nucleic acids is referred to as a fusion nucleic acid. In some embodiments, the fusion nucleic acid includes a nucleic acid encoding fos fused directly or indirectly (through a linker) to a nucleic acid encoding an activator. In some embodiments, the fusion nucleic acid comprises a fusion of a 5' fos-encoding sequence to a 3' activator nucleic acid, for example as in an FmTB converter. In some embodiments, the activator is tTA or rtTA. In some embodiments, the Fos coding sequence encodes wild-type fos protein (SEQ ID NO: 32): mmfsgfnadyeasssrcssaspagdslsyyhspadsfssmgspvnaqdfctdlayssanfiptvtaistspdlqwlvqpalvssvaps qtraphpfgvpapsagaysragyvktmtggraqsigrrgkveqlspeeeekrrirrernkmaaakernrrreltdtlqaetdqledek salqteianllkekeklefilaahrpackipddlgfpeemsvasldltgglpevatpeseeaftlpllndpepkpsvepvksissmelkte pfddflfpassrpsgsetarsvpdmdlsgsfyaadweplhsgslgmgpmateleplctpvvtctpsctaytssfvftypeadsfpsca aahrkgsssnepssdslssptllal. In some embodiments, the converter at least 20 amino acids are absent from the c terminus of wild-type fos, for example, at least 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, or 200 amino acids, or an amount that is within a range defined by any two of the aforementioned values.

As used herein, the term "vector" refers to a polynucleotide construct, typically a plasmid or a virus, used to transmit genetic material to a host cell. Vectors can be, for example, viruses, plasmids, cosmids, or phage. A vector as used herein can be composed of either DNA or RNA. In some embodiments, a vector is composed of DNA. An "expression vector" is a vector that is capable of directing the expression of a protein encoded by one or more genes carried by the vector when it is present in the appropriate environment. Vectors are preferably capable of autonomous replication. Typically, an expression vector comprises a transcription promoter, a gene, and a transcription terminator. Gene expression is usually placed under the control of a promoter, and a gene is said to be "operably linked to" the promoter.

As used herein "AAV system" or "AAV expression system" refers to nucleic acids for expressing at least one transcript-encoding nucleic acid, and which are disposed on one or more AAV vectors. As used herein, "activity-dependent expression" (and variations of this root term) refers to nucleic acid expression that will be induced upon a change in a particular type of activity of a cell containing the nucleic acid, for example depolarization of the cell. In some embodiments, the cell is a neuron, and depolarization of the neuron in response to a stimulus induces "activity-dependent" nucleic acid expression.

As used herein, the term "operably linked" is used to describe the connection between regulatory elements and a gene or its coding region. Typically, gene expression is placed under the control of one or more regulatory elements, for example, without limitation, constitutive or inducible promoters, tissue-specific regulatory elements, and enhancers. A gene or coding region is said to be "operably linked to" or "operatively linked to" or "operably associated with" the regulatory elements, meaning that the gene or coding region is controlled or influenced by the regulatory element. For instance, a promoter is operably linked to a coding sequence if the promoter effects transcription or expression of the coding sequence.

As used herein "upstream" refers to positions 5' of a location on a polynucleotide, and positions toward the N-terminus of a location on a polypeptide. As used herein "downstream" refers to positions 3' of a location on nucleotide, and positions toward the C-terminus of a location on a polypeptide.

The term "construct," as used herein, refers to a recombinant nucleic acid that has been generated for the purpose of the expression of a specific nucleotide sequence(s), or that is to be used in the construction of other recombinant nucleotide sequences.

As used herein, the terms "nucleic acid" and "polynucleotide" are interchangeable and refer to any nucleic acid, whether composed of phosphodiester linkages or modified linkages such as phosphotriester, phosphoramidate, siloxane, carbonate, carboxymethylester, acetamidate, carbamate, thioether, bridged phosphoramidate, bridged methylene phosphonate, bridged phosphoramidate, bridged phosphoramidate, bridged methylene phosphonate, phosphorothioate, methylphosphonate, phosphorodithioate, bridged phosphorothioate or sultone linkages, and combinations of such linkages. The terms "nucleic acid" and "polynucleotide" also specifically include nucleic acids composed of bases other than the five biologically occurring bases (adenine, guanine, thymine, cytosine and uracil).

As used herein, the term "promoter" is a nucleotide sequence that permits binding of RNA polymerase and directs the transcription of a gene. Typically, a promoter is located in the 5' non-coding region of a gene, proximal to the transcriptional start site of the gene. Sequence elements within promoters that function in the initiation of transcription are often characterized by consensus nucleotide sequences. Examples of promoters include, but are not limited to, promoters from bacteria, yeast, plants, viruses, and mammals (including humans). A promoter can be inducible, repressible, and/or constitutive. Inducible promoters initiate increased levels of transcription from DNA under their control in response to some change in culture conditions, such as a change in temperature.

As used herein, the terms "immediate early gene" (IEG) is a gene whose expression is increased immediately following a stimulus to a cell comprising the IEG. For example, genes expressed by neurons that exhibit a rapid increase in expression immediately following neuronal stimulation are neuronal IEGs. Such neuronal IEGs have been found to encode a wide variety of polypeptides including transcription factors, cytoskeletal polypeptides, growth factors, and metabolic enzymes as well as polypeptides involved in signal transduction. The identification of neuronal IEGs and the polypeptides they encode provides important information about the function of neurons in, for example, learning, memory, synaptic transmission, tolerance, and neuronal plasticity. It is noted that an IEG that is responsive to a stimulus to a cell can also be responsive to a stimulus or simulated stimulus in a suitable cell free-environment.

As used herein, the term "enhancer" refers to a type of regulatory element that can modulate the efficiency of transcription, regardless of the distance or orientation of the enhancer relative to the start site of transcription.

As used herein, the term "antibody" is used in the broadest sense and specifically covers human, non-human (e.g., murine) and humanized monoclonal antibodies (including full-length monoclonal antibodies), polyclonal antibodies, multi-specific antibodies (e.g., bispecific antibodies), and antibody fragments so long as they exhibit the desired biological activity. Various antibodies can be expressed using the system and method disclosed herein. "Antibodies" and "immunoglobulins" are usually heterotetrameric glycoproteins, composed of two identical light (L) chains and two identical heavy (H) chains. Each light chain is linked to a heavy chain by a disulfide bond. The number of disulfide linkages varies among the heavy chains of different immunoglobulin isotypes. Each heavy chain comprises a variable domain ($V_H$) followed by a number of constant domains. Each light chain comprises a variable domain at one end ($V_L$) and a constant domain at its other end. The constant domain of the light chain is aligned with the first constant domain of the heavy chain, and the light-chain variable domain is aligned with the variable domain of the heavy chain. While antibodies exhibit binding specificity to a specific antigen, immunoglobulins include both antibodies and other antibody-like molecules that lack antigen specificity. Polypeptides of the latter kind are, for example, produced at low levels by the lymph system and at increased levels by myelomas.

As used herein, the term "variant" refers to a polynucleotide (or polypeptide) having a sequence substantially similar to a reference polynucleotide (or polypeptide). In the case of a polynucleotide, a variant can have deletions, substitutions, additions of one or more nucleotides at the 5' end, 3' end, and/or one or more internal sites in comparison to the reference polynucleotide. Similarities and/or differences in sequences between a variant and the reference polynucleotide can be detected using conventional techniques known in the art, for example polymerase chain reaction (PCR) and hybridization techniques. Variant polynucleotides also include synthetically derived polynucleotides, such as those generated, for example, by using site-directed mutagenesis. Generally, a variant of a polynucleotide, including, but not limited to, a DNA, can have at least about 50%, about 55%, about 60%, about 65%, about 70%, about 75%, about 80%, about 85%, about 90%, about 91%, about 92%, about 93%, about 94%, about 95%, about 96%, about 97%, about 98%, about 99% or more sequence identity to the reference polynucleotide as determined by sequence alignment programs known by skilled artisans. In the case of a polypeptide, a variant can have deletions, substitutions, additions of one or more amino acids in comparison to the reference polypeptide. Similarities and/or differences in sequences between a variant and the reference polypeptide can be detected using conventional techniques known in the art, for example Western blot. Generally, a variant of a polypeptide, can have at least about 60%, about 65%, about 70%, about 75%, about 80%, about 85%, about 90%, about 91%, about 92%, about 93%, about 94%, about 95%, about 96%, about 97%, about 98%, about 99% or more sequence identity to the reference polypeptide as determined by sequence alignment programs known by skilled artisans.

As used herein, the term "transfection" refers to the introduction of a nucleic acid into a host cell, such as by contacting the cell with a recombinant AAV vector as described herein.

As used herein, the term "label" refers to a detectable molecule. A number of suitable labels comprise polypeptides. As such, as used herein, a "label nucleic acid" refers to a nucleic acid encoding a label. In some embodiments, the AAV vector systems comprise a label polynucleotide. Thus, in some embodiments, for example embodiments in which a regulatable promoter is operatively linked to the label polynucleotide, the AAV vectors described herein comprise a reporter. Example labels that are suitable in accordance with embodiments herein include, but are not limited to, green fluorescent protein (GFP), including, for example, *Aequoria victoria* GFP, *Rentlla muelleri* GFP, *Rentlla reniformis* GFP, *Renilla ptilosarcus*, blue fluorescent protein (BFP), yellow fluorescent protein (YFP), red fluorescent protein (RFP), cyan fluorescent protein (CFP), orange fluorescent proteins (OFP). Additional reporter genes include, but are not limited to neomycin, phosphoro-transferase, chloramphenicol acetyl transferase, thymidine kinase, luciferase, β-glucuronidase, aminoglycoside, phosphotransferase, hygromycin B, xanthine-guanine phosphoribosyl, luciferases (e.g., renilla, firefly, etc.), DHFR/methotrexate, β-galactosidase, alkaline phosphatase, turbo and tagRFP, and nuclear targeted versions of any of the aforementioned reporter genes. In some embodiments, the polypeptide of interest comprises the label itself, for example when production of label in active cells is desired.

In some embodiments, the label comprises a tag on another gene product. For example, the label can be fused to a polypeptide of interest, either at the N-terminal, C-terminal, or internally. For example, the label can be covalently bound to the polypeptide of interest. In some embodiments, for example when a polypeptide of interest comprises or consists of a label, a polypeptide-encoding nucleic acid comprises a label nucleic acid. In some embodiments, the label nucleic acid is controlled by the same promoter (e.g. a regulatable promoter) as a nucleic acid encoding a polypeptide of interest, so that the label nucleic acid can be transcribed in the same transcript as the transcript-encoding nucleic acid, but the label is not fused to another polypeptide encoded by the polypeptide-encoding nucleic acid. For example, the nucleic acid encoding a label can be separated from a nucleic acid encoding a different polypeptide encoding nucleic acid by an IRES or the like, or the label can be separated in-frame from the encoded polypeptide by an in-frame 2A site or the like, so that the label and encoded polypeptide are expressed as separate molecules. Optionally, the label can be fused or otherwise covalently bound (directly or indirectly) to the encoded polypeptide.

In some embodiments, the polypeptide of interest, encoded by the AAV vector and under the control of the regulatable promoter is a label, a receptor, a growth factor, a hormone, a neurotransmitter, a receptor, or other polypeptide of interest that is capable of expression in the AAV vector system described herein. Examples include, but are not limited to growth hormones (GHs) and variants thereof; insulin-like growth factors (IGFs) and variants thereof; granulocyte colony-stimulating factors (G-CSFs) and variants thereof; erythropoietin (EPO) and variants thereof; insulin, such as proinsulin, preproinsulin, insulin, insulin analogs, and the like.

AAV Vectors and AAV Vector Systems

Various vectors can be used to express gene products of interest in mammals or mammalian cells as described herein, for example, for gene therapy. In some embodiments, the vector comprises an AAV vector. A variety of AAV vectors can be used in inducible expression systems in accordance with embodiments herein. In some embodiments, the AAV vector system is a single-vector system, so that all of the components of the system are contained on a single AAV vector. In some embodiments, the AAV vector system is a multi-vector system. Thus, in some embodiments, the vector system can include 2, 3, 4, 5, or more vectors.

AAV vectors are a class of relatively compact vectors that can be used to stably introduce a transgene into a host cell without integrating into the host genome. As such, AAV vectors can introduce a transgene without disruption host genomic sequences, and expression of a transgene from an AAV vector can persist for a long time, for example months or years. AAV vectors are described in detail in U.S. Pub. No. 2012/0232133, the entirety of which is incorporated by reference herein. Because AAV vectors are compact, the gene insert should be about 3 kb or less in order for the AAV vector system to function. Accordingly, skilled design of the AAV vector system is required, including careful selection of the appropriate gene insert and corresponding regulatory elements. AAV is a replication-deficient parvovirus, the single-stranded DNA genome of which is about 4.7 kb in length including 145 nucleotide inverted terminal repeat (ITRs). The ITRs can play a role in integration of the AAV DNA into the host cell genome. However, in the absence of the rep gene, integration by AAV vectors is typically negligible. It is contemplated that integration of AAV's into a host genome can create a risk of inducing rearrangements of the host genome. For example if a first AAV integrates at a first genomic location, and a second AAV integrates at a second genomic location, induced recombination between the two AAVs could occur, and thus rearrange portions of the host genome. Accordingly, preferably the AAV vectors in accordance with embodiments herein are configured not to integrate with the host genome. In some embodiments, the AAV vectors lack a functional rep gene. In some embodiments, the rep gene is deleted from the AAV vectors. In some embodiments, the ITRs of the AAVs are configured to minimize or eliminate integration. In some embodiments, AAV vector sequences such as ITRs flank an IEG and its activator nucleic acid, so that an AAV vector sequence is 5' of the IEG, and another AAV vector sequence (e.g. a nucleic acid comprising an ITR) is 3' of the activator nucleic acid. Thus, in some embodiments is a 5' AAV ITR and a 3' AAV ITR. Without being limited by any theory, it is contemplated that the ITRs can facilitate efficient expression of the activator nucleic acid.

Accounting for the ITRs (about 0.3 kb), AAV vectors can typically contain up to about 4.4 kb of nucleic acid sequence of interest. As such, AAV vectors are much more compact than adenovirus vectors, which can typically contain up to about 7.5 kb of nucleic acid sequence of interest. When an AAV vector infects a host cell, the viral genome integrates into the host's chromosome resulting in latent infection of the cell. In a natural system, a helper virus (for example, adenovirus or herpesvirus) provides genes that allow for production of AAV vector in the infected cell. In the case of adenovirus, genes E1A, E1B, E2A, E4 and VA provide helper functions. Upon infection with a helper virus, the AAV provirus is rescued and amplified, and both AAV and adenovirus are produced. Due to the size of some IEG promoters, such as the c-fos promoter leaves limited space within an AAV for additional genetic elements of interest. In some embodiments, the AAV comprises ITRs. The ITRs can flank a nucleic acid inserted Described in accordance with some embodiments herein are engineered compact c-fos promoters, which are fused with an activator to form a converter, for example an FmTB converter, and nucleic acids encoding the same ("converter nucleic acids"). In some embodiments, the FmTB converter is about 623 base pairs in length.

Generation of the AAV vectors in accordance with various embodiments herein can be accomplished using any suitable genetic engineering technique well known in the art, including, without limitation, the standard techniques of restriction endonuclease digestion, ligation, transformation, plasmid purification, and DNA sequencing, for example as described in Sambrook et al. (Molecular Cloning: A Laboratory Manual. Cold Spring Harbor Laboratory Press, N.Y. (1989)).

The AAV vector can incorporate sequences from the genome of any known organism. The sequences can be incorporated in their native form or can be modified in any way to obtain a desired activity. For example, the sequences can comprise insertions, deletions, or substitutions.

The AAV vector described herein can include a prokaryotic replicon (that is, a DNA sequence having the ability to direct autonomous replication and maintenance of the recombinant DNA molecule extrachromosomally in a prokaryotic host cell), such as a bacterial host cell, transformed therewith. Such replicons are well known in the art. In addition, vectors that include a prokaryotic replicon may also include a gene whose expression confers a detectable marker such as a drug resistance. Typical bacterial drug resistance genes are those that confer resistance to ampicillin or tetracycline.

Some embodiments herein include an AAV vector system that comprises an IEG promoter operatively linked to a fos coding sequence fused to an activator nucleic acid, and further comprises a silencer nucleic acid. The nucleic acid comprising a fos coding sequence, can comprise upstream sequences that are not transcribed, and fos exons and introns fused to the activator nucleic acid, which are transcribed. For example, the activator, can comprise tTA. Thus, the IEG promoter is driving not only tTA expression, but also expression of a fos protein, which is fused to the tTA. The activator nucleic acid can thus be under the control of an IEG promoter. The silencer nucleic acid can be under the control of another promoter, for example a constitutive promoter such as a CMV promoter. The regulatable promoter (which can be regulated by the activator and/or silencer) can be operably linked to a transcript-encoding nucleic acid (for example, a label nucleic acid, or a polypeptide-encoding nucleic acid and a label nucleic acid, or a nucleic acid encoding a ribozyme, an antisense RNA, or a small interfering RNA), and/or can be operably linked to an insertion site, so that a polypeptide-encoding nucleic acid can be placed under the control of the regulatable promoter. The activator can comprise a gene product that induces transcription by the regulatable promoter, and the silencer can comprise a gene product that reduces or prevents transcription by the regulatable promoter. In some embodiments, an activator and a silencer can regulate the transcriptional activity of the regulatable promoter. In some embodiments, the activator, silencer, and regulatable promoter comprise a tTA, rtTS, and TRE promoter, respectively, so that in the presence of doxycycline, the activator activates the regulatable promoter. In some embodiments, the AAV vector system comprises the regulatable promoter, the activator nucleic acid and the silencer nucleic acid. In some embodiments, the AAV vector system comprises the regulatable promoter operably linked to the activator nucleic acid. In some embodiments, the AAV vector system comprises a promoter and the silencer nucleic acid.

Some embodiments herein include an activity-dependent AAV vector expression system that comprises a converter which comprises an immediate early gene (IEG) promoter fused to a tetracycline regulated transcriptional activator (tTA). In some embodiments, the AAV vector system further comprises a reverse tetracycline transcriptional silencer (rtTS), and also comprises a tetracycline regulatable element (TRE) promoter operably linked to a transcript-encoding nucleic acid (for example a polypeptide-encoding nucleic acid) or insertion site. In some embodiments, the IEG comprises a promoter, such as a fos promoter or a cyclic AMP response element promoter. In some embodiments, the IEG and converter nucleic acid (e.g. encoding an N-terminal portion of fos fused to a downstream tTA) are on a first AAV, and the silencer (e.g. rtTS) and regulatable promoter (e.g., TRE promoter) operably linked to the transcript-encoding nucleic acid or insertion site are on a second AAV. In some embodiments, the IEG promoter, converter nucleic acid (encoding the activator fused to an N-terminal portion of fos), and silencer (e.g. rtTS) are on a first AAV, and the regulatable promoter (e.g. TRE promoter) operably linked to the transcript-encoding nucleic acid (e.g. a polypeptide-encoding nucleic acid such as a label) or insertion site is on a second AAV. In some embodiments, the activator comprises tTA, the silencer comprises rtTS, and the regulatable promoter comprises a TRE promoter.

In some embodiments, the AAV vector system is injectable. In some embodiments, the AAV vector system is usable across multiple species (for example, at least two of mice, rabbits, non-human primates, non-human mammals, and/or humans).

Optionally, the AAV vector further comprises a polyadenylation site. The polyadenylation site can be positioned downstream (3') of the WPRE and upstream (5') of the second ITR. In some embodiments, the polyadenylation site comprises a SV40 polyadenylation site as described herein. In some embodiments, the polyadenylation site comprises a synthetic polyadenylation site as described herein.

In some embodiments, an AAV vector comprises an AAV sequence comprising a first ITR. The vector can comprise an IEG promoter downstream (3') of the first ITR, a converter nucleic acid encoding an N-terminal portion of FOS downstream (3') of the promoter, and an activator nucleic acid downstream (3') of and fused to the N-terminal portion of FOS. The vector can comprise an insertion site downstream (3') of the activator such that the activator is operably linked to any transcript-encoding nucleic acid (for example, a polynucleotide encoding a gene product of interest, for example a polypeptide of interest, or a label as described herein) that is inserted in the insertion site. The vector can comprise a polyadenylation site downstream (3') of the insertion site. The vector can comprise a second ITR downstream of the polyadenylation site.

In some embodiments, an AAV vector comprises an other promoter (other than the regulatable promoter and IEG promoter) and a silencer nucleic acid downstream (3') of, and operably linked to this other promoter. In some embodiments, the other promoter comprises a constitutive promoter. A number of suitable "other promoters" are known to the skilled artisan. Examples of suitable "other promoters" can be found, for example, in the Biobricks catalog. A catalog of Biobricks components is accessible on the world wide web at parts.igem.org. In some embodiments, the other promoter comprises a CMV promoter. In some embodiments, a label is positioned upstream (3') upstream of a ChR2 cassette cloned in the 3' to 5' orientation, and flanked by inverted FRT sites.

In some embodiments, an AAV vector comprises an IEG promoter operatively linked to a converter nucleic acid downstream (3') of the promoter, and further comprises a WPRE downstream (3') of the converter nucleic acid. In some embodiments, the vector also includes a polyadenylation site downstream (3') of the WPRE. In some embodiments, the vector includes a flag-encoding sequence downstream (3') of the promoter and upstream (5') of the WPRE.

In some embodiments, an AAV vector comprises, from 5' to 3', an IEG promoter (e.g., a fos promoter or CRE promoter), a converter nucleic acid comprising a nucleic acid sequence encoding an N-terminal portion of FOS (which can comprise exons and introns), a linker, an activator, and an insertion site configured to contain a transcript-encoding nucleic acid (e.g. a polypeptide-encoding nucleic acid), and/or the transcript-encoding nucleic acid itself. In some embodiments, the N-terminal portion of FOS is 5' of and fused to the linker, which is 5' of and fused to the activator through the linker. In some embodiments, the transcript-encoding nucleic acid encodes an gene product, for example an RNA or a polypeptide. Example gene products that can be encoded by a transcript-encoding interest nucleic acid include a label, a reporter, a receptor, a growth factor, a hormone, or other polypeptide of interest that is capable of being expressed within the AAV vector system, a ribozyme, an antisense RNA, or a small interfering RNA. In some embodiments, an AAV vector comprises, from 5' to 3', a promoter (other than the regulatable promoter and IEG promoter), a silencer nucleic acid, a transcript-encoding nucleic acid (e.g. a polypeptide-encoding nucleic acid), and a WPRE element. In some embodiments, the polypeptide-encoding nucleic acid is a YFP-ChR2 element in the 3' to 5' orientation. In some embodiments, the silencer nucleic acid is on the same AAV vector as the IEG promoter, converter nucleic acid, and insertion site.

In some embodiments, a second AAV vector comprises, from 5' to 3', a regulatable promoter, a flag element, and a WPRE element.

In some embodiments, the AAV vectors described herein include insertion sites positioned for insertion of a particular polynucleotide or element of interest encoding a desired gene product in a desired location. The insertion site can be operably linked to a regulatable promoter, so that the desired gene product can be transcribed when the regulatable promoter is active as described herein. Furthermore, the various elements described herein can be combined in various combinations or ordering within the scope of various embodiments.

Also described in accordance with some embodiments here are AAV vector systems in which a desired polynucleotide-encoding nucleic acid can readily be placed under the control of the TRE promoter as described herein. In some embodiments, the AAV vector comprises an insertion site rather than a polynucleotide-encoding nucleic acid, so that optionally, a transcript-encoding nucleic acid of interest can later be inserted into the insertion site, and be under the control of the TRE promoter. In some embodiments, the insertion site is configured for the insertion of a polynucleotide of interest, for example encoding a gene product of interest. In some embodiments, the insertion site is configured for the insertion of two or more polynucleotides of interest, each encoding gene products of interest, and separated by a cleavage polynucleotide. In some embodiments, the insertion site is configured for insertion of a single polynucleotide comprising the two or more polynucleotides encoding gene products of interest (optionally with a cleavage polynucleotide or IRES positioned there between). In some embodiments, the insertion site configured for insertion of a first polynucleotide encoding a first gene product of interest and a second polynucleotide encoding a second gene product of interest. Such an insertion site can optionally comprise a cleavage polynucleotide or IRES positioned there between. The cleavage site can be configured to encode a cleavage site in-frame with the sequences encoding the gene products of interest. As such, the AAV vector can be configured to simultaneously express two or more gene products of interest. In some embodiments, the gene products of interest comprise the light chain and the heavy chain of an immunoglobulin, for example an antibody. In some embodiments, the gene products of interest comprise multimeric subunits of a gene product to be expressed in gene therapy, for example a multimeric extracellular receptor.

In some embodiments provided herein is a transcript-encoding nucleic acid can be present in an AAV vector as described herein. By way of example, the transcript-encoding nucleic acid can encode a nucleic acid or polypeptide gene productExample gene products that can be encoded by a transcript-encoding interest nucleic acid include a label, a reporter, a receptor, a growth factor, a hormone, or other polypeptide of interest that is capable of being expressed within the AAV vector system, a ribozyme, an antisense RNA, or a small interfering RNA. In some embodiments, the AAV vector further comprises a promoter operably linked to a converter that is fused to a downstream tetracycline regulated transcriptional activator (tTA). The AAV vector can include a tetracycline regulatable element (TRE) promoter operably linked to the transcript-encoding nucleic acid or to an insertion site, or to an insertion site containing the transcript-encoding nucleic acid. In some embodiments, the IEG promoter comprises a fos promoter or a cyclic AMP response element (CRE) promoter operatively linker to a converter nucleic acid that encodes an N-terminal portion (which can comprise introns and exons) of FOS fused to an activator. Optionally, the polypeptide-encoding nucleic acid can encode a label as described herein. Optionally, the AAV vector can comprise an insertion site instead of the polypeptide-encoding nucleic acid, or the polypeptide-encoding nucleic acid can be in the insertion site.

The AAV vectors as provided herein may include various configurations. Without being limited in scope, but by way of example, several various configurations are described in detail herein. One of skill in the art will recognize that the examples provided herein, and the various components thereof may be modified, combined, or rearranged in numerous configurations within the scope.

FIG. 1 schematically illustrates an AAV vector in accordance with some embodiments herein. FIG. 1 shows an AAV vector comprising a FmTB converter that is operatively linked to a cfos proximal promoter that extends 5' to the HindIII site at −600 bp from the transcription start site. The vector includes introns I, II, and III. Intron I includes negative regulatory elements that suppress transcription in the absence of stimulation. The construct includes FOS coding sequence to amino acid 315, a leucine zipper motif in exon IV, with mutation of three leucine residues (L3-L4-L5 to V3-A4-V5) to abolish interaction with Jun and having the ability to transactivate target genes, Myc epitope tag 2× as spacer/tag, tTA2, and the same polyadenylation site from bovine growth hormone gene as used in Fos::eGFP mice.

Figure 3:
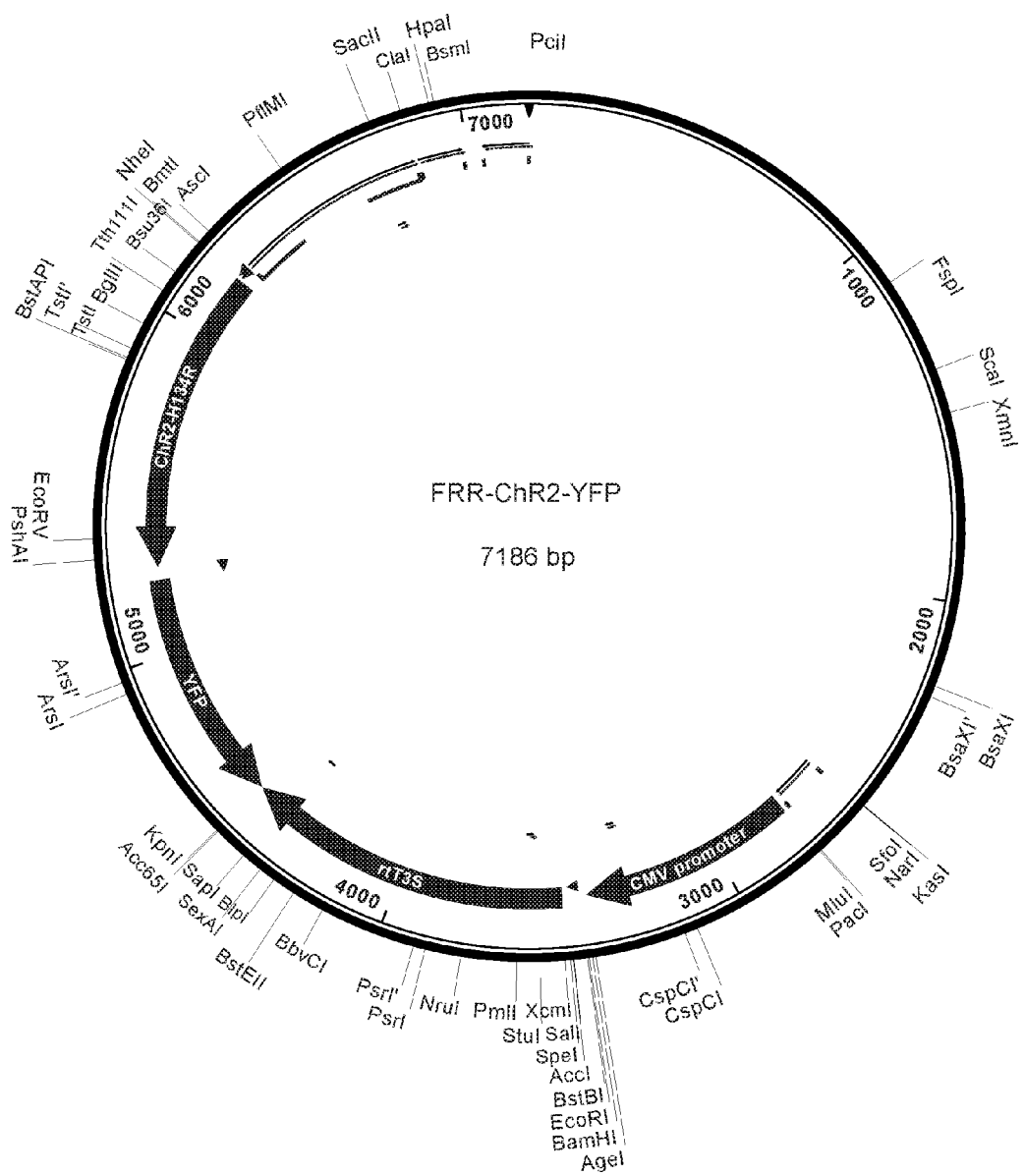
FIG. 3 is a vector map illustrating an AAV vector according to some embodiments herein. Depicted is vector FRR-ChR2-YFP (SEQ ID NO: 15).

FIG. 3 schematically illustrates an AAV vector in accordance with some embodiments herein. FIG. 1 shows a dual function AAV vector that suppresses transcription from TRE (tet-responsive element) promoter-driven vectors in a DOX-dependent manner and yields FLP recombinase-dependent expression of the light gated ion channel Channelrhodopsin-2. The construct includes an ITR-R. rtTS with high DOX sensitivity was synthesized by fusing the KRAB repressor domain of human ZNF10 to the c-terminus of the reverse tetracycline repressor protein rTetR$^S$-M2. This rtTS is upstream of a ChR2 cassette cloned in the 3' to 5' orientation, and this 5'-rtTS-3'_3'-ChR2-5' cassette is flanked by inverted FRT sites. The construct is located in a CMV promoter-driven vector containing a WPRE and a modified polyadenylation sequence from SV40. This configuration also includes a YFP, a V5 epitope tag, a ChR2-H134R, and an FRT.

Figure 5:
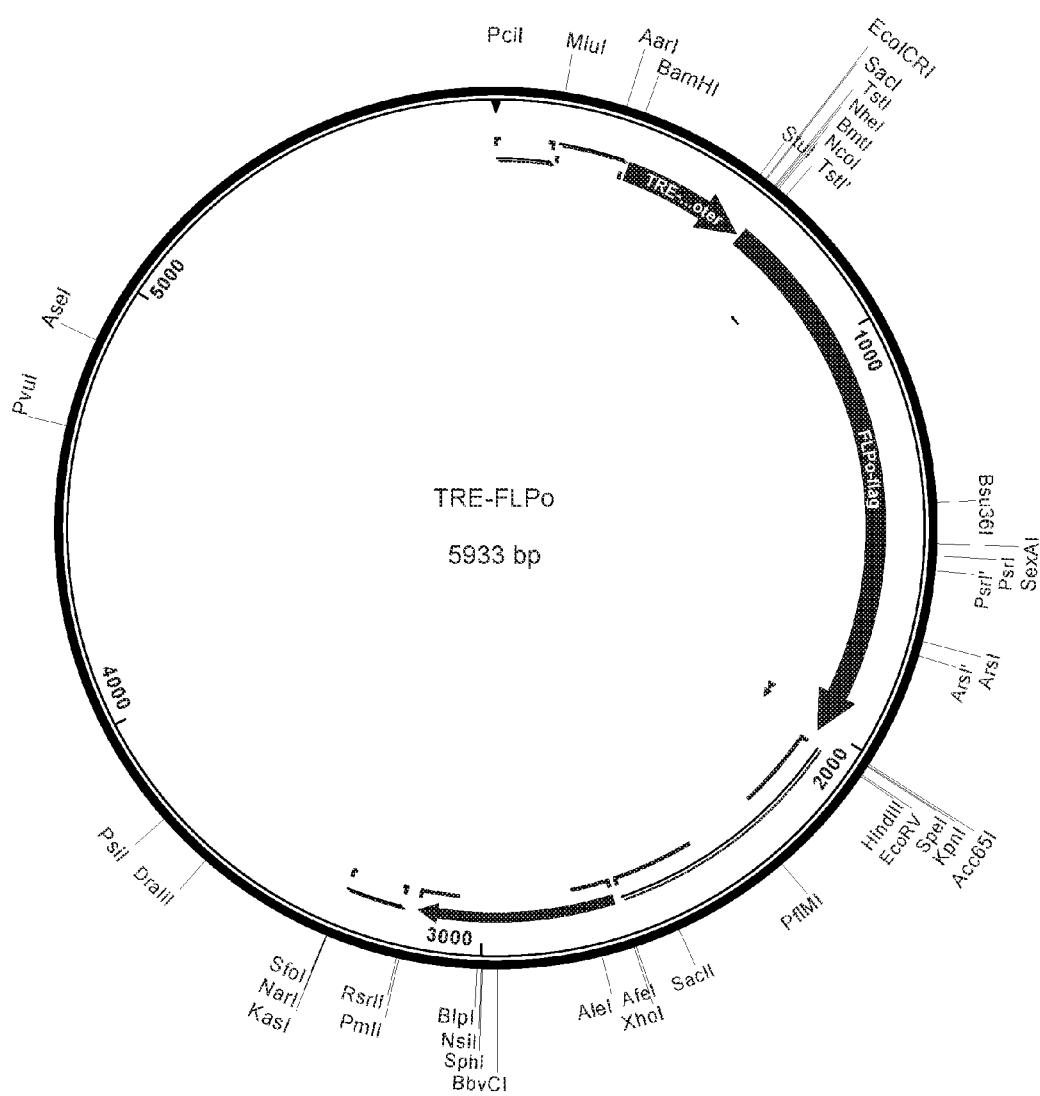
FIG. 5 is a vector map illustrating an AAV vector according to some embodiments herein. Depicted is vector TRE-FLPo (SEQ ID NO: 26).
Figure 7:
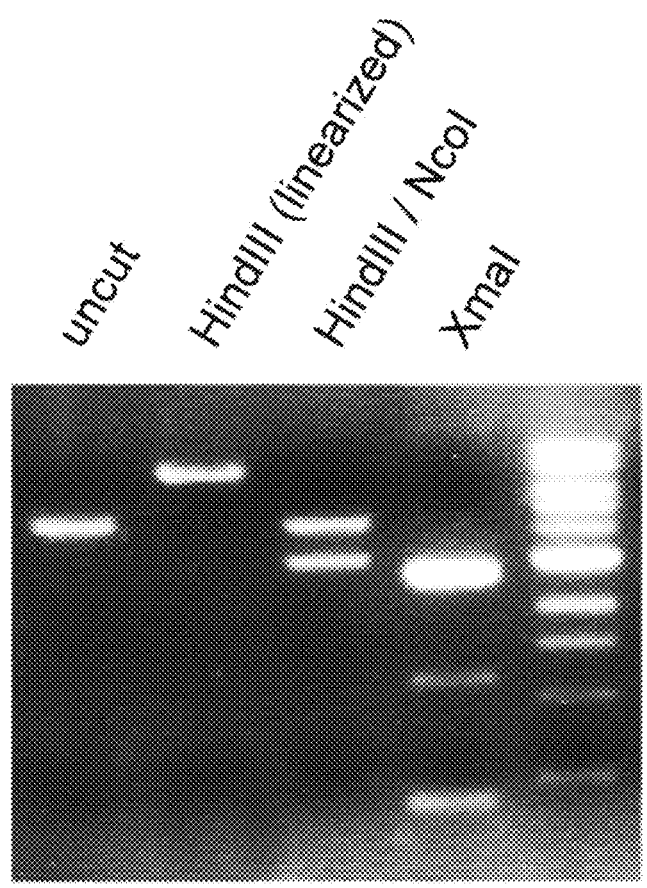
FIG. 7 is an image of a gel, showing a diagnostic digest of the AAV vector including cfos-FmTB (7.22 kb vector), in accordance with some embodiments herein. The digest provides a contrast between uncut DNA and linearized DNA (HindIII digest), and indicates that the plasmid is supercoiled. HindIII/NcoI releases the expected insert size (3 kb from 4.25 kb vector). The XmaI digest confirms that the inverted terminal repeats (ITRs) are intact, and expected fragments are observed at 0.4 (doublet), 1.15, 2.6, and 2.7 kb fragments.
Figure 8:
FIG. 8 is a schematic diagram illustrating an AAV vector, wherein the immediate early gene (IEG) is a Fos proximal promoter, in accordance with some embodiments herein. The Fos proximal promoter extends 5' to the HindIII site at −600 bp from the transcription start site. Intron I includes negative regulatory elements that suppress transcription in the absence of stimulation. Without being limited by any theory, the negative regulatory elements are contemplated to improve signal to noise ratio. The construct includes Fos coding sequence to amino acid 315. The construct also includes mutation of three leucine residues (L3-L4-L5 to V3-A4-V5) that make up the leucine zipper, which can be involved in for dimerization with Jun and transactivation of targets. Without being limited by any theory, it is contemplated that mutating the leucine zipper can abolish interactions with Jun and transactivation. The construct includes a Fos proximal promoter, introns I, II, and III, FOS coding sequence to amino acid 315, a leucine zipper motif in exon IV mutated to abolish interaction with Jun and having the ability to transactivate target genes, Myc epitope tag 2× as spacer/tag, tTA2, and the same polyadenylation site from bovine growth hormone gene as used in Fos::eGFP mice.
Figure 9:
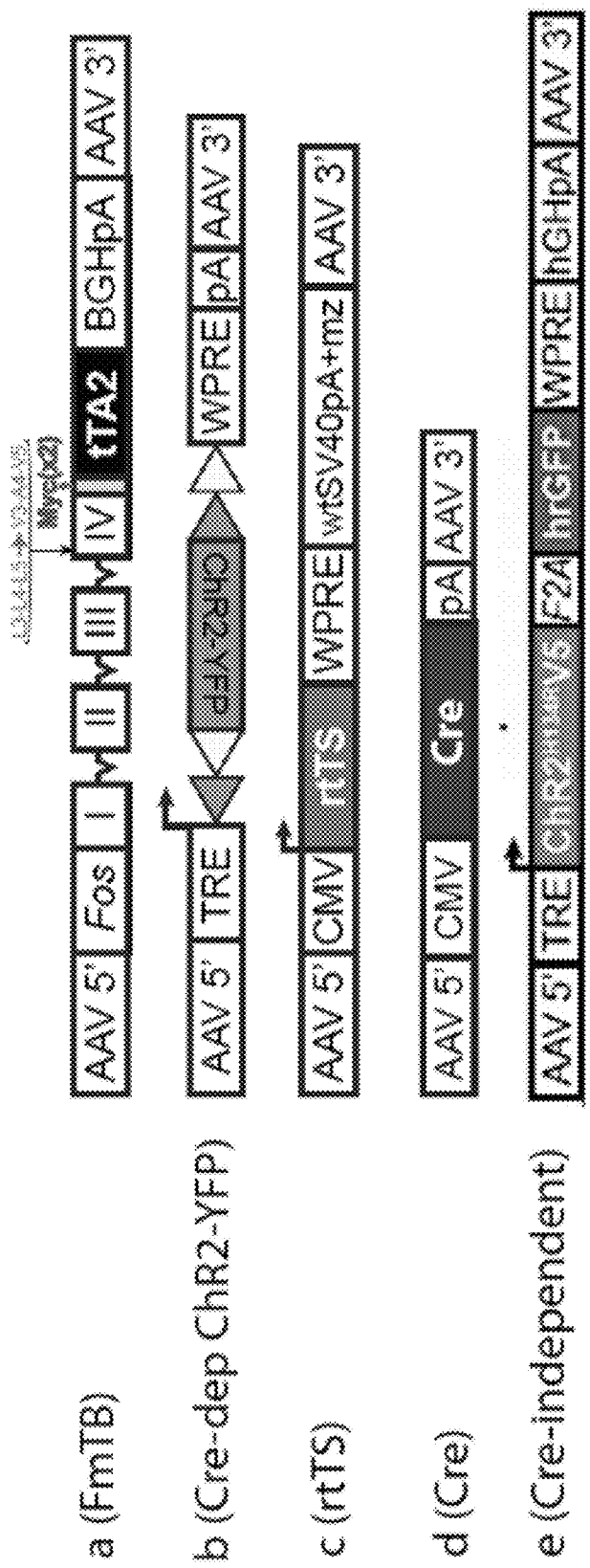
FIG. 9 is a schematic diagram illustrating the components of an AAV vector activity-dependent expression system, in accordance with some embodiments herein. Construct "a" (Fos proximal promoter, introns I, II, and III, FOS coding sequence to amino acid 315, a leucine zipper motif in exon IV mutated to abolish interaction with Jun and having the ability to transactivate target genes, Myc epitope tag 2× as spacer/tag, tTA2, and the same polyadenylation site from bovine growth hormone gene as used in Fos::eGFP mice) is the FmTB virus construct as detailed in FIG. 8. Construct "b" is a Cre-dependent, tetracycline-regulatable element (TRE)-driven effector (ChR2-YFP), including a woodchuck hepatitis virus post-transcriptional regulatory element (WPRE). Construct "c" is a constitutively expressed "leak suppressor" virus encoding a constitutively transcribed reverse-tetracycline regulated transcriptional silencer (rtTS), and including cytomegalovirus promoter-enhancer (CMV) and a polyadenylation addition site from wildtype SV40 virus (wtSV40pA). Construct "d" is a Cre-expressing virus (CMV-driven, constitutive). Construct "e" is FmTB-activated effector-reporter virus including ChR2$^{H134R}$V5-F2A-hrGFP, H134R mutation of channelrhodopsin-2, V5 epitope tag, human renilla GFP (hrGFP), and human growth hormone polyadenylation site (hGHpA).
Figure 11A:
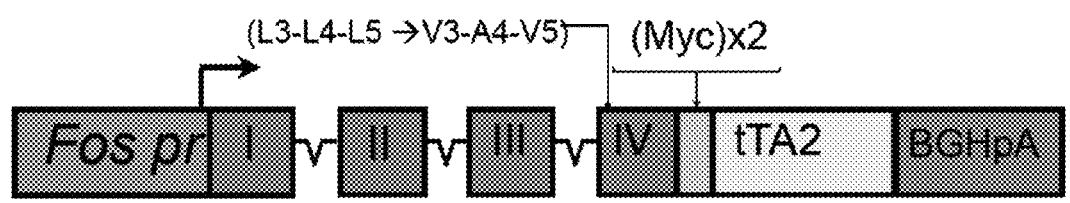
FIG. 11A is a diagram of a Fos construct as described in some embodiments herein.
Figure 11B:
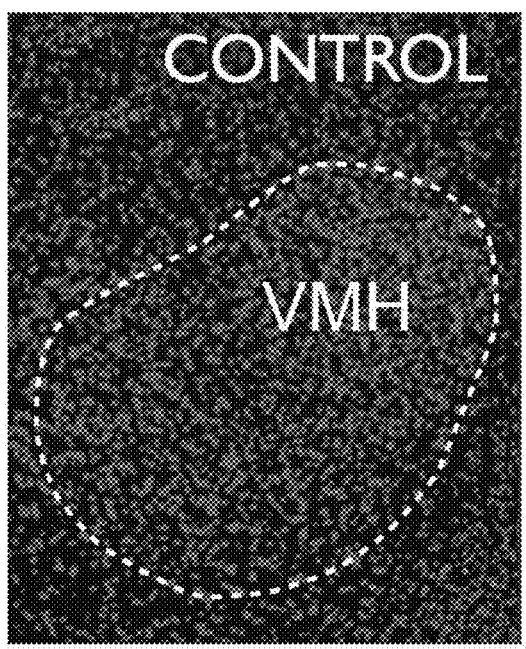
FIGS. 11B-11C are a set of microscope images providing a magnified view of tTA induction in VMHvl following an aggressive interaction with Fos-FmTB transgenic mouse in the hypothalamus.
Figure 11C:
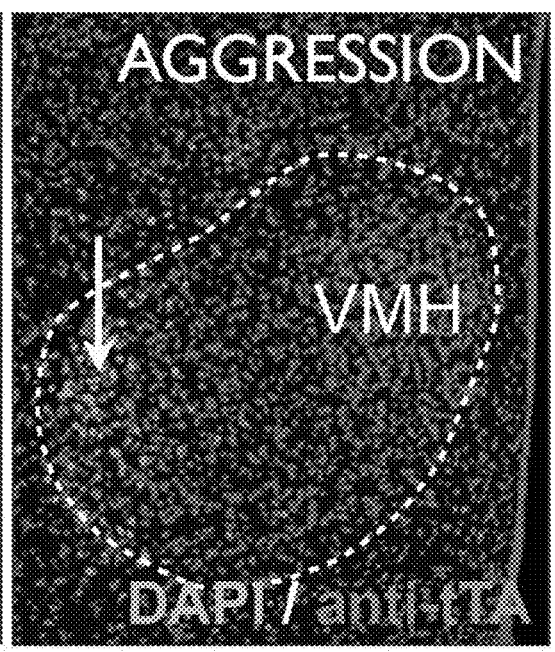
Figure 12A:
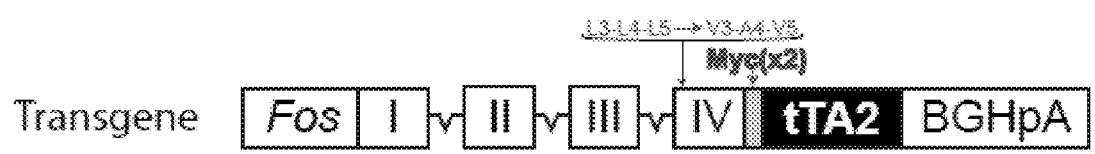
FIG. 12A is a diagram of a Fos construct as described in some embodiments herein.
Figure 12B:
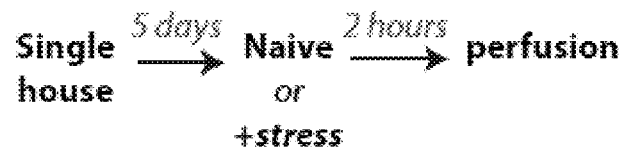
FIG. 12B describes the protocol for methods according to some embodiments described herein.
Figure 13A:
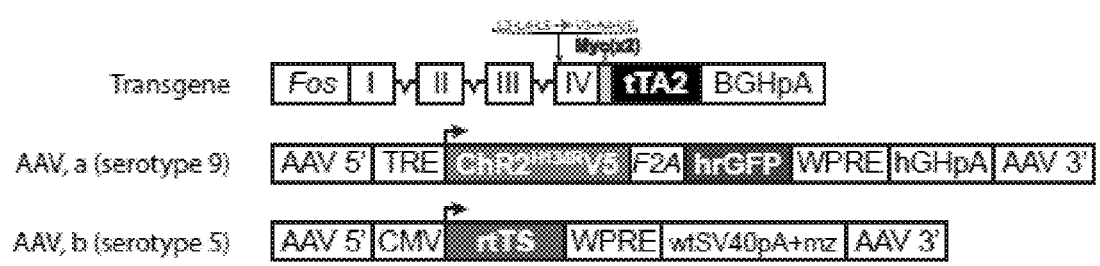
FIGS. 13A-13N demonstrate a 3-component system for tetracycline-regulated activity-dependent cell marking (TRACM) for channel rhodopsin-2 expression in vivo in accordance with some embodiments herein. The construct provided in FIG. 13A includes a transgenic mouse harboring the FmTB transgene and two virally encoded components injected into the hippocampus, including a TRE-driven ChR2 virus (AAV, "a") and a CMB-driven rtTS (AAV, "b"). The rtTS is activated by doxycycline (DOX, an analog of tetracycline) and binds to the TRE to prevent leakage expression when FmTB is not induced. In panels H-M, the neurons are activated in the hippocampus by injecting the animal with kainic acid (kainate), a glutamate receptor agonist. ChR2 expression is visualized using an antibody to the V % epitope tag. This demonstrates a strong induction in kainate-treated animals (FIG. 13M) compared to saline-injected controls (FIG. 13G).
Figure 13B:
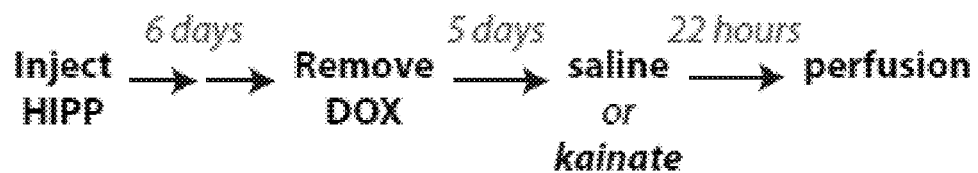
Figure 14A:
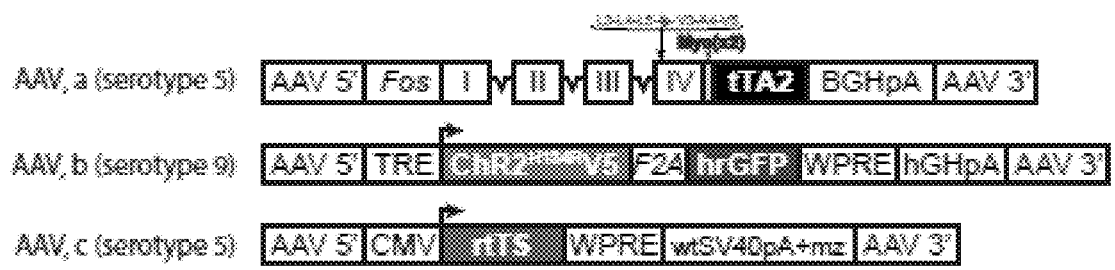
FIGS. 14A-14N demonstrate a 3-component system for TRACM-regulated channel rhodopsin-2 in vivo according to some embodiments herein. The system includes three virally encoded components and does not require a specific transgenic mouse line.
Figure 14B:
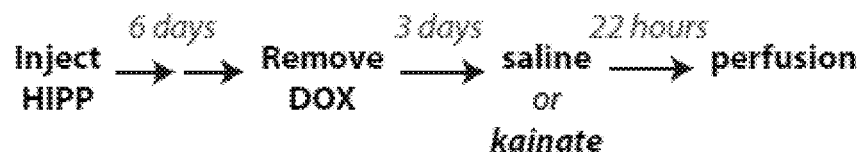
Figure 15A:
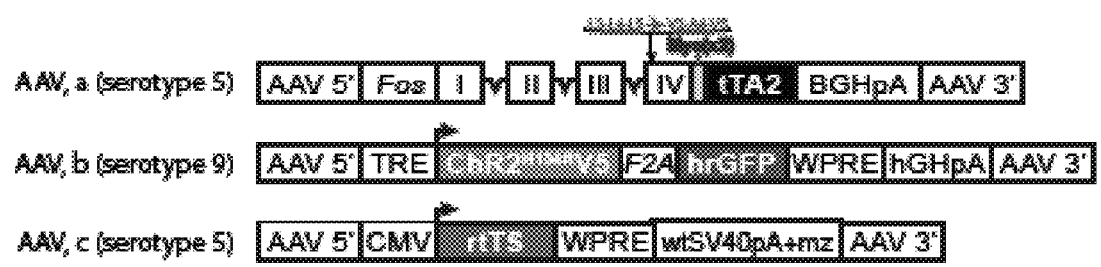
Figure 15B:
Figures 15G, 15H:
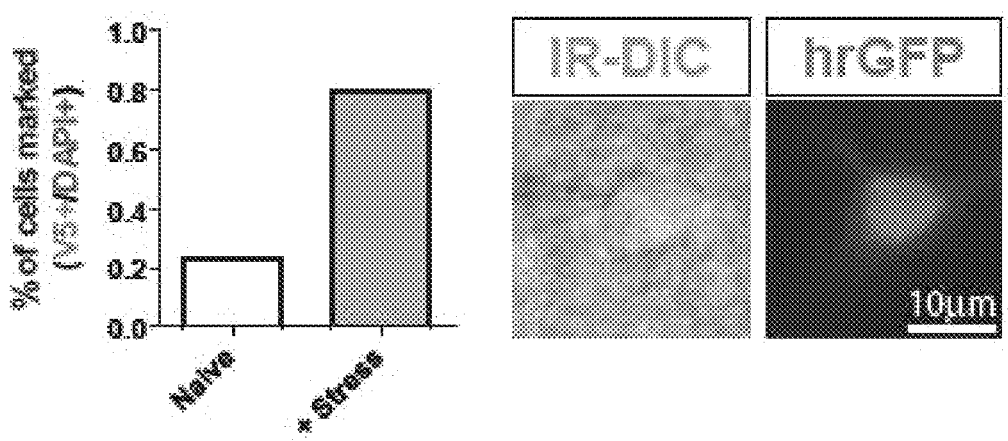
Figure 15I:
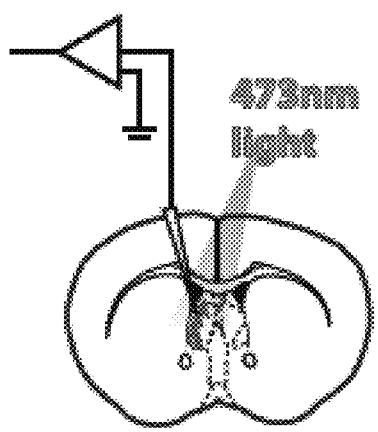
Figure 16A:
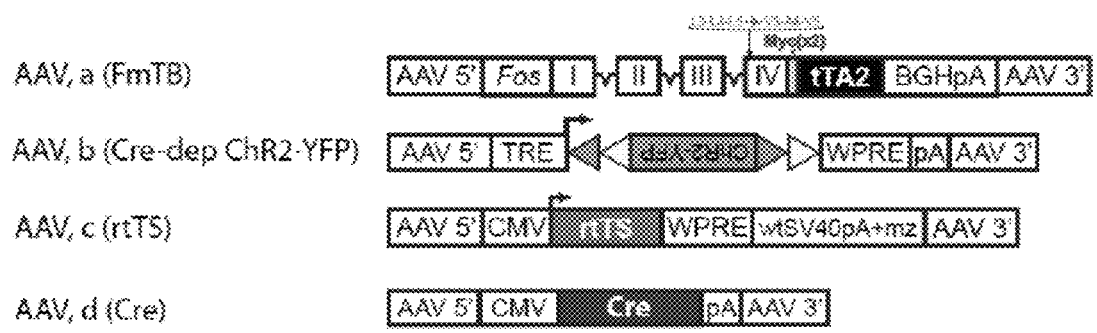
Figure 16B:
Figure 18A:
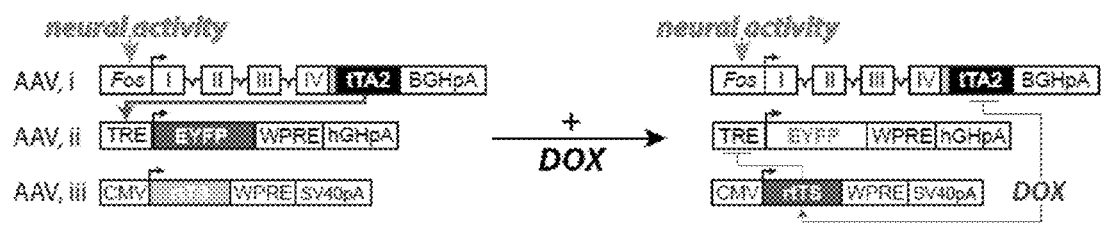
Figure 18B:
Figure 18I:
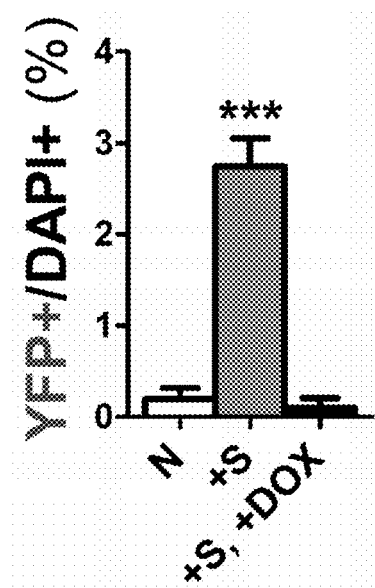
Figure 18J:
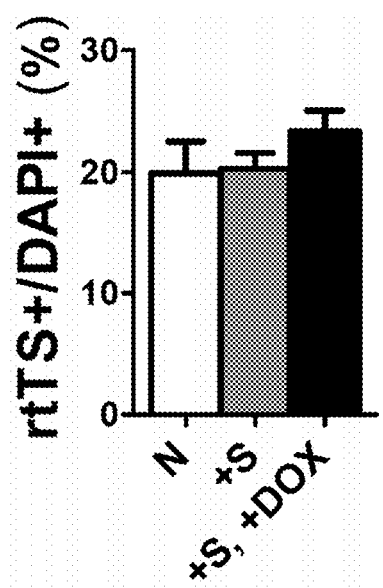

FIG. 5 schematically illustrates an AAV vector in accordance with some embodiments herein. FIG. 5 shows a codon optimized FLPo cassette from the vector pFLPo which included a 2× FLAG epitope tag (SEQ ID NO: 29) at the C-terminus. This cassette is present in an AAV vector containing a 5' polyA (SEQ ID NO: 29), a Tet response element (TRE) from vector pTRE-Tight (Clontech) (SEQ ID NO: 28), a WPRE (SEQ ID NO: 30), and a polyadenylation sequence from human growth hormone (hGHpA; SEQ ID NO: 31).

Optionally, for any of the configurations described herein, the transcript-encoding nucleic acid (e.g. polypeptide-encoding polynucleotide, such as a label-encoding polynucleotide) can be replaced with an insertion site as describe herein, for example, to facilitate the placement of a nucleotide encoding a gene product of choice for selective activity-dependent expression of the gene product of choice by an AAV system as described herein.

Cleavage Sites

As used herein "cleavage site" refers to a sequence that mediates the separation of a first polypeptide that would otherwise be in cis to a second polypeptide. Accordingly, for simplicity, "cleavage," "cleavage site," and the like as used herein refer to the separation of any two polypeptides that are encoded by a single polynucleotide in cis. Thus, "cleavage" and "cleavage site," can, but do not necessarily refer to proteolytic sites and events, and can also refer to other mechanisms for mediating the separation of polypeptides, for example ribosomal skipping. As used herein "cleavage polynucleotide" refers to a polynucleotide encoding a cleavage site. In some embodiments, a cleavage site mediates the separation via an intra-ribosomal, translational termination-and-restart event during the synthesis of the nascent polypeptide chains so that a peptide bond is not formed between an upstream amino acid residue and a downstream amino acid residue. For example, such a cleavage site can include a 2A polypeptide as described herein. In some embodiments, a cleavage site includes a protease target site. For example, such a protease target site can comprise a furin cleavage site (Arg-X-X-Arg, preferably Arg-X-Lys/Arg-Arg). As used herein, "cleavage polynucleotide" refers to a polynucleotide that encodes a cleavage site.

As used herein, 2A sequences or elements refer to small peptides introduced as a linker between two proteins, allowing autonomous intraribosomal self-processing of polyproteins (See e.g., de Felipe. (2004) Genetic Vaccines and Ther. 2:13; deFelipe et al. (2004) Traffic 5:616-626). These short peptides allow co-expression of multiple proteins from a single vector. Many 2A elements are known in the art. Examples of 2A sequences that can be used in the methods and system disclosed herein, without limitation, include 2A sequences from the foot-and-mouth disease virus (F2A), equine rhinitis A virus (E2A), *Thosea asigna* virus (T2A), and porcine teschovirus-1 (P2A) as described in U.S. Patent Publication No. 2007/0116690. In some embodiments, a cleavage site comprises a 2A polypeptide.

Recombinases and Recombinase Target Sites

Recombination systems can mediate recombination between recombinase target sites, and depending on the orientation of the recombinase target sites, can either excise or flip sequences flanked by the recombinase target sites. According to some embodiments herein, recombinase target sites in the same orientation can flank portions of AAV vectors as described herein, and can facilitate the insertion and/or removal of a nucleic acid, for example a transcript-encoding nucleic acid into and/or out of an insertion site as described herein.

A variety of recombinases and corresponding recombinase target sites can be used in accordance with embodiments herein. "Recombinases," as used herein, refer to gene products and synthetic analogs thereof that catalyze recombination between a first and second polynucleotide. It is noted that recombinases typically can catalyze recombination between polynucleotide sequences in cis (i.e. on the same polynucleotide strand) or in trans (i.e. on different polynucleotide strands). "Recombinase target sites" refer to polynucleotide sequences on which recombinases specifically act to induce recombination. A particular recombinase may have specificity for a single nucleic acid sequence, or a plurality of nucleic acid sequences. Such a plurality of sequences can be described by a consensus sequence. In some embodiments, a recombinase polypeptide is provided. In some embodiments, a polynucleotide encoding a recombinase polypeptide (a "recombinase polynucleotide") is provided. Exemplary recombinases and recombinase target sites that can be used in accordance with embodiments herein include, but are not limited to, Cre-lox and FLP-FRT.

The Cre-lox system, derived from bacteriophage P1, is a well-characterized recombinase and recombinase target site system (see, e.g., Lakso et al., 1992, Proc. Natl. Acad. Sci. USA 89: 6232-6236; Orban et al., 1992, Proc. Natl. Acad. Sci. USA 89: 6861-6865, each of which is incorporated by reference herein in its entirety) that can be used in accordance with some embodiments herein. Cre recombinase catalyzes site-specific recombination, which can excise or invert an intervening target sequence or transgene located between lox sequences. Canonically, loxP sequences are targets for Cre recombinase. A loxP sequence comprises a 34 base pair polynucleotide sequence of SEQ ID NO: 33 (ATAACTTCGTATAGCATACATTATACGAAGTTAT). It is appreciated that variants loxP sequences, for example lox2272 and loxN can also be used as a Cre recombinase target in accordance with embodiments herein (see Livet et al., 2007, Nature, 450, 56-62, incorporated by reference in its entirety). Transgenic strategies for combinatorial expression of fluorescent proteins in the nervous system. Lox2272 comprises the polynucleotide sequence of SEQ ID NO: 34 (ATAACTTCGTATAAAGTATCCTATACGAAGTTAT). LoxN comprises the polynucleotide sequence of SEQ ID NO: 35 (ATAACTTCGTATAGTATACCTTATACGAAGTTAT). Without being limited to any particular theory, Cre recombinase can work on any of the loxP or variant lox sites described herein. While Cre recombinase can induce recombination between a pair of identical lox sites (e.g. two loxP sites, or two lox2272 sites), Cre recombinase typically cannot induce recombination between a pair of non-identical lox sites (e.g. cannot induce recombination between a loxP and a lox2272 site, or a loxN and a lox2272 site). As such, according to some embodiments herein, for each lox sequence in the AAV vector, there is at least one additional identical lox sequence in the vector.

The orientation of lox sequences can determine whether the intervening transgene is excised or inverted when Cre recombinase is present (Abremski et al., 1984, J. Biol. Chem. 259:1509-1514). Cre can catalyze the excision of the transgene when the lox sequences are oriented as direct repeats (e.g. in the same orientation on the same strand) and catalyzes inversion of the transgene when lox sequences are oriented as inverted repeats (e.g. in opposite orientations on the strand. As such, in some embodiments, two or more lox sequences are oriented in the same direction on a polynucleotide strand. In some embodiments, 2, 3, 4, 5, 6, 7, 8, 9, 10, 11, 12, 13, 14, 15, 16, 17, 18, 19, or 20 lox sequences are oriented in the same direction on a polynucleotide strand. In some embodiments, all of the lox sequences on a strand are oriented in the same direction.

The FLP recombinase system, derived from of *Saccharomyces cerevisiae* (see, e.g., O'Gorman et al., 1991, Science 251: 1351-1355; PCT publication WO 92/15694, each of which is incorporated by reference herein in its entirety) can be used to generate in vivo site-specific genetic recombination, similar to the Cre-lox system. In some embodiments a FLP recombinase target (FRT) site comprises the sequence of SEQ ID NO: 36 (GAAGTTCCTATTCTCTAGAAAGTATAGGAACTTC). A number of functional variant FRTs are known in the art, for example GAAGTTCCTATTCCGAAGTTCCTATTCTCTAGAAAGTATAGGAACTTC.

Accordingly, in some embodiments, a variant FRT site is used. Without being limited by any particular theory, FLPase recombinase can work on any of the FRT or variant FRT sites described herein. While FLP recombinase can induce recombination between a pair of identical FLP sites, it typically cannot induce recombination between a pair of non-identical FRT sites. Similar to Cre, FLP recombinase can catalyze the excision of a sequence positioned between two FRT sites in the same orientation, and can catalyze the inversion of a sequence positioned between two FRT sites in opposite orientations. Accordingly, in some embodiments, at least two FRT sequences are oriented in the same direction on a polynucleotide strand. In some embodiments, 2, 3, 4, 5, 6, 7, 8, 9, 10, 11, 12, 13, 14, 15, 16, 17, 18, 19, or 20 FRT sequences are oriented in the same direction on a polynucleotide strand. In some embodiments, all of the FRT sequences on a strand are oriented in the same direction.

IEG Promoters

A number of suitable IEG promoters can be used in accordance with various embodiments herein. It is noted that in view of the size and capacity of AAV vectors, in some embodiments, a suitable IEG promoter is about 3 kb or less. In some embodiments, the IEG promoter comprises c-Fos, c-Fos is a nuclear proto-oncogene which has been implicated in a number of important cellular events, including cell proliferation (Holt et al. (1986) Proc. Natl. Acad. Sci. USA 831:4794-4798; Riabowol et al. (1988) Mol. Cell. Biol. 8:1670-1676), differentiation (Distel et al. (1987) Cell 49: 835-844; Lord et al. (1993) Mol Cell. Biol. 13:841-851), and tumorigenesis (Cantor et al. (1993) Proc. Natl. Acad. Sci. USA 90:10932-10936; Miller et al. (1984) Cell 36:51-60; Ruther et al. (1989) Oncogene 4:861-865, each of which is incorporated by reference in its entirety herein). c-Fos encodes a 62 kDa protein which forms heterodimers with c-Jun, forming an AP-1 transcription factor which binds to DNA at an AP-1 element and stimulates transcription. Fos gene products can also repress gene expression. Sassone et al. (1988) Nature 334:314-319 showed c-Fos inhibits its own promoter, and Gius et al. (Gius et al. (1990) Mol. Cell. Biol. 10:4243-4255) and Hay et al. (1989) Genes Dev. 3:293-303 showed c-Fos inhibits early response genes Egr-1 and c-myc. AP-1 factors have also been shown to inhibit expression of the MiFIC class I and PEPCK genes (see Gurney et al. (1992) J. Biol. Chem. 267:18133-18139).

Cyclic AMP response elements (CREs) are enhancer sequences which mediate signal transduction involving cyclic AMP by interacting with transcription factors and/or associated proteins of the transcriptional complex. Suitable CRE promoters can comprise multimerized CRE elements (for example CRE×3 or CRE×6).

In some embodiments herein, transcription of a transcript-encoding nucleic acid is driven by an IEG promoter, for example, a c-Fos promoter or a CRE promoter. In some embodiments, c-Fos drives expression of an activator, including, for example, tTA or rtTA. In some embodiments, the activator is downstream (3') of the promoter.

Expression by a Regulatable Promoter

As used herein a "regulatable promoter" refers to a promoter that can be induced to driving transcription of a nucleic acid operably linked to the regulatable promoter, for example by an active activator and/or in the absence of an active silencer, and can also, under some circumstances, not drive expression of the nucleic acid, for example in the absence of an active activator, and/or in the presence of an active silencer. For example, the TRE promoter, in accordance with some embodiments herein, is a regulatable promoter that can be activated by tTA or rtTA, and repressed by rtTS.

As used herein an "activator" refers to a gene product that induces transcription by a regulatable promoter. In some embodiments, the activator comprises tTA. In some embodiments, the activator can be regulated. For example, an activator can be inhibited or activated by a transcriptional modulator compound. In some embodiments, the transcriptional modulator compound comprises a tetracycline, doxycycline, or a derivative of tetracycline. The type of modulation will be understood based on the particular combination of transcriptional modulator compound and activator. For example, a transcriptional modulator compound that comprises tetracycline, doxycycline, and some derivitives of these compounds can inhibit a tTA activator, but can activate a rTA activator. Moreover an "activator nucleic acid" refers to a nucleic acid that encodes an activator. In some embodiments tTA is encoded by the activator nucleic acid of SEQ ID NO: 11. In some embodiments, the activator comprises reverse tetracycline transcriptional activator (rtTA), which can be encoded, for example, by the activator nucleic acid of SEQ ID NO: 13. Whereas tTA is inhibited by tetracycline or an analogue thereof, rtTA is activated by tetracycline or an analogue thereof.

As used herein, "silencer" refers to a gene product that reduces or prevents transcription by a promoter. The reduction or prevention of transcription by the silencer can be modulated by a transcriptional modulator compound, for example tetracycline, doxycycline, or a derivative of tetracycline. For example, the silencer can require a transcriptional modulator compound in order to reduce or prevent transcription. In some embodiments, the silencer activity of rtTS is activated or induced by a transcriptional modulator compound such as tetracycline or doxycycline. Moreover a "silencer nucleic acid" refers to a nucleic acid that encodes an activator. In some embodiments, the silencer comprises rtTS. In some embodiments the rtTS silencer is encoded by the silencer nucleic acid in SEQ ID NO: 19. It is contemplated that since the activity of a silencer such as a rtTS can depend on the activity of an inhibitor compound, leakage can be minimized by expressing the silencer under a strong or constitutive promoter (e.g. the CMV promoter), and controlling silencing by adding or removing a transcriptional modulator compound as described herein.

The silencers and activators as used herein can regulate the transcriptional activity of a "regulatable promoter." For example tTA and rtTS can respectively activate and repress, dependent upon the presence of tetracycline, doxycycline, or a tetracycline analogue.

As used herein, "transcriptional modulator compound" refers to a compound that can bind to and inhibit the transcriptional activating activity of a transcriptional activator. For example several antibiotic compounds such as doxycycline or tetracycline or tetracycline analogs, can bind to tTA and prevent its binding to TRE, thereby inhibiting activation of TRE. In some embodiments, the transcriptional modulator compound comprises doxycycline, tetracycline, or another tetracycline analog.

Tetracycline regulated transcriptional element, or tetracycline transactivator (tTA) is a fusion protein that combines the tetracycline repressor protein (tetR) DNA binding domain with the transcriptional activation domain of VP-16, such that when tTA binds to a minimal promoter containing tetR sequences, transcription of the target gene is activated. Tetracycline binding to tTA prevents activation by causing a conformational change in the tetR portion of tTA which blocks binding of tTA to tetR (Hinrichs, W., et al., (1994) Science 264:418-420); gene activation is achieved by removing tetracycline (Gossen, M. & Bujard, H., (1992) Proc. Natl. Acad. Sci. USA 89:5547-5551). Derivatives or analogues of tetracycline may also be used, including, for example, doxycycline (DOX), minocycline, metacycline, sancycline, chloro-tetracycline, demeclocycline, and tigecycline.

The addition of rtTS enables enhanced DOX-induced suppression of TRE promoter-drive reporter constructs, thereby preventing leaks and enhancing the specificity of activity-dependent marking.

Regulatory Elements

Vectors according to some embodiments herein, for example AAV vectors, can include various regulatory elements, such as a transcription initiation region and/or a transcriptional termination region. Examples of transcription termination region include, but are not limited to, polyadenylation signal sequences. Examples of polyadenylation signal sequences include, but are not limited to, Bovine growth hormone (BGH) poly(A), SV40 late poly(A), rabbit beta-globin (RBG) poly(A), thymidine kinase (TK) poly(A) sequences, and any variants thereof. In some embodiments, the transcriptional termination region is located downstream of the posttranscriptional regulatory element. In some embodiments, the transcriptional termination region is a polyadenylation signal sequence. In some embodiments, the transcriptional termination region comprises a 5' upstream poly(A) sequence, for example the polynucleotide sequence of SEQ ID NO: 2 (AATAAAATATCTTTATTTTCATTACATCTGTGTGT-TGGTTTTTTGTGTGAATCGAT AGTACTAACAT-ACGCTCTCCATCAAAACAAAAC-GAAACAAAACAAACTAGCAAAA TAGGCTGTCCCCAGTGCAAGTGCAGGTGCCA-GAACATTTCTCT) or a polynucleotides with at least about 80% identity thereto, for example 80%, 81%, 82%, 83%, 84%, 85%, 86%, 87%, 88%, 89%, 90%, 91%, 92%, 93%, 94%, 95%, 96%, 97%, 98%, and 99% identity. In some embodiments, the transcriptional termination region comprises a synthetic poly(A) sequence. In some embodiments, the transcriptional termination region comprises a poly(A) sequence, for example the polynucleotide sequence of SEQ ID NO: 27 (AACGCAATAAAATATCTTTATTTTCATTA-CATCTGTGTGTTGGTTTTTTGTGTGAA TCGATAG-TACTAACATACGCTCTCCATCAAAACAAAAC-GAAACAAAACAAACTAG CAAAATAGGCTGTCCCCAGTGCAAGTGCAGGTGC-CAGAACATTTCTCTATTT), or a polynucleotides with at least about 80% identity thereto, for example 80%, 81%, 82%, 83%, 84%, 85%, 86%, 87%, 88%, 89%, 90%, 91%, 92%, 93%, 94%, 95%, 96%, 97%, 98%, and 99% identity.

Various posttranscriptional regulatory elements can be used in the viral vectors, for example to increase expression level of the protein of interest in a host cell. In some embodiments, the posttranscriptional regulatory element can be a viral posttranscriptional regulatory element. Non-limiting examples of viral posttranscriptional regulatory element include woodchuck hepatitis virus posttranscriptional regulatory element (WPRE), hepatitis B virus posttranscriptional regulatory element (HBVPRE), RNA transport element (RTE), and any variants thereof.

A variety of WPRE's can be used in accordance with embodiments herein. In some embodiments, the WPRE is "full-length." comprising the nucleic acid sequence of SEQ ID NO: 23 (CCGATAATCAACCTCTGGATTA-CAAAATTTGTGAAAGATTGACTGGTATTCTTAA CTATGTTGCTCCTTTTACGCTATGTGGATACGCT-GCTTTAATGCCTTTGTATCATG CTATTGCTTCCCG-TATGGCTTTCATTTTCTCCTCCTTGTATAAATCCTG-GTTGCTGT CTCTTTATGAGGAGTTGTGGCCCGTTGTCAG-GCAACGTGGCGTGGTGTGCACTGT GTTTGCT-GACGCAACCCCCACTGGTTGGGGCATTGCCAC-CACCTGTCAGCTCCTTT CCGGGACTTTCGCTTTCCCCCTCCCTATTGCCACG-GCGGAACTCATCGCCGCCTGC CTTGCCCGCT-GCTGGACAGGGGCTCGGCTGTTGGGCACT-GACAATTCCGTGGTGT TGTCGGGGAAATCATCGTCCTTTCCTTGGCT-GCTCGCCTGTGTTGCCACCTGGATT CTGCGCGGGACGTCCTTCTGCTACGTCCCTTCGGC-CCTCAATCCAGCGGACCTTCC TTCCCGCGGCCT- GCTGCCGGCTCTGCGGCCTCTTCCGCGTCTTCGCCTTCGCCCTCAGACGAGTCGGATCTCCCTTTGGGCCGCCTCCCCGC). It is contemplated herein that to increase cloning capacity of adeno-associated viral vectors, in some embodiments, a shorter WPRE is used. A variety of shorter WPREs can function comparably to the full-length WPRE to mediate gene expression. In some embodiments, a "short WPRE" is used. In some embodiments, a variant of SEQ ID NO: 23 is used. Accordingly, in some embodiments, the adeno-associated vector comprises a WPRE with at least about 69% identity to the full-length WPRE, for example, at least about 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical, including ranges between any two of the listed values. In some embodiments, the WPRE is at least about 69% identical to the "short" WPRE, for example, at least about 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical, including ranges between any two of the listed values.

The RTE can comprise a rev response element (RRE), for example, a lentiviral RRE. A non-limiting example is bovine immunodeficiency virus rev response element (RRE). In some embodiments, the RTE is a constitutive transport element (CTE). Examples of CTE include, but are not limited to Mason-Pfizer Monkey Virus CTE and Avian Leukemia Virus CTE.

In some embodiments, the AAV vector includes a gene for a selectable marker that is effective in a eukaryotic cell, such as a drug resistance selection marker. This selectable marker gene can encode a factor necessary for the survival or growth of transformed host cells grown in a selective culture medium. Host cells not transformed with the vector containing the selection gene will not survive in the culture medium. Typical selection genes encode proteins that confer resistance to antibiotics or other toxins, e.g., ampicillin, neomycin, methotrexate, kanamycin, gentamycin, Zeocin, or tetracycline, complement auxotrophic deficiencies, or supply critical nutrients withheld from the media.

The AAV vectors disclosed herein can also include one or more adenine (A) nucleotides immediately after an insertion site downstream of the promoter, where the insertion site allows the insertion of a polynucleotide encoding the protein(s) of interest. For example, one or more A nucleotides are located immediately after the TAA stop codon of the protein of interest after the insertion of the polynucleotide encoding the protein of interest into the vector. In some embodiments, at least one A nucleotide, two A nucleotides, three A nucleotides, or more are located immediately after the restriction site, including ranges between any two of the listed values. In some embodiments, at least one A nucleotide, two A nucleotides, three A nucleotides, or more are located immediately after the TAA stop codon of the protein of interest, including ranges between any two of the listed values.

It is contemplated that AAV vector systems in accordance with various embodiments herein can comprise a "cross-platform" system that is suitable for activity-dependent expression in different types of organisms. For example, AAV vector systems in accordance with various embodiments herein can be administered to a variety of types of host cells, in vivo or in vitro. In some embodiments, the AAV vector systems can be administered to two or more different types of mammals, for example two or more different types of non-human mammals, two or more different types of primates, or to two or more different types of mammals that can be human or non-human. In some embodiments, the AAV vectors can include additional sequences that make the vectors suitable for replication and integration in eukaryotes. In some embodiments, the AAV vectors disclosed herein can include a shuttle element that makes the vectors suitable for replication and integration in both prokaryotes and eukaryotes. In some embodiments, the AAV vectors can include additional transcription and translation initiation sequences, such as promoters and enhancers; and additional transcription and translation terminators, such as polyadenylation signals.

In some embodiments, the AAV vectors can include a regulatory sequence that allows, for example, the translation of multiple proteins from a single mRNA. Non-limiting examples of such regulatory sequences include internal ribosome entry site (IRES) and "cleavage polynucleotides" encoding cleavage sites such as 2A self-processing sequence. In some embodiments, the 2A sequence is a 2A peptide site from foot-and-mouth disease virus (F2A sequence). In some embodiments, the F2A sequence has a standard furin cleavage site.

The AAV vectors can also, in some embodiments, have one or more restriction site(s) located near the promoter sequence to provide for the insertion of nucleic acid sequences encoding one or more proteins of interest and other protein(s).

Insertion Sites

In some embodiments, the AAV vector includes one or more insertion sites. An insertion site can be positioned for the insertion of a polynucleotide in a desired location on the AAV vector. In some embodiments, the insertion site is for inserting a polynucleotide encoding a desired gene product in a desired location. In some embodiments, the insertion site includes at least one cleavage polynucleotide (for example a 2A polynucleotide) positioned between a site for inserting a first polynucleotide encoding a gene product and a site for inserting a second polynucleotide encoding a gene product.

In some embodiments, an insertion site can be positioned in an AAV vector to facilitate insertion of a polynucleotide encoding a gene product of interest that is operatively linked to the promoter of the AAV vector. The insertion site can be positioned 3' to the promoter, for example about 10 bp, 20, 30, 40, 50, 100, 150, 200, 250, 300, 400, 500, 600, 700, 800, 900, 1000, 1100, 1200, 1500, or 2000 bp 3' to the promoter.

In some embodiments, the insertion site is configured for the insertion of a first polynucleotide encoding a first gene product of interest and a second polynucleotide encoding a second gene product of interest. The insertion site can comprise a cleavage polynucleotide positioned 3' of a site in which the first polynucleotide can be inserted, and can be configured to be in-frame with the coding sequence of the first polynucleotide. The cleavage polynucleotide can be positioned 5' of a site in which the second polynucleotide can be inserted, and can be configured to be in-frame with the coding sequence of the second polynucleotide. In some embodiments, the cleavage polynucleotide encodes a 2A sequence or 2A variant as described herein.

In some embodiments, the insertion site comprises one or more restriction endonuclease sites. In some embodiments, the insertion site comprises a multiple cloning site (MCS). In some embodiments, the insertion site comprises enzymatic targets, for example recombinase sites or the like. In some embodiments, the insertion site comprises a GATEWAY destination site.

Kits

In some embodiments kits are provided. The kit can comprise an AAV vector activity-dependent expression system as described herein, including a AAV vector for expressing a gene product of interest as described herein and a transcriptional modulator compound as described herein, for example a tTA inhibitor (which can also function as a rtTS inducer) such as tetracycline, doxycycline, or another tetracycline analog. In some embodiments, the kit comprises at least one type of cell for expressing the activity-dependent expression system as described herein. In some embodiments, the cell comprises a mammalian cell suitable for production of gene products, for example a Chinese hamster ovary (CHO) cell, baby hamster kidney (BHK) cell, HeLa cell, monkey kidney cell (COS), human hepatocellular carcinoma cell (e.g. Hep G2), or the like. In some embodiments, the cell comprises a cell suitable for functional application in the brain.

In some embodiments, the kit comprises packaging, instructions, and the like.

Methods of Activity-Dependent Expression

In some embodiments, methods of activity-dependent expression of a nucleic acid of an animal cell are provided. In some embodiments, the method is useful for activity-dependent expression in any cell that expresses an IEG, for example Fos and/or CRE. Optionally, the method is an in vivo method. Optionally, the method is an in vitro method. The method can comprise contacting an adeno-associated virus (AAV) vector system in the animal cell with a transcriptional modulator compound. The AAV vector system can comprise an immediate early gene (IEG) promoter operably linked to an activator nucleic acid, and a regulatable promoter operably linked to a polypeptide-encoding nucleic acid. The regulatable promoter can be configured to be activated by the activator. Optionally, the AAV vector system further includes a silencer encoding nucleic acid operably linked to a first promoter. The silencer can be configured to inhibit transcription by the regulatable promoter.

In some embodiments, if expressed, the activator can be configured to be inhibited by the transcriptional modulator compound, for example a tTA activator. In some embodiments, the method can comprise ceasing contacting the AAV vector system in the animal cell with the transcriptional modulator compound so that an activator is no longer inhibited. When the activator is no longer inhibited, the polypeptide-encoding nucleic acid can be expressed from the regulatable promoter. Optionally the polypeptide-encoding nucleic acid encodes a label. Optionally, the activator comprises tetracycline regulated transcriptional activator (tTA), the silencer comprises reverse tetracycline transcriptional silencer (rtTS), and the regulatable promoter comprises a tetracycline regulatable element (TRE) promoter. In some embodiments, the IEG promoter comprises a fos promoter as described herein. Optionally, the activator comprises tetracycline regulated reverse transcriptional activator (rtTA), the silencer is not present, and the regulatable promoter comprises a tetracycline regulatable element (TRE) promoter In some embodiments, if expressed, the activator can be configured to be turned on in the presence of the transcriptional modulator compound (for example rtTA can be turned on, and thus can induce transcription, in the presence of doxycycline). In some embodiments, the method can comprise contacting the AAV vector system in the animal cell with the transcriptional modulator compound that activates the activator, so that the activator can induce transcription by a regulatable promoter. When the activator is active, the polypeptide-encoding nucleic acid can be expressed from the regulatable promoter. Optionally the polypeptide-encoding nucleic acid encodes a label. In some embodiments, the IEG promoter comprises a fos promoter as described herein. In some embodiments, the activator comprises reverse tetracycline regulated transcriptional activator (rtTA).

In some embodiments, the method includes administering an activity-dependent AAV vector expression system for selectively labeling cells as described herein to an animal cell. In the case of an in vivo method, the activity-dependent AAV vector expression system can be administered The activity-dependent AAV vector expression system can be directly administered to an animal or animal cell for example via injection or infusion. Any suitable injection method is contemplated (e.g., intravenous, subcutaneous, parenteral, iontophoresis, or stereotaxic). In some embodiments, the animal is a mammal. In some embodiments, the animal is a non-human mammal. In some embodiments, the animal is a human. In some embodiments, the animal is a non-human primate. In some embodiments, the animal is a mouse. In some embodiments, the activity-dependent AAV expression system is administered to a cell, cell culture, or tissue in vitro. In some embodiments, the AAV expression system is already present in the animal or in vitro cells or tissue, and as such, the administration step is optional.

The method can include administering a transcriptional modulator compound to the animal or cell. Suitable transcriptional inhibitors compound can correspond to the activity-dependent AAV vector expression system, for example doxycycline or tetracycline for an AAV vector expression system comprising tTA and rtTS.

When selective labeling is desired, contact between the activity-dependent AAV vector expression system and the transcriptional modulator compound can be changed. It will be appreciated that the effect of the transcriptional modulator compound will depend on the particular combination of transcriptional modulator compound and activator (and optional silencer). For example, addition of tetracycline or doxycline to an AAV expression system comprising a tTA activator will inhibit transcription, while ceasing the contacting of the tetracycline or doxycline will activate transcription. For example, addition of tetracycline or doxycline to an AAV expression system comprising a rtTA activator will activate transcription, and can be useful, for example, in obtaining transcription by the direct addition of tetracycline or doxycline. On the other hand obtaining transcription by ceasing the addition of transcriptional modulator compound (for example if the AAV system comprises a tTA activator and/or an rtTS silencer) can involve first establishing a "baseline" state in which transcriptional modulator compound is contacted with the activator and optional silencer, and transcription is achieved by subsequently ceasing the contacting. In some embodiments, the transcriptional modulator compound is injected or infused, and, if applicable the contact is ceased by ceasing injection or infusion. In some embodiments, the transcriptional modulator compound is applied topically, and, if applicable, contacting is ceased by ceasing topical administration. In some embodiments, the transcriptional modulator compound is sequestered, so as to cease the contacting. In some embodiments, the transcriptional modulator compound is chemically modified to an inert form, so as to cease the contacting. In some embodiments, the transcriptional modulator compound is applied and removed via diet.

It is contemplated that it can be useful to permit activity-dependent expression for a particular period of time, for example a particular window of time preceding, following, or encompassing a stimulus to a cell of interest. In some embodiments, activity-dependent expression is for a particular period of time, for example a time in which the animal or animal cell is exposed to a particular stimulus. In some embodiments, ceasing contact with the transcriptional modulator compound so as to permit activity-dependent transcription is for a particular period of time (for example, if the activator comprises tTA). In some embodiments, contact with the transcriptional modulator so as to permit activity-dependent transcription for a particular period of time compound (for example if the activator comprises rtTA). As such, animal cells that respond to that particular activity can be labeled. In some embodiments, the particular period of time (for which transcription is permitted) comprises at least about 1 second, for example at least about 1 second, 2, 3, 4, 5, 6, 7, 8, 9, 10, 11, 12, 13, 14, 15, 16, 17, 18, 19, 20, 21, 22, 23, 24, 25, 25, 27, 28, 29, 30, 35, 30, 45, 50, 55 seconds, 1 minute, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45 50, 55, or 60 minutes, including ranges between any two of the listed values, for example about 1 second to 60 minutes, 1 second to 10 minutes, 1 second to 1 minute, 1 second to 45 seconds, 1 second to 30 seconds, 1 second to 15 seconds, 1 second to 10 seconds, 1 second to 5 seconds, 5 seconds to 60 minutes, 5 seconds to 10 minutes, 5 seconds to 1 minute, 5 seconds to 45 seconds, 5 seconds to 30 seconds, 5 seconds to 15 seconds, 5 seconds to 10 seconds, 10 seconds to 60 minutes, 10 seconds to 10 minutes, 10 seconds to 1 minute, 10 seconds to 45 seconds, 10 seconds to 30 seconds, 10 seconds to 15 seconds, 30 seconds to 60 minutes, 30 seconds to 10 minutes, 30 seconds to 1 minute, 30 seconds to 45 seconds, 1 minute to 60 minutes, 1 minute to 10 minutes, or 10 minutes to 60 minutes. In some embodiments, ceasing contact is performed for at least about 1 hour, for example, at least about 1 hour, 2, 3, 4, 5, 6, 7, 8, 9, 10, 11, 12, 13, 14, 15, 16, 17, 18, 19, 20, 21, 22, 23, 24, 30, 36, 42, 48, 60, or 72 hours, including ranges between any two of the listed values.

In some embodiments, the method comprises activating cells comprising the activity-dependent AAV vector expression system as described herein. In some embodiments, an activated cell has been activated by a stimulus, for example a neuron activated by an action potential. Stimuli can include a natural stimulus, a chemical stimulus, such as, for example, activation by a sensory cue, a behavioral experience, or in response to a particular drug, such as by kainate. Activated cells, including activated neural cells experience a change in polarity. Without being limited by any theory, activation of the cells can stimulate the IEG promoter. In the absence of a transcriptional inhibitor (for example, tetracycline, doxycycline, or other tetracycline analogue), the activator, (for example, tTA), binds to the regulatable promoter, for example, TRE. By placing the regulatable promoter upstream of any transcript-encoding nucleic acid, that transcript-encoding nucleic acid can be regulated by the activator (e.g., if the activator is tTA, and the regulatable promoter is TRE, the transcript-encoding nucleic acid can be regulated by expression of tTA). On the other hand, if the transcriptional inhibitor is present, the activator is inhibited by binding of the transcriptional inhibitor to the activator. The binding of the transcriptional inhibitor to the activator prevents the binding of the activator to TRE, thereby inhibiting activation of TRE. Thus, a polypeptide of interest is regulated based on the binding of the activator to the TRE, which is regulated by the presence of the transcriptional inhibitor. In some embodiments, the polypeptide of interest is a label. Optionally, the method can further include determining the presence or absence of the label, for example by microscopy, magnetic resonance imaging, bioluminescence (e.g., detecting luciferase with a luminometer), or photometry (e.g., using implanted fibers to measure changes in fluorescence).

Example 1: Generation of Fos-FmTB AAV Vector

The following example demonstrates the method for preparing a Fos-FmTB AAV construct, as shown in FIG. 1, SEQ ID NO: 1.

The Fos-FmTB AAV construct was assembled in three steps as follows. First, the Fos gene, including the cfos promoter (SEQ ID NO: 4 (CAAGCTTTCCTTTAG-GAACAGAGGCTTCGAGCCTTTAAGGCTGCGTACTT-GCTTC TCCTAATACCAGAGACTCAAAAAAAAAA AAAAAGTTCCAGATTGCTGGACAATGA CCCGGGTCTCATCCCTTGACCCTGGGAACCGGGTC-CACATTGAATCAGGTGCGAA TGTTCGCTCGCCT-TCTCTGCCTTTCCCGCCTCCCCTCCCCGGCCGCG-GCCCCGGT TCCCCCCCTGCGCTGCACCCTCAGAGTTGGCTGCA-GCCGGCGAGCTGTTCCCGTC AATCCCTCCCTCCTT-TACACAGGATGTCCATATTAGGACATCTGCGTCA-GCAGGTT TCCACGGCCGGTCCCTGTTGT-TCTGGGGGGGGGACCATCTCCGAAATCCTACACG CGGAAGGTCTAGGAGACCCCCTAAGATCCCAAAT-GTGAACACTCATAGGTGAAA GATGTATGC-CAAGACGGGGGTTGAAAGCCTGGGGCGTAGAGTT-GACGACAGAGC GCCCGCAGAGGGCCTTGGGGCGCGCTTC-CCCCCCCTTCCAGTTCCGCCCAGTGAC GTAG-GAAGTCCATCCATTCACAGCGCTTC-TATAAAGGCGCCAGCTGAGGCGCCTA CTACTCCAACCGCGACTG) and Fos exon I (SEQ ID NO: 5 (CAGCGAGCAACTGAGAAGACTGGATA-GAGCCGGCGGTTCCGCGAACGAGCAGT GAC-CGCGCTCCCACCCAGCTCTGCTCTGCAGCTCCCAC-CAGTGTCTACCCCTGGA CCCCTTGCCGGGCTTTCCCCAAACTTCGACCAT-GATGTTCTCGGGTTTCAACGCCG ACTACGAGGCGT-CATCCTCCCGCTGCAGTAGCGCCTCCCCGGC-CGGGGACAGCCT TTCCTACTACCATTCCCCAGCCGACTCCTTCTCCA-GCATGGGCTCTCCTGTCAACA CACAG)), Fos exon II (SEQ ID NO: 6 (GACTTTTGCGCAGATCTGTC-CGTCTCTAGTGCCAACTTTATCCCCACGGTGACAG CCATCTCCACCAGCCCAGACCTGCAGTGGCTGGT-GCAGCCCACTCTGGTCTCCTC CGTGGC-CCCATCGCAGACCAGAGCGCCCCATCCTTACG-GACTCCCCACCCAGTCT GCTGGGGCTTACGCCAGAGCGGGAATGGT-GAAGACCGTGTCAGGAGGCAGAGCG CAGAG-CATCGGCAGAAGGGGCAAAGTAGAGCAG)), Fos exon III (SEQ ID NO: 7 (CTATCTCCTGAAGAGGAAGA-GAAACGGAGAATCCAAGGGAACGGAATAAGAT GGCTGCAGCCAAGTGCCGGAATCGGAG-GAGGGAGCTGACAGATACACTCCAAGC)), and Fos exon IV (SEQ ID NO: 8 (GAGACAGATCAACTT-GAAGATGAGAAGTCTGCGGTGCAGACTGAGATT-GCCAAT GCCCTGAAAGAGAAGGAAAAAGTG-GAGTTTATTTTGGCAGCCCACCGACCTGCCT GCAAGATCCCCGATGACCTTGGCTTCCCAGAGGA-GATGTCTGTGGCCTCCCTGGA TTTGACTGGAG-GTCTGCCTGAGGCTTCCACCCCAGAGTCTGAG- GAGGCCTTCACC CTGCCCCTTCTCAACGACCCTGAGCCCAAGCCATC-CTTGGAGCCAGTCAAGAGCA TCAGCAACGTG-GAGCTGAAGGCAGAACCCTTTGATGACTTCTT-GTTTCCGGCATC ATCTAGGCCCAGTGGCTCAGAGACCTCCCGCTCT-GTGCCAGATGTGGACCTGTCC GGTTCCTTCTAT-GCAGCAGACTGGGAGCCTCTGCACAGCAATTCCT-TGGGGATGG GGCCCATG)) was PCR amplified from murine bacterial artificial chromosome clone RP24-233K from the HindIII site at −622 to the NcoI site at +2363 (relative to the transcription start site). During this amplification, a leucine zipper motif shown previously to mediate complex formation with Jun/AP-1 (Schuermann, M. et al. The leucine repeat motif in Fos protein mediates complex formation with Jun/AP-1 and is required for transformation. Cell, 1989, 56, 507-516, which is incorporated by reference herein in its entirety) was mutated by changing the leucine residues at amino acid positions 179, 186, and 193 to valine, alanine, and valine, respectively (L3-L4-L5 mutation).

Second, the tTA2 gene (SEQ ID NO: 11 (TCTAGACTG-GACAAGAGCAAAGTCATAAACTCTGCTCTGGAAT-TACTCAATGAA GTCGGTATCGAAGGCCTGACGA-CAAGGAAACTCGCTCAAAAGCTGGGAGTTGAG CAGCCTACCCTGTACTGGCACGT-GAAGAACAAGCGGGCCCTGCTCGATGCCCTGG CAATCGAGATGCTGGACAGGCATCATACCCACT-TCTGCCCCTGGAAGGCGAGTC ATG-GCAAGACTTTCTGCGGAACAACGCCAAGTCATTC-CGCTGTGCTCTCCTCTCA CATCGCGACGGGGCTAAAGTGCATCTCGGCAC-CCGCCCAACAGAGAAACAGTAC GAAACCCTG-GAAAATCAGCTCGCGTTCCTGTGTCAGCAAGGCT-TCTCCCTGGAGA ACGCACTGTACGCTCTGTCCGCCGTGGGCCACTT-TACACTGGGCTGCGTATTGGA GGATCAGGAGCAT-CAAGTAGCAAAAGAGGAAAGAGAGACACCTAC-CACCGATTC TATGCCCCCACTTCTGAGACAAGCAATTGAGCTGT-TCGACCATCAGGGAGCCGAA CCTGCCTTC-CTTTTCGGCCTGGAACTAATCATATGTGGCCTGGA-GAAACAGCTAA AGTGCGAAAGCGGCGGGCCGGCCGACGCCCTT-GACGATTTTGACTTAGACATGCT CCCAGCCGATGC-CCTTGACGACTTTGACCTTGATATGCTGCCTGCT-GACGCTCTTG ACGATTTTGACCTTGACATGCTCCCCGGG)) was amplified from the vector pTet-Off-Advanced (Clontech) using a 5' primer including two Myc epitope tags (SEQ ID NO: 9 (GAGCAGAAGCTGATCTCCGAGGAGGAC-CTG) and 8× glycine-asparagine (GN) flexible linker (SEQ ID NO: 10 (GGCAACGGAAATGGCAATGGAAACG-GCAATGGCAACGGAAATGGAAAC)), and a 3' primer including the BGHpA sequence (SEQ ID NO: 14 (AGCTCGCTGATCAGCCTCGACTGTGCCTTCTAGTT-GCCAGCCATCTGTTGTTTGC CCCTCCCCGTGCCT-TCCTTGACCCTGGAAGGTGCCACTCCCACTGTC-CTTTCCTA ATAAAATGAGGAAATTGCATCGCATTGTCTGAG-TAGGTGTCATTCTATTCTGGGG GGTGGGGTGGGCAGGACAGCAAGGGGGAGGAT-TGGGAAGACAATAGCAGGCA TGCTGGGGATGCG-GTGGGCTCTATGGCTTCTGAGGCGGAAAGAACCA-GCTGGGG CTCGAA)).

Third, these two cassettes were inserted into an AAV vector containing an upstream 5' pA sequence (to minimize transcription from the upstream ITR; SEQ ID NO: 2) to generate the vector AAV-Fos-FmTB, which contains (5' to 3'): ITR-R_5'pA_Fos gene (−622 to +2363, with L3-L4-L5 mutation)-Myc(×2)-GN×8-tTA2-BGHpA_ITR-L. This vector was fully sequenced to confirm integrity of all components.

Thus, AAV vectors for regulated activity-dependent cell marking, comprising an IEG, and activator nucleic acid in accordance with some embodiments herein can be produced.

Example 2: Generation of FRR-ChR2-YFP AAV Vector

The following example demonstrates the method for preparing the FRR-ChR2-YFP AAV construct, shown in FIG. 3, SEQ ID NO: 15.

FRR-ChR2-YFP is a dual function AAV vector that 1) DOX-dependently suppresses transcription from TRE (tet-responsive element) promoter-driven vectors and 2) yields FLP recombinase-dependent expression of the light gated ion channel Channelrhodopsin-2. The construct includes an ITR-R (SEQ ID NO: 16 (CCCTGCAGGCAGCT-GCGCGCTCGCTCGCTCACTGAGGCCGC-CCGGGCAAAGCCC GGGCGTCGGGCGACCTTTG-GTCGCCCGGCCTCAGTGAGCGAGCGAGCGCGCAGA GAGGGGAGTGGCCAACTCCATCACTAGGGGTTCCT)) and ITR-L (SEQ ID NO: 25 (CAGGAACCCCTAGT-GATGGAGTTGGCCACTCCCTCTCT-GCGCGCTCGCTCGCTCA CTGAGGCCGGGCGAC-CAAAGGTCGCCCGACGCCCGGGCTTTGCCCGGGC-GGCCT CAGTGAGCGAGCGAGCGCGCAGCTGCCT-GCAGG).

This construct was generated as follows. First, a novel reverse tetracycline-controlled transcriptional Silencer (rtTS; SEQ ID NO: 19 (ATGTCCAGACTGGACAAGAG-CAAAGTCATAAACGGAGCTCTGGAATTACTCAAT GGTGTCGGTATCGAAGGCCTGACGA-CAAGGAAACTCGCTCAAAAGCTGGGAGTT GAGCAGCCTACCCTGTACTGGCACGT-GAAGAACAAGCGGGCCCTGCTCGATGCCC TGC-CAATCGAGATGCTGGACAGGCATCATACCCACT-TCTGCCCCCTGGAAGGCGA GTCATGGCAAGACTTTCTGCGGAACAACGC-CAAGTCATACCGCTGTGCTCTCCTC TCACATCGC-GACGGGGCTAAAGTGCATCTCGGCACCCGC-CCAACAGAGAAACAGT ACGAAACCCTGGAAAATCAGCTCGCGTTCCTGT-GTCAGCAAGGCTTCTCCCTGGA GAACGCACTG-TACGCTCTGTCCGCCGTGGGCCACTTTA-CACTGGGCTGCGTATTG GAGGAACAGGAGCATCAAGTAGCAAAAGAG-GAAAGAGAGACACCTACCACCGAT TCTATGC-CCCCACTTCTGAGACAAGCAATTGAGCTGTTCGAC-CGGCAGGGAGCCG AACCTGCCTTCCTTTTCGGCCTGGAACTAATCATAT-GTGGCCTGGAGAAACAGCT AAAGTGC-GAAAGCGGGTCGCCAAAAAAGAAGAGAAAGGTG-GACGGCGGTGGTG CTTTGTCTCCTCAGCACTCTGCTGTCACT-CAAGGAAGTATCATCAAGAACAAGGA GGGCATG-GATGCTAAGTCACTAACTGCCTGGTCCCGGA-CACTGGTGACCTTCAAG GATGTATTTGTGGACTTCACCAGGGAGGAGTG-GAAGCTGCTGGACACTGCTCAGC AGATCGTGTA-CAGAAATGTGATGCTGGAGAACTATAAGAACCTG-GTTTCCTTGGG TTATCAGCTTACTAAGCCAGATGTGATCCTCCGGT-TGGAGAAGGGAGAAGAGCCC TGGCTGGTGGAGA-GAGAAATTCACCAAGAGACCCATCCTGATTCAGA- GACTGCAT TTGAAATCAAATCATCAGTTTAA) with high DOX sensitivity was synthesized by fusing the KRAB repressor domain of human ZNF10 (amplified from pLVCT-rtTRKRAB-2SM2) to the C-terminus of the reverse tet repressor protein rTetR$^S$-M2 (Urlinger, S. et al. Exploring the sequence space for tetracycline-dependent transcriptional activators: novel mutations yield expanded range and sensitivity. PNAS, 2000, 97, 7963-7968), amplified from the vector pSLIKneo. This rtTS was then inserted upstream of a ChR2 cassette cloned in the 3' to 5' orientation, and this 5'-rtTS-3'_3'-ChR2-5' cassette was flanked by inverted FRT sites (SEQ ID NO: 18). Finally, this construct was moved into a CMV promoter-driven vector (SEQ ID NO: 17 (ACGCGTCTAGTTATTAATAGTAATCAAT-TACGGGGTCATTAGTTCATAGCCCATA TATGGAGT-TCCGCGTTACATAACTTACGGTAAATGGCCCGC-CTGGCTGACCGCCC AACGACCCCCGCCCATTGACGTCAATAATGACG-TATGTTCCCATAGTAACGCCAA TAGGGACTTTCCAT-TGACGTCAATGGGTGGAGTATTTACGGTAAACTGC-CCACTT GGCAGTACATCAAGTGTATCATATGCCAAGTACGC-CCCCTATTGACGTCAATGAC GGTAAATGGCCCGC-CTGGCATTATGCCCAGTACATGACCT-TATGGGACTTTCCTA CTTGGCAGTACATCTACGTATTAGTCATCGCTAT-TACCATGGTGATGCGGTTTTGG CAGTACAT-CAATGGGCGTGGATAGCGGTTTGACT-CACGGGGATTTCCAAGTCTCC ACCCCATTGACGTCAATGGGAGTTTGTTTTGGCAC-CAAAATCAACGGGACTTTCC AAAATGTCG-TAACAACTCCGCCCCATTGACGCAAATGGGCGG-TAGGCGTGTACGG TGGGAGGTCTATATAAGCAGAGCTCGTTTAGT-GAACCGTCAGATCGCCTGGAGAC GCCATC-CACGCTGTTTTGACCTCCATAGAAGACAC-CGGGACCGATCCAGCCTC)) containing a WPRE (SEQ ID NO: 23) and a modified polyadenylation sequence from 5V40 (wtSV40pA+mz; SEQ ID NO: 24 (TGCTTTATTT-GTGAAATTTGTGATACTATTGCTTTATTTGTAACCAT-TATAAGCTG CAATAAACAAGTTAACAACAACAATT-GCATTCATTTTATTGTTTCAGGTTCAGGG GGAGGTGTGGGAGGTTTTTTAAAG)).

This construct includes a YFP (SEQ ID NO: 20 (CT-CACTTGTACAGCTCGTCCATGCCGAGAGTGATC-CCGGCGGCGGTCACGAACTC CAGCAGGACCATGT-GATCGCGCTTCTCGTTGGGGTCTTTGCTCAGGGCG-GACTGG TAGCTCAGGTAGTGGTTGTCGGGCAGCA-GCACGGGGCCGTCGCCGATGGGGGTG TTCTGCTG-GTAGTGGTCGGCGAGCTGCACGCTGCCGTCCTC-GATGTTGTGGCGGA TCTTGAAGTTCACCTTGATGCCGTTCTTCTGCTT-GTCGGCCATGATATAGACGTTG TGGCTGTTGTAGT-TGTACTCCAGCTTGTGCCCCAGGATGTTGCCGTC-CTCCTTGAA GTCGATGCCCTTCAGCTCGATGCGGTTCACCA-GGGTGTCGCCCTCGAACTTCACC TCG-GCGCGGGTCTTGTAGTTGCCGTCGTCCTT-GAAGAAGATGGTGCGCTCCTGGA CGTAGCCTTCGGGCATGGCGGACTT-GAAGAAGTCGTGCTGCTTCATGTGGTCGGG GTAGCGGGCGAAGCCGTACGCCAGGCCGTAGC-CGAAGGTGGTCACGAGGGTGGGCCA GGGCACGGGCAGCTTGCCGGTGGTGCAGAT-GAACTTCAGGGTCAGCTTGCCGTA GGTG-GCATCGCCCTCGCCCTCGCCGGACACGCTGAACTT-GTGGCCGTTTACGTCG CCGTCCAGCTCGACCAGGATGGGCACCACCCCG-GTGAACAGCTCCTCGCCCTTGC TCAC)), a V5 epitope tag (SEQ ID NO: 21 (CGTAGAATCGAGACCGAGGA-GAGGGTTAGGGATAGGCTTCCC)), a ChR2-H134R (SEQ ID NO: 22 (TGGCACGGCTCCGGCCTCGGCT-TCGTCTTCGACGAGAGTCTCGACCTCGATCTCC GTTCCGCCGATGTTCAGTTTGGTGGTTTTGCGGA-TATCTCCGTGAATCAATATGTG CTCGTGGATCAG-GACGCGCAGGTAGTGTCCCAACAAC-CCCCAACAATTTTTACTC ATCAGATCAATAATCGTGTGACCTACGGTGGAGC-CATAGACGCTCAGGACGCCAA AACCTTCGGGC-CCCAAAATGAAGAGAATTGGGAACATACCCCA-GCTCACGAAAA ACAGCCATGCCATGCCGGTCACGACCTGGCG-GCACCGACCCTTTGGCACAGTATG ATAACCCTCGA-TATATGCTTTGGCGGCGTGAAAAAATGTGT-TCGCGCCATAGCAC AATCCAAGACAAAAGAAGATGACTTTAACATAGC-CGGTTGCCATGGCGCTGGTAG CCCCCCACACGA-TAGTCCCGATGTCTGAGACAAGGAGTCCCATGGT-TCTCCTGCT GTAGTCGTTGCTCAGGCCGGTGAGGTTGCTCAG-GCGGATAAGGATGACAGGACA AGTGAGCAGC-CACTCTGCATAGCGCAGCCACTGCACCCGGTGTC-CTGTGGCAAGG TAGAGCATAGAGGGATTCTTAAACT-CAAAAAAGAACTCGAGAATCACCTTAACCA TTTCAATGGCGCACACATAGATCTCCTCCCAGCCG-CATGTAGATTTCCAGGTTTG GTAGGCATA-GAACATCAGCAGCAAAATGCTGAATCCTGCTG-CAAGCCACTGCAGG ACATTTGACGCGGTCTGAGCGCCGTTCGTGCCGC-GAGATTCAATCCATCCGGCAC AGTAACATTGATC-CTCAGGGACCAGGACGGACCCGTTCACCACCACA-GGATTAGT AACGAACAAAAGTTCGCGTCCGACGGCAGA-CAAAGCGCCGCCATAGTCCAT)), and an FRT (SEQ ID NO: 18).

Thus, AAV vectors for regulated activity-dependent cell marking, comprising a regulatable promoter and polypeptide (label)-encoding nucleic acid in accordance with some embodiments herein can be produced.

Example 3: Generation of TRE-FLPo AAV Vector

The following example demonstrates the method for preparing the TRE-FLPo AAV construct, shown in FIG. 5, SEQ ID NO: 26.

PCR was used to amplify a codon optimized FLPo cassette from the vector pFLPo which included a 2× FLAG epitope tag (SEQ ID NO: 29 (ATGGCTC-CTAAGAAGAAGAGGAAGGTGATGAGCCAGTTCGA-CATCCTGTGCAAG ACCCCCCCCAAGGTGCTGGT-GCGGCAGTTCGTGGAGAGATTCGAGAGGCCCAGC GGCGAGAAGATCGCCAGCTGTGCCGCCGAGCT-GACCTACCTGTGCTGGATGATCA CCCACAACG-GCACCGCCATCAAGAGGGCCACCTTCATGAGCTA-CAACACCATCAT CAGCAACAGCCTGAGCTTCGACATCGT-GAACAAGAGCCTGCAGTTCAAGTACAAG ACCCA-GAAGGCCACCATCCTGGAGGCCAGCCT-GAAGAAGCTGATCCCCGCCTGG GAGTTCACCATCATCCCTTACAACGGCCA-GAAGCACCAGAGCGACATCACCGACA TCGTGTC-CAGCCTGCAGCTGCAGTTCGAGAGCAGCGAGGAG-GCCGACAAGGGCA ACAGCCACAGCAAGAAGATGCTGAAGGCCCTGCTGTCCGAGGGCGAGAGCATCT GGGAGATCACCGAGAAGATCCTGAACAGCTTCGAGTACACCAGCAGGTTCACCA AGACCAAGACCCTGTACCAGTTCCTGTTCCTGGCCACATTCATCAACTGCGGCAG GTTCAGCGACATCAAGAACGTGGACCCCAAGAGCTTCAAGCTGGTGCAGAACAA GTACCTGGGCGTGATCATTCAGTGCCTGGTGACCGAGACCAAGACAAGCGTGTCC AGGCACATCTACTTTTTCAGCGCCAGAGGCAGGATCGACCCCCTGGTGTACCTGG ACGAGTTCCTGAGGAACAGCGAGCCCGTGCTGAAGAGAGTGAACAGGACCGGCA ACAGCAGCAGCAACAAGCAGGAGTACCAGCTGCTGAAGGACAACCTGGTGCGCA GCTACAACAAGGCCCTGAAGAAGAACGCCCCCTACCCCATCTTCGCTATCAAGAA CGGCCCTAAGAGCCACATCGGCAGGCACCTGATGACCAGCTTTCTGAGCATGAAG GGCCTGACCGAGCTGACAAACGTGGTGGGCAACTGGAGCGACAAGAGGGCCTCC GCCGTGGCCAGGACCACCTACACCCACCAGATCACCGCCATCCCCGACCACTACT TCGCCCTGGTGTCCAGGTACTACGCCTACGACCCCATCAGCAAGGAGATGATCGC CCTGAAGGACGAGACCAACCCCATCGAGGAGTGGCAGCACATCGAGCAGCTGAA GGGCAGCGCCGAGGGCAGCATCAGATACCCCGCCTGGAACGGCATCATCAGCCA GGAGGTGCTGGACTACCTGAGCAGCTACATCAACAGGCGGATCAGATCTGGCGG CGACTACAAGGACGACGACGACAAGGACTACAAGGACGACGACGACAAG)) at the C-terminus. This cassette was cloned into an AAV vector containing a 5' polyA (SEQ ID NO: 27), the Tet response element (TRE) from vector pTRE-Tight (Clontech) (SEQ ID NO: 28 (CGAGTTTACTCCCTATCAGTGATAGAGAACGTATGTCGAGTTTACTCCCTATCAG TGATAGAGAACGATGTCGAGTTTACTCCCTATCAGTGATAGAGAACGTATGTCGA GTTTACTCCCTATCAGTGATAGAGAACGTATGTCGAGTTTACTCCCTATCAGTGAT AGAGAACGTATGTCGAGTTTATCCCTATCAGTGATAGAGAACGTATGTCGAGTTT ACTCCCTATCAGTGATAGAGAACGTATGTCGAGGTAGGCGTGTACGGTGGGAGG CCTATATAAGCAGAGCTCGTTTAGTGAACCGTCAGATCGCC)), a WPRE (SEQ ID NO: 30 (GCTTATCGATAATCAACCTCTGGATTACAAAATTTGTGAAAGATTGACTGGTATT CTTAACTATGTTGCTCCTTTTACGCTATGTGGATACGCTGCTTTAATGCCTTTGTA TCATGCTATTGCTTCCCGTATGGCTTTCATTTTCTCCTCCTTGTATAAATCCTGGTT GCTGTCTCTTTATGAGGAGTTGTGGCCCGTTGTCAGGCAACGTGGCGTGGTGTGC ACTGTGTTTGCTGACGCAACCCCCACTGGTTGGGGCATTGCCACCACCTGTCAGC TCCTTTCCGGGACTTTCGCTTTCCCCCTCCCTATTGCCACGGCGGAACTCATCGCC GCCTGCCTTGCCCGCTGCTGGACAGGGGCTCGGCTGTTGGGCACTGACAATTCCG TGGTGTTGTCGGGGAAATCATCGTCCTTTCCTTGGCTGCTCGCCTATGTTGCCACC TGGATTCTGCGCGGGACGTCCTTCTGCTACGTCCCTTCGGCCCTCAATCCAGCGG ACCTTCCTTCCCGCGGCCTGCTGCCGGCTCTGCGGCCTCTTCCGCGTCTTCGCCTT CGCCCTCAGACGAGTCGGATCTCCCTTTGGGCCGCCTCCCCGCATCGATACCG)), and the polyadenylation sequence from human growth hormone (hGHpA; SEQ ID NO: 31 (TACGGGTGGCATCCCTGTGACCCCTCCCCAGTGCCTCTCCTGGCCCTGGAAGTTG CCACTCCAGTGCCCACCAGCCTTGTCCTAATAAAATTAAGTTGCATCATTTTGTCT GACTAGGTGTCCTTCTATAATATTATGGGGTGGAGGGGGGTGGTATGGAGCAAG GGGCAAGTTGGGAAGACAACCTGTAGGGCCTGCGGGGTCTATTGGGAACCAAGC TGGAGTGCAGTGGCACAATCTTGGCTCACTGCAATCTCCGCCTCCTGGGTTCAAG CGATTCTCCTGCCTCAGCCTCCCGAGTTGTTGGGATTCCAGGCATGCATGACCAG GCTCAGCTAATTTTTGTTTTTTTGGTAGAGACGGGGTTTCACCATATTGGCCAGGC TGGTCTCCAACTCCTAATCTCAGGTGATCTACCCACCTTGGCTCTCCCAAATTGCTG GGATTACAGGCGTGAACCACTGCTCCCTTCCCTGTCCTT)).

Thus, AAV vectors for regulated activity-dependent cell marking, comprising a codon optimized FLPo cassette in accordance with some embodiments herein can be produced.

Example 4: Generation of Fos-FmTB Transgenic Mice

The following example demonstrates the method of preparing Fos-FmTB transgenic mice.

AAV-Fos-FmTB was digested with HindIII/NotI to release the Fos-FmTB insert from the AAV vector backbone, purified from a low melting agarose gel using Elutip-d minicolumns (Whatman), drop dialyzed into injection buffer (5 mM Tris, pH 7.4, 5 mM NaCl, 0.1 mM EDTA), and diluted to 3 ng/μl for pronuclear injection into B6CBAF1/J embryos (UCLA Transgenic Core Facility). Founder lines were identified using PCR, and backcrossed onto a C57Bl/6N background.

Thus, transgenic mice comprising Fos-FmTB in accordance with some embodiments herein were produced.

Example 5: Viral Packaging of AAV Constructs

Endotoxin-free AAV-Fos-FmTB, TRE-FLPo, and FRR-ChR2-YFP plasmid DNA was prepared and submitted to the viral core facility at the University of Pennsylvania for packaging into AAV serotype 5.

Example 6: All Viral TRACM System for Marking LS Neurons

The following example shows that an all viral TRACM system robustly and specifically marks LS acute stress-activated neurons.

TRACM AAV vectors are used for transient expression of reporter or effector molecules, as shown in FIG. 18. Neural activity-induced Fos expression produces a DOX-suppressible tetracycline transactivator (tTA) fusion protein (i) that in turn activates expression from TRE-driven reporter vectors (ii). Inclusion of the DOX-activated reverse Tet silencer (rtTS, iii) increases signal to noise by actively suppressing expression from the TRE promoter. Panels b-f show that in the absence of DOX, significant induction of YFP native fluorescence is observed in immobilization stressed (+S) but not unstressed naive (N) mice (panels c and d); stress does not induce YFP in the presence of DOX (+S, +DOX) (panel e). ***P<0.001; one-way ANOVA with Tukey's Multiple Comparisons Test. Panel g illustrates that constitutively expressed rtTS serves as an internal control; no significant differences in LS rtTS⁻ cell counts are detectable, demonstrating comparable infections across all experimental groups. Total DAPI⁺ cells: N=5,580; +S=5,076; +S,+DOX=3,164.

Accordingly, an all viral system comprising AAV vectors in accordance with some embodiments herein can be used to specifically mark LS neurons.

Example 7: Stable Activity-Dependent Genetic Marking Using TRACM

Figure 19A:
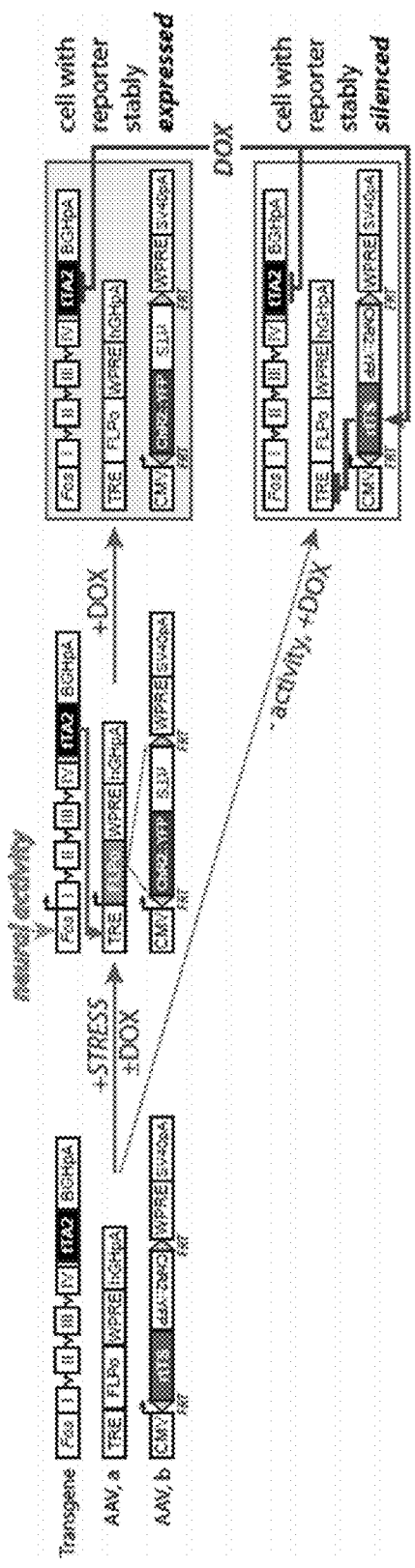
Figure 19B:
Figure 19F:
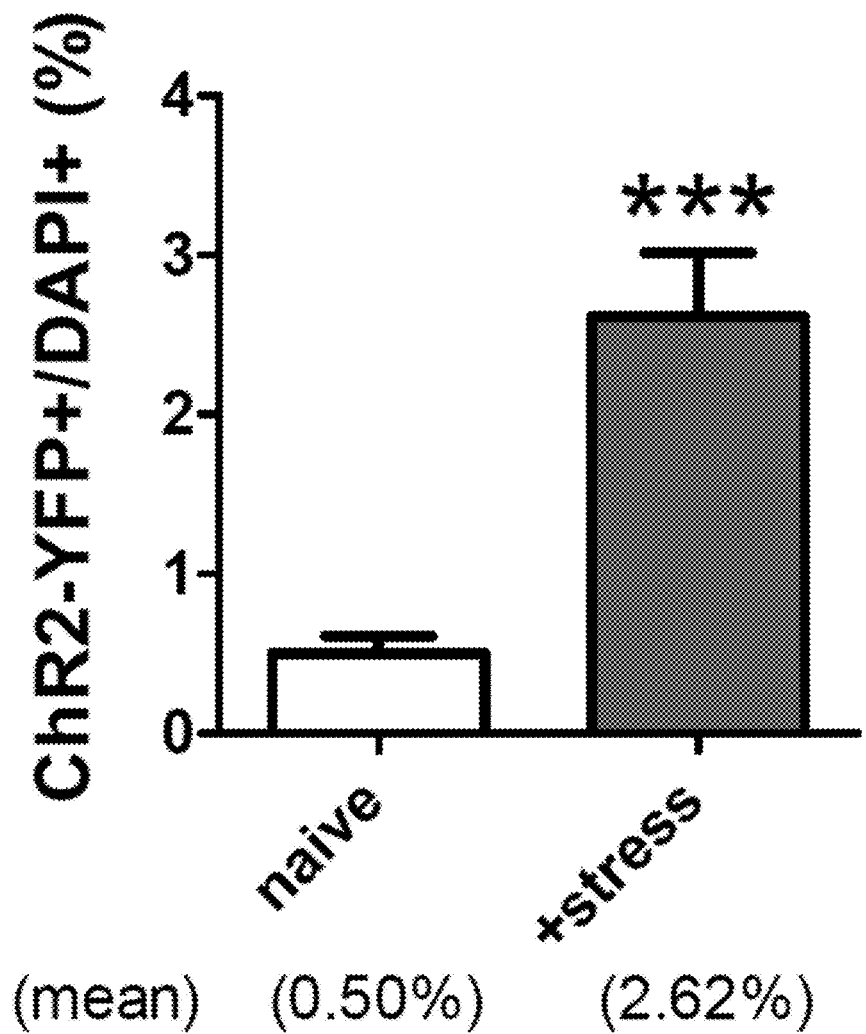

As shown in FIG. 19, the TRACM transgene and AAV vectors may be used for stable expression of reporter or effector molecules. In panel a of FIG. 19, the AAV that expresses rtTS also contains a second gene (here, ChR2::YFP) which is in the reverse 3' to 5' orientation relative to rtTS and the CMV promoter; both rtTS and ChR2::YFP are flanked by inverted FRT sites. Therefore, neural activity results in the induction of codon optimized FLPo recombinase, which mediates inversion of the rtTS-ChR2 cassette such that ChR2::YFP is inverted into the correct, 5' to 3' orientation. Upon placing subjects onto high concentrations of DOX, cells in which such a recombination event occurred will yield stable expression of the reporter, whereas cells that did not undergo a recombination event will be stably silenced. Panels b-f show that 8 days following stereotactic injections of AAV constructs "a"+"b" into Fos-FmTB transgenics, mice were either left undisturbed in their home cages (naive) or subjected to immobilization stress (+stress). At 24 hours following completion of immobilization, all animals were placed onto DOX, and 12 days later, perfused for histological analysis. Stressed animals showed significantly more ChR2-YFP+ neurons than naive mice (panels c, d, and f), and stressed mice that received DOX from day 0 (panel e) showed similar ChR2-YFP expression as naives. Total DAPI+ cells: naive=2,922; +stress=2,879.

Accordingly, an all viral system comprising AAV vectors in accordance with some embodiments herein can be used to for stable expression of reporter or effector molecules.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

All patents and publications mentioned in the specification are indicative of the levels of those skilled in the art to which the invention pertains. All patents and publications are herein incorporated by reference to the same extent as if each individual publication was specifically and individually indicated to be incorporated by reference.

While the present invention has been described in some detail for purposes of clarity and understanding, one skilled in the art will appreciate that various changes in form and detail can be made without departing from the true scope of the invention.

The term "comprising" as used herein is synonymous with "including," "containing," or "characterized by," and is inclusive or open-ended and does not exclude additional, unrecited elements or method steps.

All numbers expressing quantities of ingredients, reaction conditions, and so forth used in the specification are to be understood as being modified in all instances by the term "about." Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

The above description discloses several methods and materials of the present invention. This invention is susceptible to modifications in the methods and materials, as well as alterations in the fabrication methods and equipment. Such modifications will become apparent to those skilled in the art from a consideration of this disclosure or practice of the invention disclosed herein. Consequently, it is not intended that this invention be limited to the specific embodiments disclosed herein, but that it cover all modifications and alternatives coming within the true scope and spirit of the invention.

The foregoing description and Examples detail certain embodiments. It will be appreciated, however, that no matter how detailed the foregoing may appear in text, the invention may be practiced in many ways and the invention should be construed in accordance with the appended claims and any equivalents thereof.

What is claimed is:

1. An activity-dependent adeno-associated virus (AAV) vector expression system comprising:
    an immediate early gene (IEG) promoter operably linked to a converter nucleic acid encoding a converter comprising an N-terminal portion of FOS fused to a nucleic acid encoding an activator, wherein the activator is downstream of the N terminal portion of FOS; and
    a regulatable promoter operably linked to an insertion site for a transcript-encoding nucleic acid, wherein transcription by the regulatable promoter is activated by the activator, and
    wherein the activator's activation of the regulatable promoter is modulated by a transcriptional modulator compound, if present.

2. The activity-dependent MV vector expression system of claim 1, further comprising another promoter operably linked to a silencer nucleic acid encoding a silencer, wherein the silencer inhibits transcription by the regulatable promoter, and wherein the silencer's inhibition of the regulatable promoter is modulated by the transcriptional modulator compound, if present.

3. The activity-dependent AAV vector expression system of claim 2, wherein the activator comprises tTA, wherein the silencer comprises rtTS, and wherein the regulatable promoter comprises a tetracycline regulatable element (TRE) promoter.

4. The activity-dependent AAV vector expression system of claim 1, wherein the activator comprises rtTA, wherein the regulatable promoter comprises a tetracycline regulatable element (TRE) promoter, and wherein the transcriptional modulator compound, if present, induces the activator's activation of the regulatable promoter.

5. The activity-dependent AAV vector expression system of claim 1, wherein the activator comprises tTA, wherein the regulatable promoter comprises a tetracycline regulatable element (TRE) promoter, and wherein the transcriptional modulator compound, if present, inhibits the activator's activation of the regulatable promoter.

6. The activity-dependent AAV vector expression system of claim 1, wherein the converter nucleic acid comprises fos exons I, II, III, and IV.

7. The activity-dependent AAV vector expression system of claim 1, wherein the IEG promoter comprises a fos promoter or a cyclic AMP response element (CRE) promoter.

8. The activity-dependent AAV vector expression system of claim 1, wherein the insertion site contains a polynucleotide encoding a label.

9. The activity-dependent AAV vector expression system of claim 1, wherein a single AAV vector comprises the converter nucleic acid, the silencer nucleic acid, the regulatable promoter, and the insertion site.

10. The activity-dependent AAV vector expression system of claim 1, wherein two or more different AAV vectors collectively comprise the converter nucleic acid, the silencer nucleic acid, the regulatable promoter, and the insertion site.

11. The activity-dependent AAV vector expression system of claim 1, wherein the converter nucleic acid encodes an FmTB converter of SEQ ID NO: 12.

12. The activity-dependent AAV vector expression system of claim 1, further comprising a first inverted terminal repeat (ITR) sequence located 5' of the IEG promoter, and a second ITR sequence located 3' of the insertion site.

13. A kit for activity-dependent nucleic acid expression in cells, the kit comprising:
    the AAV vector system of claim 1; and
    a transcriptional modulator compound.

14. The kit of claim 13, wherein the transcriptional modulator compound comprises doxycycline or tetracycline.

* * * * *

UNITED STATES PATENT AND TRADEMARK OFFICE
CERTIFICATE OF CORRECTION

| | | |
|---|---|---|
| PATENT NO. | : 10,266,844 B2 | Page 1 of 2 |
| APPLICATION NO. | : 15/222554 | |
| DATED | : April 23, 2019 | |
| INVENTOR(S) | : David J. Anderson et al. | |

It is certified that error appears in the above-identified patent and that said Letters Patent is hereby corrected as shown below:

On the Title Page

Item (56), Page 2, Column 2, Line 22, Under Other Publications, "Rüüther" should be --Rüther--.

In the Specification

Column 7, Line 18, "rtTS⁻" should be --rtTS$^+$--.

Column 7, Line 38, "FIG." should be --FIGs.--.

Column 17, Line 39, "Aequoria" should be --Aequorea--.

Column 17, Line 39, "Rentlla" should be --Renilla--.

Column 17, Line 39, "Rentlla" should be --Renilla--.

Column 22, Line 48, "productExample" should be --product. Example--.

Column 26, Line 67, "derivitives" should be --derivatives--.

Column 31, Line 59, "promoter" should be --promoter.--.

Column 32, Line 12, "administered" should be --administered.--.

Column 32, Line 40, "doxycline." should be --doxycycline.--.

Column 32, Line 42, "doxycline." should be --doxycycline.--.

Column 32, Line 43, "doxycline." should be --doxycycline.--.

Signed and Sealed this
Thirtieth Day of July, 2019

Andrei Iancu
*Director of the United States Patent and Trademark Office*

Column 32, Line 47, "doxycline." should be --doxycycline.--.

Column 37, Line 39, "5V40" should be --SV40--.

Column 41, Line 4, "rtTS$^-$" should be --rtTS$^+$--.

In the Claims

Column 85, Line 28 (approx.), In Claim 2, "MV" should be --AAV--.

SEQUENCE LISTING

```
<160> NUMBER OF SEQ ID NOS: 36

<210> SEQ ID NO 1
<211> LENGTH: 7223
<212> TYPE: DNA
<213> ORGANISM: Artificial Sequence
<220> FEATURE:
<223> OTHER INFORMATION: AAV cfos-FmTB-comp+5'pA

<400> SEQUENCE: 1
acatgtgagc aaaaggccag caaaaggcca ggaaccgtaa aaaggccgcg ttgctggcgt      60
ttttccatag gctccgcccc cctgacgagc atcacaaaaa tcgacgctca agtcagaggt     120
ggcgaaaccc gacaggacta taaagatacc aggcgtttcc ccctggaagc tccctcgtgc     180
gctctcctgt tccgaccctg ccgcttaccg gatacctgtc cgcctttctc ccttcggaa      240 gcgtggcgct ttctcatagc tcacgctgta ggtatctcag ttcggtgtag gtcgttcgct     300
ccaagctggg ctgtgtgcac gaaccccccg ttcagcccga ccgctgcgcc ttatccggta     360
actatcgtct tgagtccaac ccggtaagac acgacttatc gccactggca gcagccactg     420
gtaacaggat tagcagagcg aggtatgtag gcggtgctac agagttcttg aagtggtggc     480
ctaactacgg ctacactaga aggacagtat ttggtatctg cgctctgctg aagccagtta     540
ccttcggaaa aagagttggt agctcttgat ccggcaaaca aaccaccgct ggtagcggtg     600
gtttttttgt ttgcaagcag cagattacgc gcagaaaaaa aggatctcaa gaagatcctt     660
tgatcttttc tacggggtct gacgctcagt ggaacgaaaa ctcacgttaa gggattttgg     720
tcatgagatt atcaaaaagg atcttcacct agatcctttt aaattaaaaa tgaagtttta     780
aatcaatcta agtatatat gagtaaactt ggtctgacag ttaccaatgc ttaatcagtg      840
aggcacctat ctcagcgatc tgtctatttc gttcatccat agttgcctga ctccccgtcg     900
tgtagataac tacgatacgg gagggcttac catctggccc cagtgctgca atgataccgc     960
gagacccacg ctcaccggct ccagatttat cagcaataaa ccagccagcc ggaagggccg    1020
agcgcagaag tggtcctgca actttatccg cctccatcca gtctattaat tgttgccggg    1080
aagctagagt aagtagttcg ccagttaata gtttgcgcaa cgttgttgcc attgctacag    1140
gcatcgtggt gtcacgctcg tcgtttggta tggcttcatt cagctccggt tcccaacgat    1200
```

```
caaggcgagt tacatgatcc cccatgttgt gcaaaaaagc ggttagctcc ttcggtcctc    1260
cgatcgttgt cagaagtaag ttggccgcag tgttatcact catggttatg gcagcactgc    1320
ataattctct tactgtcatg ccatccgtaa gatgcttttc tgtgactggt gagtactcaa    1380
ccaagtcatt ctgagaatag tgtatgcggc gaccgagttg ctcttgcccg cgtcaatac    1440
gggataatac cgcgccacat agcagaactt taaaagtgct catcattgga aaacgttctt    1500
cggggcgaaa actctcaagg atcttaccgc tgttgagatc cagttcgatg taacccactc    1560
gtgcacccaa ctgatcttca gcatctttta ctttcaccag cgtttctggg tgagcaaaaa    1620
caggaaggca aaatgccgca aaaagggaa taagggcgac acggaaatgt tgaatactca    1680
tactcttcct ttttcaatat tattgaagca tttatcaggg ttattgtctc atgagcggat    1740
acatatttga atgtatttag aaaaataaac aatagggt tccgcgcaca tttccccgaa    1800
aagtgccacc tgacgtctaa gaaaccatta ttatcatgac attaacctat aaaaataggc    1860
gtatcacgag gccctttcgt ctcgcgcgtt tcggtgatga cggtgaaaac ctctgacaca    1920
tgcagctccc ggagacggtc acagcttgtc tgtaagcgga tgccgggagc agacaagccc    1980
gtcagggcgc gtcagcgggt gttggcgggt gtcgggctg gcttaactat gcggcatcag    2040
agcagattgt actgagagtg caccataaaa ttgtaaacgt taatattttg ttaaaattcg    2100
cgttaaattt ttgttaaatc agctcatttt ttaaccaata ggccgaaatc ggcaaaatcc    2160
cttataaatc aaaagaatag cccgagatag ggttgagtgt tgttccagtt tggaacaaga    2220
gtccactatt aaagaacgtg gactccaacg tcaagggcg aaaaccgtc tatcagggcg    2280
atggcccact acgtgaacca tcacccaaat caagttttt ggggtcgagg tgccgtaaag    2340
cactaaatcg aaccctaaa gggagccccc gatttagagc ttgacgggga agccggcga    2400
acgtggcgag aaaggaaggg aagaaagcga aaggagcggg cgctagggcg ctggcaagtg    2460
tagcggtcac gctgcgcgta accaccacac ccgccgcgct taatgcgccg ctacagggcg    2520
cgtactatgg ttgctttgac gtatgcggtg tgaaataccg cacagatgcg taaggagaaa    2580
ataccgcatc aggcgcccct gcaggcagct gcgcgctcgc tcgctcactg aggccgcccg    2640
ggcaaagccc gggcgtcggg cgaccttttgg tcgcccggcc tcagtgagcg agcgagcgcg    2700
cagagaggga gtggccaact ccatcactag gggttcctgc ggccgcacct taattaagca    2760
ataaatatc tttattttca ttacatctgt gtgttggttt tttgtgtgaa tcgatagtac    2820
taacatacgc tctccatcaa aacaaaacga aacaaaacaa actagcaaaa taggctgtcc    2880
ccagtgcaag tgcaggtgcc agaacatttc tctggcctaa ctggccggta ccaagctttc    2940
ctttaggaac agaggcttcg agcctttaag gctgcgtact tgcttctcct aataccagag    3000
actcaaaaaa aaaaaaaaag ttccagattg ctggacaatg acccgggtct catcccttga    3060
ccctgggaac cgggtccaca ttgaatcagg tgcgaatgtt cgctcgcctt ctctgccttt    3120
cccgcctccc ctccccggc cgcggccccg gttccccccc tgcgctgcac cctcagagtt    3180
ggctgcagcc ggcgagctgt tcccgtcaat ccctccctcc tttacacagg atgtccatat    3240
taggacatct gcgtcagcag gtttccacgg ccggtccctg ttgttctggg gggggaccaa    3300
tctccgaaat cctacacgcg gaaggtctag gagacccct aagatcccaa atgtgaacac    3360
tcataggtga aagatgtatg ccaagacggg ggttgaaagc ctgggcgta gagttgacga    3420
cagagcgccc gcagagggcc ttggggcgcg cttccccccc cttccagttc cgcccagtga    3480
cgtaggaagt ccatccattc acagcgcttc tataaaggcg ccagctgagg cgcctactac    3540
tccaaccgcg actgcagcga gcaactgaga agactggata gagccggcgg ttccgcgaac    3600
```

```
gagcagtgac cgcgctccca cccagctctg ctctgcagct cccaccagtg tctacccctg    3660 gacccettgc cgggctttcc ccaaacttcg accatgatgt tctcgggttt caacgccgac    3720
tacgaggcgt catcctcccg ctgcagtagc gcctccccgg ccggggacag cctttcctac    3780
taccattccc cagccgactc cttctccagc atgggctctc ctgtcaacac acaggtgagt    3840
ttggctttgt gtagccgcca ggtccgcgct gagggtcgcc gtggaggaga cactggggtg    3900
tgactcgcag gggcggggg gtcttccttt ttcgctctgg agggagactg gcgcggtcag    3960
agcagcctta gcctgggaac caggacttg tctgagcgcg tgcacacttg tcatagtaag    4020
acttagtgac cccttcccgc gcggcaggtt tattctgagt ggcctgcctg cattcttctc    4080
tcggccgact tgtttctgag atcagccggg gccaacaagt ctcgagcaaa gagtcgctaa    4140
ctagagtttg ggaggcggca aaccgcggca atccccctc ccggggcagc ctggagcagg    4200
gaggagggag gagggaggag ggtgctgcgg gcgggtgtgt aaggcagttt cattgataaa    4260
aagcgagttc attctggaga ctccggagca gcgcctgcgt cagcgcagac gtcagggata    4320
tttataacaa accccctttc gagcgagtga tgccgaaggg ataacgggaa cgcagcagta    4380
ggatggagga gaaaggctgc gctgcggaat tcaaggaggg atattgggag agcttttatc    4440
tccgatgagg tgcatacagg aagacataag cagtctctga ccggaatgct tctctctccc    4500
tgcttcatgc gacactaggg ccacttgctc cacctgtgtc tggaacctcc tcgctcacct    4560
ccgctttcct ctttttgttt tgtttcagga cttttgcgca gatctgtccg tctctagtgc    4620
caactttatc cccacggtga cagccatctc caccagccca gacctgcagt ggctggtgca    4680
gcccactctg gtctcctccg tggccccatc gcagaccaga gcgcccatc cttacggact    4740 ccccacccag tctgctgggg cttacgccag agcgggaatg tgtgaagaccg tgtcaggagg    4800 cagagcgcag agcatcggca gaaggggcaa agtagagcag gtgagcagcg attctggacc    4860
tttgtgggct ggggggggg gggggggcgg agactgacgc acagaccaca caacagagaa    4920
gggacgctac tgactgcact tcctgaccag gagctgtggc tgctagccct ttccctccct    4980
tgtcagattt tgacagttgg acccaagaca aactctagac agtttccctg acagcttcct    5040
acttcattct ctagccgggg agcttctttg ttccctgct aaagatctca ctttaaatgc    5100
aaatcacact ctgcctgcca actgcaggtt agaaaaactg cttcaccgag aggtgcgggt    5160
gctgtaggag ccagttcac tggggtgact gaatggaggt gacactagac aaccttaact    5220
gaatgttggt cctttcttc tatagctatc tcctgaagag aagagaaac ggagaatccg    5280 aagggaacgg aataagatgg ctgcagccaa gtgccggaat cggaggaggg agctgacaga    5340
tacactccaa gcggtaggtt gaaccagctg ctgctcctga aactttatta aagttggagc    5400
ttgggactat gggcgcaggg tccttgagca tgcccgtgtc ttatgctttc ttatatctct    5460
ccctatgcag gagacagatc aacttgaaga tgagaagtct gcggtgcaga ctgagattgc    5520
caatgccctg aaagagaagg aaaaagtgga gtttattttg gcagcccacc gacctgcctg    5580
caagatcccc gatgaccttg gcttcccaga ggagatgtct gtggcctccc tggattttgac    5640 tggaggtctg cctgaggctt ccaccccaga gtctgaggag ccttcaccc tgccccttct    5700 caacgaccct gagcccaagc catccttgga gccagtcaag agcatcagca acgtggagct    5760
gaaggcagaa cccttttgatg acttcttgtt tccggcatca tctaggccca gtggctcaga    5820
gacctcccgc tctgtgccag atgtggacct gtccggttcc ttctatgcag cagactggga    5880
gcctctgcac agcaattcct tggggatggg gcccatggag cagaagctga tctccgagga    5940
```

```
ggacctggag cagaagctga tctccgagga ggacctgggc aacggaaatg gcaatggaaa    6000
cggcaatggc aacggaaatg gaaactctag actggacaag agcaaagtca taaactctgc    6060
tctggaatta ctcaatgaag tcggtatcga aggcctgacg acaaggaaac tcgctcaaaa    6120
gctgggagtt gagcagccta ccctgtactg gcacgtgaag aacaagcggg ccctgctcga    6180
tgccctggca atcgagatgc tggacaggca tcatacccac ttctgccccc tggaaggcga    6240
gtcatggcaa gactttctgc ggaacaacgc caagtcattc cgctgtgctc tcctctcaca    6300
tcgcgacggg gctaaagtgc atctcggcac ccgcccaaca gagaaacagt acgaaaccct    6360
ggaaaatcag ctcgcgttcc tgtgtcagca aggcttctcc ctggagaacg cactgtacgc    6420
tctgtccgcc gtgggccact ttacactggg ctgcgtattg gaggatcagg agcatcaagt    6480
agcaaaagag gaaagagaga cacctaccac cgattctatg cccccacttc tgagacaagc    6540
aattgagctg ttcgaccatc agggagccga acctgccttc cttttcggcc tggaactaat    6600
catatgtggc ctggagaaac agctaaagtg cgaaagcggc gggccggccg acgcccttga    6660
cgattttgac ttagacatgc tcccagccga tgcccttgac gactttgacc ttgatatgct    6720
gcctgctgac gctcttgacg attttgacct tgacatgctc cccgggtaaa cgcgtggcgc    6780
gccagctcgc tgatcagcct cgactgtgcc ttctagttgc cagccatctg ttgtttgccc    6840
ctcccccgtg ccttccttga ccctggaagg tgccactccc actgtccttt cctaataaaa    6900
tgaggaaatt gcatcgcatt gtctgagtag gtgtcattct attctggggg gtggggtggg    6960
gcaggacagc aagggggagg attgggaaga caatagcagg catgctgggg atgcggtggg    7020
ctctatggct tctgaggcgg aaagaaccag ctggggctcg aaggtacctc gagagcggcc    7080
gcaggaaccc ctagtgatgg agttggccac tccctctctg cgcgctcgct cgctcactga    7140
ggccgggcga ccaaaggtcg cccgacgccc gggctttgcc cggcggcct cagtgagcga    7200 gcgagcgcgc agctgcctgc agg                                            7223

<210> SEQ ID NO 2
<211> LENGTH: 154
<212> TYPE: DNA
<213> ORGANISM: Artificial Sequence
<220> FEATURE:
<223> OTHER INFORMATION: Upstream 5' pA

<400> SEQUENCE: 2
aataaaatat ctttattttc attacatctg tgtgttggtt ttttgtgtga atcgatagta     60
ctaacatacg ctctccatca aaacaaaacg aaacaaaaca aactagcaaa ataggctgtc    120
cccagtgcaa gtgcaggtgc cagaacattt ctct                                154

<210> SEQ ID NO 3
<211> LENGTH: 1709
<212> TYPE: DNA
<213> ORGANISM: Artificial Sequence
<220> FEATURE:
<223> OTHER INFORMATION: fos coding sequence

<400> SEQUENCE: 3
caagctttcc tttaggaaca gaggcttcga gcctttaagg ctgcgtactt gcttctccta     60
ataccagaga ctcaaaaaaa aaaaaaagt tccagattgc tggacaatga cccgggtctc    120
atcccttgac cctggaacc gggtccacat tgaatcaggt gcgaatgttc gctcgccttc    180
tctgcctttc ccgcctcccc tccccgggcc gcggccccgg ttccccccct gcgctgcacc    240
ctcagagttg gctgcagccg cgagctgttt cccgtcaatc cctccctcct ttacacagga    300
```

```
tgtccatatt aggacatctg cgtcagcagg tttccacggc cggtccctgt tgttctgggg      360
ggggaccat ctccgaaatc ctacacgcgg aaggtctagg agacccccta agatcccaaa       420
tgtgaacact cataggtgaa agatgtatgc caagacgggg gttgaaagcc tggggcgtag      480
agttgacgac agagcgcccg cagagggcct tggggcgcgc ttccccccc ttccagttcc       540
gcccagtgac gtaggaagtc catccattca cagcgcttct ataaaggcgc cagctgaggc      600
gcctactact ccaaccgcga ctgcagcgag caactgagaa gactggatag agccggcggt     660
tccgcgaacg agcagtgacc gcgctcccac ccagctctgc tctgcagctc ccaccagtgt     720
ctaccctgg acccttgcc gggctttccc caaacttcga ccatgatgtt ctcgggtttc        780
aacgccgact acgaggcgtc atcctcccgc tgcagtagcg cctccccggc cggggacagc     840
ctttcctact accattcccc agccgactcc ttctccagca tgggctctcc tgtcaacaca    900
caggactttt gcgcagatct gtccgtctct agtgccaact ttatccccac ggtgacagcc    960
atctccacca gccagacct gcagtggctg gtgcagccca ctctggtctc ctccgtggcc      1020
ccatcgcaga ccagagcgcc ccatccttac ggactcccca cccagtctgc tggggcttac   1080
gccagagcgg gaatggtgaa gaccgtgtca ggaggcagag cgcagagcat cggcagaagg   1140
ggcaaagtag agcagctatc tcctgaagag gaagagaaac ggagaatccg aagggaacgg   1200
aataagatgg ctgcagccaa gtgccggaat cggaggaggg agctgacaga tacactccaa   1260
gcgagacaga tcaacttgaa gatgagaagt ctgcggtgca gactgagatt gccaatgccc   1320
tgaaagagaa ggaaaaagtg gagtttattt tggcagccca ccgacctgcc tgcaagatcc   1380
ccgatgacct tggcttccca gaggagatgt ctgtggcctc cctggatttg actggaggtc   1440
tgcctgaggc ttccaccca gagtctgagg aggccttcac cctgccccttt ctcaacgacc   1500
ctgagcccaa gccatccttg gagccagtca agagcatcag caacgtggag ctgaaggcag   1560
aaccctttga tgacttcttg tttccggcat catctaggcc cagtggctca gagacctccc   1620
gctctgtgcc agatgtggac ctgtccggtt ccttctatgc agcagactgg gagcctctgc   1680
acagcaattc cttggggatg gggcccatg                                       1709
```

<210> SEQ ID NO 4
<211> LENGTH: 623
<212> TYPE: DNA
<213> ORGANISM: Artificial Sequence
<220> FEATURE:
<223> OTHER INFORMATION: cfos Promoter

<400> SEQUENCE: 4

```
caagctttcc tttaggaaca gaggcttcga gcctttaagg ctgcgtactt gcttctccta      60
ataccagaga ctcaaaaaaa aaaaaaaagt tccagattgc tggacaatga cccgggtctc    120
atcccttgac cctgggaacc gggtccacat tgaatcaggt gcgaatgttc gctcgccttc    180
tctgcctttc ccgcctcccc tccccgggcc gcggccccgg ttccccccct gcgctgcacc    240
ctcagagttg gctgcagccg gcgagctgtt cccgtcaatc cctccctcct ttacacagga    300
tgtccatatt aggacatctg cgtcagcagg tttccacggc cggtccctgt tgttctgggg    360
ggggaccat ctccgaaatc ctacacgcgg aaggtctagg agacccccta agatcccaaa     420
tgtgaacact cataggtgaa agatgtatgc caagacgggg gttgaaagcc tggggcgtag    480
agttgacgac agagcgcccg cagagggcct tggggcgcgc ttccccccc ttccagttcc     540
gcccagtgac gtaggaagtc catccattca cagcgcttct ataaaggcgc cagctgaggc    600
```

```
gcctactact ccaaccgcga ctg                                          623
```

<210> SEQ ID NO 5
<211> LENGTH: 280
<212> TYPE: DNA
<213> ORGANISM: Artificial Sequence
<220> FEATURE:
<223> OTHER INFORMATION: Fos Exon I

<400> SEQUENCE: 5

```
cagcgagcaa ctgagaagac tggatagagc cggcggttcc gcgaacgagc agtgaccgcg    60
ctcccaccca gctctgctct gcagctccca ccagtgtcta cccctggacc ccttgccggg   120 cttccccaa acttcgacca tgatgttctc gggtttcaac gccgactacg aggcgtcatc    180
ctcccgctgc agtagcgcct ccccggccgg ggacagcctt cctactacc attccccagc    240 cgactccttc tccagcatgg gctctcctgt caacacacag                         280
```

<210> SEQ ID NO 6
<211> LENGTH: 252
<212> TYPE: DNA
<213> ORGANISM: Artificial Sequence
<220> FEATURE:
<223> OTHER INFORMATION: Fos Exon II

<400> SEQUENCE: 6

```
gactttgcg cagatctgtc cgtctctagt gccaacttta tccccacggt gacagccatc     60
tccaccagcc cagacctgca gtggctggtg cagcccactc tggtctcctc cgtggcccca   120
tcgcagacca gagcgcccca tccttacgga ctccccaccc agtctgctgg ggcttacgcc   180
agagcgggaa tggtgaagac cgtgtcagga ggcagagcgc agagcatcgg cagaaggggc   240
aaagtagagc ag                                                       252
```

<210> SEQ ID NO 7
<211> LENGTH: 107
<212> TYPE: DNA
<213> ORGANISM: Artificial Sequence
<220> FEATURE:
<223> OTHER INFORMATION: Fos Exon III

<400> SEQUENCE: 7

```
ctatctcctg aagaggaaga gaaacggaga atccgaaggg aacggaataa gatggctgca    60
gccaagtgcc ggaatcggag gagggagctg acagatacac tccaagc                 107
```

<210> SEQ ID NO 8
<211> LENGTH: 447
<212> TYPE: DNA
<213> ORGANISM: Artificial Sequence
<220> FEATURE:
<223> OTHER INFORMATION: Fos Exon IV

<400> SEQUENCE: 8

```
gagacagatc aacttgaaga tgagaagtct gcggtgcaga ctgagattgc caatgccctg    60
aaagagaagg aaaaagtgga gtttatttg gcagcccacc gacctgcctg caagatcccc   120
gatgaccttg gcttcccaga ggagatgtct gtggcctccc tggatttgac tggaggtctg   180
cctgaggctt ccaccccaga gtctgaggag gccttcaccc tgccccttct caacgaccct   240
gagcccaagc catccttgga gccagtcaag agcatcagca acgtggagct gaaggcagaa   300
ccctttgatg acttcttgtt tccggcatca tctaggccca gtggctcaga gacctcccgc   360
tctgtgccag atgtggacct gtccggttcc ttctatgcag cagactggga gcctctgcac   420
```
agcaattcct tgggatgggg gcccatg                                           447

<210> SEQ ID NO 9
<211> LENGTH: 30
<212> TYPE: DNA
<213> ORGANISM: Artificial Sequence
<220> FEATURE:
<223> OTHER INFORMATION: Myc #1

<400> SEQUENCE: 9
gagcagaagc tgatctccga ggaggacctg                                        30

<210> SEQ ID NO 10
<211> LENGTH: 48
<212> TYPE: DNA
<213> ORGANISM: Artificial Sequence
<220> FEATURE:
<223> OTHER INFORMATION: Linker

<400> SEQUENCE: 10
ggcaacggaa atggcaatgg aaacggcaat ggcaacggaa atggaaac                    48

<210> SEQ ID NO 11
<211> LENGTH: 741
<212> TYPE: DNA
<213> ORGANISM: Artificial Sequence
<220> FEATURE:
<223> OTHER INFORMATION: tTA

<400> SEQUENCE: 11
tctagactgg acaagagcaa agtcataaac tctgctctgg aattactcaa tgaagtcggt        60
atcgaaggcc tgacgacaag gaaactcgct caaaagctgg gagttgagca gcctaccctg       120
tactggcacg tgaagaacaa gcgggccctg ctcgatgccc tggcaatcga gatgctggac       180
aggcatcata cccacttctg cccccctgga aggcgagtca tggcaagactt tctgcggaac      240 aacgccaagt cattccgctg tgctctcctc tcacatcgcg acggggctaa agtgcatctc       300
ggcacccgcc caacagagaa acagtacgaa accctggaaa atcagctcgc gttcctgtgt       360
cagcaaggct tctccctgga gaacgcactg tacgctctgt ccgccgtggg ccactttaca       420
ctgggctgcg tattggagga tcaggagcat caagtagcaa agaggaaag agagacacct        480 accaccgatt ctatgcccc acttctgaga caagcaattg agctgttcga ccatcaggga       540
gccgaacctg ccttcctttt cggcctggaa ctaatcatat gtggcctgga gaacagcta       600 aagtgcgaaa gcggcgggcc ggccgacgcc cttgacgatt ttgacttaga catgctccca       660
gccgatgccc ttgacgactt tgaccttgat atgctgcctg ctgacgctct tgacgatttt       720
gaccttgaca tgctccccgg g                                                 741

<210> SEQ ID NO 12
<211> LENGTH: 1935
<212> TYPE: DNA
<213> ORGANISM: Artificial Sequence
<220> FEATURE:
<223> OTHER INFORMATION: FmTB converter

<400> SEQUENCE: 12
cagcgagcaa ctgagaagac tggatagagc cggcggttcc gcgaacgagc agtgaccgcg        60
ctcccaccca gctctgctct gcagctccca ccagtgtcta cccctggacc ccttgccggg       120
cttttcccca acttcgacca tgatgttctc gggtttcaac gccgactacg aggcgtcatc       180

| | |
|---|---|
| ctcccgctgc agtagcgcct ccccggccgg ggacagcctt tcctactacc attccccagc | 240 |
| cgactccttc tccagcatgg gctctcctgt caacacacag gacttttgcg cagatctgtc | 300 |
| cgtctctagt gccaacttta tccccacggt gacagccatc tccaccagcc cagacctgca | 360 |
| gtggctggtg cagcccactc tggtctcctc cgtggcccca tcgcagacca gagcgcccca | 420 |
| tccttacgga ctccccaccc agtctgctgg ggcttacgcc agagcgggaa tggtgaagac | 480 |
| cgtgtcagga ggcagagcgc agagcatcgg cagaaggggc aaagtagagc agctatctcc | 540 |
| tgaagaggaa gagaaacgga gaatccgaag ggaacggaat aagatggctg cagccaagtg | 600 |
| ccggaatcgg aggagggagc tgacagatac actccaagcg agacagatca acttgaagat | 660 |
| gagaagtctg cggtgcagac tgagattgcc aatgccctga agagaaggaa aaagtggag | 720 |
| tttattttgg cagcccaccg acctgcctgc aagatccccg atgaccttgg cttcccagag | 780 |
| gagatgtctg tggcctccct ggatttgact ggaggtctgc ctgaggcttc caccccagag | 840 |
| tctgaggagg ccttcaccct gccccttctc aacgaccctg agcccaagcc atccttggag | 900 |
| ccagtcaaga gcatcagcaa cgtggagctg aaggcagaac cctttgatga cttcttgttt | 960 |
| ccggcatcat ctaggcccag tggctcagag acctcccgct ctgtgccaga tgtggacctg | 1020 |
| tccggttcct tctatgcagc agactgggag cctctgcaca gcaattcctt ggggatgggg | 1080 |
| cccatggagc agaagctgat ctccgaggag gacctggagc agaagctgat ctccgaggag | 1140 |
| gacctgggca acggaaatgg caatggaaac ggcaatggca acggaaatgg aaactctaga | 1200 |
| ctggacaaga gcaaagtcat aaactctgct ctggaattac tcaatgaagt cggtatcgaa | 1260 |
| ggcctgacga caaggaaact cgctcaaaag ctgggagttg agcagcctac cctgtactgg | 1320 |
| cacgtgaaga acaagcgggc cctgctcgat gccctggcaa tcgagatgct ggacaggcat | 1380 |
| catacccact tctgccccct ggaaggcgag tcatggcaag actttctgcg gaacaacgcc | 1440 |
| aagtcattcc gctgtgctct cctctcacat cgcgacgggg ctaaagtgca tctcggcacc | 1500 |
| cgcccaacag agaaacagta cgaaaccctg gaaaatcagc tcgcgttcct gtgtcagcaa | 1560 |
| ggcttctccc tggagaacgc actgtacgct ctgtccgccg tgggccactt tacactgggc | 1620 |
| tgcgtattgg aggatcagga gcatcaagta gcaaaagagg aaagagagac acctaccacc | 1680 |
| gattctatgc ccccacttct gagacaagca attgagctgt cgaccatca gggagccgaa | 1740 |
| cctgccttcc ttttcggcct ggaactaatc atatgtggcc tggagaaaca gctaaagtgc | 1800 |
| gaaagcggcg ggccggccga cgcccttgac gattttgact tagacatgct cccagccgat | 1860 |
| gcccttgacg actttgacct tgatatgctg cctgctgacg ctcttgacga ttttgacctt | 1920 |
| gacatgctcc ccggg | 1935 |

<210> SEQ ID NO 13
<211> LENGTH: 1008
<212> TYPE: DNA
<213> ORGANISM: Artificial Sequence
<220> FEATURE:
<223> OTHER INFORMATION: rtTA

<400> SEQUENCE: 13

| | |
|---|---|
| ctacccaccg tactcgtcaa ttccaagggc atcggtaaac atctgctcaa actcgaagtc | 60 |
| ggccatatcc agagcgccgt aggggcgga gtcgtggggg gtaaatcccg gacccgggga | 120 |
| atccccgtcc cccaacatgt ccagatcgaa atcgtctagc gcgtcggcat gcgccatcgc | 180 |
| cacgtcctcg ccgtctaagt ggagctcgtc ccccaggctc acatcggtcg gggggccgt | 240 |
| cgacagtctg cgcgtgtgtc ccgcggggag aaaggacagg cgcggagccg ccagccccgc | 300 |

```
ctcttcgggg gcgtcgtcgt ccgggagatc gagcaggccc tcgatggtag acccgtaatt      360
gtttttcgta cgcgcgcggc tgtacgcgga cccactttca catttaagtt gtttttctaa      420
tccgcatatg atcaattcaa ggccgaataa gaaggctggc tctgcacctt ggtgatcaaa      480
taattcgata gcttgtcgta ataatggcgg catactatca gtagtaggtg tttccctttc      540
ttctttagcg acttgatgct cttgatcttc caatacgcaa cctaaagtaa aatgccccac      600
agcgctgagt gcatataacg cgttctctag tgaaaaacct tgttggcata aaaggctaa       660 ttgattttcg agagtttcat actgtttttc tgtaggccgt gtatctgaat gtacttttgc      720
tccattgcga tgacttagta aagcacatct aaaactttta gcgttattgc gtaaaaaatc      780
ttgccagctt tccccttta aagggcaaaa gtgagtatgg tgcctatcta acatctcaat      840
ggctaaggcg tcgagcaaag cccgcttatt ttttacatgc aatacagtg taggctgctc       900 tacaccaagc ttctgggcga gtttacgggt tgttaaacct tcgattccga cctcattaag      960
cagctctaat gcgctgttaa tcactttact tttatctaat ctagacat                  1008
```

<210> SEQ ID NO 14
<211> LENGTH: 279
<212> TYPE: DNA
<213> ORGANISM: Artificial Sequence
<220> FEATURE:
<223> OTHER INFORMATION: BGHpA from IRES-EGFP

<400> SEQUENCE: 14

```
agctcgctga tcagcctcga ctgtgccttc tagttgccag ccatctgttg tttgcccctc       60
ccccgtgcct tccttgaccc tggaaggtgc cactcccact gtcctttcct aataaaatga      120
ggaaattgca tcgcattgtc tgagtaggtg tcattctatt ctgggggtg gggtggggca       180 ggacagcaag ggggaggatt gggaagacaa tagcaggcat gctggggatg cggtgggctc      240
tatggcttct gaggcggaaa gaaccagctg gggctcgaa                             279
```

<210> SEQ ID NO 15
<211> LENGTH: 7186
<212> TYPE: DNA
<213> ORGANISM: Artificial Sequence
<220> FEATURE:
<223> OTHER INFORMATION: FRR-ChR2-YFP

<400> SEQUENCE: 15

```
acatgtgagc aaaaggccag caaaaggcca ggaaccgtaa aaaggccgcg ttgctggcgt       60
ttttccatag gctccgcccc cctgacgagc atcacaaaaa tcgacgctca agtcagaggt      120
ggcgaaaccc gacaggacta taaagatacc aggcgtttcc ccctggaagc tccctcgtgc      180
gctctcctgt tccgaccctg ccgcttaccg gatacctgtc cgcctttctc ccttcgggaa      240
gcgtggcgct ttctcatagc tcacgctgta ggtatctcag ttcggtgtag gtcgttcgct      300
ccaagctggg ctgtgtgcac gaaccccccg ttcagcccga ccgctgcgcc ttatccggta      360
actatcgtct tgagtccaac ccggtaagac acgacttatc gccactggca gcagccactg      420
gtaacaggat tagcagagcg aggtatgtag gcggtgctac agagttcttg aagtggtggc      480
ctaactacgg ctacactaga aggacagtat ttggtatctg cgctctgctg aagccagtta      540
ccttcggaaa aagagttggt agctcttgat ccggcaaaca aaccaccgct ggtagcggtg      600
gtttttttgt ttgcaagcag cagattacgc gcagaaaaaa aggatctcaa gaagatcctt      660
tgatcttttc tacggggtct gacgctcagt ggaacgaaaa ctcacgttaa gggattttgg      720
```

```
tcatgagatt atcaaaaagg atcttcacct agatccttt  aaattaaaaa tgaagttta      780
aatcaatcta aagtatatat gagtaaactt ggtctgacag ttaccaatgc ttaatcagtg      840
aggcacctat ctcagcgatc tgtctatttc gttcatccat agttgcctga ctccccgtcg      900
tgtagataac tacgatacgg gagggcttac catctggccc cagtgctgca atgataccgc      960
gagacccacg ctcaccggct ccagatttat cagcaataaa ccagccagcc ggaagggccg     1020
agcgcagaag tggtcctgca actttatccg cctccatcca gtctattaat tgttgccggg     1080
aagctagagt aagtagttcg ccagttaata gtttgcgcaa cgttgttgcc attgctacag     1140
gcatcgtggt gtcacgctcg tcgtttggta tggcttcatt cagctccggt tcccaacgat     1200
caaggcgagt tacatgatcc cccatgttgt gcaaaaaagc ggttagctcc ttcggtcctc     1260
cgatcgttgt cagaagtaag ttggccgcag tgttatcact catggttatg gcagcactgc     1320
ataattctct tactgtcatg ccatccgtaa gatgctttc tgtgactggt gagtactcaa     1380
ccaagtcatt ctgagaatag tgtatgcggc gaccgagttg ctcttgcccg cgtcaatac     1440
gggataatac cgcgccacat agcagaactt taaaagtgct catcattgga aaacgttctt     1500
cggggcgaaa actctcaagg atcttaccgc tgttgagatc cagttcgatg taacccactc     1560
gtgcacccaa ctgatcttca gcatctttta ctttcaccag cgtttctggg tgagcaaaaa     1620
caggaaggca aaatgccgca aaaaagggaa taagggcgac acggaaatgt tgaatactca     1680
tactcttcct ttttcaatat tattgaagca tttatcaggg ttattgtctc atgagcggat     1740
acatatttga atgtatttag aaaaataaac aaataggggt tccgcgcaca tttccccgaa     1800
aagtgccacc tgacgtctaa gaaaccatta ttatcatgac attaacctat aaaaataggc     1860
gtatcacgag gcccttcgt ctcgcgcgtt tcggtgatga cggtgaaaac ctctgacaca     1920
tgcagctccc ggagacggtc acagcttgtc tgtaagcgga tgccgggagc agacaagccc     1980
gtcagggcgc gtcagcgggt gttggcgggt gtcgggctg gcttaactat gcggcatcag     2040
agcagattgt actgagagtg caccataaaa ttgtaaacgt taatattttg ttaaaattcg     2100
cgttaaattt ttgttaaatc agctcatttt ttaaccaata ggccgaaatc ggcaaaatcc     2160
cttataaatc aaaagaatag cccgagatag ggttgagtgt tgttccagtt tggaacaaga     2220
gtccactatt aaagaacgtg gactccaacg tcaagggcg aaaaaccgtc tatcagggcg     2280
atggcccact acgtgaacca tcacccaaat caagttttt ggggtcgagg tgccgtaaag     2340
cactaaatcg gaaccctaaa gggagccccc gatttagagc ttgacgggga agccggcga     2400
acgtggcgag aaaggaaggg aagaaagcga aaggagcggg cgctaggcg ctggcaagtg     2460
tagcggtcac gctgcgcgta accaccacac ccgccgcgct taatgcgccg ctacagggcg     2520
cgtactatgg ttgcttgac gtatgcggtg tgaaataccg cacagatgcg taaggagaaa     2580
ataccgcatc aggcgcccct gcaggcagct gcgcgctcgc tcgctcactg aggccgcccg     2640
ggcaaagccc gggcgtcggg cgaccttgg tcgcccggcc tcagtgagcg agcgagcgcg     2700
cagagaggga gtgccaact ccatcactag gggttcctgc ggccgcacct taattaaacg     2760
cgtctagtta ttaatagtaa tcaattacgg ggtcattagt tcatagccca tatatggagt     2820
tccgcgttac ataacttacg gtaaatggcc cgcctggctg accgcccaac gacccccgcc     2880
cattgacgtc aataatgacg tatgttccca tagtaacgcc aatagggact ttccattgac     2940
gtcaatgggt ggagtattta cggtaaactg cccacttggc agtacatcaa gtgtatcata     3000
tgccaagtac gcccctattt gacgtcaatg acggtaaatg gcccgctgg cattatgccc     3060
agtacatgac cttatgggac tttcctactt ggcagtacat ctacgtatta gtcatcgcta     3120
```

```
ttaccatggt gatgcggttt tggcagtaca tcaatgggcg tggatagcgg tttgactcac    3180
ggggatttcc aagtctccac cccattgacg tcaatgggag tttgttttgg caccaaaatc    3240
aacgggactt tccaaaatgt cgtaacaact ccgccccatt gacgcaaatg ggcggtaggc    3300
gtgtacggtg gaggtctat ataagcagag ctcgtttagt gaaccgtcag atcgcctgga    3360
gacgccatcc acgctgtttt gacctccata gaagacaccg ggaccgatcc agcctcaccg    3420
gtagaggatc cagagaattc gaagttccta ttctctagaa agtataggaa cttcgtcgac    3480
agaactagtc accatgtcca gactggacaa gagcaaagtc ataaacggag ctctggaatt    3540
actcaatggt gtcggtatcg aaggcctgac gacaaggaaa ctcgctcaaa agctgggagt    3600
tgagcagcct accctgtact ggcacgtgaa gaacaagcgg ccctgctcg atgccctgcc    3660 aatcgagatg ctggacaggc atcataccca cttctgcccc ctggaaggcg agtcatggca    3720
agactttctg cggaacaacg ccaagtcata ccgctgtgct ctcctctcac atcgcgacgg    3780
ggctaaagtg catctcggca cccgcccaac agagaaacag tacgaaaccc tggaaaatca    3840
gctcgcgttc ctgtgtcagc aaggcttctc cctggagaac gcactgtacg ctctgtccgc    3900
cgtgggccac tttacactgg gctgcgtatt ggaggaacag gagcatcaag tagcaaaaga    3960
ggaaagagag acacctacca ccgattctat gcccccactt ctgagacaag caattgagct    4020
gttcgaccgg cagggagccg aacctgcctt ccttttcggc ctggaactaa tcatatgtgg    4080
cctggagaaa cagctaaagt gcgaaagcgg gtcgccaaaa agaagagaa aggtggacgg    4140 cggtggtgct ttgtctcctc agcactctgc tgtcactcaa ggaagtatca tcaagaacaa    4200
ggagggcatg gatgctaagt cactaactgc ctggtcccgg acactggtga ccttcaagga    4260
tgtatttgtg gacttcacca gggaggagtg gaagctgctg gacactgctc agcagatcgt    4320
gtacagaaat gtgatgctgg agaactataa gaacctggtt tccttgggtt atcagcttac    4380
taagccagat gtgatcctcc ggttggaaaa gggagaagag ccctggctgg tggagagaga    4440
aattcaccaa gagacccatc ctgattcaga gactgcattt gaaatcaaat catcagttta    4500
aggtacctca cttgtacagc tcgtccatgc cgagagtgat cccggcggcg gtcacgaact    4560
ccagcaggac catgtgatcg cgcttctcgt tggggtcttt gctcagggcg gactggtagc    4620
tcaggtagtg gttgtcgggc agcagcacgg ggccgtcgcc gatgggggtg ttctgctggt    4680
agtggtcggc gagctgcacg ctgccgtcct cgatgttgtg gcggatcttg aagttcacct    4740
tgatgccgtt cttctgcttg tcggccatga tatagacgtt gtggctgttg tagttgtact    4800
ccagcttgtg ccccaggatg ttgccgtcct ccttgaagtc gatgcccttc agctcgatgc    4860
ggttcaccag ggtgtcgccc tcgaacttca cctcggcgcg gtcttgtag ttgccgtcgt    4920 ccttgaagaa gatggtgcgc tcctggacgt agccttcggg catggcggac ttgaagaagt    4980
cgtgctgctt catgtggtcg gggtagcggg cgaagcactg caggccgtag ccgaaggtgg    5040
tcacgagggt gggccaggc acgggcagct tgccggtggt gcagatgaac ttcagggtca    5100
gcttgccgta ggtggcatcg ccctcgccct cgccggacac gctgaacttg tggccgttta    5160
cgtcgccgtc cagctcgacc aggatgggca ccaccccggt gaacagctcc tcgcccttgc    5220
tcaccgtaga atcgagaccg aggagagggt tagggatagg cttccctggc acggctccgg    5280
cctcggcttc gtcttcgacg agagtctcga cctcgatctc cgttccgccg atgttcagtt    5340
tggtggtttt gcggatatct ccgtgaatca atatgtgctc gtggatcagg acgcgcaggt    5400
agtgtcccaa caaccccccaa caatttttac tcatcagatc aataatcgtg tgacctacgg    5460
```

| | |
|---|---|
| tggagccata gacgctcagg acgccaaaac cttcgggccc caaaatgaag agaattggga | 5520 |
| acataccca gctcacgaaa aacagccatg ccatgccggt cacgacctgg cggcaccgac | 5580 |
| cctttggcac agtatgataa ccctcgatat atgctttggc ggcgtgaaaa aatgtgttcg | 5640 |
| cgccatagca caatccaaga caaaagaaga tgactttaac atagccggtt gccatggcgc | 5700 |
| tggtagcccc ccacacgata gtcccgatgt ctgagacaag gagtcccatg gttctcctgc | 5760 |
| tgtagtcgtt gctcaggccg gtgaggttgc tcaggcggat aaggatgaca ggacaagtga | 5820 |
| gcagccactc tgcatagcgc agccactgca cccggtgtcc tgtggcaagg tagagcatag | 5880 |
| agggattctt aaactcaaaa aagaactcga gaatcacctt aaccatttca atggcgcaca | 5940 |
| catagatctc ctcccagccg catgtagatt tccaggtttg gtaggcatag aacatcagca | 6000 |
| gcaaaatgct gaatcctgct gcaagccact gcaggacatt tgacgcggtc tgagcgccgt | 6060 |
| tcgtgccgcg agattcaatc catccggcac agtaacattg atcctcaggg accaggacgg | 6120 |
| acccgttcac caccacagga ttagtaacga acaaaagttc gcgtccgacg gcagacaaag | 6180 |
| cgccgccata gtccatggtg gctagcgaag ttcctatact ttctagagaa taggaacttc | 6240 |
| ggcgcgccga taatcaacct ctggattaca aaatttgtga agattgact ggtattctta | 6300 |
| actatgttgc tcctttacg ctatgtggat acgctgcttt aatgcctttg tatcatgcta | 6360 |
| ttgcttcccg tatggctttc attttctcct ccttgtataa atcctggttg ctgtctcttt | 6420 |
| atgaggagtt gtggcccgtt gtcaggcaac gtggcgtggt gtgcactgtg tttgctgacg | 6480 |
| caaccccac tggttgggc attgccacca cctgtcagct cctttccggg actttcgctt | 6540 |
| tccccctccc tattgccacg gcggaactca tcgccgcctg ccttgcccgc tgctggacag | 6600 |
| gggctcggct gttgggcact gacaattccg tggtgttgtc ggggaaatca tcgtcctttc | 6660 |
| cttggctgct cgcctgtgtt gccacctgga ttctgcgcgg gacgtccttc tgctacgtcc | 6720 |
| cttcggccct caatccagcg gaccttcctt cccgcggcct gctgccggct ctgcggcctc | 6780 |
| ttccgcgtct tcgccttcgc cctcagacga gtcggatctc cctttgggcc gcctccccgc | 6840 |
| atcgatcgag tgctttattt gtgaaatttg tgatactatt gctttatttg taaccattat | 6900 |
| aagctgcaat aaacaagtta acaacaacaa ttgcattcat tttattgttt caggttcagg | 6960 |
| gggaggtgtg ggaggttttt taaggggga gggggtacgt agataagtag catggcgggt | 7020 |
| taatcattaa ctcgagagcg gccgcaggaa ccctagtga tggagttggc cactccctct | 7080 |
| ctgcgcgctc gctcgctcac tgaggccggg cgaccaaagg tcgcccgacg cccgggcttt | 7140 |
| gcccgggcgg cctcagtgag cgagcgagcg cgcagctgcc tgcagg | 7186 |

<210> SEQ ID NO 16
<211> LENGTH: 142
<212> TYPE: DNA
<213> ORGANISM: Artificial Sequence
<220> FEATURE:
<223> OTHER INFORMATION: ITR-R

<400> SEQUENCE: 16

| | |
|---|---|
| ccctgcaggc agctgcgcgc tcgctcgctc actgaggccg cccgggcaaa gcccgggcgt | 60 |
| cgggcgacct ttggtcgccc ggcctcagtg agcgagcgag cgcgcagaga gggagtggcc | 120 |
| aactccatca ctaggggttc ct | 142 |

<210> SEQ ID NO 17
<211> LENGTH: 659
<212> TYPE: DNA
<213> ORGANISM: Artificial Sequence
<220> FEATURE:
<223> OTHER INFORMATION: CMV Promoter

<400> SEQUENCE: 17

```
acgcgtctag ttattaatag taatcaatta cggggtcatt agttcatagc ccatatatgg      60
agttccgcgt tacataactt acggtaaatg gcccgcctgg ctgaccgccc aacgacccc      120
gcccattgac gtcaataatg acgtatgttc ccatagtaac gccaataggg actttccatt    180
gacgtcaatg ggtggagtat ttacggtaaa ctgcccactt ggcagtacat caagtgtatc    240
atatgccaag tacgcccct attgacgtca atgacggtaa atggcccgcc tggcattatg     300
cccagtacat gaccttatgg gactttccta cttggcagta catctacgta ttagtcatcg   360
ctattaccat ggtgatgcgg ttttggcagt acatcaatgg gcgtggatag cggtttgact   420
cacggggatt tccaagtctc cacccccattg acgtcaatgg gagtttgttt tggcaccaaa  480
atcaacggga ctttccaaaa tgtcgtaaca actccgcccc attgacgcaa atgggcggta   540
ggcgtgtacg gtgggaggtc tatataagca gagctcgttt agtgaaccgt cagatcgcct   600
ggagacgcca tccacgctgt tttgacctcc atagaagaca ccgggaccga tccagcctc    659
```

<210> SEQ ID NO 18
<211> LENGTH: 34
<212> TYPE: DNA
<213> ORGANISM: Artificial Sequence
<220> FEATURE:
<223> OTHER INFORMATION: FRT

<400> SEQUENCE: 18

```
gaagttccta ttctctagaa agtataggaa cttc                                34
```

<210> SEQ ID NO 19
<211> LENGTH: 1008
<212> TYPE: DNA
<213> ORGANISM: Artificial Sequence
<220> FEATURE:
<223> OTHER INFORMATION: rtT3S

<400> SEQUENCE: 19

```
atgtccagac tggacaagag caaagtcata acggagctc tggaattact caatggtgtc      60
ggtatcgaag gcctgacgac aaggaaactc gctcaaaagc tgggagttga gcagcctacc   120
ctgtactggc acgtgaagaa caagcgggcc ctgctcgatg ccctgccaat cgagatgctg   180
gacaggcatc atacccactt ctgccccctg gaaggcgagt catggcaaga ctttctgcgg   240
aacaacgcca gtcataccg ctgtgctctc ctctcacatc gcgacggggc taaagtgcat    300
ctcggcaccc gcccaacaga gaaacagtac gaaaccctgg aaaatcagct cgcgttcctg   360
tgtcagcaag gcttctccct ggagaacgca ctgtacgctc tgtccgccgt gggccacttt   420
acactgggct gcgtattgga ggaacaggag catcaagtag caaaagagga agagagaca    480
cctaccaccg attctatgcc cccacttctg agacaagcaa ttgagctgtt cgaccggcag   540
ggagccgaac tgccttcct tttcggcctg gaactaatca tatgtggcct ggagaaacag    600
ctaaagtgcg aaagcgggtc gccaaaaaag aagagaaagg tggacggcgg tggtgctttg   660
tctcctcagc actctgctgt cactcaagga agtatcatca gaacaaggga gggcatggat   720
gctaagtcac taactgcctg gtcccggaca ctggtgacct tcaaggatgt atttgtggac   780
ttcaccaggg aggagtggaa gctgctggac actgctcagc agatcgtgta cagaaatgtg   840
atgctggaga actataagaa cctggttttcc ttgggttatc agcttactaa gccagatgtg   900
```

| | |
|---|---|
| atcctccggt tggagaaggg agaagagccc tggctggtgg agagagaaat tcaccaagag | 960 |
| acccatcctg attcagagac tgcatttgaa atcaaatcat cagtttaa | 1008 |

<210> SEQ ID NO 20
<211> LENGTH: 718
<212> TYPE: DNA
<213> ORGANISM: Artificial Sequence
<220> FEATURE:
<223> OTHER INFORMATION: YFP

<400> SEQUENCE: 20

| | |
|---|---|
| ctcacttgta cagctcgtcc atgccgagag tgatcccggc ggcggtcacg aactccagca | 60 |
| ggaccatgtg atcgcgcttc tcgttggggt ctttgctcag gcggactgg tagctcaggt | 120 |
| agtggttgtc gggcagcagc acggggccgt cgccgatggg ggtgttctgc tggtagtggt | 180 |
| cggcgagctg cacgctgccg tcctcgatgt tgtggcggat cttgaagttc accttgatgc | 240 |
| cgttcttctg cttgtcggcc atgatataga cgttgtggct gttgtagttg tactccagct | 300 |
| tgtgccccag gatgttgccg tcctccttga agtcgatgcc cttcagctcg atgcggttca | 360 |
| ccagggtgtc gccctcgaac ttcacctcgg cgcgggtctt gtagttgccg tcgtccttga | 420 |
| agaagatggt gcgctcctgg acgtagcctt cgggcatggc ggacttgaag aagtcgtgct | 480 |
| gcttcatgtg gtcggggtag cgggcgaagc actgcaggcc gtagccgaag gtggtcacga | 540 |
| gggtgggcca gggcacgggc agcttgccgg tggtgcagat gaacttcagg gtcagcttgc | 600 |
| cgtaggtggc atcgccctcg ccctcgccgg acacgctgaa cttgtggccg tttacgtcgc | 660 |
| cgtccagctc gaccaggatg ggcaccaccc cggtgaacag ctcctcgccc ttgctcac | 718 |

<210> SEQ ID NO 21
<211> LENGTH: 42
<212> TYPE: DNA
<213> ORGANISM: Artificial Sequence
<220> FEATURE:
<223> OTHER INFORMATION: V5 Epitope Tag

<400> SEQUENCE: 21

| | |
|---|---|
| cgtagaatcg agaccgagga gagggttagg gataggcttc cc | 42 |

<210> SEQ ID NO 22
<211> LENGTH: 930
<212> TYPE: DNA
<213> ORGANISM: Artificial Sequence
<220> FEATURE:
<223> OTHER INFORMATION: ChR2-H134R

<400> SEQUENCE: 22

| | |
|---|---|
| tggcacggct ccggcctcgg cttcgtcttc gacgagagtc tcgacctcga tctccgttcc | 60 |
| gccgatgttc agtttggtgg ttttgcggat atctccgtga atcaatatgt gctcgtggat | 120 |
| caggacgcgc aggtagtgtc ccaacaaccc ccaacaattt ttactcatca gatcaataat | 180 |
| cgtgtgacct acggtggagc catagacgct caggacgcca aaaccttcgg gccccaaaat | 240 |
| gaagagaatt gggaacatac cccagctcac gaaaaacagc catgccatgc cggtcacgac | 300 |
| ctggcggcac cgaccctttg gcacagtatg ataaccctcg atatatgctt ggcggcgtg | 360 |
| aaaaaatgtg ttcgcgccat agcacaatcc aagacaaaag aagatgactt taacatagcc | 420 |
| ggttgccatg cgctggtag ccccccacac gatagtcccg atgtctgaga caaggagtcc | 480 |
| catggttctc ctgctgtagt cgttgctcag gccggtgagg ttgctcaggc ggataaggat | 540 |
| gacaggacaa gtgagcagcc actctgcata gcgcagccac tgcacccggt gtcctgtggc | 600 |

```
aaggtagagc atagagggat tcttaaactc aaaaaagaac tcgagaatca ccttaaccat    660
ttcaatggcg cacacataga tctcctccca gccgcatgta gatttccagg tttggtaggc    720
atagaacatc agcagcaaaa tgctgaatcc tgctgcaagc cactgcagga catttgacgc    780
ggtctgagcg ccgttcgtgc cgcgagattc aatccatccg gcacagtaac attgatcctc    840
agggaccagg acggacccgt tcaccaccac aggattagta acgaacaaaa gttcgcgtcc    900
gacggcagac aaagcgccgc catagtccat                                     930

<210> SEQ ID NO 23
<211> LENGTH: 594
<212> TYPE: DNA
<213> ORGANISM: Artificial Sequence
<220> FEATURE:
<223> OTHER INFORMATION: WPRE

<400> SEQUENCE: 23
ccgataatca acctctggat tacaaaattt gtgaaagatt gactggtatt cttaactatg     60
ttgctccttt tacgctatgt ggatacgctg ctttaatgcc tttgtatcat gctattgctt    120
cccgtatggc tttcattttc tcctccttgt ataaatcctg gttgctgtct ctttatgagg    180
agttgtggcc cgttgtcagg caacgtggcg tggtgtgcac tgtgtttgct gacgcaaccc    240
ccactggttg gggcattgcc accacctgtc agctcctttc cgggactttc gctttccccc    300
tccctattgc cacggcggaa ctcatcgccg cctgccttgc ccgctgctgg acaggggctc    360
ggctgttggg cactgacaat tccgtggtgt tgtcggggaa atcatcgtcc tttccttggc    420
tgctcgcctg tgttgccacc tggattctgc gcgggacgtc cttctgctac gtcccttcgg    480
ccctcaatcc agcggacctt ccttcccgcg gcctgctgcc ggctctgcgg cctcttccgc    540
gtcttcgcct tcgccctcag acgagtcgga tctccctttg ggccgcctcc ccgc          594

<210> SEQ ID NO 24
<211> LENGTH: 135
<212> TYPE: DNA
<213> ORGANISM: Artificial Sequence
<220> FEATURE:
<223> OTHER INFORMATION: wtSV40pA+Mz

<400> SEQUENCE: 24
tgctttattt gtgaaatttg tgatactatt gctttatttg taaccattat aagctgcaat     60
aaacaagtta caacaacaa ttgcattcat tttattgttt caggttcagg gggaggtgtg    120
ggaggttttt taaag                                                    135

<210> SEQ ID NO 25
<211> LENGTH: 142
<212> TYPE: DNA
<213> ORGANISM: Artificial Sequence
<220> FEATURE:
<223> OTHER INFORMATION: ITR-L

<400> SEQUENCE: 25
caggaacccc tagtgatgga gttggccact ccctctctgc gcgctcgctc gctcactgag     60
gccgggcgac caaaggtcgc ccgacgcccg ggctttgccc gggcggcctc agtgagcgag    120
cgagcgcgca gctgcctgca gg                                            142

<210> SEQ ID NO 26
<211> LENGTH: 5933
<212> TYPE: DNA
```

<213> ORGANISM: Artificial Sequence
<220> FEATURE:
<223> OTHER INFORMATION: TRE-FLPo

<400> SEQUENCE: 26

```
cctgcaggca gctgcgcgct cgctcgctca ctgaggccgc ccgggcaaag cccgggcgtc      60
gggcgacctt tggtcgcccg gcctcagtga gcgagcgagc gcgcagagag ggagtggcca     120
actccatcac taggggttcc tgcggccgca cgcgtaacgc aataaaatat ctttattttc     180
attacatctg tgtgttggtt ttttgtgtga atcgatagta ctaacatacg ctctccatca     240
aaacaaaacg aaacaaaaca aactagcaaa ataggctgtc cccagtgcaa gtgcaggtgc     300
cagaacattt ctctatttct cgactggatc ccgagtttac tccctatcag tgatagagaa     360
cgtatgtcga gtttactccc tatcagtgat agagaacgat gtcgagttta ctccctatca     420
gtgatagaga acgtatgtcg agtttactcc ctatcagtga tagagaacgt atgtcgagtt     480
tactccctat cagtgataga gaacgtatgt cgagtttatc cctatcagtg atagagaacg     540
tatgtcgagt ttactcccta tcagtgatag agaacgtatg tcgaggtagg cgtgtacggt     600
gggaggccta taagcagagc tcgtttag tgaaccgtca gatcgccgct agccaccatg     660
gctcctaaga agaagaggaa ggtgatgagc cagttcgaca cctgtgcaa gacccccccc     720
aaggtgctgg tgcggcagtt cgtggagaga ttcgagaggc ccagcggcga aagatcgcc     780
agctgtgccg ccgagctgac ctacctgtgc tggatgatca cccacaacgg caccgccatc     840
aagagggcca ccttcatgag ctacaacacc atcatcagca acagcctgag cttcgacatc     900
gtgaacaaga gcctgcagtt caagtacaag acccagaagg ccaccatcct ggaggccagc     960
ctgaagaagc tgatccccgc ctgggagttc accatcatcc cttacaacgg ccagaagcac    1020
cagagcgaca tcaccgacat cgtgtccagc ctgcagctgc agttcgagag cagcgaggag    1080
gccgacaagg gcaacagcca gcagcaagaag atgctgaagg ccctgctgtc cgagggcgag    1140
agcatctggg agatcaccga aagatcctg aacagcttcg agtacaccag caggttcacc    1200
aagaccaaga ccctgtacca gttcctgttc ctggccacat tcatcaactg cggcaggttc    1260
agcgacatca gaacgtgga ccccaagagc ttcaagctgg tgcagaacaa gtacctgggc    1320
gtgatcattc agtgcctggt gaccgagacc aagacaagcg tgtccaggca catctacttt    1380
ttcagcgcca gaggcaggat cgaccccctg gtgtacctgg acgagttcct gaggaacagc    1440
gagcccgtgc tgaagagagt gaacaggacc ggcaacagca gcagcaacaa gcaggagtac    1500
cagctgctga aggacaacct ggtgcgcagc tacaacaagg ccctgaagaa gaacgccccc    1560
tacccatct tcgctatcaa gaacggccct aagagccaca tcggcaggca cctgatgacc    1620
agctttctga gcatgaaggg cctgaccgag ctgacaaacg tggtgggcaa ctggagcgac    1680
aagagggcct ccgccgtggc caggaccacc tacacccacc agatcaccgc catccccgac    1740
cactacttcg ccctggtgtc caggtactac gcctacgacc ccatcagcaa ggagatgatc    1800
gccctgaagg acgagaccaa ccccatcgag gagtggcagc acatcgagca gctgaagggc    1860
agcgccgagg gcagcatcag ataccccgcc tggaacggca tcatcagcca ggaggtgctg    1920
gactacctga gcagctacat caacaggcgg atcagatctg cggcgactac aaggacgac    1980
gacgacaagg actacaagga cgacgacgac aagtgaggta ccactagtgc ctcctcaatt    2040
cgatatcaag cttatcgata atcaacctct ggattacaaa atttgtgaaa gattgactgg    2100
tattcttaac tatgttgctc cttttacgct atgtggatac gctgctttaa tgcctttgta    2160
tcatgctatt gcttcccgta tggctttcat tttctcctcc ttgtataaat cctggttgct    2220
```

```
gtctctttat gaggagttgt ggcccgttgt caggcaacgt ggcgtggtgt gcactgtgtt      2280
tgctgacgca accccactg gttggggcat gccaccacc tgtcagctcc tttccgggac       2340
tttcgctttc ccctcccta ttgccacggc ggaactcatc gccgcctgcc ttgcccgctg      2400
ctggacaggg gctcggctgt tgggcactga caattccgtg gtgttgtcgg ggaaatcatc    2460
gtcctttcct tggctgctcg cctatgttgc cacctggatt ctgcgcggga cgtccttctg    2520
ctacgtccct tcggccctca atccagcgga ccttccttcc cgcggcctgc tgccggctct    2580
gcggcctctt ccgcgtcttc gccttcgccc tcagacgagt cggatctccc tttgggccgc    2640
ctccccgcat cgataccgag cgctgctcga gagatctacg ggtggcatcc ctgtgacccc    2700
tccccagtgc ctctcctggc cctggaagtt gccactccag tgcccaccag ccttgtccta    2760
ataaaattaa gttgcatcat tttgtctgac taggtgtcct tctataatat tatgggtgg     2820 agggggggtgg tatggagcaa ggggcaagtt gggaagacaa cctgtagggc ctgcggggtc    2880
tattgggaac caagctggag tgcagtggca caatcttggc tcactgcaat ctccgcctcc    2940
tgggttcaag cgattctcct gcctcagcct cccgagttgt tgggattcca ggcatgcatg    3000
accaggctca gctaattttt gtttttttgg tagagacggg gtttcaccat attggccagg    3060
ctggtctcca actcctaatc tcaggtgatc tacccacctt ggcctcccaa attgctggga    3120
ttacaggcgt gaaccactgc tcccttccct gtccttctga ttttgtaggt aaccacgtgc    3180
ggaccgagcg gccgcaggaa cccctagtga tggagttggc cactccctct ctgcgcgctc    3240
gctcgctcac tgaggccggg cgaccaaagg tcgcccgacg cccgggcttt gcccgggcgg    3300
cctcagtgag cgagcgagcg cgcagctgcc tgcaggggcg cctgatgcgg tattttctcc    3360
ttacgcatct gtgcggtatt tcacaccgca tacgtcaaag caaccatagt acgcgccctg    3420
tagcggcgca ttaagcgcgg cgggtgtggt ggttacgcgc agcgtgaccg ctacacttgc    3480
cagcgcccta gcgcccgctc ctttcgcttt cttcccttcc tttctcgcca cgttcgccgg    3540
ctttccccgt caagctctaa atcggggggct ccctttaggg ttccgattta gtgctttacg    3600
gcacctcgac cccaaaaaac ttgatttggg tgatggttca cgtagtgggc catcgccctg    3660
atagacggtt tttcgccctt tgacgttgga gtccacgttc tttaatagtg gactcttgtt    3720
ccaaactgga acaacactca accctatctc gggctattct tttgatttat aagggatttt    3780
gccgatttcg gcctattggt taaaaaatga gctgatttaa caaaaattta acgcgaattt    3840
taacaaaata ttaacgttta caattttatg gtgcactctc agtacaatct gctctgatgc    3900
cgcatagtta agccagcccc gacacccgcc aacacccgct gacgcgccct gacgggcttg    3960
tctgctcccg gcatccgctt acagacaagc tgtgaccgtc tccgggagct gcatgtgtca    4020
gaggttttca ccgtcatcac cgaaacgcgc gagacgaaag gcctcgtga tacgcctatt    4080 tttataggtt aatgtcatga taataatggt ttcttagacg tcaggtggca cttttcgggg    4140
aaatgtgcgc ggaaccccta tttgtttatt tttctaaata cattcaaata tgtatccgct    4200
catgagacaa taaccctgat aaatgcttca ataatattga aaaggaaga gtatgagtat    4260 tcaacatttc cgtgtcgccc ttattccctt tttgcggca ttttgccttc ctgtttttgc    4320
tcacccagaa acgctggtga agtaaaaga tgctgaagat cagttgggtg cacgagtggg    4380
ttacatcgaa ctggatctca acagcggtaa gatccttgag agttttcgcc ccgaagaacg    4440
ttttccaatg atgagcactt ttaaagttct gctatgtggc gcggtattat cccgtattga    4500
cgccgggcaa gagcaactcg gtcgccgcat acactattct cagaatgact tggttgagta    4560
```

| | |
|---|---|
| ctcaccagtc acagaaaagc atcttacgga tggcatgaca gtaagagaat tatgcagtgc | 4620 |
| tgccataacc atgagtgata acactgcggc caacttactt ctgacaacga tcggaggacc | 4680 |
| gaaggagcta accgcttttt tgcacaacat gggggatcat gtaactcgcc ttgatcgttg | 4740 |
| ggaaccggag ctgaatgaag ccataccaaa cgacgagcgt gacaccacga tgcctgtagc | 4800 |
| aatggcaaca acgttgcgca aactattaac tggcgaacta cttactctag cttcccggca | 4860 |
| acaattaata gactgatgg aggcggataa agttgcagga ccacttctgc gctcggccct | 4920 |
| tccggctggc tggtttattg ctgataaatc tggagccggt gagcgtgggt ctcgcggtat | 4980 |
| cattgcagca ctggggccag atggtaagcc ctcccgtatc gtagttatct acacgacggg | 5040 |
| gagtcaggca actatggatg aacgaaatag acagatcgct gagataggtg cctcactgat | 5100 |
| taagcattgg taactgtcag accaagttta ctcatatata ctttagattg atttaaaact | 5160 |
| tcatttttaa tttaaaagga tctaggtgaa gatcctttt gataatctca tgaccaaaat | 5220 |
| cccttaacgt gagttttcgt tccactgagc gtcagacccc gtagaaaaga tcaaaggatc | 5280 |
| ttcttgagat ccttttttc tgcgcgtaat ctgctgcttg caaacaaaaa aaccaccgct | 5340 |
| accagcggtg gtttgtttgc cggatcaaga gctaccaact cttttccga aggtaactgg | 5400 |
| cttcagcaga gcgcagatac caaatactgt ccttctagtg tagccgtagt taggccacca | 5460 |
| cttcaagaac tctgtagcac cgcctacata cctcgctctg ctaatcctgt taccagtggc | 5520 |
| tgctgccagt ggcgataagt cgtgtcttac cgggttggac tcaagacgat agttaccgga | 5580 |
| taaggcgcag cggtcgggct gaacggggggg ttcgtgcaca cagcccagct tggagcgaac | 5640 |
| gacctacacc gaactgagat acctacagcg tgagctatga gaaagcgcca cgcttcccga | 5700 |
| agggagaaag gcggacaggt atccggtaag cggcagggtc ggaacaggag agcgcacgag | 5760 |
| ggagcttcca gggggaaacg cctggtatct ttatagtcct gtcgggtttc gccacctctg | 5820 |
| acttgagcgt cgatttttgt gatgctcgtc agggggcgg agcctatgga aaaacgccag | 5880 |
| caacgcggcc ttttacggt tcctggcctt ttgctggcct tttgctcaca tgt | 5933 |

<210> SEQ ID NO 27
<211> LENGTH: 163
<212> TYPE: DNA
<213> ORGANISM: Artificial Sequence
<220> FEATURE:
<223> OTHER INFORMATION: 5' polyA

<400> SEQUENCE: 27

| | |
|---|---|
| aacgcaataa aatatcttta ttttcattac atctgtgtgt tggttttttg tgtgaatcga | 60 |
| tagtactaac atacgctctc catcaaaaca aaacgaaaca aaacaaacta gcaaaatagg | 120 |
| ctgtccccag tgcaagtgca ggtgccagaa catttctcta ttt | 163 |

<210> SEQ ID NO 28
<211> LENGTH: 316
<212> TYPE: DNA
<213> ORGANISM: Artificial Sequence
<220> FEATURE:
<223> OTHER INFORMATION: TRE-Tight Promoter

<400> SEQUENCE: 28

| | |
|---|---|
| cgagtttact ccctatcagt gatagagaac gtatgtcgag tttactccct atcagtgata | 60 |
| gagaacgatg tcgagtttac tccctatcag tgatagagaa cgtatgtcga gtttactccc | 120 |
| tatcagtgat agagaacgta tgtcgagttt actccctatc agtgatagag aacgtatgtc | 180 |
| gagtttatcc ctatcagtga tagagaacgt atgtcgagtt tactccctat cagtgataga | 240 |

```
gaacgtatgt cgaggtaggc gtgtacggtg ggaggcctat ataagcagag ctcgtttagt    300
gaaccgtcag atcgcc                                                    316
```

<210> SEQ ID NO 29
<211> LENGTH: 1356
<212> TYPE: DNA
<213> ORGANISM: Artificial Sequence
<220> FEATURE:
<223> OTHER INFORMATION: FLPo-flag

<400> SEQUENCE: 29

```
atggctccta agaagaagag gaaggtgatg agccagttcg acatcctgtg caagacccc     60 cccaaggtgc tggtgcggca gttcgtggag agattcgaga ggcccagcgg cgagaagatc    120
gccagctgtg ccgccgagct gacctacctg tgctggatga tcacccacaa cggcaccgcc    180
atcaagaggg ccaccttcat gagctacaac accatcatca gcaacagcct gagcttcgac    240
atcgtgaaca gagcctgca gttcaagtac aagacccaga aggccaccat cctggaggcc     300
agcctgaaga agctgatccc cgcctgggag ttcaccatca tcccttacaa cggccagaag    360
caccagagcg acatcaccga catcgtgtcc agcctgcagc tgcagttcga gagcagcgag    420
gaggccgaca agggcaacag ccacagcaag aagatgctga aggccctgct gtccgagggc    480
gagagcatct gggagatcac cgagaagatc ctgaacagct cgagtacac cagcaggttc    540 accaagacca agaccctgta ccagttcctg ttcctggcca cattcatcaa ctgcggcagg    600
ttcagcgaca tcaagaacgt ggaccccaag agcttcaagc tggtgcagaa caagtacctg    660
ggcgtgatca ttcagtgcct ggtgaccgag accaagacaa gcgtgtccag gcacatctac    720
tttttcagcg ccagaggcag gatcgacccc ctggtgtacc tggacgagtt cctgaggaac    780
agcgagcccg tgctgaagag agtgaacagg accggcaaca gcagcagcaa caagcaggag    840
taccagctgc tgaaggacaa cctggtgcgc agctacaaca aggccctgaa gaagaacgcc    900
ccctacccca tcttcgctat caagaacggc cctaagagcc acatcggcag gcacctgatg    960 accagcttc tgagcatgaa gggcctgacc gagctgacaa acgtggtggg caactggagc    1020
gacaagaggg cctccgccgt ggccaggacc acctacaccc accagatcac cgccatcccc    1080
gaccactact cgccctggt gtccaggtac tacgcctacg accccatcag caaggagatg    1140
atcgccctga aggacgagac caaccccatc gaggagtggc agcacatcga gcagctgaag    1200
ggcagcgccg agggcagcat cagataccc gcctggaacg gcatcatcag ccaggaggtg    1260
ctggactacc tgagcagcta catcaacagg cggatcagat ctggcggcga ctacaaggac    1320
gacgacgaca aggactacaa ggacgacgac gacaag                              1356
```

<210> SEQ ID NO 30
<211> LENGTH: 609
<212> TYPE: DNA
<213> ORGANISM: Artificial Sequence
<220> FEATURE:
<223> OTHER INFORMATION: TRE WPRE

<400> SEQUENCE: 30

```
gcttatcgat aatcaacctc tggattacaa aatttgtgaa agattgactg gtattcttaa    60
ctatgttgct ccttttacgc tatgtggata cgctgcttta atgcctttgt atcatgctat    120
tgcttcccgt atggctttca ttttctcctc cttgtataaa tcctggttgc tgtctcttta    180
tgaggagttg tggcccgttg tcaggcaacg tggcgtggtg tgcactgtgt ttgctgacgc    240
```

```
aaccccccact ggttggggca ttgccaccac ctgtcagctc ctttccggga ctttcgcttt      300
cccctcccct attgccacgg cggaactcat cgccgcctgc cttgcccgct gctggacagg      360
ggctcggctg ttgggcactg acaattccgt ggtgttgtcg gggaaatcat cgtcctttcc      420
ttggctgctc gcctatgttg ccacctggat tctgcgcggg acgtccttct gctacgtccc      480
ttcggccctc aatccagcgg accttccttc ccgcggcctg ctgccggctc tgcggcctct      540
tccgcgtctt cgccttcgcc ctcagacgag tcggatctcc ctttgggccg cctccccgca      600
tcgataccg                                                              609
```

<210> SEQ ID NO 31
<211> LENGTH: 480
<212> TYPE: DNA
<213> ORGANISM: Artificial Sequence
<220> FEATURE:
<223> OTHER INFORMATION: hGH polyA

<400> SEQUENCE: 31

```
tacgggtggc atccctgtga cccctcccca gtgcctctcc tggccctgga agttgccact       60
ccagtgccca ccagccttgt cctaataaaa ttaagttgca tcattttgtc tgactaggtg      120
tccttctata atattatggg gtggaggggg gtggtatgga gcaaggggca agttgggaag      180
acaacctgta gggcctgcgg ggtctattgg gaaccaagct ggagtgcagt ggcacaatct      240
tggctcactg caatctccgc ctcctgggtt caagcgattc tcctgcctca gcctcccgag      300
ttgttgggat tccaggcatg catgaccagg ctcagctaat ttttgttttt ttggtagaga      360 cggggttttca ccatattggc caggctggtc tccaactcct aatctcaggt gatctaccca      420
ccttggcctc ccaaattgct gggattacag gcgtgaacca ctgctccctt ccctgtcctt      480
```

<210> SEQ ID NO 32
<211> LENGTH: 380
<212> TYPE: PRT
<213> ORGANISM: Homo sapiens

<400> SEQUENCE: 32

```
Met Met Phe Ser Gly Phe Asn Ala Asp Tyr Glu Ala Ser Ser Ser Arg
 1               5                  10                  15

Cys Ser Ser Ala Ser Pro Ala Gly Asp Ser Leu Ser Tyr Tyr His Ser
            20                  25                  30

Pro Ala Asp Ser Phe Ser Ser Met Gly Ser Pro Val Asn Ala Gln Asp
        35                  40                  45

Phe Cys Thr Asp Leu Ala Val Ser Ser Ala Asn Phe Ile Pro Thr Val
    50                  55                  60

Thr Ala Ile Ser Thr Ser Pro Asp Leu Gln Trp Leu Val Gln Pro Ala
65                  70                  75                  80

Leu Val Ser Ser Val Ala Pro Ser Gln Thr Arg Ala Pro His Pro Phe
                85                  90                  95

Gly Val Pro Ala Pro Ser Ala Gly Ala Tyr Ser Arg Ala Gly Val Val
            100                 105                 110

Lys Thr Met Thr Gly Gly Arg Ala Gln Ser Ile Gly Arg Arg Gly Lys
        115                 120                 125

Val Glu Gln Leu Ser Pro Glu Glu Glu Lys Arg Arg Ile Arg Arg
    130                 135                 140

Glu Arg Asn Lys Met Ala Ala Ala Lys Cys Arg Asn Arg Arg Arg Glu
145                 150                 155                 160

Leu Thr Asp Thr Leu Gln Ala Glu Thr Asp Gln Leu Glu Asp Glu Lys
```

```
             165                 170                 175
Ser Ala Leu Gln Thr Glu Ile Ala Asn Leu Leu Lys Glu Lys Glu Lys
        180                 185                 190

Leu Glu Phe Ile Leu Ala Ala His Arg Pro Ala Cys Lys Ile Pro Asp
        195                 200                 205

Asp Leu Gly Phe Pro Glu Glu Met Ser Val Ala Ser Leu Asp Leu Thr
        210                 215                 220

Gly Gly Leu Pro Glu Val Ala Thr Pro Glu Ser Glu Glu Ala Phe Thr
225                 230                 235                 240

Leu Pro Leu Leu Asn Asp Pro Glu Pro Lys Pro Ser Val Glu Pro Val
                245                 250                 255

Lys Ser Ile Ser Ser Met Glu Leu Lys Thr Glu Pro Phe Asp Asp Phe
                260                 265                 270

Leu Phe Pro Ala Ser Ser Arg Pro Ser Gly Ser Glu Thr Ala Arg Ser
                275                 280                 285

Val Pro Asp Met Asp Leu Ser Gly Ser Phe Tyr Ala Ala Asp Trp Glu
                290                 295                 300

Pro Leu His Ser Gly Ser Leu Gly Met Gly Pro Met Ala Thr Glu Leu
305                 310                 315                 320

Glu Pro Leu Cys Thr Pro Val Val Thr Cys Thr Pro Ser Cys Thr Ala
                325                 330                 335

Tyr Thr Ser Ser Phe Val Phe Thr Tyr Pro Glu Ala Asp Ser Phe Pro
                340                 345                 350

Ser Cys Ala Ala Ala His Arg Lys Gly Ser Ser Ser Asn Glu Pro Ser
                355                 360                 365

Ser Asp Ser Leu Ser Ser Pro Thr Leu Leu Ala Leu
                370                 375                 380

<210> SEQ ID NO 33
<211> LENGTH: 34
<212> TYPE: DNA
<213> ORGANISM: Artificial Sequence
<220> FEATURE:
<223> OTHER INFORMATION: loxP

<400> SEQUENCE: 33
ataacttcgt atagcataca ttatacgaag ttat                              34

<210> SEQ ID NO 34
<211> LENGTH: 34
<212> TYPE: DNA
<213> ORGANISM: Artificial Sequence
<220> FEATURE:
<223> OTHER INFORMATION: lox2272

<400> SEQUENCE: 34
ataacttcgt ataaagtatc ctatacgaag ttat                              34

<210> SEQ ID NO 35
<211> LENGTH: 34
<212> TYPE: DNA
<213> ORGANISM: Artificial Sequence
<220> FEATURE:
<223> OTHER INFORMATION: loxN

<400> SEQUENCE: 35
ataacttcgt atagtatacc ttatacgaag ttat                              34

<210> SEQ ID NO 36
```

```
<211> LENGTH: 34
<212> TYPE: DNA
<213> ORGANISM: Artificial Sequence
<220> FEATURE:
<223> OTHER INFORMATION: FLP recombinase

<400> SEQUENCE: 36
gaagttccta ttctctagaa agtataggaa cttc                              34
```